United States Patent
Hotta et al.

(10) Patent No.: US 12,084,698 B2
(45) Date of Patent: Sep. 10, 2024

(54) VIRUS-LIKE PARTICLES AND USE THEREOF

(71) Applicant: KYOTO UNIVERSITY, Kyoto (JP)

(72) Inventors: Akitsu Hotta, Kyoto (JP); Peter David Gee, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 900 days.

(21) Appl. No.: 17/258,288

(22) PCT Filed: Jul. 12, 2019

(86) PCT No.: PCT/JP2019/027708
§ 371 (c)(1),
(2) Date: Jan. 6, 2021

(87) PCT Pub. No.: WO2020/013317
PCT Pub. Date: Jan. 16, 2020

(65) Prior Publication Data
US 2021/0269790 A1    Sep. 2, 2021

(30) Foreign Application Priority Data
Jul. 13, 2018 (JP) ................. 2018-133682

(51) Int. Cl.
| | | |
|---|---|---|
| *C12N 9/90* | (2006.01) | |
| *A61K 31/436* | (2006.01) | |
| *A61K 35/76* | (2015.01) | |
| *C07K 14/16* | (2006.01) | |
| *C12N 7/00* | (2006.01) | |
| *C12N 9/22* | (2006.01) | |
| *C12N 15/113* | (2010.01) | |
| *C12N 15/62* | (2006.01) | |
| *C12N 15/87* | (2006.01) | |

(52) U.S. Cl.
CPC .............. *C12N 9/90* (2013.01); *A61K 31/436* (2013.01); *A61K 35/76* (2013.01); *C07K 14/161* (2013.01); *C12N 7/00* (2013.01); *C12N 9/22* (2013.01); *C12N 15/113* (2013.01); *C12N 15/625* (2013.01); *C12N 15/87* (2013.01); *C12Y 502/00* (2013.01)

(58) Field of Classification Search
CPC ... C12N 9/90; C12N 7/00; C12N 9/22; C12N 15/113; C12N 15/625; C12N 15/87; C12N 15/907; C12N 15/111; C12N 2310/20; C12N 2330/51; C12N 2740/16023; C12N 2740/16042; C12N 2740/16222; A61K 31/436; A61K 35/76; A61K 48/0041; A61K 48/005; C07K 14/161; C07K 14/005; C12Y 502/00
See application file for complete search history.

(56) References Cited

FOREIGN PATENT DOCUMENTS

| | | |
|---|---|---|
| WO | WO 2013/148302 A1 | 10/2013 |
| WO | WO 2013/174999 A1 | 11/2013 |
| WO | WO 2016/150992 A1 | 9/2016 |
| WO | WO 2017/068077 A1 | 4/2017 |

OTHER PUBLICATIONS

Banaszynski et al., "Characterization of the FKBP-Rapamycin-FRB Ternary Complex", JACS, Published Mar. 9, 2005, vol. 127, pp. 4715-4716. (Year: 2005).*
Kaczmarczyk et al., "Protein delivery using engineered virus-like particles", PNAS, Published Oct. 11, 2011, vol. 108, pp. 16998-16999. (Year: 2011).*
Choi et al., "Lentivirus pre-packed with Cas9 protein for safer gene editing", Gene Ther., Jul. 2016, 23(7): 627-633.
Gao et al., "Self-processing of ribozyme-flanked RNAs into guide RNAs in vitro and in vivo for CRISPR-mediated genome editing", J Integr Plant Biol., Apr. 2014, 56(4): 343-349.
International Search Report for PCT International Patent Application No. PCT/JP2019/027708, mailed Oct. 8, 2019, with English translation, 4 pages.
Liang et al., "Engineering the ABA plant stress pathway for regulation of induced proximity", Sci Signal, Mar. 15, 2011, 4(164): rs2.
Miyamoto et al., "Rapid and orthogonal logic gating with a gibberellin-induced dimerization system", Nat Chem Biol., Mar. 25, 2012, 8(5): 465-470.
Yoshioka et al., "Development of a mono-promoter-driven CRISPR/Cas9 system in mammalian cells", Sci Rep., Dec. 16, 2015, 5: 18341.

* cited by examiner

*Primary Examiner* — Brian Whiteman
*Assistant Examiner* — Stephanie L Sullivan
(74) *Attorney, Agent, or Firm* — Lathrop GPM LLP; Brian C. Trinque; Tanya D'Souza

(57) ABSTRACT

A virus-like particle encapsulating a target protein is provided. The virus-like particle contain a Gag protein, and the Gag protein forms a dimer with the target protein.

6 Claims, 50 Drawing Sheets
Specification includes a Sequence Listing.

(a)

(b)

(c)

(a) FKBP12-Gag$^{HIV}$ (b) FRB-Luc (c)

(a) Jurkat (T lympohcyte) cells (b) Jurkat (T lymphocyte) cells

(a) Cortical neurons differentiated from iPSCs

*SAMHD1* gene locus sgRNA #2: CTCAAACACCCCTTCCGCAG AGG
SEQ ID NO: 31
PAM sgRNA #1: GTCATCGCAACGGGGACGCT TGG
SEQ ID NO: 30
PAM

(b)

(c)

anti-SAMHD1 VLP — — #1 #2
T7E1 — + + +

% Indels    0    0    36    36

(a)

(b)

(c)

(d)

VIRUS-LIKE PARTICLES AND USE THEREOF

SEQUENCE LISTING

The instant application contains a Sequence Listing which has been submitted electronically in ASCII format and is hereby incorporated by reference in its entirety. Said ASCII file, created on Mar. 11, 2024, is named 712472_SIW-023US_ST25.txt and is 109,179 bytes in size.

TECHNICAL FIELD

The present invention relates to a virus-like particle encapsulating a target protein and/or target RNA and use of the virus-like particle. More specifically, the present invention relates to a virus-like particle encapsulating a Cas family protein or a Cas family protein/RNA RNP complex, a method for manufacturing the virus-like particle, a kit for manufacturing the virus-like particle, and a method for manufacturing a cell with genomic DNA cleaved in a sequence-specific manner.

BACKGROUND ART

The introduction of a genome-editing enzyme such as CRISPR-Cas9/gRNA RNP complex into cells or living organisms makes it possible to induce DNA cleavage, base substitution, epigenetic modification, and the like at any genomic site.

As methods for introducing a Cas9 protein, a Cas9 gene, gRNA, and the like into cells, various methods have been developed, such as lipofection or a lipid nanoparticle (LNP) method using lipid, electroporation or microinjection as a physical introduction method, and a viral vector method that exploits the mechanism of viral entry into cells.

Among these, the viral vector method is widely used, and particularly, an adeno-associated virus (AAV) vector, a lentiviral vector, and the like are known to exhibit high introduction efficiency and low cytotoxicity.

However, the viral vector-mediated expression of exogenous genes persists for a long period of time. Therefore, for example, in a case where a Cas9 gene is introduced into cells by the viral vector method, the expression of the Cas9 protein persists for a long period of time in the cells. As a result, the risk of introducing an off-target mutation that cleaves sequences other than a target sequence increases.

Therefore, a technique has been developed which uses a virus-like particle (hereinafter, called "VLP" in some cases) composed only of the envelope of a virus so as to utilize only the mechanism of viral entry into cells while ruling out the replication mechanism and infection persistency of the virus. Once entering cells, VLPs release the exogenous gene contained in the particles and then disappear. The transient expression pattern is a major characteristic of VLPs. Virus-like particles are particles which contain at least one or more virus-derived proteins and have a diameter of 1,000 nm or less. Such virus-like particles are classified into particles having a lipid bilayer membrane and particles devoid of such a membrane.

For example, Non-Patent Literature 1 reports a method of encapsulating a Cas9 protein in VLPs by using a fusion protein of a lentiviral Gag structure protein and a Cas9 protein.

Clontech Laboratories, Inc. sells a GESICLE system more efficient in encapsulating a Cas9 protein in VLPs. In the Gesicle system, an iDimerize Inducible Heterodimer System is used to cause Cherry Picker as a membrane localization-type fluorescent protein and a Cas9 protein to associate with each other in a compound A/C Heterodimerizer-dependent manner. In this way, the CAS9 protein is more efficiently encapsulated in VLPs.

CITATION LIST

Non-Patent Literature

[Non-Patent Literature 1]
Choi J. G., et al., Lentivirus pre-packed with Cas9 protein for safer gene editing, Gene Therapy, vol 23, 627-633, 2016.

SUMMARY OF INVENTION

Technical Problem

However, the method described in Non-Patent Literature 1 is inefficient in encapsulating a Cas9 protein in VLPs and inducing genomic cleavage.

Furthermore, the Gesicle system of Clontech Laboratories, Inc. is sometimes inefficient in encapsulating Cas9 because the Cherry Picker fluorescent protein is not specifically incorporated into VLPs.

In addition, it is not easy to manufacture VLPs containing a sufficient amount of an active Cas9/gRNA RNP complex. In order to form an active Cas9/gRNA RNP complex in VLPs, first, sufficient amounts of Cas9 and gRNA need to be encapsulated in VLPs. In order for gRNA to be efficiently encapsulated in VLPs, gRNA needs to be transported to the cytoplasm (from the nucleus) in VLP-producing cells and localized in the vicinity thereof at the time of budding of VLPs.

However, in the method that has been conventionally used, gRNA tends to stay in the nucleus of the producing cells and is difficult to be encapsulated in VLPs.

An object of the present invention is to provide a technique for efficiently encapsulating a target protein or a target protein and a target RNA in a virus-like particle (VLP).

Solution to Problem

As a solution to the problems of the conventional technique, the inventors of the present invention have found that in a case where a target protein and Gag protein are expressed in VLP-producing cells, and these proteins are expressed as a fusion protein with either an FK506-binding protein (FKBP12) or an FKBP12-rapamycin-associated protein 1, FRAP1 fragment (FRB), the target protein is efficiently encapsulated in VLPs depending on the presence of a rapamycin compound.

Furthermore, the inventors of the present invention have found that in a case where a gRNA sequence is interposed between two self-splicing RNA (Self-cleaving RNA, hereinafter, called ribozyme in some cases) sequences, a packaging signal of retrovirus is disposed on the upstream thereof, and mRNA transcribed under the control of an LTR promoter is expressed, the mRNA is actively encapsulated in VLPs, the gRNA is automatically cleaved from the mRNA, and the obtained VLPs exhibit higher Cas9 activity in each particle compared to the conventional VLPs.

Based on these findings, the inventors of the present invention have accomplished the present invention.

That is, the present invention includes the following aspects.

[1] A virus-like particle encapsulating a target protein, containing Gag protein, in which the Gag protein forms a dimer with the target protein.

[2] The virus-like particle described in [1], in which one of the Gag protein and the target protein is a fusion protein with an FK506-binding protein (FKBP12) and the other is a fusion protein with an FKBP12-rapamycin-associated protein 1, FRAP1 fragment (FRB), and the FKBP12, rapamycin or a rapamycin derivative, and the FRB are bound together in the dimer.

[3] The virus-like particle described in [1] or [2], in which the target protein is a Cas family protein.

[4] The virus-like particle described in [3] further encapsulating mRNA or a self-cleavage product of the mRNA, in which the mRNA has a gRNA sequence interposed between a first ribozyme sequence and a second ribozyme sequence and a packaging signal sequence.

[5] A method for manufacturing a genome-edited cell, including inoculating the cell with the virus-like particle described in [4].

[6] A method for manufacturing a virus-like particle encapsulating a target protein, including the following steps (1) and (2): (1) a step of letting a cell to express a fusion protein of FKBP12 and Gag protein and a fusion protein of FRB and the target protein, or to express a fusion protein of FRB and Gag protein and a fusion protein of FKBP12 and the target protein in the presence of rapamycin or a rapamycin derivative, and (2) a step of obtaining a medium containing the virus-like particle encapsulating the target protein.

[7] The method for manufacturing described in [6], in which in step (1), a nucleic acid encoding the fusion protein is introduced into the cell by lipofection or electroporation.

[8] A method for manufacturing a virus-like particle encapsulating a Cas family protein and a gRNA, including the following steps (1) and (2): (1) a step of letting a cell to express a fusion protein of FKBP12 and Gag protein and a fusion protein of FRB and a Cas family protein, or a fusion protein of FRB and Gag protein and a fusion protein of FKBP12 and the Cas family protein, and an mRNA having the gRNA sequence interposed between a first ribozyme sequence and a second ribozyme sequence and a packaging signal sequence in the presence of rapamycin or a rapamycin derivative, and (2) a step of obtaining a medium containing the virus-like particle encapsulating the Cas family protein and the gRNA.

[9] The method for manufacturing described in [8], in which in step (1), a nucleic acid encoding the fusion protein or the mRNA is introduced into the cells by lipofection or electroporation.

[10] A kit for manufacturing a virus-like particle encapsulating a target protein, including an expression vector for a fusion protein of FKBP12 and Gag protein or an expression vector for a fusion protein of FRB and Gag protein.

[11] A kit for manufacturing a virus-like particle encapsulating a Cas family protein, including an expression vector for a fusion protein of FKBP12 and Gag protein and an expression vector for a fusion protein of FRB and the Cas family protein or an expression vector for a fusion protein of FRB and Gag protein and an expression vector for a fusion protein of FKBP12 and the Cas family protein.

[12] The kit described in [11], further including an expression vector for mRNA having a base sequence of a target RNA or a multiple cloning site, which is interposed between a first ribozyme sequence and a second ribozyme sequence, and a packaging signal sequence.

[13] A virus-like particle encapsulating a target RNA, containing Gag protein, in which the target RNA is encapsulated in the form of mRNA or in the form of a self-cleavage product of the mRNA, in which the mRNA has a base sequence of the target RNA, which is interposed between a first ribozyme sequence and a second ribozyme sequence, and a packaging signal sequence.

[14] A method for manufacturing a virus-like particle encapsulating a target RNA, including the following steps (1) and (2): (1) a step of letting a cell to express a Gag protein and an mRNA having a base sequence of the target RNA, which is interposed between a first ribozyme sequence and a second ribozyme sequence, and a packaging signal sequence and (2) a step of obtaining the virus-like particle which are contained in a medium of the cells and encapsulate the target RNA in the form of the mRNA or in the form of a self-cleavage product of the mRNA.

[15] The method for manufacturing described in [14], in which in step (1), a nucleic acid encoding the mRNA is introduced into the cells by lipofection or electroporation.

[16] A kit for manufacturing a virus-like particle encapsulating a target RNA, including an expression vector for Gag protein and an expression vector for mRNA having a base sequence of the target RNA or a multiple cloning site, which is interposed between a first ribozyme sequence and a second ribozyme sequence, and a packaging signal sequence.

[17] An agent for treating diseases caused by genetic mutation, infections, or cancer, the agent containing the virus-like particle described in [1] to [4] or [13] as an active component.

Advantageous Effects of Invention

According to the present invention, it is possible to provide a technique for efficiently encapsulating a target protein in a virus-like particle.

BRIEF DESCRIPTION OF DRAWINGS

FIG. 1(*b*) is a schematic view showing the structure of a fusion protein obtained by adding an FKBP12 domain to the N-terminal of Gag-Pol of HIV (hereinafter, called "FKBP12-Gag-Pol$^{HIV}$" in some cases). FIG. 1(*c*) is a schematic view showing the structure of a fusion protein obtained by adding an FKBP12 domain to the N-terminal of Gag of HIV (hereinafter, called "FKBP12-Gag$^{HIV}$" in some cases).

DESCRIPTION OF EMBODIMENTS

[Virus-Like Particles Encapsulating Target Protein]

Figure 1:
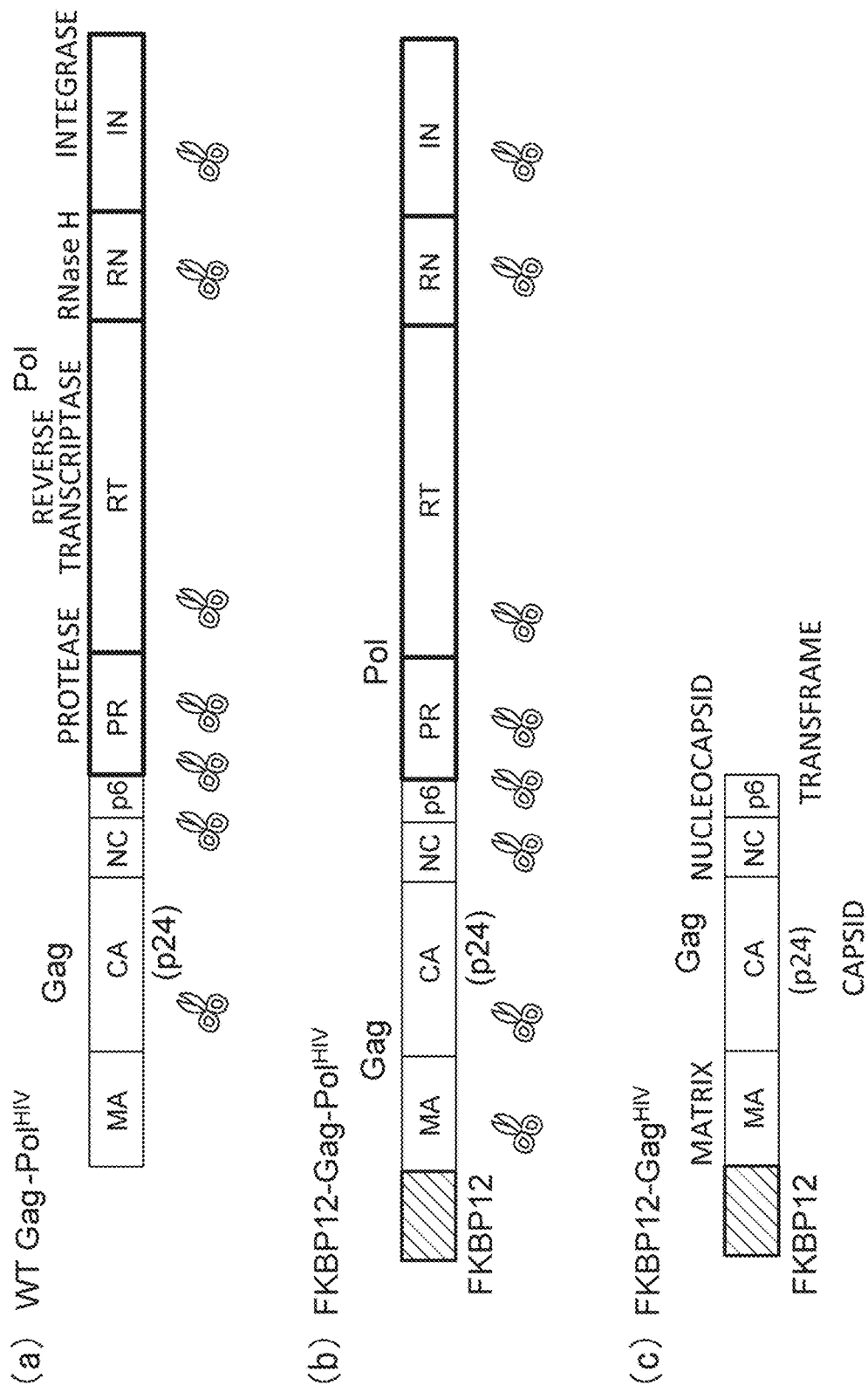
FIG. 1(*a*) is a schematic view showing the structure of Gag-Pol of HIV (hereinafter, called "WT Gag-Pol$^{HIV}$" in some cases).

In an embodiment, the present invention provides virus-like particles encapsulating a target protein. The virus-like particles contain Gag protein, and the Gag protein forms a dimer with the target protein.

As will be described later in Examples, a target protein can be efficiently encapsulated in the virus-like particles (hereinafter, called "VLPs" in some cases) of the present embodiment. By letting VLPs of the present embodiment to enter cells, it is possible to efficiently introduce the target protein into the cells.

VLP is a particle composed only of the envelope of a virus so as to rule out the replication mechanism and infection persistency of the virus. VLPs of the present embodiment contain Gag protein. Examples of the Gag protein include Gag protein derived from a retrovirus. As the Gag protein, Gag protein derived from human immunodeficiency virus (HIV), Gag protein derived from murine leukemia virus (MLV), and the like can be suitably used.

The amino acid sequence of the HIV-derived Gag protein is shown in SEQ ID NO: 1, and the amino acid sequence of the MLV-derived Gag protein is shown in SEQ ID NO: 2. The Gag protein may have a mutation as long as the effect of VLPs of the present embodiment can be obtained.

In VLPs of the present embodiment, the Gag protein may be cleaved into a matrix (MA), a capsid (CA), a nucleocapsid (NC), or the like, or these may remain bound together.

As will be described later in Examples, it is preferable that VLPs of the present embodiment not contain retrovirus-derived Pol. In a case where VLPs contain Pol, sometimes the target protein is broken down by the protease of Pol.

Incidentally, in order to let VLPs to enter cells, a process of membrane fusion between a viral membrane and a cell membrane is required. A viral protein called envelope protein is responsible for the process of membrane fusion. The envelope (Env) protein is present on the surface of an enveloped virus and has an ability to induce membrane fusion.

The envelope of VLPs of the present embodiment may contain a viral envelope protein known in the related art. As the envelope protein, for example, the Env protein of viruses belonging to the family Retroviridae (such as human immunodeficiency virus (HIV), simian immunodeficiency virus (SIV), feline immunodeficiency virus (FIV), equine infectious anemia virus (EIAV), human T-lymphotropic virus (HTLV), murine leukemia virus (MLV), feline leukemia virus (FLV), Rouse sarcoma virus (RSV), and endogenous retrovirus), the Env protein (G protein) of viruses belonging to the family Rhabdoviridae (such as vesicular stomatitis virus (VSV), rabies virus, and Mokola virus), the Env protein of viruses belonging to the family Arenaviridae (such as Lymphocytic choriomeningitis virus (LCMV)), the Env protein of the family Togaviridae (such as sindbis virus), the Env protein (hemagglutinin (HA) protein and fusion (F) protein) of viruses belonging to the family Paramyxoviridae (such as measles virus), the envelope protein (hemagglutinin (HA) protein and neuraminidase (NA) protein) of viruses belonging to the family Orthomyxoviridae (such as influenza virus), and the like can be suitably used. Among these, VSV-G which is a glycoprotein derived from VSV can be particularly suitably used. The amino acid sequence of VSV-G is shown in SEQ ID NO: 3. Examples of host cells into which VLPs will enter include human-derived cells, nonhuman animal-derived cells, cells in organisms, and the like. Examples of the organisms include human beings and nonhuman animals.

The target protein in VLPs of the present embodiment is not particularly limited, and examples thereof include sequence-specific DNA cleavage enzymes such as RNA-induced nuclease and artificial nuclease; cell reprogramming-inducing proteins such as Oct3/4 protein, Sox2 protein, Klf4 protein, and c-Myc protein; cell type-converting proteins such as MyoD protein, GATA4 protein, MEF2C protein, TBX5 protein, FOXA1 protein, FOXA2 protein, FOXA3 protein, HNF4A protein, ASCL1 protein, BRN2 protein, and MYT1L protein; fluorescent proteins (such as mCherry); luciferase protein, and the like.

In a case where the target protein is a sequence-specific DNA cleavage enzyme, by letting VLPs of the present embodiment to enter cells, it is possible to efficiently introduce the sequence-specific DNA cleavage enzyme into the cells. As a result, DNA cleavage, base substitution, epigenetic modification, and the like can be induced at any genomic site.

The sequence-specific DNA cleavage enzyme is roughly classified into RNA-induced nuclease and artificial nuclease. The sequence-specific DNA cleavage enzyme may be the RNA-induced nuclease or the artificial nuclease.

The RNA-induced nuclease is an enzyme in which a short chain RNA as a guide binds to a target sequence and recruits a nuclease having two DNA cleavage domains (nuclease domains) so as to induce sequence-specific cleavage. Examples of the RNA-induced nuclease include CRISPR-Cas family proteins.

Examples of the CRISPR-Cas family proteins include Cas9, Cpf1 (also known as Cas12a), C2C1 (also known as Cas12b), C2C2 (also known as Cas13a), CasX, CasY, Cas1, Cas2, Cas3, Cas4, Cas5, Cas6, Cas7, Cas8, Cas10, and the like. The RNA-induced nuclease may be a homologue of the CRISPR-Cas family protein or a modified CRISPR-Cas family protein. For example, the RNA-induced nuclease may be a nickase-modified nuclease obtained by modifying one of two wild-type nuclease domains into an inactive domain, or dCas9 obtained by modifying both of two wild-type nuclease domains into inactive domains. Alternatively, Cas9-HF, HiFi-Cas9, eCas9, and the like with enhanced target specificity may be used. In addition, proteins obtained by the fusion of these Cas9 proteins with other proteins (enzyme and the like) may be used.

Cas9 is derived, for example, from *Streptococcus pyogenes, Staphylococcus aureus, Streptococcus thermophilus, Geobacillus stearothermophilus*, and the like. Cpf1 is derived, for example, from Acidaminococcus, Lachnospiraceae, *Chlamydomonas, Francisella novicida*, and the like.

The amino acid sequence of the Cas9 protein derived from *Streptococcus pyogenes* (hereinafter, called "SpCas9 protein" in some cases) is shown in SEQ ID NO: 4.

The artificial nuclease is an artificial restriction enzyme having a DNA binding domain designed and prepared to specifically bind to a target sequence, and a nuclease domain (such as a DNA cleavage domain of FokI which is a restriction enzyme). Examples of the artificial nuclease include, but are not limited to, Zinc finger nuclease (ZFN), Transcription activator-like effector nuclease (TALEN), meganuclease, and the like.

In VLPs of the present embodiment, the Gag protein forms a dimer with the target protein. Forming a dimer means that the proteins are reversibly bound together. Therefore, it is preferable that the Gag protein not be a fusion protein with the target protein.

The Gag protein and the target protein can be dissociated from each other. Therefore, in a case where VLPs of the present embodiment are caused to enter target cells so that the target protein is introduced into the cells, and then the Gag protein is dissociated from the target protein, the target protein can fully perform its function.

Furthermore, because the Gag protein and the target protein form a dimer, the target protein can be efficiently encapsulated in VLPs in VLP-producing cells.

The means by which the Gag protein and the target protein form a dimer is not particularly limited. For example, it is possible to use a system in which FK506-binding protein (FKBP12) and FKBP12-rapamycin-associated protein 1, FRAP1 fragment (FRB) form a heterodimer in the presence of rapamycin or a rapamycin derivative. Alternatively, it is possible to use a system in which GAI (Gibberellin insensitive) and GID1 (Gibberellin insensitive dwarf1) form a heterodimer in the presence of gibberellin or GA3-AM (for example, see Miyamoto T., et al., Rapid and Orthogonal Logic Gating with a Gibberellin-induced Dimerization System, Nat Chem Biol., 8 (5), 465-470, 2012), a system in which PyL (PYR1-like, consisting of the $33^{rd}$ to $209^{th}$ amino acids) and ABI1 (consisting of the $126^{th}$ to $423^{rd}$ amino acids) form a heterodimer in the presence of S-(+)-abscisic acid (ABA) (for example, see, Liang F. S., et al., Engineering the ABA plant stress pathway for regulation of induced proximity, Sci Signal., 4 (164), rs2, 2011), and the like.

In the present specification, the term "rapamycin derivative" includes "rapamycin analog", and sometimes "rapamycin" and "rapamycin derivative" will be called "rapamycin compound".

Specifically, by culturing VLP-producing cells (cells expressing envelope-constituting proteins) in the presence of rapamycin or a rapamycin derivative, and letting one of the Gag protein and the target protein to be expressed as a fusion protein with FKBP12 and the other to be expressed as a fusion protein with FRB in the VLP-producing cells, it is possible to dimerize the FKBP12 domain and the FRB domain through the rapamycin or the rapamycin derivative.

Furthermore, the fusion protein (fusion protein of FKBP12 or FRB with Gag) may have an amino acid sequence that promotes the localization of the protein in the cell membrane (hereinafter, such an amino acid sequence will be called cell membrane localization sequence in some cases). In a case where the fusion protein is localized in the cell membrane of the VLP-producing cells, by the FKBP12 domain-FRB domain interaction, the target protein is efficiently recruited to the vicinity of the cell membrane, and the aforementioned dimer can be formed in the vicinity of the cell membrane. As a result, the dimer is efficiently encapsulated in VLPs during the budding of VLPs. Accordingly, it is possible to manufacture VLPs containing more target proteins compared to VLPs prepared by the conventional method. In the present disclosure, "localized in the cell membrane" refers to a state where the target molecule is bound to the lipid or protein constituting the cell membrane directly or through other factors.

Examples of the cell membrane localization sequence include a sequence promoting post-translational protein modification such as farnesylation, palmitoylation, myristoylation, and GPI anchorization, a sequence that constitutes a transmembrane domain consisting of hydrophobic amino acid residues, a sequence of a domain or peptide binding to proteins present in cell membrane structures, and the like. As these sequences, those well known in the related art can be appropriately used without particular limitation. Among these, the sequence promoting post-translational protein modification (including lipid modification) can be suitably used.

For example, as will be described later in Examples, FKBP12 may be fused with the Gag protein, and FRB may be fused with the target protein. For instance, in a case where the target protein is a Cas9 protein, it is preferable to fuse FKBP12 with the N-terminal side of the Gag protein. Furthermore, it is preferable to fuse FRB with the N-terminal side of the Cas9 protein.

The amino acid sequence of the FKBP12 protein is shown in SEQ ID NO: 5, and the amino acid sequence of the FRB protein is shown in SEQ ID NO: 6. As long as the effect of VLPs of the present embodiment is obtained, the FKBP12 protein or the FRB protein may have a mutation.

As the rapamycin derivative, for example, AP21967 (C-16-(S)-7-methylindole rapamycin) can be suitably used.

[Virus-Like Particles Encapsulating Target Protein and Target RNA]

VLPs of the present embodiment may further encapsulate a target RNA in addition to the target protein. For example, the target protein may be a Cas family protein, and the target RNA may be gRNA. In this case, by letting VLPs to enter cells, genome editing can be induced at a target sequence site of genomic DNA of the cells.

gRNA is usually a short RNA chain consisting of about 100 or less bases. Conventionally, short chain RNAs such as gRNA cannot be efficiently encapsulated in VLPs.

As a solution to this problem, the inventors of the present invention let VLP-producing cells to express mRNA having a gRNA sequence interposed between a first ribozyme sequence and a second ribozyme sequence and a packaging signal sequence as will be described later in Examples. As a result, the inventors succeeded in efficiently encapsulating the mRNA in VLPs. In VLPs or target cells in which genome editing is to be induced, the mRNA cleaves a gRNA portion by the self-cleaving activity of ribozyme and generates gRNA as a self-cleavage product.

That is, VLPs of the present embodiment may further encapsulate mRNA or a self-cleavage product of the mRNA, in which the mRNA includes a gRNA sequence interposed between a first ribozyme sequence and a second ribozyme sequence and a packaging signal sequence.

The packaging signal sequence is a base sequence essential for the genomic RNA of retrovirus to be incorporated into a viral particle. The packaging signal sequence of the genomic RNA of retrovirus is known to have a characteristic secondary structure and bind specifically to the nucleocapsid (NC) on Gag protein.

As the packaging signal sequence, a retroviral Ψ sequence can be suitably used. It is known that in a case where the packaging signal sequence is an Extended packaging signal (Ψ+) including the leading portion of Gag, proteins are more efficiently encapsulated in VLPs. The base sequence of Ψ derived from HIV is shown in SEQ ID NO: 7. The base sequence of Ψ+ derived from HIV is shown in SEQ ID NO: 8.

In the aforementioned mRNA, the position of the packaging signal sequence is not particularly limited. In the aforementioned mRNA, for example, the packaging signal sequence, the first ribozyme sequence, the gRNA sequence, and the second ribozyme sequence may be arranged in this order, or the first ribozyme sequence, the gRNA sequence, the second ribozyme sequence, and the packaging signal sequence may be arranged in this order.

Furthermore, the aforementioned mRNA may further include one or more arbitrary RNA sequences on the 5' or 3' side of the packaging signal sequence. Those arbitrary RNA sequences may encode, for example, proteins.

In a case where the aforementioned mRNA includes one arbitrary RNA sequence, in the mRNA, for example, the arbitrary RNA sequence, the packaging signal sequence, the first ribozyme sequence, the gRNA sequence, and the second ribozyme sequence may be arranged in this order; the packaging signal sequence, the arbitrary RNA sequence, the first ribozyme sequence, the gRNA sequence, and the second ribozyme sequence may be arranged in this order; the first ribozyme sequence, the gRNA sequence, the second ribozyme sequence, the arbitrary RNA sequence, and the packaging signal sequence may be arranged in this order; or the first ribozyme sequence, the gRNA sequence, the second ribozyme sequence, the packaging signal sequence, and the arbitrary RNA sequence may be arranged in this order.

Furthermore, in a case where the aforementioned mRNA includes a plurality of arbitrary RNA sequences, the RNA sequences may be at different positions in the mRNA.

Usually, gRNA is transcribed from polymerase III promoters such as a U6 promoter and an H1 promoter. Therefore, it is difficult to lengthen gRNA. As a solution to this problem, as will be described later in Examples, the inventors of the present invention expressed a long mRNA consisting of 300 or more bases that includes the packaging signal sequence, the first ribozyme sequence, the gRNA sequence, and the second ribozyme sequence arranged in this order by using polymerase II promoters such as an LTR promoter and an EF1α promoter, so that the gRNA portion is cleaved by the self-cleaving activity of ribozyme. The inventors have revealed that in this way, the efficiency in encapsulating gRNA in VLPs is greatly increased.

In addition, as will be described later in Examples, in a case where VLPs encapsulating a Cas9 protein and gRNA by the above method are caused to enter cells, it is possible to obtain genome editing activity significantly higher than genome editing activity of the conventional VLPs.

As the first ribozyme sequence and the second ribozyme sequence, it is possible to use the hammerhead (HH) ribozyme sequence, the hepatitis delta virus (HDV) ribozyme sequence, the Varkud satellite ribozyme, the hairpin ribozyme, the glmS ribozyme, and the like. The first ribozyme sequence and the second ribozyme sequence may be the same sequence or different sequences.

An example of the hammerhead (HH) ribozyme sequence is shown in SEQ ID NO: 9. Furthermore, an example of the HDV ribozyme sequence is shown in SEQ ID NO: 10.

gRNA may be a complex of CRISPR RNA (crRNA) and trans-activating CRISPR RNA (tracrRNA), or may be a single gRNA (sgRNA) that is a combination of tracrRNA and crRNA.

In a case where gRNA is a complex of crRNA and tracrRNA, two kinds of mRNAs, mRNA having the packaging signal sequence, the first ribozyme sequence, the crRNA sequence, and the second ribozyme sequence arranged in this order and mRNA having the packaging signal sequence, the first ribozyme sequence, the tracrRNA sequence, and the second ribozyme sequence arranged in this order, may be encapsulated in VLPs.

Alternatively, for example, one kind of mRNA having the packaging signal sequence, the first ribozyme sequence, the crRNA sequence, the second ribozyme sequence, a third ribozyme sequence, the tracrRNA sequence, and a fourth ribozyme sequence arranged in this order can be encapsulated in VLPs. The third and fourth ribozyme sequences may be the same sequences as the first and second ribozyme sequences. In addition, the position of the crRNA sequence may be switched with the position of the tracrRNA sequence.

As a result, in VLPs or in target cells in which genome editing is to be induced, crRNA and tracrRNA are generated by the self-cleaving activity of ribozyme, and a complex of crRNA and tracrRNA is formed.

As the base sequence of crRNA and tracrRNA, for example, the following base sequence can be established. First, from a target base sequence, a protospacer adjacent motif (PAM) sequence is removed, thereby obtaining a spacer base sequence. Then, a base sequence is designed by connecting a scaffold sequence to the 3' end of the spacer base sequence, thereby obtaining a base sequence of crRNA. For example, in a case where the base sequence obtained by removing the PAM sequence from the target base sequence is (SEQ ID NO: 11)
"5'-NNNNNNNNNNNNNNNNNNNNN-3'", the base sequence of crRNA can be (SEQ ID NO: 12)
"5'-NNNNNNNNNNNNNNNNNNNNNGUUUUAGAGCUAUGCUGUUUUG-3'".

In addition, the base sequence of tracrRNA can be, for example,

"5'-CAAAACAGCAUAGCAAGUUAAAAUAAGGCUAGUCCGUUAUCAACU (SEQ ID NO: 13)

UGAAAAAGUGGCACCGAGUCGGUGC-3'".

In a case where gRNA is sgRNA, mRNA having the base sequence of sgRNA interposed between the first ribozyme sequence and the second ribozyme sequence and the packaging signal sequence may be encapsulated in VLPs. As a result, in VLPs or in target cells in which genome editing is to be induced, sgRNA is generated by the self-cleaving activity of ribozyme.

As the base sequence of sgRNA, for example, the following base sequence can be established. First, a PAM sequence is removed from a target base sequence, thereby obtaining a spacer base sequence. Then, a base sequence is designed by connecting a scaffold sequence to the 3' terminal of the spacer base sequence. For example, in a case where the base sequence obtained by removing the PAM sequence from the target base sequence is

"5'-NNNNNNNNNNNNNNNNNNNNN-3'", (SEQ ID NO: 11)

the base sequence of sgRNA that specifically recognizes the target base sequence can be

"5'-NNNNNNNNNNNNNNNNNNNNNGUUUUAGAGCUAGAAAUAGCAAGUU (SEQ ID NO: 14)

AAAAUAAGGCUAGUCCGUUAUCAACUUGAAAAAGUGGCACCGAGUCGGU

GCUUUUUUU-3'".

VLPs of the present embodiment can provide a novel genome editing therapy in the medical field. For example, by encapsulating CRISPR-Cas9 or CRISPR-Cas9 RNP in VLPs and injecting the VLPs into muscle tissue, it is possible to induce the intended genome editing in muscle cells. Furthermore, by injecting the VLPs into liver tissue, it is possible to induce the intended genome editing in liver cells.

In the present specification, genome editing means DNA cleavage, cleavage of single-stranded DNA, induction of homologous recombination, base editing, induction or removal of DNA methylation, control of gene expression level, and the like.

In addition, it is possible to provide genome editing therapy such as inoculating the collected cells, for example, hematopoietic stem cells, with VLPs and re-transplanting the cells in which the intended genome editing is induced. This technique can be a novel method for treating diseases caused by genetic mutation. Furthermore, it is considered that this technique may be applicable to infection therapy for destroying viral receptors, anti-cancer therapy combined with CAR-T cells, and the like.

Moreover, in the livestock and fishing industries, by inoculating the reproductive cells, fertilized eggs, early embryos, or individuals of target animals with VLPs, it is possible to induce bread improvement according to the genome editing site.

VLPs of the present embodiment may further contain donor DNA (double-stranded DNA or single-stranded DNA) for inducing gene recombination by the homologues recombination (HR) pathway.

[Method for Manufacturing Genome-Edited Cells]

In an embodiment, the present invention provides a method for manufacturing genome-edited cells, which includes inoculating the cells with VLPs encapsulating a Cas family protein and gRNA. By the method for manufacturing of the present embodiment, sequence-specifically genome-edited cells can be manufactured.

Herein, inoculating cells with VLPs ultimately means that VLPs are caused to enter the cells. For example, VLPs may be brought into contact with the cells or may be added to a medium of the cells.

[Method for Manufacturing VLPs Encapsulating Target Protein]

In an embodiment, the present invention provides a method for manufacturing VLPs encapsulating a target protein, including letting cells to express a combination of a fusion protein of FKBP12 and Gag protein and a fusion protein of FRB and a target protein or express a combination of a fusion protein of FRB and Gag protein and a fusion protein of FKBP12 and a target protein in the presence of rapamycin or a rapamycin derivative, so that VLPs encapsulating the target protein are released into a medium of the cells. By the method for manufacturing of the present embodiment, VLPs encapsulating a target protein can be manufactured.

It can also be said that the method for manufacturing of the present embodiment is a method for manufacturing VLPs encapsulating a target protein, including the following steps (1) and (2).

(1) A step of letting cells to express a fusion protein of FKBP12 and Gag protein and a fusion protein of FRB and a target protein or express a fusion protein of FRB and Gag protein and a fusion protein of FKBP12 and a target protein in the presence of rapamycin or a rapamycin derivative.

(2) A step of obtaining a medium containing VLPs encapsulating the target protein.

In step (1), it is preferable to introduce a nucleic acid encoding the fusion protein into the cells by lipofection or electroporation (including flow electroporation). After the nucleic acid is introduced, the cells may be treated with endonuclease.

The flow electroporation is electroporation which makes it possible to introduce DNA, mRNA, siRNA, proteins, and the like into various cells with high efficiency and high viability at a volume on a scale of 50 µL to 1 L. Therefore, in a case where the flow electroporation is adopted, VLPs can be easily mass-produced.

In addition, as will be described later in Examples, by introducing the nucleic acid into the cells by flow electroporation and then treating the cells with endonuclease, the amount of formed VLPs can be increased. It is considered that this is because the endonuclease treatment may increase the viability of the cells by removing unintroduced nucleic acids.

In order to apply VLPs to medical use, it is preferable to manufacture VLPs without using animal-derived components (xeno-free). Therefore, the medium of the cells is preferably a serum-free medium.

In the method for manufacturing of the present embodiment, the fusion protein of FKBP12 and Gag protein, the fusion protein of FRB and a target protein, the fusion protein of FRB and Gag protein, and the fusion protein of FKBP12 and a target protein may be expressed using expression vectors that function in VLP-producing cells. In addition, VLPs released into the medium can be concentrated, for example, by ultracentrifugation, polyethylene glycol (PEG) precipitation, column chromatography, ion exchange chromatography, and the like.

In the method for manufacturing of the present embodiment, VLPs, the target protein, the rapamycin derivative, the Gag protein, FKBP12, and FRB are the same as those described above. Furthermore, as the VLP-producing cells, human cells and non-human animal cells can be used. However, in a case where VLPs are inoculated into an organism, from the viewpoint of reducing immunogenicity, it is preferable to use cells derived from the same species as the recipient as the VLP-producing cells. The specific VLP-producing cells are not particularly limited, and for example, HEK293T cells, HEK293 cells, and the like which are human embryonic kidney-derived cell strains can be used.

Compared to the conventional technique, the method for manufacturing of the present embodiment makes it possible to more efficiently encapsulate a target protein in VLPs. Therefore, more target proteins can be encapsulated in (incorporated into) VLPs. The number of target protein molecules that can be encapsulated in one VLP is, for example, 3 or greater, preferably 4 or greater, more preferably 5 or greater, even more preferably 6 or greater, and most preferably 7 or greater.

[Method for Manufacturing VLPs Encapsulating Cas Family Protein and gRNA]

In an embodiment, the present invention provides a method for manufacturing VLPs each encapsulating a Cas family protein and gRNA. The method for manufacturing includes letting cells to express a combination of a fusion protein of FKBP12 and Gag protein and a fusion protein of FRB and a Cas family protein or a combination of a fusion protein of FRB and Gag protein and a fusion protein of FKBP12 and a Cas family protein and mRNA having a gRNA sequence interposed between a first ribozyme sequence and a second ribozyme sequence and a packaging signal sequence in the presence of rapamycin or a rapamycin derivative, so that VLPs encapsulating the Cas family protein and gRNA are released into a medium of the cells.

It can also be said that the method for manufacturing of the present embodiment is a method for manufacturing VLPs encapsulating a Cas family protein and gRNA, including the following steps (1) and (2).

(1) A step of letting cells to express a fusion protein of FKBP12 and Gag protein and a fusion protein of FRB and a Cas family protein or a fusion protein of FRB and Gag protein and a fusion protein of FKBP12 and a Cas family protein, and mRNA having a gRNA sequence interposed between a first ribozyme sequence and a second ribozyme sequence and a packaging signal sequence in the presence of rapamycin or a rapamycin derivative.

(2) A step of obtaining a medium containing VLPs encapsulating the Cas family protein and gRNA.

In step (1), it is preferable to introduce a nucleic acid encoding the fusion protein or the mRNA into the cells by lipofection or electroporation (including flow electroporation). After the nucleic acid is introduced, the cells may be treated with endonuclease. The medium of the cells is preferably a serum-free medium. The flow electroporation and the endonuclease treatment are the same as those described above.

Compared to the conventional technique, the method for manufacturing of the present embodiment makes it possible to more efficiently encapsulate a Cas family protein and gRNA in VLPs. Therefore, more Cas family protein-gRNA complex (ribonucleoprotein, RNP) can be encapsulated in VLPs. The number of RNP molecules that can be encapsulated in one VLP is, for example, 3 or greater, preferably 4 or greater, more preferably 5 or greater, even more preferably 6 or greater, and most preferably 7 or greater.

By the method for manufacturing of the present embodiment, it is possible to manufacture VLPs encapsulating a Cas family protein and gRNA. In addition, VLPs released into the medium can be concentrated, for example, by ultracentrifugation, PEG precipitation, column chromatography, ion exchange chromatography, and the like.

In the method for manufacturing of the present embodiment, VLPs, the Cas family protein, gRNA, the rapamycin derivative, the Gag protein, FKBP12, FRB, the packaging signal sequence, the ribozyme sequences, and the VLP-producing cells are the same as those described above.

In the method for manufacturing of the present embodiment, the fusion protein of FKBP12 and Gag protein, the fusion protein of FRB and a Cas family protein, the fusion protein of FRB and Gag protein, the fusion protein of FKBP12 and a Cas family protein, and mRNA having a gRNA sequence interposed between a first ribozyme sequence and the second ribozyme sequence and a packaging signal sequence may be expressed using expression vectors that function in the VLP-producing cells.

Particularly, it is preferable that mRNA having a gRNA sequence interposed between a first ribozyme sequence and a second ribozyme sequence and a packaging signal sequence be expressed using a polymerase II promoter. Examples of the polymerase II promoter include an LTR promoter (5' LTR of lentivirus), an EF1α promoter, and the like. As the LTR promoter, 5'LTR of HIV can be particularly suitably used.

Furthermore, in a case where mRNA having a gRNA sequence interposed between a first ribozyme sequence and a second ribozyme sequence and packaging signal sequence is expressed using the LTR promoter, it is preferable to let the VLP-producing cells to express a Tat protein.

[Kit for Manufacturing VLPs Encapsulating Target Protein]

In an embodiment, the present invention is a kit for manufacturing VLPs encapsulating a target protein. The kit includes an expression vector for a fusion protein of FKBP12 and Gag protein or an expression vector for a fusion protein of FRB and Gag protein. With the kit of the present embodiment, VLPs encapsulating a target protein can be manufactured.

In the kit of the present embodiment, VLPs, the target protein, the Gag protein, FKBP12, and FRB are the same as those described above.

The kit of the present embodiment may further include a vector for preparing an expression vector for a fusion protein of FKBP12 and a target protein, an expression vector for a fusion protein of FKBP12 and a target protein, a vector for preparing an expression vector for a fusion protein of FRB and a target protein, an expression vector for a fusion protein of FRB and a target protein, and the like.

Examples of the vector for preparing an expression vector for a fusion protein of FKBP12 and a target protein include a vector having an FKBP12-encoding gene and a multiple cloning site on the downstream of a promoter.

In the present specification, the multiple cloning site is a region in which one or more base sequences recognized by restriction enzymes are arranged. The multiple cloning site may include one restriction enzyme site or a plurality of restriction enzyme sites.

By incorporating a gene encoding a target protein into the multiple cloning site of the aforementioned vector, the expression vector for a fusion protein of FKBP12 and a target protein can be prepared. The multiple cloning site may be positioned on the 5' side or 3' side of the FKBP12-encoding gene.

Examples of the vector for preparing an expression vector for a fusion protein of FRB and a target protein include a vector having an FRB-encoding gene and a multiple cloning site on the downstream of a promoter. By incorporating a gene encoding the target protein into the multiple cloning site, the expression vector for a fusion protein of FRB and a target protein can be prepared. The multiple cloning site may be positioned on the 5' side or 3' side of the FRB-encoding gene.

The kit of the present embodiment may further contain rapamycin or a rapamycin derivative, VLP-producing cells, and the like. The rapamycin or rapamycin derivative and the VLP-producing cells are the same as those described above.

[Kit for Manufacturing VLPs Encapsulating Cas Family Protein]

In an embodiment, the present invention provides a kit for manufacturing VLPs encapsulating a Cas family protein. The kit includes a combination of an expression vector for a fusion protein of FKBP12 and Gag protein and an expression vector for a fusion protein of FRB and a Cas family protein or includes a combination of an expression vector for a fusion protein of FRB and Gag protein and an expression vector for a fusion protein of FKBP12 and a Cas family protein. With the kit of the present embodiment, VLPs encapsulating a Cas family protein can be manufactured.

In the kit of the present embodiment, VLPs, the Cas family protein, the Gag protein, FKBP12, and FRB are the same as those described above.

For example, as will be described later in Examples, FKBP12 may be fused with the Gag protein, and FRB may be fused with the Cas family protein. In this case, it is preferable to fuse FKBP12 with the N-terminal side of the Gag protein. Furthermore, it is preferable to fuse FRB to the N-terminal side of the Cas family protein.

The kit of the present embodiment may further include an expression vector for mRNA having a base sequence of a target RNA or a multiple cloning site, which is interposed between a first ribozyme sequence and a second ribozyme sequence, and a packaging signal sequence. In this case, with the kit of the present embodiment, VLPs encapsulating a Cas family protein and a target RNA can be manufactured.

Herein, the packaging signal sequence and the ribozyme sequences are the same as those described above. Examples of the target RNA include a short chain RNA such as gRNA. In the present specification, examples of the short chain RNA include an RNA chain consisting of about, for example, 200 or less bases, 150 or less bases, or 100 or less bases.

By incorporating a DNA fragment encoding the target RNA into the multiple cloning site of the expression vector for mRNA having the multiple cloning site interposed between the first ribozyme sequence and the second ribozyme sequence and the packaging signal sequence, it is possible to prepare an expression vector for mRNA having a base sequence of a target RNA interposed between the first ribozyme sequence and the second ribozyme sequence and the packaging signal sequence.

The kit of the present embodiment may further contain rapamycin or a rapamycin derivative, VLP-producing cells, and the like. The rapamycin or rapamycin derivative and the VLP-producing cells are the same as those described above.

[VLPs Encapsulating Target RNA]

In an embodiment, the present invention provides VLPs encapsulating a target RNA. The VLPs contain Gag protein, and the target RNA is encapsulated in VLPs in the form of mRNA or in the form of a self-cleavage product of the mRNA, in which the mRNA has a base sequence of the target RNA interposed between a first ribozyme sequence and a second ribozyme sequence and a packaging signal sequence.

The VLPs of the present embodiment encapsulate a target RNA instead of a target protein, which is a key difference between VLPs of the present embodiment and VLPs described above.

As will be described later in Examples, a target RNA can be efficiently encapsulated in VLPs of the present embodiment. By letting VLPs of the present embodiment to enter cells, it is possible to efficiently introduce the target RNA into the cells.

Examples of the target RNA include a short chain RNA. In the present specification, examples of the short chain RNA include an RNA chain consisting of about, for example, 200 or less bases, 150 or less bases, or 100 or less bases. Examples of the target RNA include siRNA, shRNA, miRNA, gRNA, and the like.

In VLPs of the present embodiment, VLPs, the Gag protein, the packaging signal sequence, the ribozyme sequences, and gRNA are the same as those described above.

[Method for Manufacturing VLPs Encapsulating Target RNA]

In an embodiment, the present invention provides a method for manufacturing VLPs encapsulating a target RNA. The method for manufacturing includes letting cells to express Gag protein and mRNA having a base sequence of a target RNA interposed between a first ribozyme sequence and a second ribozyme sequence and a packaging signal sequence, so as to obtain virus-like particles encapsulating the target RNA that are released to a medium of the cells, in which the target RNA is encapsulated in the virus-like particles in the form of the mRNA or in the form of a self-cleavage product of the mRNA.

It can also be said that the method for manufacturing of the present embodiment is a method for manufacturing VLPs encapsulating a target RNA, including the following steps (1) and (2).

(1) A step of letting cells to express Gag protein and mRNA having a base sequence of a target RNA interposed between a first ribozyme sequence and a second ribozyme sequence and a packaging signal sequence.

(2) A step of obtaining a medium containing VLPs encapsulating the target RNA in the form of the mRNA or in the form of a self-cleavage product of the mRNA.

In step (1), it is preferable to introduce a nucleic acid encoding the mRNA into the cells by lipofection or electroporation (including flow electroporation). After the nucleic acid is introduced, the cells may be treated with endonuclease. The medium of the cells is preferably a serum-free medium. The flow electroporation and the endonuclease treatment are the same as those described above.

By the method for manufacturing of the present embodiment, VLPs encapsulating a target RNA can be manufactured. In the method for manufacturing of the present embodiment, VLPs, the Gag protein, the packaging signal sequence, the first ribozyme sequence, the target RNA, the second ribozyme sequence, and the VLP-producing cells are the same as those described above. In addition, VLPs released into the medium can be concentrated, for example, by ultracentrifugation, PEG precipitation, column chromatography, ion exchange chromatography, and the like.

Compared to the conventional technique, the method for manufacturing of the present embodiment makes it possible to more efficiently encapsulate a target RNA in VLPs. Therefore, more target RNA can be encapsulated in VLPs. The number of target RNA molecules that can be encapsulated in one VLP is, for example, 3 or greater, preferably 4 or greater, more preferably 5 or greater, even more preferably 6 or greater, particularly preferably 7 or greater, and most preferably 8 or greater.

[Kit for Manufacturing VLPs Encapsulating Target RNA]

In an embodiment, the present invention provides a kit for manufacturing VLPs encapsulating a target RNA. The kit includes an expression vector for Gag protein and an expression vector for mRNA having a base sequence of the target RNA or a multiple cloning site, which is interposed between a first ribozyme sequence and a second ribozyme sequence, and a packaging signal sequence. With the kit of the present embodiment, it is possible to manufacture VLPs in which the target RNA is efficiently encapsulated.

In the kit of the present embodiment, VLPs, the target RNA, the packaging signal sequence, the ribozyme sequences, and the multiple cloning site are the same as those described above.

As described above, by incorporating a DNA fragment encoding the target RNA into the multiple cloning site of the expression vector for mRNA having the multiple cloning site interposed between the first ribozyme sequence and the second ribozyme sequence and the packaging signal sequence, it is possible to prepare an expression vector for mRNA having a base sequence of the target RNA interposed between the first ribozyme sequence and the second ribozyme sequence and the packaging signal sequence.

Furthermore, as described above, in a case where the VLP-producing cells are caused to express the Gag protein and mRNA having the base sequence of the target RNA interposed between the first ribozyme sequence and the second ribozyme sequence and the packaging signal sequence, the packaging signal sequence on the mRNA has a characteristic secondary structure and binds specifically to the nucleocapsid (NC) on the Gag protein. As a result, the target RNA is efficiently encapsulated in VLPs.

The kit of the present embodiment may further contain VLP-producing cells and the like. The VLP-producing cells are the same as those described above.

[Agent for Treating Diseases Caused by Genetic Mutation, Infections, or Cancer]

In an embodiment, the present invention provides an agent for treating diseases caused by genetic mutation, infections, or cancer, which contains the virus-like particles described above as an active component. Examples of the diseases caused by genetic mutation include, but are not limited to, Duchenne muscular dystrophy (DMD), myotonic dystrophy, facioscapulohumeral muscular dystrophy, hemophilia, congenital encephalopathy, phenylketonuria, disorders of biopterin metabolism, maple syrup urine disease, homocystinuria, albinism, xeroderma pigmentosum, and the like. The administration of the treatment agent of the present embodiment induces exon skipping by genome editing, repairs genetic mutation, or deletes abnormal genes, and in this way, the diseases caused by genetic mutation can be treated.

Examples of the infections include AIDS, hepatitis B, EBV infection, and the like. The administration of the treatment agent of the present embodiment disrupts the genes of viruses or bacteria causing the infections or disrupts the receptor genes necessary for causing viral or bacterial infections, and in this way, the infections can be treated.

In the present specification, "cancer" means not only cancer that develops from epithelial cells but all kinds of malignant tumors. Examples of the cancer include congenital childhood cancer. The administration of the treatment agent of the present embodiment disrupts the genes essential for the survival of cancer cells or cancer genes or repairs the mutation of cancer suppressor genes, and in this way, cancer can be treated.

The administration method and dose of the treatment agent of the present embodiment are not particularly limited, and may be appropriately determined according to the symptoms, body weight, age, gender, and the like of the patient. For example, the treatment agent may be administered in the form of intravenous injection, intraarterial injection, intramuscular injection, and the like.

Other Embodiments

In an embodiment, the present invention provides a method for treating diseases caused by genetic mutation, infections, or cancer, including administering an effective dose of VLPs to a patient in need of treatment, in which the VLPs encapsulate a target protein, a target RNA, or a target protein and a target RNA.

In an embodiment, the present invention provides VLPs for treating diseases caused by genetic mutation, infections, or cancer, in which the VLPs encapsulate a target protein, a target RNA, or a target protein and a target RNA.

In an embodiment, the present invention provides the use of VLPs for manufacturing an agent for treating diseases caused by genetic mutation, infections, or cancer, in which the VLPs encapsulate a target protein, a target RNA, or a target protein and a target RNA.

In each of the above embodiments, the VLPs encapsulating a target protein, the VLPs encapsulating a target RNA, and the VLPs encapsulating a target protein and a target RNA are the same as those described above.

In each of the above embodiments, the VLPs encapsulate a target protein or encapsulate a target protein and a target RNA. The target protein may be a Cas family protein, and the target RNA may be gRNA. Alternatively, the VLPs may encapsulate a target RNA, and the target RNA may be siRNA, shRNA, miRNA, gRNA, or the like.

EXAMPLES

Next, the present invention will be more specifically described with reference to examples, but the present invention is not limited to the following examples.

Experimental Method (Cell Culture)

HEK293T cells as a human embryonic kidney-derived cell strain, HEK293T cells into which a reporter construct EGxxFP was introduced (hereinafter, called "HEK293T EGxxFP cells" in some cases), and HEK293T EGxxFP cells caused to constantly express sgRNA DMD #1 (the target sequence is shown in SEQ ID NO: 15) targeting the 5' side (near the splicing acceptor) of exon 45 of the human DMD gene were cultured in DMEM containing 10% bovine fetal serum, penicillin, and streptomycin.

iPS cells (404C2 strain and 138D2 strain) derived from healthy human beings were cultured in StemFit AK03N medium (AJINOMOTO HEALTHY SUPPLY CO., INC.) on a culture dish coated with iMatix 511-E8. iPS cells derived from a patient with Duchenne muscular dystrophy (DMD) were cultured in StemFit AK03N medium on a culture dish coated with iMatix 511-E8.

C2C12 cells as a cell strain derived from the mouse striated muscle were cultured in DMEM containing 15% fetal bovine serum, 0.1 mM essential amino acids, 100 mM sodium pyruvate, 100 mM 2-mercaptoethanol, penicillin, and streptomycin.

As a differentiation-inducing medium for the C2C12 cells, DMEM containing 5% horse serum, 0.1 mM essential amino acids, 100 mM sodium pyruvate, 100 mM 2-mercaptoethanol, 0.5% penicillin, and streptomycin was used.

(Method for Preparing VLPs)

HEK293T cells ($3 \times 10^6$ cells) were seeded on a 10-cm plate. On the next day, by using lipofectamine 2000 (Thermo Fisher Scientific Inc.), the cells were transfected with 10 µg of pHLS-EF1a-FKBP12-Gag$^{HIV}$ (SEQ ID NO: 16), 10 µg of pHLS-EF1a-FRB-SpCas9-A (SEQ ID NO: 17), 10 µg of pL-sin-RGR-AmCyan-A (SEQ ID NO: 18), 2 µg of pcDNA3.1-Tat$^{HIV}$ (SEQ ID NO: 19), and 5 µg of pMD-VSVG (SEQ ID NO: 20). Each of these expression vectors was appropriately modified by experiments.

Subsequently, on the next day, the medium was replaced with 10 mL of a new medium containing 300 nM AP21967 (Clontech Laboratories, Inc.). Thereafter, 36 to 48 hours after the transfection, the culture supernatant was collected, cell debris was removed using a syringe filter having a pore size of 0.45 µm, and the filtrate was centrifuged for 3 hours at 100,000×g by using an Avanti JXN-30 centrifuge (Beckman Coulter, Inc.) so that VLPs were concentrated.

Then, the precipitate containing VLPs was resuspended in 100 µL of HBSS (Thermo Fisher Scientific Inc.), dispensed into 1.5 mL tubes, and stored at −80° C.

(Introduction of VLPs into Cell)

The HEK293T EGxxFP cells were seeded on a 48-well plate at $2.5 \times 10^4$ to $5.0 \times 10^4$ cells/well. On the next day, the VLP solution was added thereto, and then after 3 days, the fluorescence of EGFP was analyzed using an LSR3 flow cytometer.

(T7EI Assay)

By using MonoFas Genomic DNA Extraction kit (GL Sciences Inc.), genomic DNA was recovered from the cultured cells according to the protocol. Then, PCR was performed using 100 ng of the genomic DNA, primers for the regions to be amplified, and PrimeSTAR GXL DNA Polymerase (Takara Bio Inc.), and the PCR product was purified using Wizard SV Gel and PCR Clean-up System (Promega Corporation).

Subsequently, 400 ng of the PCR product was thermally denatured in NEBuffer 2.1 (New England Biolabs) at 95° C. for 5 minutes and then reannealed by slow cooling. The PCR product was cooled to 85° C. from 95° C. at −2° C./sec and then to 25° C. from 85° C. at −0.1° C./sec. Subsequently, 10 units of T7 endonuclease I (T7EI) enzyme was added thereto and reacted at 37° C. for 15 minutes. Thereafter, 6 mM of EDTA was added thereto so that the reaction stopped. Then, the cleavage products were analyzed using DS1000 High Sensitivity Screen Tape and Tape Station 2200 (Agilent Technologies, Inc.).

Experimental Example 1

(Examination on Cas9 Delivery by VLPs)

The Cas9 protein was delivered by VLPs using Gag-Pol or Gag, and an SSA-EGFP reporter experiment was performed to evaluate the genome editing efficiency.

FIG. 1(a) is a schematic view showing the structure of Gag-Pol of HIV (hereinafter, called "WT Gag-Pol$^{HIV}$" in some cases). As shown in FIG. 1(a), the Gag portion is constituted with a matrix (MA), a capsid (CA, also called p24), a nucleocapsid (NC), and p6 (transframe). In addition, Pol is constituted with protease (PR), reverse transcriptase (RT), RNase H (RN), and integrase (IN).

FIG. 1(b) is a schematic view showing the structure of a fusion protein obtained by adding an FKBP12 domain to the N-terminal of Gag-Pol of HIV (hereinafter, called "FKBP12-Gag-Pol$^{HIV}$" in some cases). FKBP12 is an FK506 binding protein.

FIG. 1(c) is a schematic view showing the structure of a fusion protein obtained by adding an FKBP12 domain to the N-terminal of Gag of HIV (hereinafter, called "FKBP12-Gag$^{HIV}$" in some cases).

The Protease (PR) which is a part of Pol originally has an activity of cleaving a specific site (indicated by scissors in FIG. 1) of a Gag-Pol protein. In VLPs from which the Pol containing PR is deleted, although the target sequence of protease remains, protein cleavage does not occur because protease is not supplied.

Figure 2:
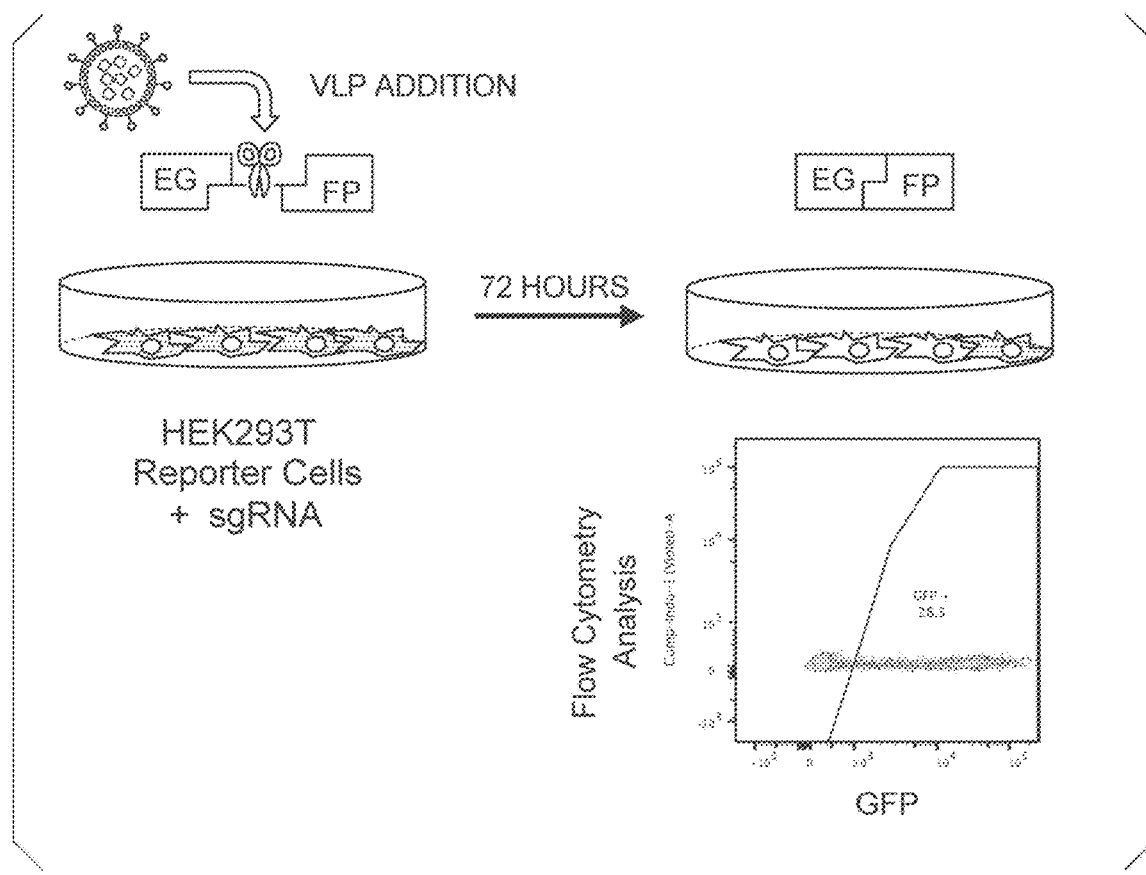
FIG. 2 is a schematic view illustrating an SSA-EGFP reporter experiment.

FIG. 2 is a schematic view illustrating an SSA-EGFP (hereinafter, called "EGxxFP" in some cases) reporter experiment. As cells, HEK293T cells were used which constantly express sgRNA targeting the human Dystrophin (DMD) gene and have genome into which the EGxxFP reporter construct (SEQ ID NO: 21) was inserted. The EGxxFP reporter construct is a construct designed by inserting a sequence including the target sequence of the sgRNA into the EGFP cDNA sequence, so that a functional EGFP protein is not expressed.

As shown in FIG. 2, in a case where VLPs encapsulating Cas9 are introduced into the cells, a complex of the Cas9 protein and the sgRNA (RNP complex) is formed, and the aforementioned insertion sequence is cleaved. Then, the cleaved EGFP cDNA is repaired by single-strand annealing (SSA). As a result, functional EGFP is expressed, and the fluorescence of EGFP can be observed. In this experimental system, by quantifying the fluorescence of EGFP in the cells by using a flow cytometer, it is possible to evaluate the target gene cleavage efficiency (genome editing efficiency) of the Cas9 protein in cell populations.

First, in the presence or absence of Darunavir (HIV protease inhibitor), VLPs (FIGS. 1(a) and 1(b)) were prepared which were constituted with wild-type Gag-Pol$^{HIV}$ or FKBP12-Gag-Pol$^{HIV}$ derived from HIV and encapsulated a Cas9 protein fused with an FRB domain (hereinafter, called "FRB-Cas9 protein" in some cases). The FKBP12 domain and the FRB (FKBP12-rapamycin-associated protein 1, FRAP1 fragment) domain are known to form a heterodimer in the presence of a drug similar to rapamycin.

Then, the prepared VLPs (15 µL) were introduced into the HEK293T EGxxFP reporter cells ($5 \times 10^4$ cells expressing sgRNA). Subsequently, after 3 days, the proportion of GFP-positive cells was analyzed with a flow cytometer.

Figure 3:
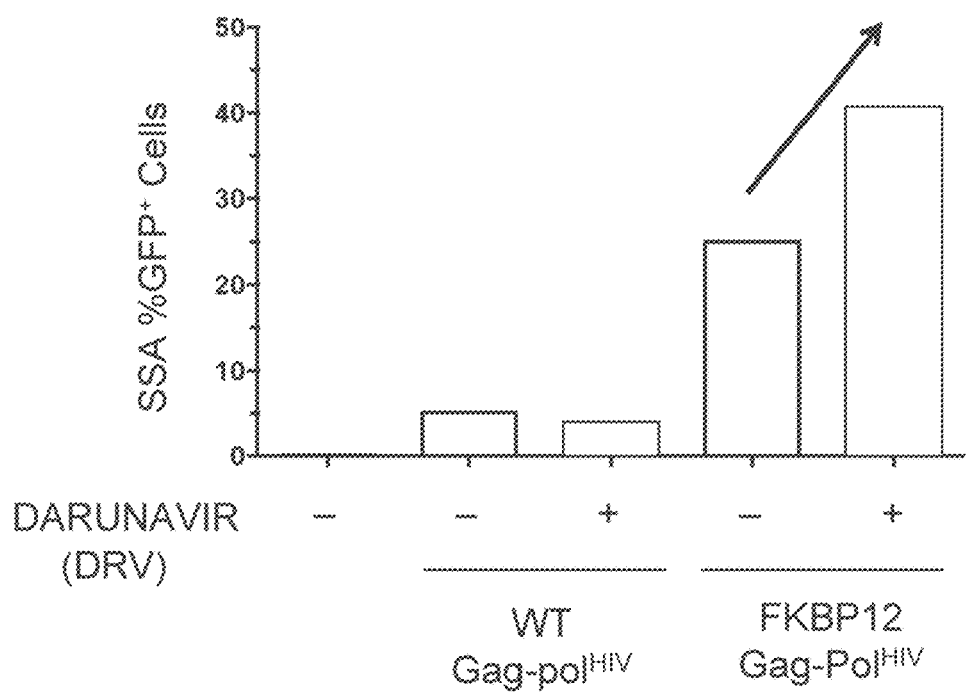
FIG. 3 is a graph showing the results of flow cytometry in Experimental Example 1.

FIG. 3 is a graph showing the results of flow cytometry. In FIG. 3, the ordinate shows the proportion of GFP-positive cells. As a result, it was revealed that in a case where FKBP12-Gag-Pol$^{HIV}$ VLP is used to deliver FRB-Cas9, the genome editing efficiency is higher than in a case where WT Gag-Pol$^{HIV}$ VLP is used (comparison between the Darunavir-free groups). Furthermore, it was revealed that in a case where Darunavir, which is an HIV protease inhibitor, is added to the cells in preparing VLPs, the genome editing efficiency is further improved in the cells into which FKBP12-Gag-Pol$^{HIV}$ VLP is introduced (in FIG. 3, the arrow shows the improvement of the genome editing efficiency).

Figure 4:
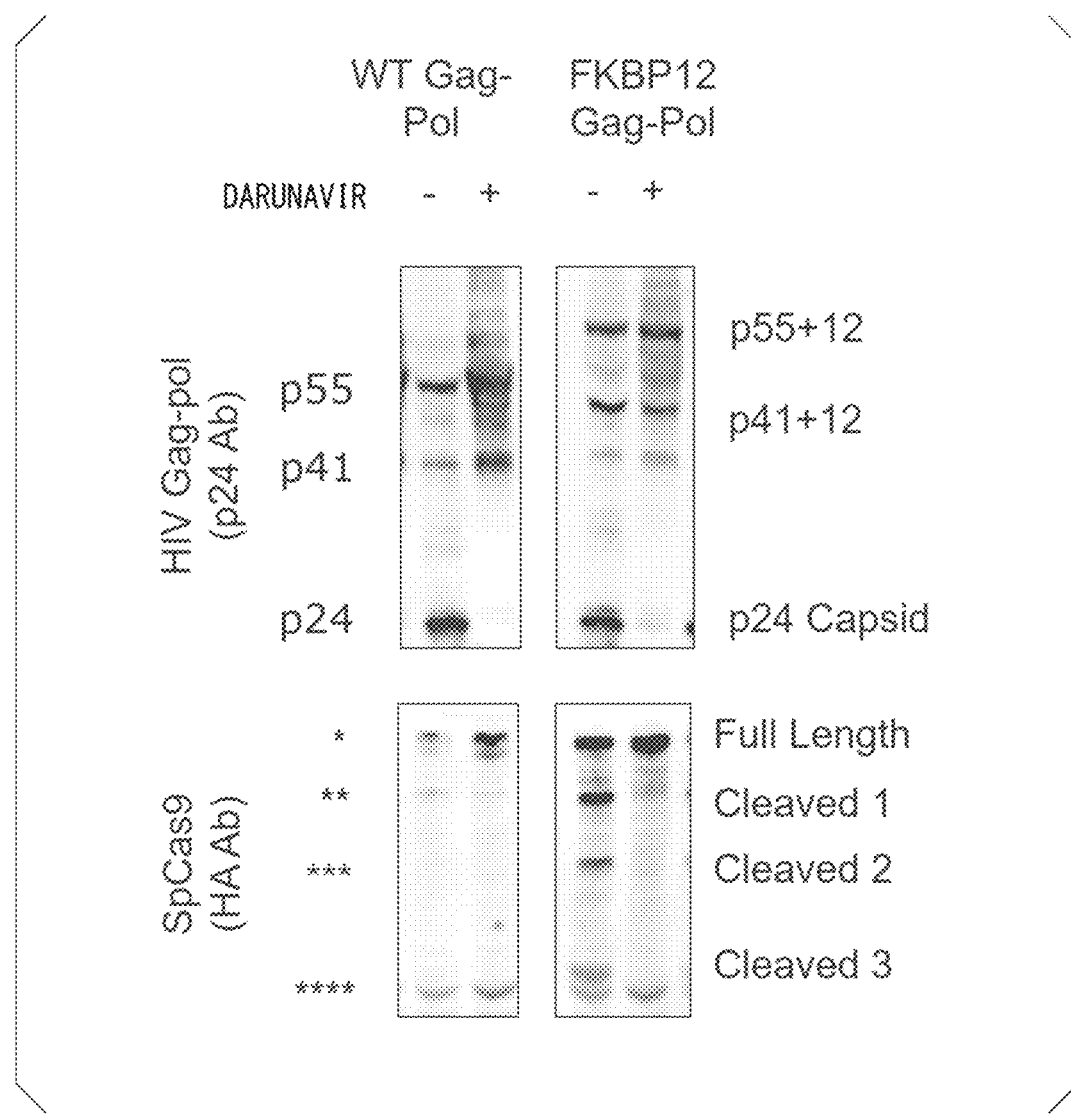
FIG. 4 is a photograph showing the results of Western blotting in Experimental Example 1.

Subsequently, FKBP12-Gag-Pol$^{HIV}$ and the HA-tagged FRB-Cas9 protein in each of the above VLPs were quantified by Western blotting. FIG. 4 is photographs showing the results of Western blotting. As shown in FIG. 4, the increase in the amount of FKBP12-Gag-Pol$^{HIV}$ ("p55+12" in FIG. 4) and the HA-tagged FRB-Cas9 protein ("Full length" in FIG. 4) was greater in VLPs to which Darunavir, an HIV protease inhibitor, was added to cells in preparing the VLPs, than in VLPs to which Darunavir was not added. On the other hand, in VLPs to which Darunavir was not added, the amount of molecular species with a lower molecular weight ("p41+12", "p24 Capsid", and "Cleaved 1, 2" in FIG. 4) increased further than in VLPs to which Darunavir was added (Comparison between "Darunavir +" and "Darunavir –"). That is, it was revealed that the cleavage of Gag protein and the degradation of Cas9 protein are inhibited in VLPs to which Darunavir is added.

Figure 5:
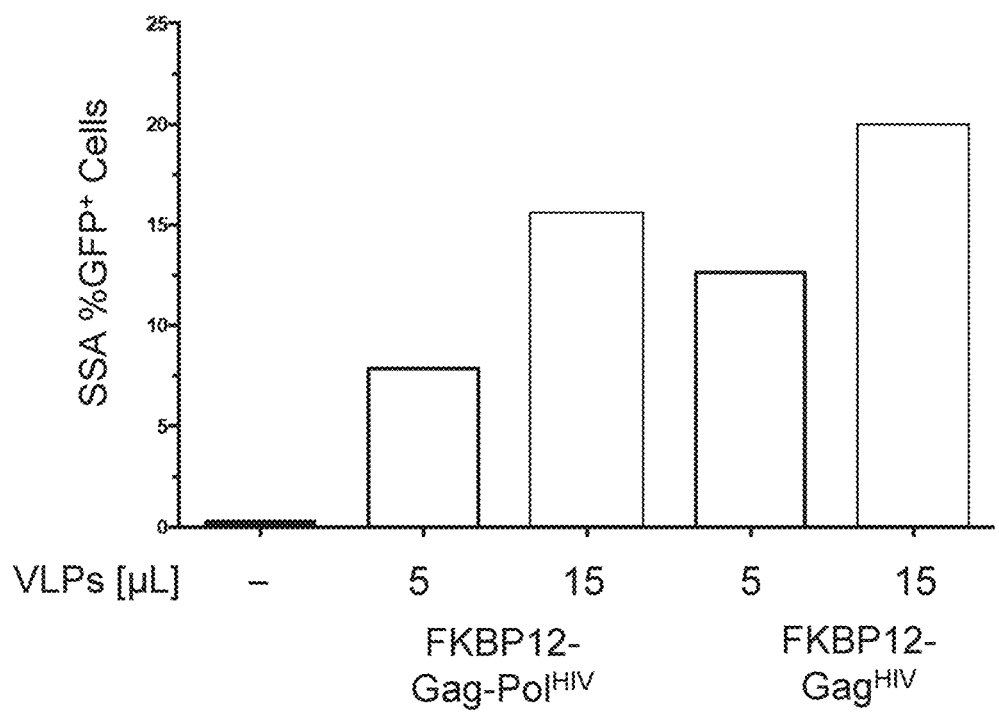
FIG. 5 is a graph showing the results of flow cytometry in Experimental Example 1.

Then, by using FKBP12-Gag$^{HIV}$ prepared by deleting the Pol portion from FKBP12-Gag-Pol$^{HIV}$ (FIG. 1(c)), VLPs encapsulating an FRB-Cas9 protein were prepared, and genome editing efficiency thereof was examined by an SSA-EGFP reporter experiment. FIG. 5 is a graph showing the results of flow cytometry. In FIG. 5, the ordinate shows the proportion of GFP-positive cells.

As a result, it was revealed that in a case where FKBP12-Gag$^{HIV}$ VLP is used to deliver FRB-Cas9, the genome editing efficiency is higher than in a case where FKBP12-Gag-Pol$^{HIV}$ VLP is used.

From these results, it was revealed that in a case where the Gag protein is expressed in the form of a protein including Pol, due to the action of protease in Pol, not only the Gag protein but also the Cas9 protein is degraded. Therefore, it is considered that in the conventional VLPs manufactured by the method of expressing the Gag protein in the form of a protein including Pol (for example, Non-Patent Literature 1), the Cas9 protein may be degraded by the protease expressed from Pol, hence the amount of the Cas9 protein retained in the VLPs may be small, and accordingly, sufficient genome cleavage efficiency may not be obtained.

Experimental Example 2

(Examination 1 on FKBP12 Domain Binding Site)

An examination was performed regarding where in VLP the FKBP12 domain should be localized for the delivery of FRB-Cas9.

Figure 6:
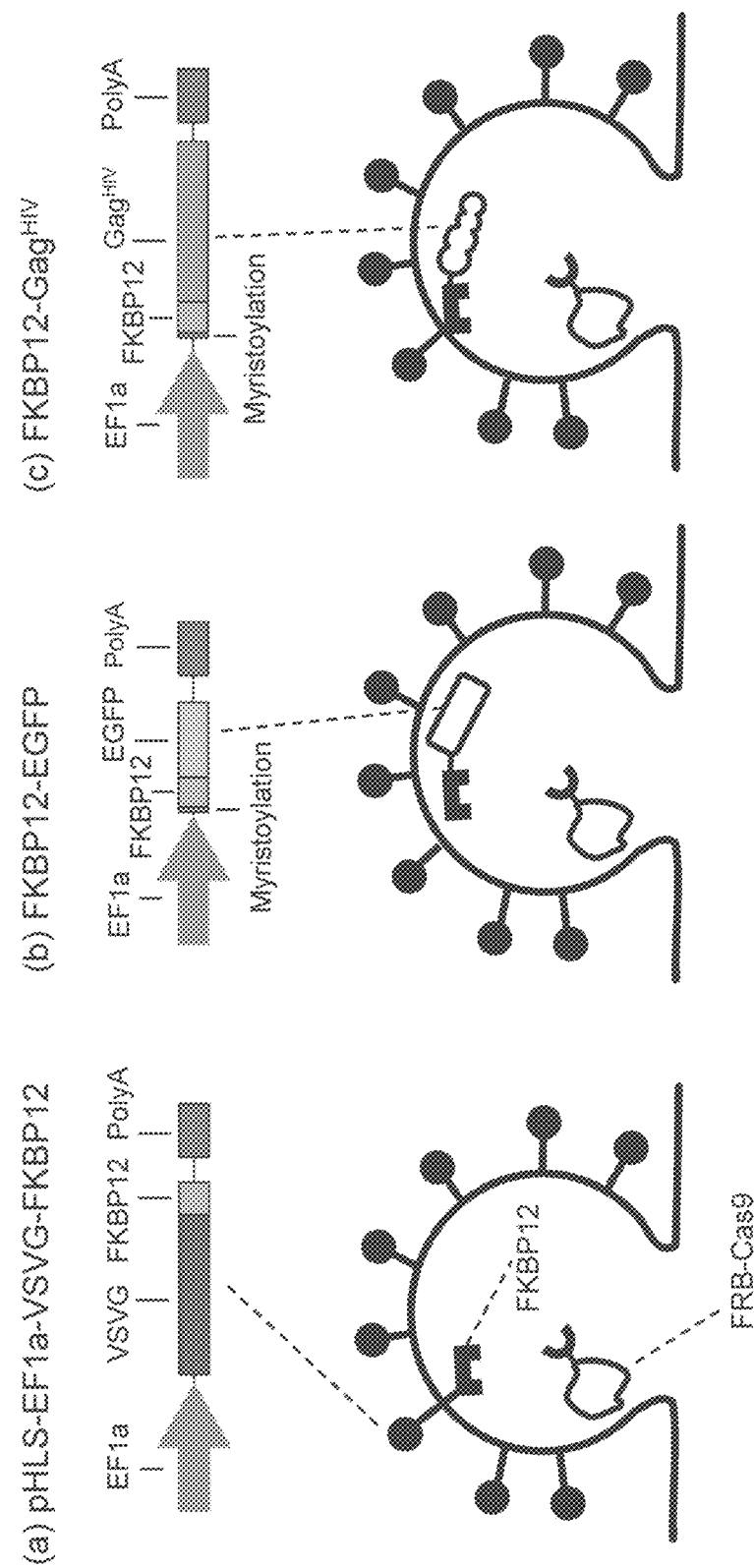
FIG. 6(a) is a schematic view showing the structure of an expression vector for a VSVG-FKPB12 fusion protein (pHLS-EF1a-VSVG-FKBP12) obtained by adding an FKBP12 domain to the C-terminal (intracytoplasmic domain side) of VSV-G (envelope protein of vesicular stomatitis virus) and the structure of VLP containing the VSVG-FKPB12 fusion protein.
FIG. 6(b) is a schematic view showing the structure of an expression vector for an FKBP12-EGFP fusion protein obtained by fusing an FKBP12 domain with the N-terminal of EGFP and the structure of VLP containing the FKBP12-EGFP fusion protein.
FIG. 6(c) is a schematic view showing the structure of an expression vector for an FKBP12-Gag$^{HIV}$ fusion protein obtained by fusing an FKBP12 domain with the N-terminal of Gag$^{HIV}$ and the structure of VLP containing the FKBP12-Gag$^{HIV}$ fusion protein.

FIG. 6(a) is a schematic view showing the structure of a VSVG-FKPB12 fusion protein expression vector (pHLS-EF1a-VSVG-FKBP12) obtained by fusing an FKBP12 domain with the C-terminal (intracytoplasmic domain side) of VSV-G (envelope protein of vesicular stomatitis virus) and the structure of VLP containing the VSVG-FKPB12 fusion protein. VSV-G is an envelope protein that has broad tropism and is generally used for preparing pseudotyped viruses of lentivirus and retrovirus. VSV-G is a main component constituting the envelope of VLPs according to the present disclosure. Therefore, the FKPB12 domain portion of the above fusion protein expressed from this vector is in the form of a portion protruding from the inner membrane of the envelope of the VLPs (localization on the membrane).

FIG. 6(b) is a schematic view showing the structure of an expression vector for an FKBP12-EGFP fusion protein obtained by the fusion of an FKBP12 domain with the N-terminal of EGFP and the structure of VLP containing the FKBP12-EGFP fusion protein. The FKPB12 domain portion of the fusion protein expressed from this vector is on the inside of VLP (localization in cytoplasm).

FIG. 6(c) is a schematic view showing the structure of an expression vector for an FKBP12-Gag$^{HIV}$ fusion protein which is obtained by the fusion of an FKBP12 domain with the N-terminal of Gag$^{HIV}$ and has a myristoylation signal on the N-terminal, and the structure of VLP containing the FKBP12-Gag$^{HIV}$ fusion protein. The FKPB12 domain portion of the above fusion protein expressed from this vector is in a state of binding to the inside of the membrane of the envelope of VLP (localization on the inside of the membrane).

First, in the presence or absence of AP21967 which is a drug similar to rapamycin, VLPs containing a VSVG-FKPB12 fusion protein, an FKBP12-EGFP fusion protein, or an FKBP12-Gag$^{HIV}$ fusion protein and encapsulating FRB-Cas9 were prepared.

Figure 7:
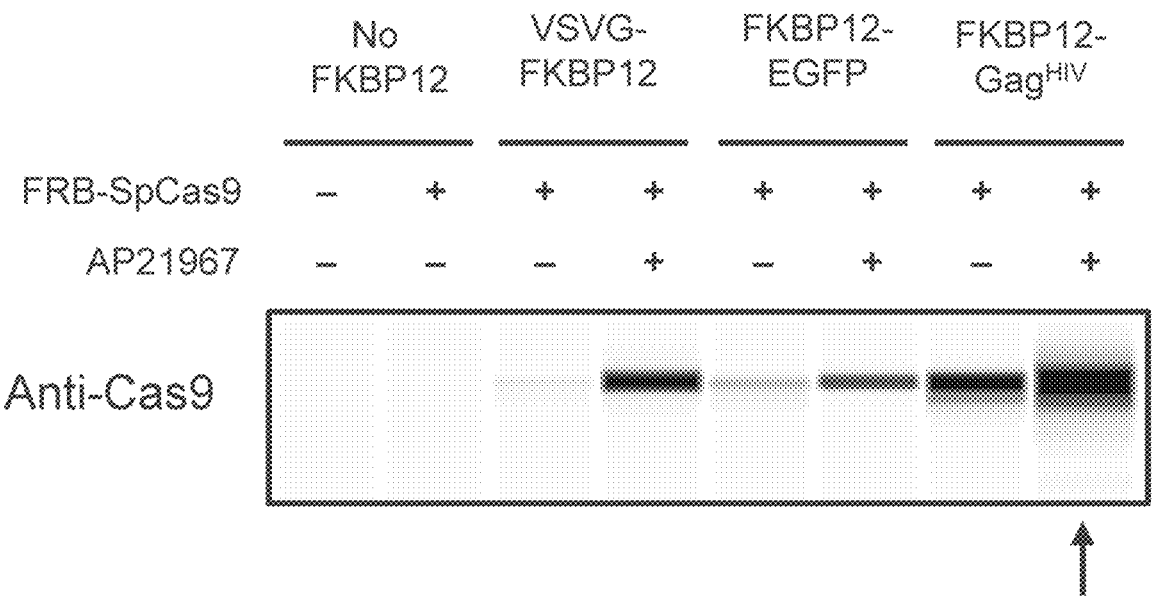
FIG. 7 is an image showing the results of Western blotting in Experimental Example 2.

Then, the amount of the FRB-Cas9 protein contained in each of the VLPs was quantified. Specifically, the concentrated VLPs were lysed in Lysis buffer (120 nM HEPES, pH 7.5, 100 mM KCl, 5 mM MgCl$_2$, 1 mM DTT, 5% glycerol, 0.1% Triton X-100, and protease inhibitor) and subjected to Western blotting using a fully automated Western blotting device Wes of ProteinSimple, Inc. and anti-Cas9 antibodies. FIG. 7 is an image showing the results of Western blotting.

As a result, as indicated by the arrow in FIG. 7, it was revealed that the amount of Cas9 encapsulated in VLPs is larger in VLPs in which the FKPB12 domain is bonded to Gag$^{HIV}$ (localization on the inside of the membrane) than in VLPs in which the FKPB12 domain is bonded to VSV-G (localization on the membrane) or EGFP (localization in the cytoplasm).

Thereafter, in order to test the amount of the Cas9 protein contained in VLPs, in vitro DNA cleavage activity was measured. Specifically, Lysis buffer was added to each of the concentrated VLPs, and the mixture was left to stand on ice for 10 minutes so that the VLPs were lysed.

Subsequently, the VLP lysate containing the Cas9 protein, DNA (700 bp) including a dystrophin target sequence, and sgRNA DMD #1 (the target sequence is shown in SEQ ID NO: 15), which was prepared by in vitro transcription (IVT) reaction and targeted the 5' side (near the splicing acceptor) of exon 45 of the human DMD gene, were mixed together in a buffer (20 mM HEPES, pH 7.5, 100 mM KCl, 5 mM MgCl$_2$, 1 mM DTT, 5% glycerol, and 0.5% BSA) and reacted at 37° C. for 1 hour. After the reaction, in order to remove sgRNA, RNase A was added thereto and reacted at 37° C. for 30 minutes. Furthermore, in order to remove proteins, proteinase K was added thereto and reacted at 50° C. for 20 minutes.

Then, these samples were subjected to electrophoresis using 2200 TapeStation (high sensitivity D1000 TapeScreen, Agilent Technologies, Inc.), and the proportion of cleaved DNA including the dystrophin target sequence was measured.

Figure 8:
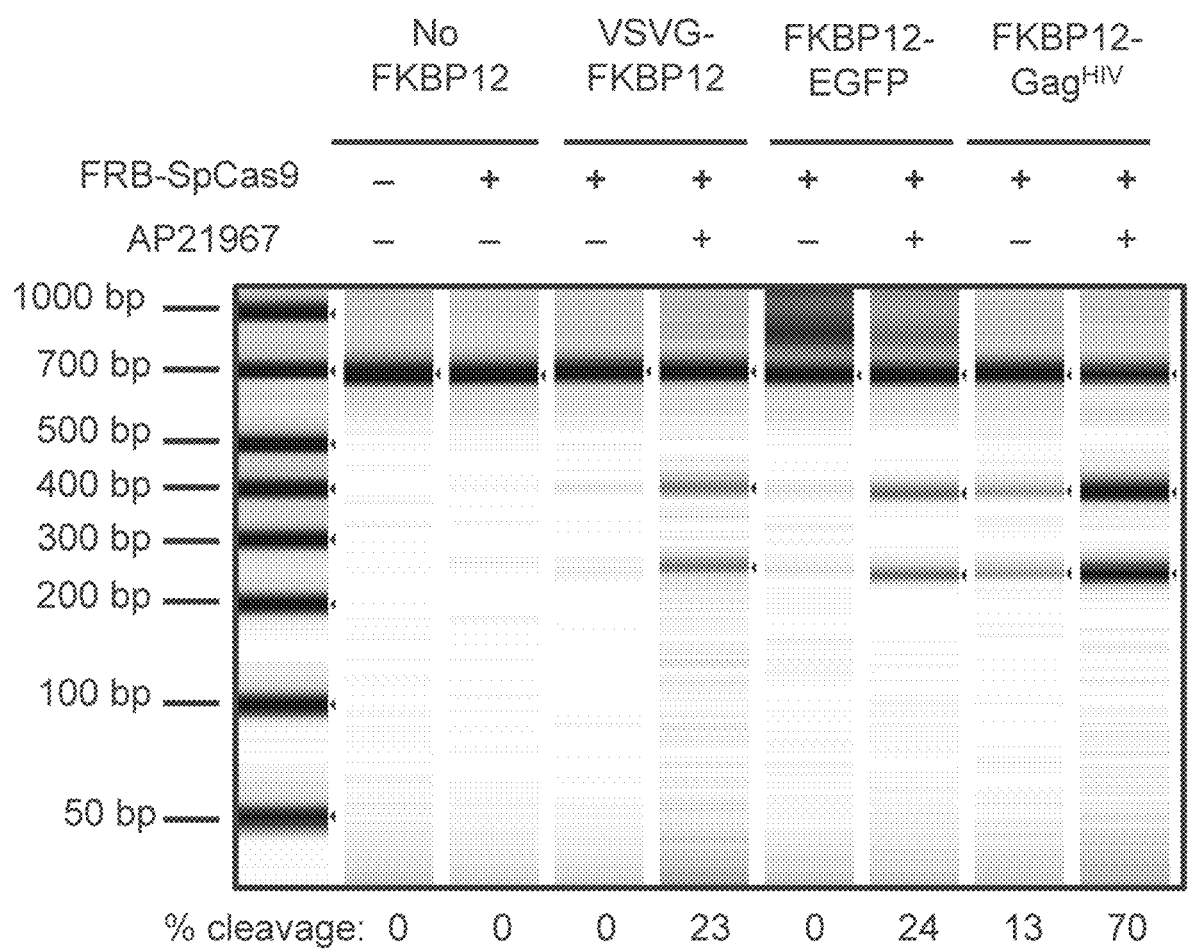
FIG. 8 is an image showing the results of electrophoresis in Experimental Example 2.
Figure 9:
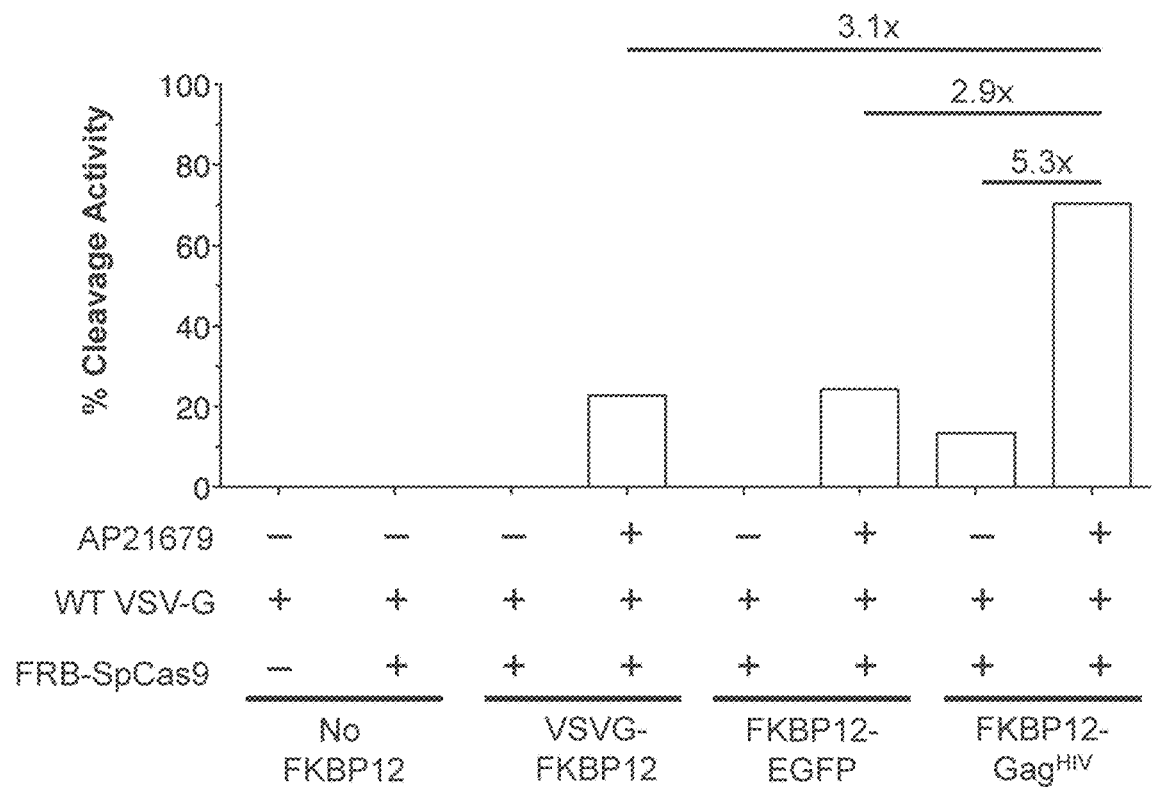
FIG. 9 is a graph numerically expressing the results shown in FIG. 8.

FIG. 8 is an image showing the results of electrophoresis. FIG. 9 is a graph numerically expressing the results shown in FIG. 8. As a result, it was revealed that VLPs containing FKBP12-Gag$^{HIV}$ exhibit the highest cleavage activity, and Cas9 is more efficiently encapsulated in VLPs by the addition of AP21967 which induces the dimerization of FKBP12 and FRB.

Experimental Example 3

(Examination 2 on FKBP12 Domain Binding Site)

An examination was performed regarding to where in VLP the FKBP12 domain should be bonded for the delivery of FRB-Cas9.

The same VLPs as those in Experimental Example 2 were introduced into HEK293T EGxxFP cells caused to constantly express sgRNA DMD #1 (the target sequence is shown in SEQ ID NO: 15). Then, the cleavage activity for the target DMD gene on the genome was measured by T7EI assay.

Specifically, first, each of the VLPs was introduced into HEK293T EGxxFP cells caused to constantly express sgRNA DMD #1 (the target sequence is shown in SEQ ID NO: 15). After 3 days, genomic DNA was extracted from each of the cells. Subsequently, the target region of the DMD gene on the genome was amplified by PCR. Thereafter, the PCR product was purified using columns, and by using 400 ng of the obtained DNA, mutation introduction efficiency was measured by T7EI assay.

Figure 10:
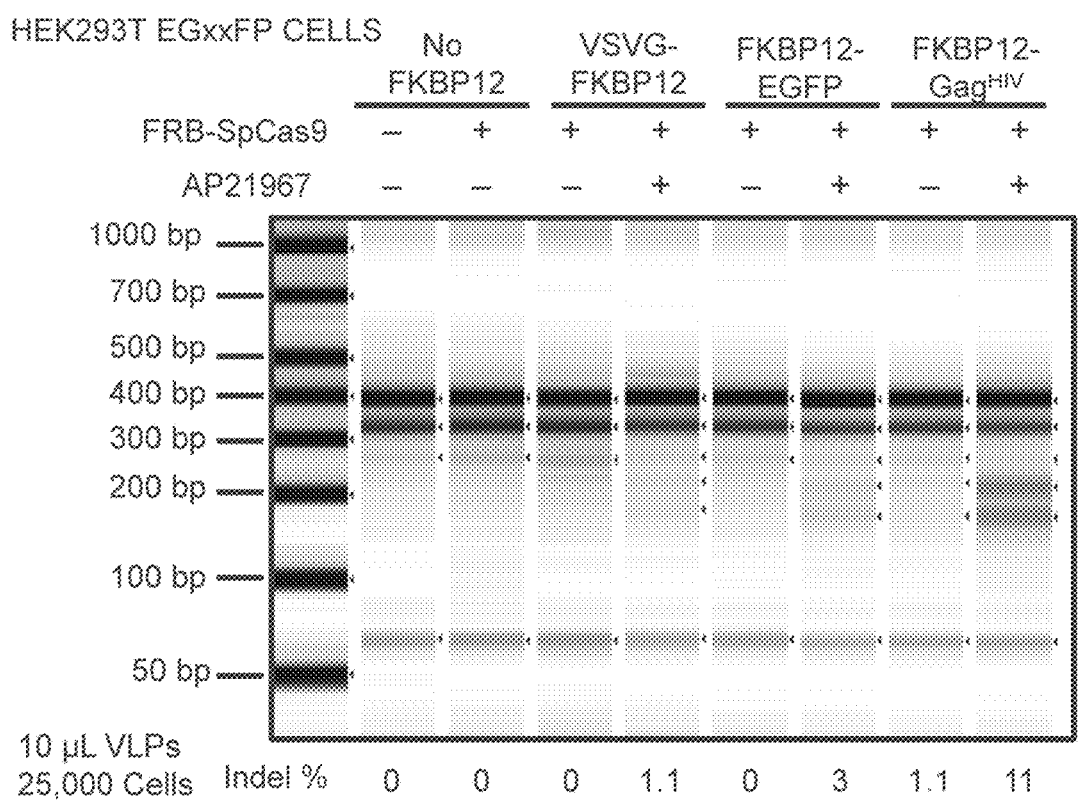
FIG. 10 is an image showing the results of T7 Endonuclease I (T7EI) assay in Experimental Example 3.
Figure 11:
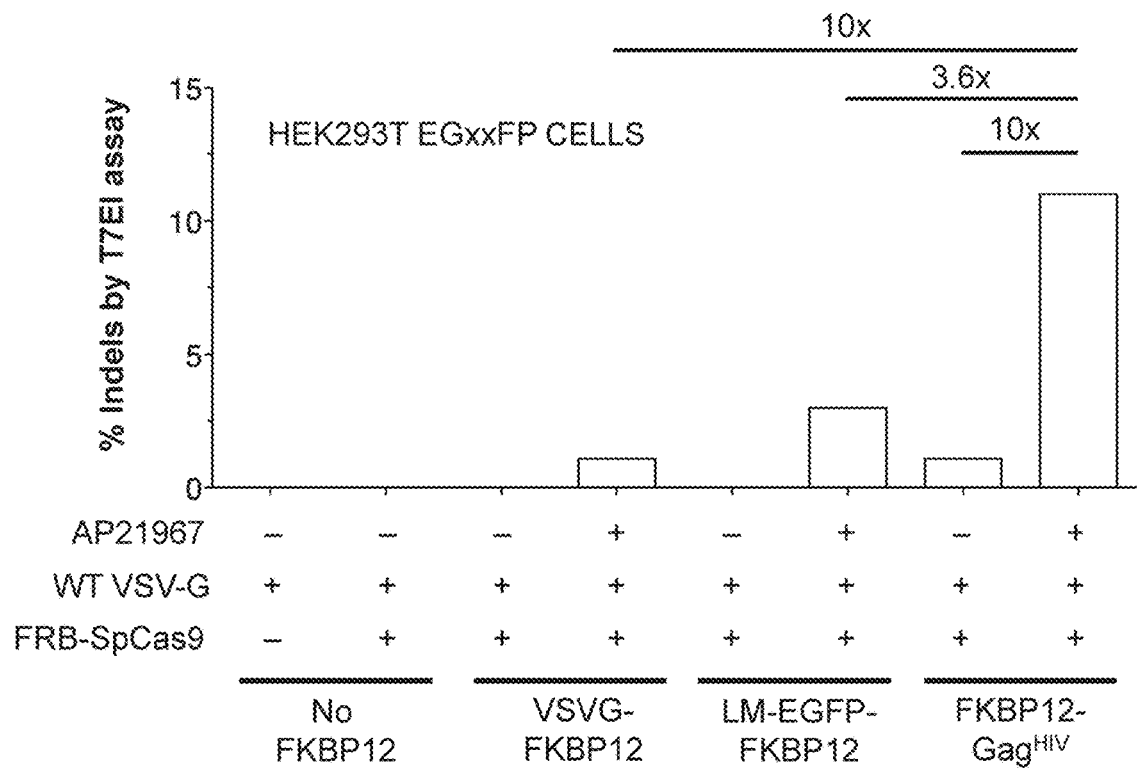
FIG. 11 is a graph numerically expressing the results shown in FIG. 10.
Figure 12:
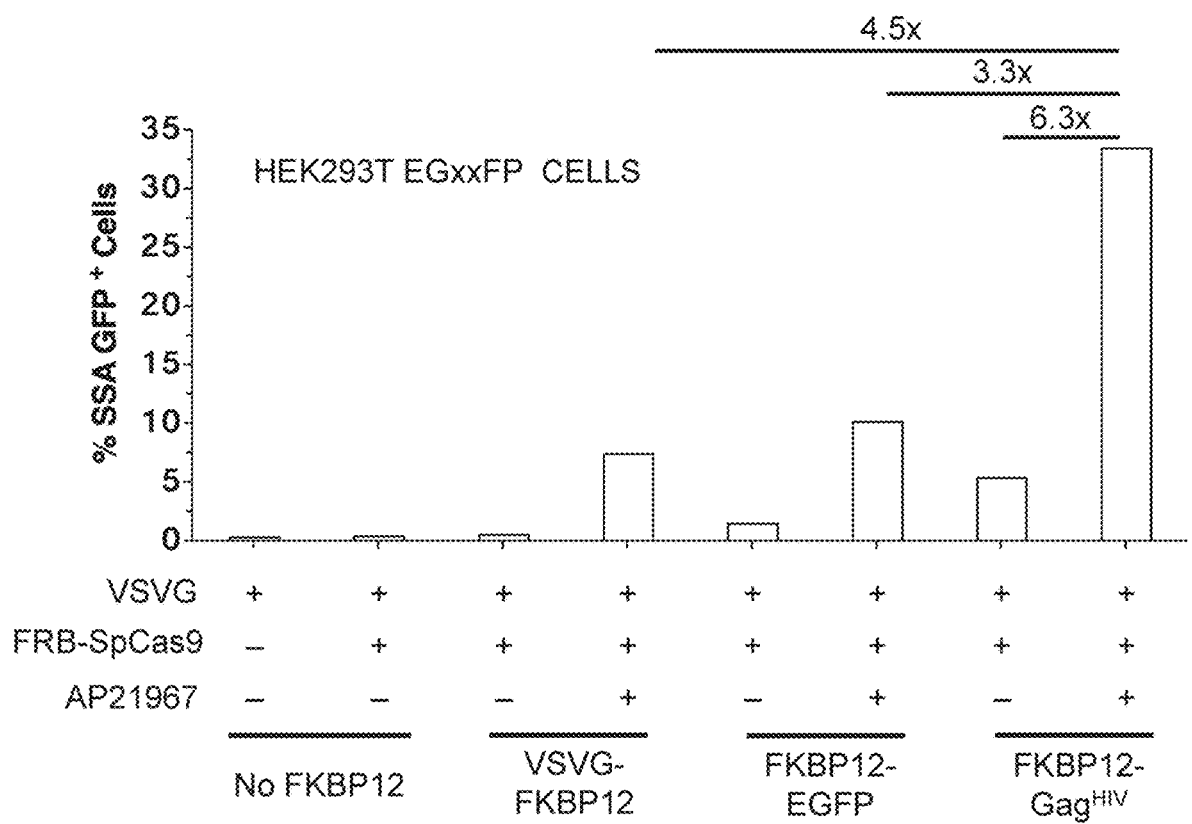
FIG. 12 is a graph showing the results of flow cytometry in Experimental Example 3.

FIG. 10 is an image showing the results of the T7EI assay. FIG. 11 is a graph numerically expressing the results shown in FIG. 10. FIG. 12 is a graph showing the results of flow cytometry performed to determine the proportion of GFP-positive cells from the EGxxFP reporter construct in each of the cells of the present experimental example.

As a result, it was revealed that VLPs containing FKBP12-Gag$^{HIV}$ exhibit the highest cleavage activity, and Cas9 is more efficiently encapsulated in VLPs by the addition of AP21967 which induces the dimerization of FKBP12 and FRB.

Experimental Example 4

(Examination 1 on Cas9 Protein Encapsulation Efficiency in VLP)

VLPs in which a Cas9 protein was encapsulated using murine leukemia virus (MLV)-derived Gag (hereinafter, called "FKBP12-Gag$^{HIV}$ VLP" in some cases) and VLPs in which a Cas9 protein was encapsulated using HIV-derived Gag (hereinafter, called "FKBP12-Gag$^{HIV}$ VLP" in some cases) were prepared, and the Cas9 protein delivery efficiency thereof was examined.

Specifically, HEK293T EGxxFP cells (2.5×10$^4$ cells) caused to constantly express sgRNA DMD #1 (the target sequence is shown in SEQ ID NO: 15) were inoculated with 10 μL of each of VLPs. As a control, cells not being inoculated with VLPs were prepared. After 3 days, the fluorescence of the EGxxFP reporter construct of each cell sample was analyzed using a flow cytometer.

Figure 13:
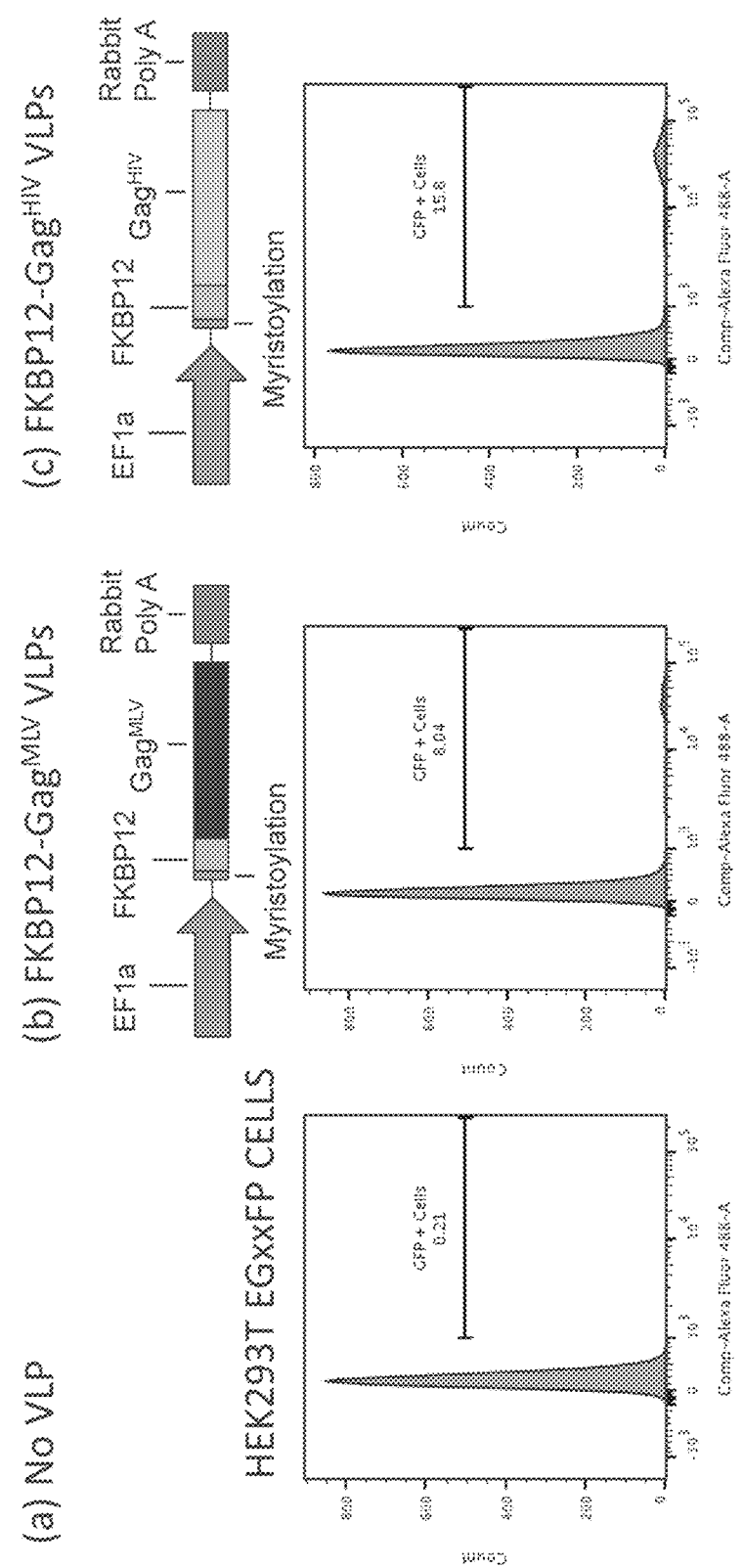
FIGS. 13(a) to 13(c) are graphs showing the results of flow cytometry in Experimental Example 4.

FIGS. 13(a) to 13(c) are graphs showing the results of flow cytometry. FIG. 13(a) shows the results obtained from the control cells. FIG. 13(b) shows the results obtained from the cells inoculated with FKBP12-Gag$^{HIV}$ VLP. FIG. 13(c) shows the results obtained from the cells inoculated with FKBP12-Gag$^{HIV}$ VLP. As a result, it was revealed that compared to FKBP12-Gag$^{HIV}$ VLP, FKBP12-Gag$^{HIV}$ VLP more efficiently delivers the Cas9 protein.

Experimental Example 5

(Examination 2 on Cas9 Protein Encapsulation Efficiency in VLP)

In the presence or absence of AP21967, VLPs containing Cas9 including the FRB domain bonded to the N-terminal, Cas9 including the FRB domain bonded to the C-terminal, or Cas9 including the FRB domain bonded to both the N-terminal and C-terminal were prepared, and the Cas9 protein encapsulation efficiency in the VLPs was examined.

AP21967 is known to specifically bind to FRB (T2098L) established by substituting threonine as the 2,098th residue in the FRB domain with leucine. Therefore, FRB (T2098L) was used as FRB.

Specifically, HEK293T EGxxFP cells (2.5×10$^4$ cells) caused to constantly express sgRNA DMD #1 (the target sequence is shown in SEQ ID NO: 15) were inoculated with 150 ng, equivalent to the amount of p24, of each of VLPs. After 3 days, the fluorescence of the EGxxFP reporter construct of each cell sample was analyzed using a flow cytometer.

Figure 14:
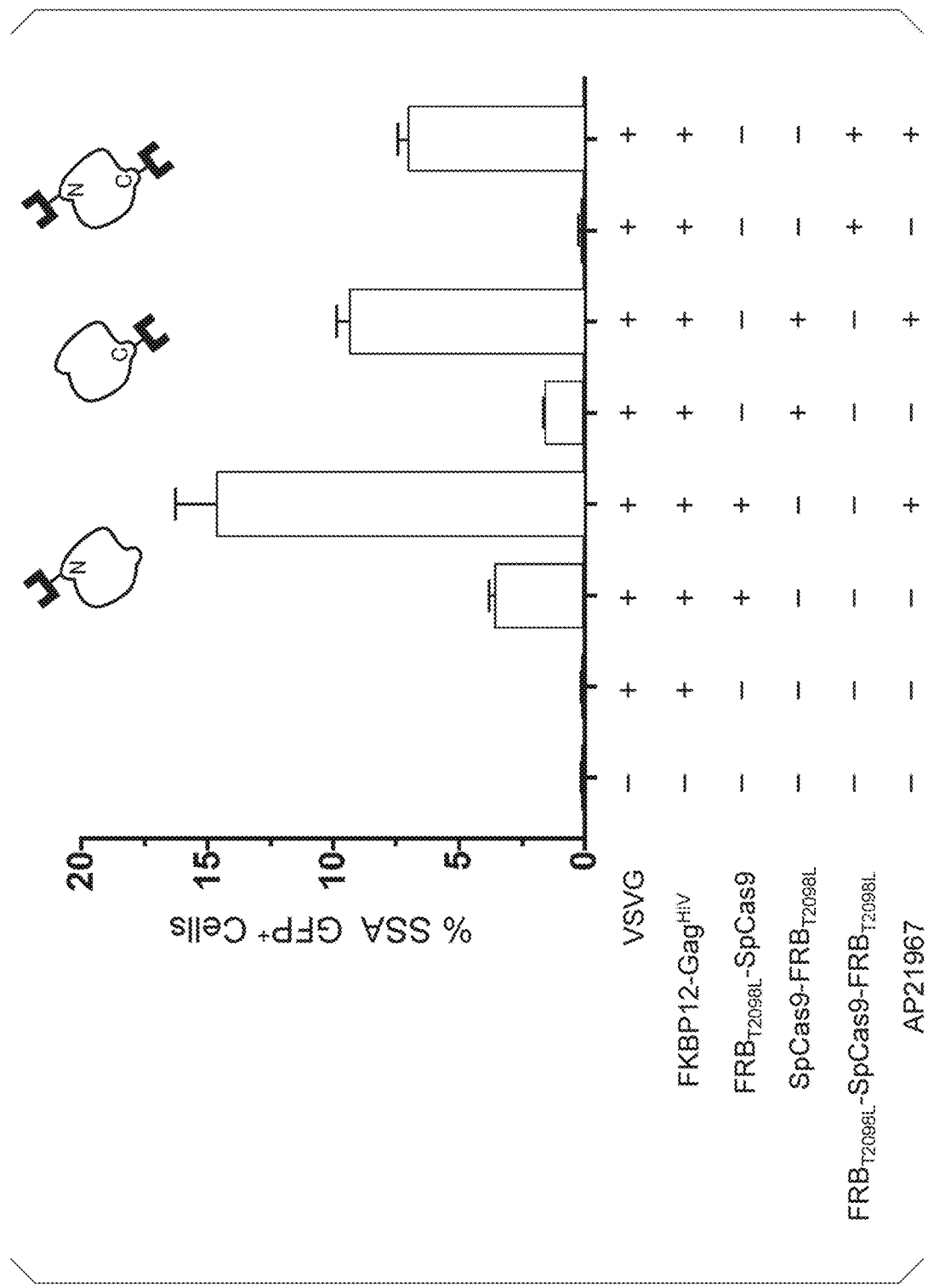
FIG. 14 is a graph showing the results of flow cytometry in Experimental Example 5.

FIG. 14 is a graph showing the results of flow cytometry. In FIG. 14, the ordinate shows the proportion of GFP-positive cells. As a result, it was confirmed that in all the VLPs, AP21967-dependent Cas9 protein delivery is carried out. Furthermore, it was revealed that the delivery of the Cas9 protein is most efficiently carried out in a case where the FRB domain is bonded to the N-terminal of the Cas9 protein.

Experimental Example 6

(Examination 3 on Cas9 Protein Encapsulation Efficiency in VLP)

By using VLPs in which a Cas9 protein was encapsulated through the binding of the FKBP12 domain to the FRB domain and VLPs in which a Cas9 protein was encapsulated by being directly fused with Gag, the Cas9 protein encapsulation efficiency in VLPs was examined.

Figure 15:
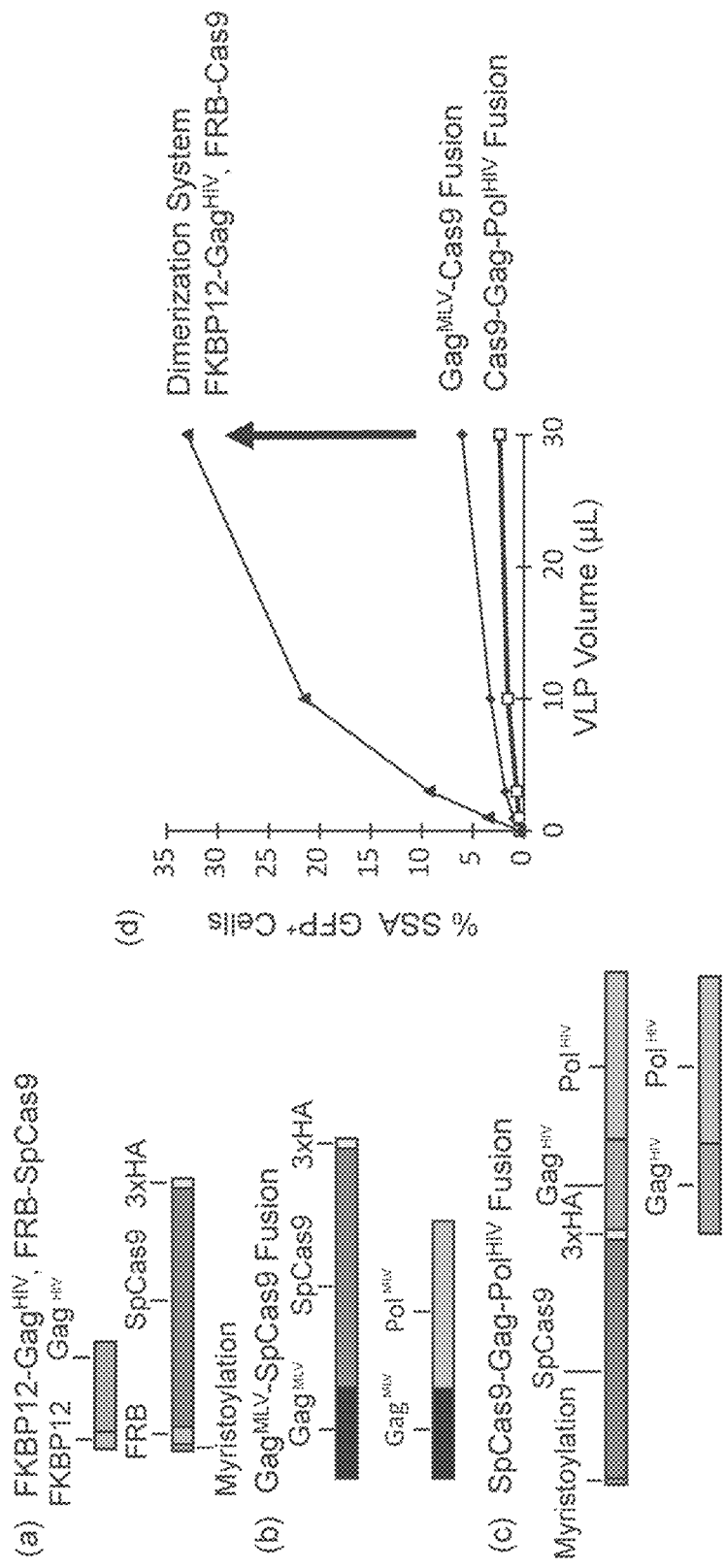
FIG. 15(a) is a schematic view showing the structure of a fusion protein of an FRB domain and a Cas9 protein and the structure of a fusion protein of an FKBP12 domain and Gag$^{HIV}$.
FIG. 15(b) is a schematic view showing the structure of a fusion protein of Gag$^{MLV}$ and a Cas9 protein and the structure of GAG-Pol$^{MLV}$.
FIG. 15(c) is a schematic view showing the structure of a fusion protein of a Cas9 protein and Gag-Pol$^{HIV}$ and the structure of GAG-Pol$^{HIV}$.
FIG. 15(d) is a graph showing the results of flow cytometry in Experimental Example 6.

FIG. 15(a) is a schematic view showing the structure of a fusion protein of the FRB domain and the Cas9 protein and the structure of a fusion protein of the FKBP12 domain and Gag$^{HIV}$. In this case, the encapsulation of the Cas9 protein in VLP was carried out by the AP21967-mediated dimerization.

FIG. 15(b) is a schematic view showing the structure of a fusion protein of Gag$^{MLV}$ and the Cas9 protein and the structure of GAG-Pol$^{MLV}$. In this case, Gag-Pol$^{MLV}$ was added to accelerate the formation of VLPs.

FIG. 15(c) is a schematic view showing the structure of a fusion protein of the Cas9 protein and Gag-Pol$^{HIV}$ and the structure of GAG-Pol$^{HIV}$. In this case, Gag-Pol$^{HIV}$ was added to accelerate the formation of VLPs.

Specifically, HEK293T EGxxFP cells caused to constantly express sgRNA DMD #1 (the target sequence is shown in SEQ ID NO: 15) were inoculated with each of the VLPs. After 3 days, the fluorescence of the EGxxFP reporter construct of each cell sample was analyzed using a flow cytometer.

FIG. 15(d) is a graph showing the results of flow cytometry. In FIG. 15(d), the ordinate shows the proportion of GFP-positive cells. As a result, it was revealed that compared to the VLPs prepared by directly fusing the Cas9 protein with Gag or Gag-Pol, the VLPs prepared by using the binding of the FKBP12 domain to the FRB domain more efficiently deliver the Cas9 protein.

Experimental Example 7

(Examination on Concentration of AP21967)

VLPs were prepared by varying the concentration of AP21967, a heterodimerizing ligand, to 0, 3, 30, and 300 nM. Then, HEK293T EGxxFP cells (5×10$^4$ cells) caused to constantly express sgRNA DMD #1 (the target sequence is shown in SEQ ID NO: 15) were inoculated with each of the VLPs. After 3 days, the fluorescence of the EGxxFP reporter construct of each cell sample was analyzed using a flow cytometer.

Figure 16:
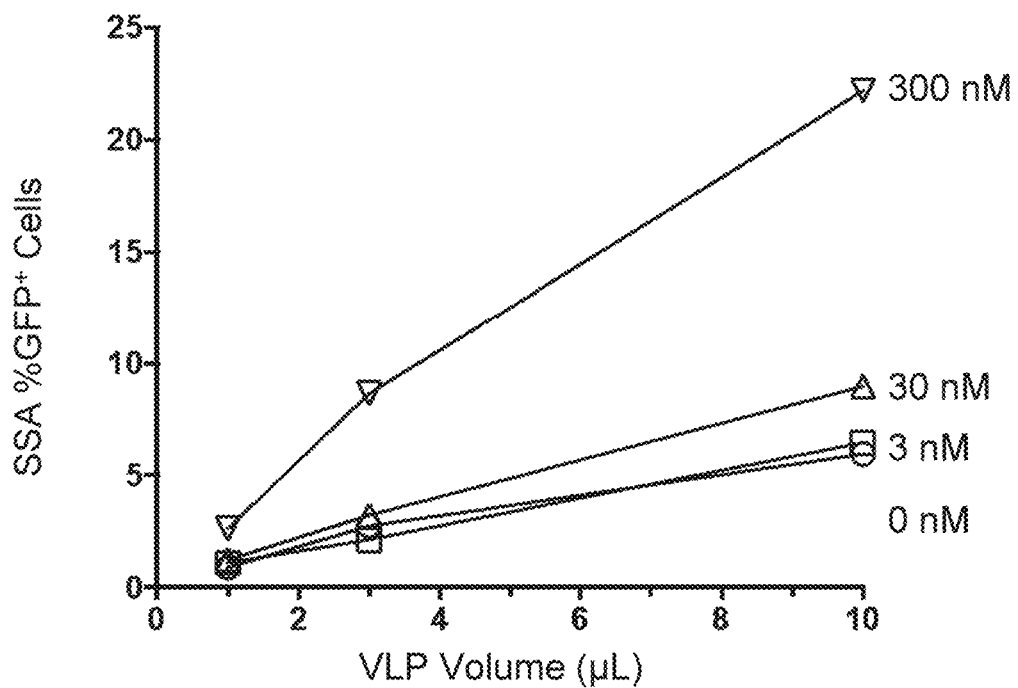
FIG. 16 is a graph showing the results of flow cytometry in Experimental Example 7.
Figure 17:
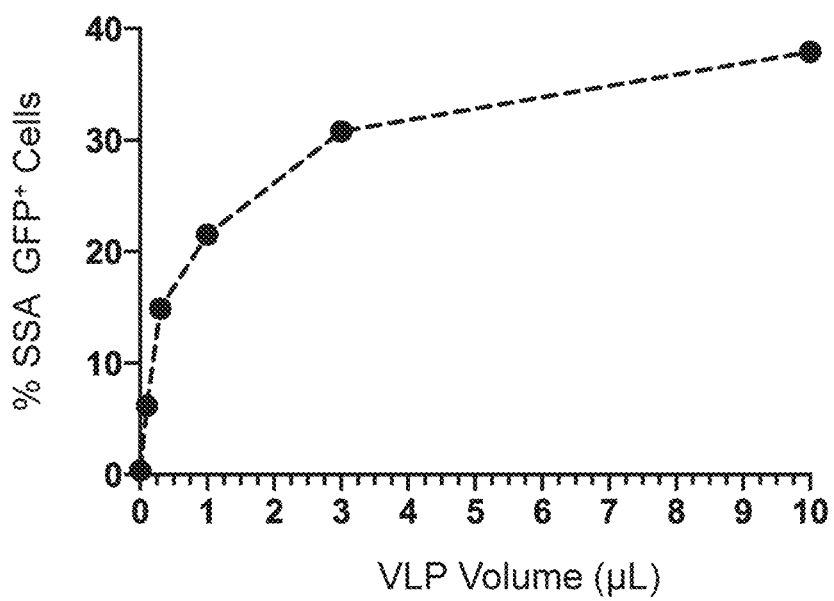
FIG. 17 is a graph showing the results of flow cytometry in Experimental Example 7.

FIGS. 16 and 17 are graphs showing the results of flow cytometry. In FIGS. 16 and 17, the ordinate shows the proportion of GFP-positive cells. As a result, the observed fluorescence indicates that the genome editing efficiency increases depending on the AP21967 concentration at the time of preparing VLPs. Furthermore, it was revealed that the VLPs prepared in the presence of AP21967 deliver Cas9 and induce genome editing depending on the inoculation dose of the VLPs.

Experimental Example 8

(Examination on FRB Domain)

AP21967 is known to specifically bind to an FRB domain (T2098L) established by substituting threonine as the 2,098th residue with leucine. Meanwhile, an FRB domain (T2098A) established by substituting threonine as the 2,098th residue with alanine is known to lose the ability to bind to AP21967.

VLPs were prepared using Cas9 including each of the FRB domains, and the genome editing efficiency was measured. Specifically, HEK293T EGxxFP cells caused to constantly express sgRNA targeting sgRNA DMD #1 (the target sequence is shown in SEQ ID NO: 15) were inoculated with each of the VLPs. After 3 days, the fluorescence of the EGxxFP reporter construct of each cell sample was analyzed using a flow cytometer.

Figure 18:
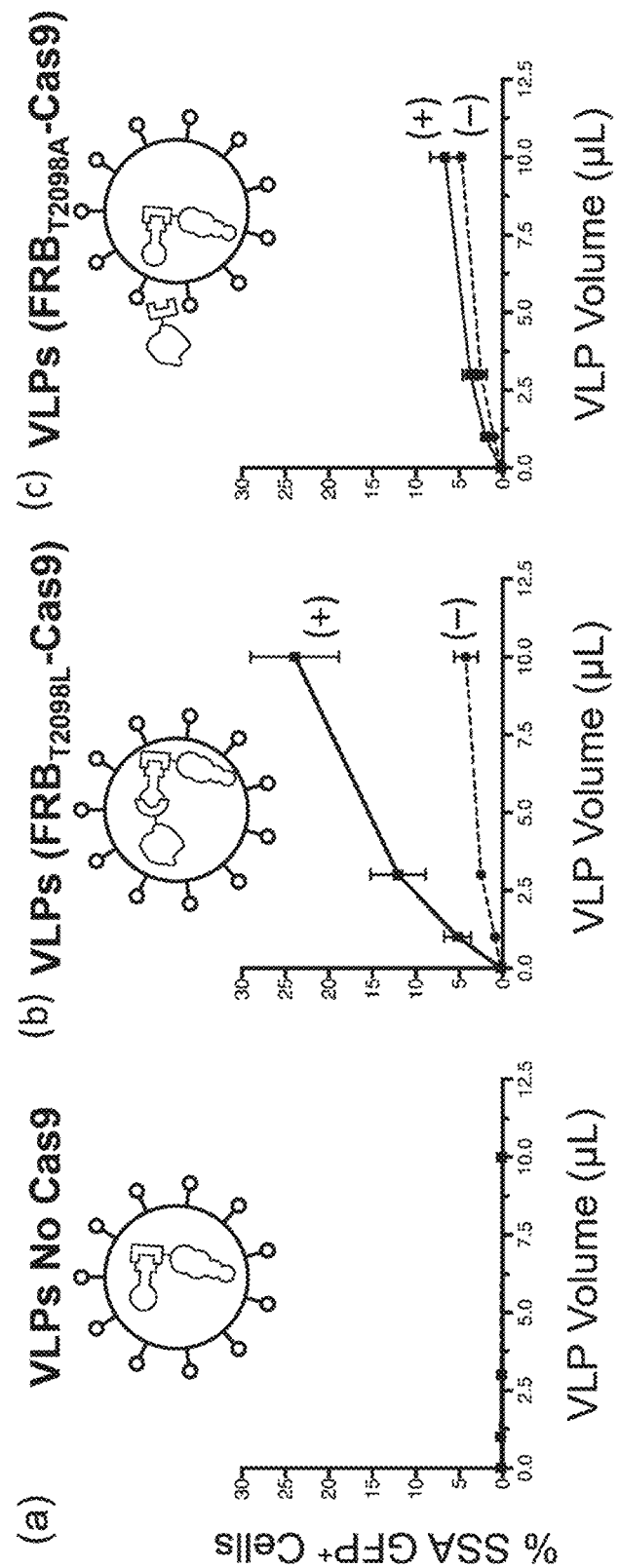
FIGS. 18(a) to 18(c) are graphs showing the results of flow cytometry in Experimental Example 8.

FIGS. 18(a) to 18(c) are graphs showing the results of flow cytometry. In FIGS. 18(a) to 18(c), the ordinate shows the proportion of GFP-positive cells. Furthermore, "+" shows that the result is obtained from VLPs prepared in the presence of AP21967, and "−" shows that the result is obtained from VLPs prepared in the absence of AP21967.

As a result, it was revealed that in VLPs containing the Cas9 protein bound to the FRB domain (T2098A) mutant, the AP21967-dependent Cas9 delivery is inhibited. This result further supports that the dimerization of the Cas9 protein and Gag through the FRB domain (T2098L) is necessary for efficient delivery of the Cas9 protein.

Experimental Example 9

(Examination on Localization of FRB-Cas9 Protein)

The intracellular localization of the FRB-Cas9 protein was examined. Specifically, VLPs were prepared which contained a fusion protein obtained by binding mCherry as a fluorescent protein to FRB-SpCas9 (with a nuclear transport signal). Then, HEK293T cells (5×10$^4$ cells) on a 48-well plate were inoculated with the concentrated VLPs (8 µL), and 20 hours after inoculation, the fluorescence of mCherry was analyzed using a 20× objective lens of a Keyence BX-700 microscope.

Figure 19:
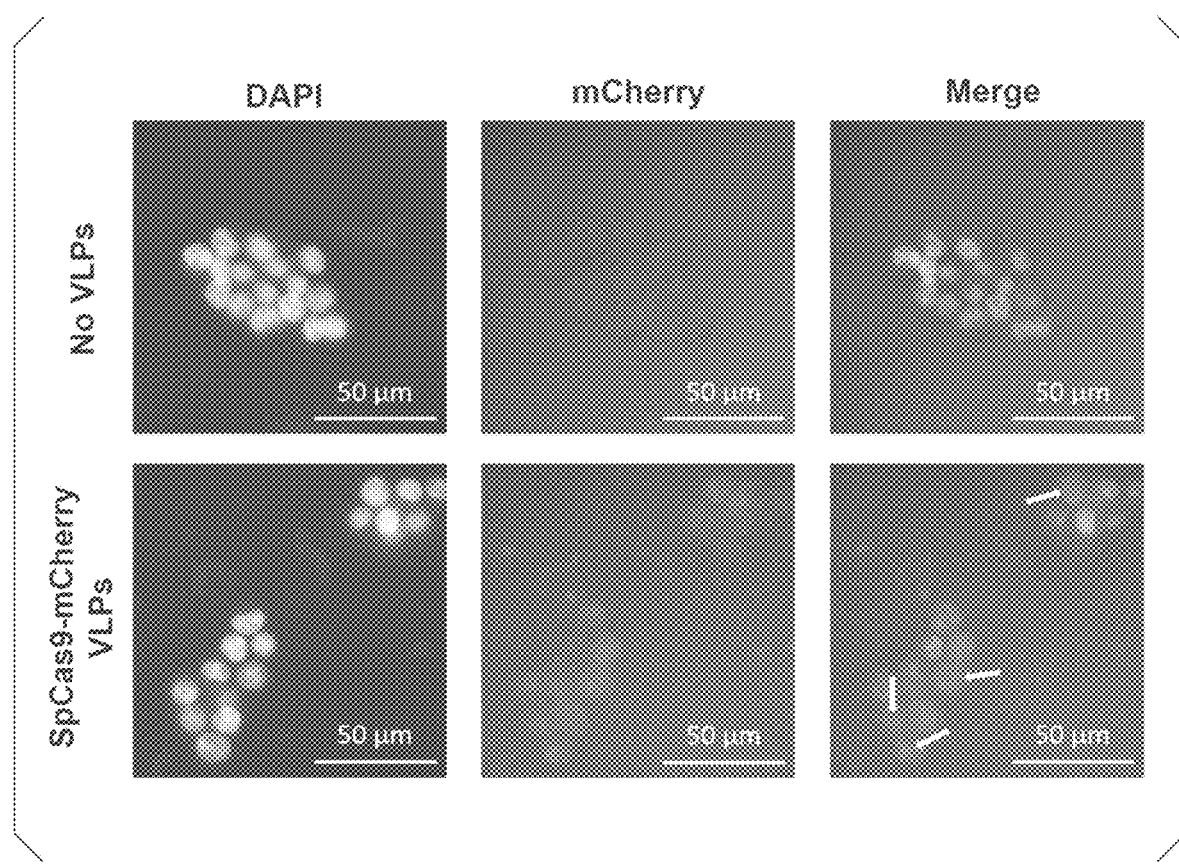
FIG. 19 is fluorescence micrographs in Experimental Example 9.

FIG. 19 is fluorescence micrographs showing the analysis results. In FIG. 19, "DAPI" represents the result obtained by staining the nucleus with 4',6-diamidino-2-phenylindole, "mCherry" represents the result of detecting fluorescence of mCherry, and "Merge" represents the result obtained by merging together the fluorescence of DAPI and the fluorescence of mCherry. As a result, it was confirmed that the FRB-Cas9 protein is localized in the nucleus. In FIG. 19, the arrows indicate the fluorescence of mCherry localized in the nucleus.

Experimental Example 10

(Examination 1 on Method of Encapsulating sgRNA in VLP)

Figure 20:
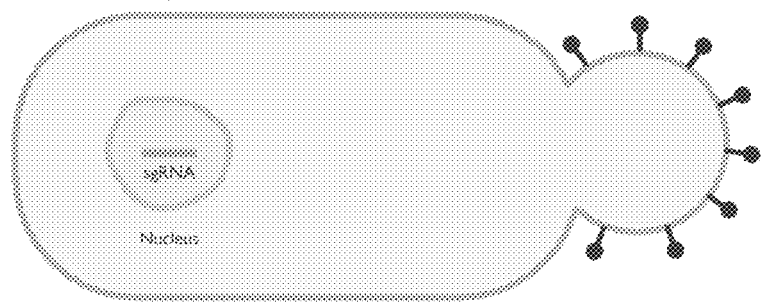
FIGS. 20(a) to 20(c) are schematic views illustrating how sgRNA behaves in a virus-like particle (VLP)-producing cell by an sgRNA expression method.
Figure 20:
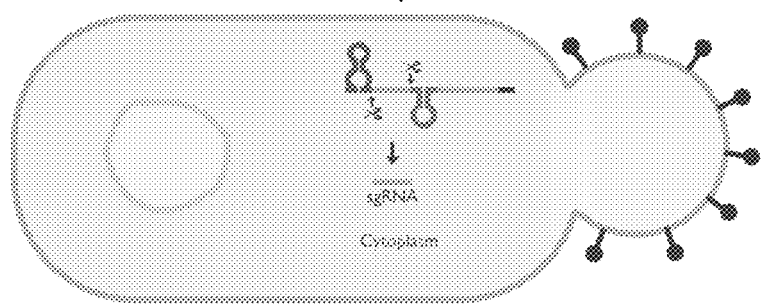
Figure 20:
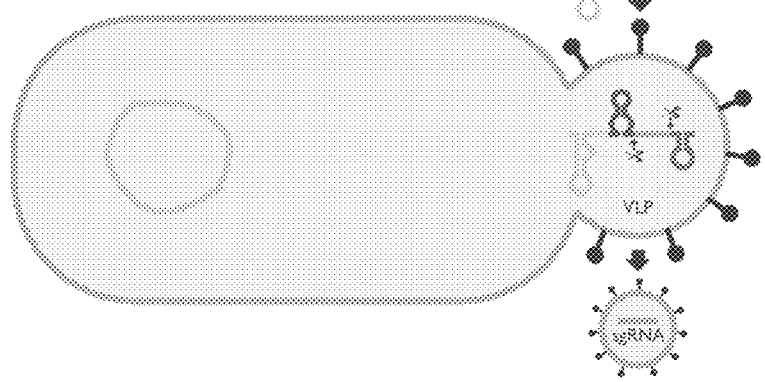

FIGS. 20(a) to 20(c) are schematic views illustrating how sgRNA behaves in a VLP-producing cell (HEK293T) by an sgRNA expression method.

FIG. 20(a) is a schematic view showing a case where sgRNA is transcribed using a polymerase III promoter. Being a short RNA consisting of about 100 bases, sgRNA is transcribed using a polymerase III promoter such as a U6 or H1 promoter in many cases. It has been reported that in this case, sgRNA mainly accumulates in the nucleus as shown in FIG. 20(a).

FIG. 20(b) is a schematic view showing a case where mRNA is transcribed using a polymerase II promoter. By adding ribozymes (hammerhead (HH) ribozyme and hepatitis delta virus (HDV) ribozyme) as self-cleaving sequences so that these sequences are positioned before and after sgRNA, mRNA longer than the original sgRNA can be transcribed from a polymerase II promoter (such as an LTR promoter or an EF1α promoter). In this case, mRNA is distributed in the cytoplasm as shown in FIG. 20(b).

FIG. 20(c) is a schematic view illustrating a method of encapsulating sgRNA in VLP, which was examined in the present experimental example. In the present experimental example, in order for sgRNA transcribed as mRNA to be more efficiently encapsulated in VLP, a method of adding an HIV-derived packaging signal (Ψ) to mRNA was examined. The packaging signal (Ψ) is a sequence found in retrovirus or lentivirus such as MLV or HIV which uses this sequence to incorporate their own genomic mRNA into viral particles.

It is known that viral genomic mRNA is incorporated into viral particles through the binding of the Gag protein to the packaging signal. The inventors of the present invention examined the application of this mechanism to the encapsulation of sgRNA in VLP.

It is known that the packaging signal sequence is more efficiently incorporated into viral particles in a case where the sequence is in the form of an Extended packaging signal (Ψ+) including the leading portion of Gag. The Ψ+ sequence was also used in the present experimental example. A mutation is inserted into the start codon in Gag in this portion so that the protein is not translated.

Figure 21:
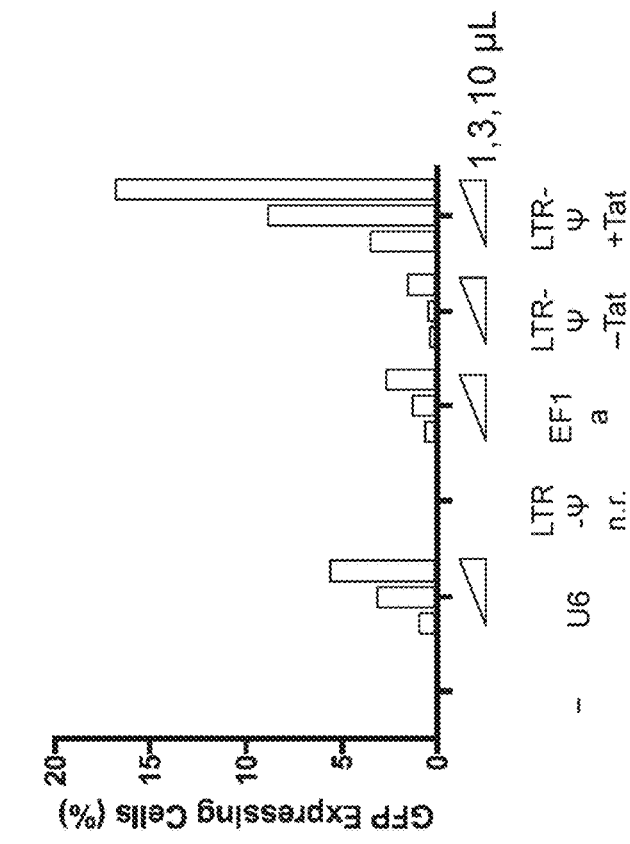
FIGS. 21(a) and 21(b) are graphs showing the results of the T7EI assay in Experimental Example 10.
Figure 21:
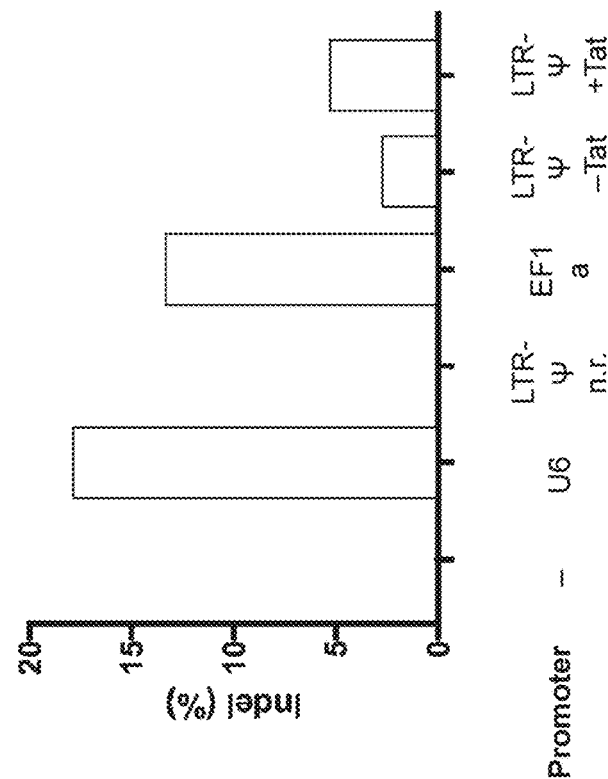

In the present experimental example, first, in the presence of FRB-Cas9, VLPs were prepared which included VLPs prepared by a method of letting sgRNA to be transcribed from the U6 promoter (represented by "U6" in FIGS. 21(a) and 21(b)), VLPs prepared by a method of letting sgRNA to be transcribed from the LTR promoter as mRNA having Ψ+ without a ribozyme sequence (represented by "LTR-Ψn.r." in FIGS. 21(a) and 21(b)), VLPs prepared by a method of letting sgRNA having Ψ+ and a ribozyme sequence to be transcribed from the EF1a promoter (represented by "EF1α" in FIGS. 21(a) and 21(b)), and VLPs prepared by a method of letting sgRNA having Ψ+ and a ribozyme sequence to be transcribed in the presence of a Tat protein (represented by "LTR-Ψ+Tat" in FIGS. 21(a) and 21(b)) activating the HIV LTR promoter or in the absence of the Tat protein (represented by "LTR-Ψ-Tat" in FIGS. 21(a) and 21(b)). Then, the genomic DNA of the VLP-producing cells was recovered, and the genome editing efficiency was examined by analyzing the target base sequence of the DMD gene by T7EI assay.

FIG. 21(a) is a graph showing the results of the T7EI assay performed on the VLP-producing cells. As a result, it was revealed that the most active sgRNA can be transcribed much from the U6 promoter. Furthermore, it was revealed that in a case where sgRNA is transcribed as mRNA from the polymerase II promoter (LTR or EF1α), the sgRNA can be cleaved as long as it has a ribozyme sequence and can induce genome editing.

Subsequently, each of the prepared VLPs was introduced in an amount of 1 μL, 3 μL, and 10 μL into HEK293T EGxxFP reporter cells ($5 \times 10^4$ cells). Subsequently, after 3 days, the proportion of GFP-positive cells was analyzed with a flow cytometer.

FIG. 21(b) is a graph showing the results of flow cytometry. In FIG. 21(b), the ordinate shows the proportion of GFP-positive cells. As a result, it was revealed that the U6 promoter exhibiting high genome editing activity in the VLP-producing cells is inefficient in encapsulating sgRNA in VLPs and exhibits low genome editing activity.

In contrast, it was revealed that in a case where sgRNA having Ψ+ and a ribozyme sequence is transcribed from the LTR promoter in the presence of Tat protein (represented by "LTR-Ψ+Tat" in FIG. 21(b)), the VLP-mediated sgRNA delivery efficiency is the highest.

Experimental Example 11

(Examination 2 on Method of Encapsulating sgRNA in VLP)

The HIV Rev protein is known to bind to the Rev responsive element (RRE) sequence on RNA and transport viral RNA with PRE to the cytoplasm. The RRE sequence is incorporated into most lentiviral vectors. The sgRNA expression vector used in Experimental Example 10 also includes the RRE sequence. Therefore, the necessity of the Rev protein was examined.

Figure 22:
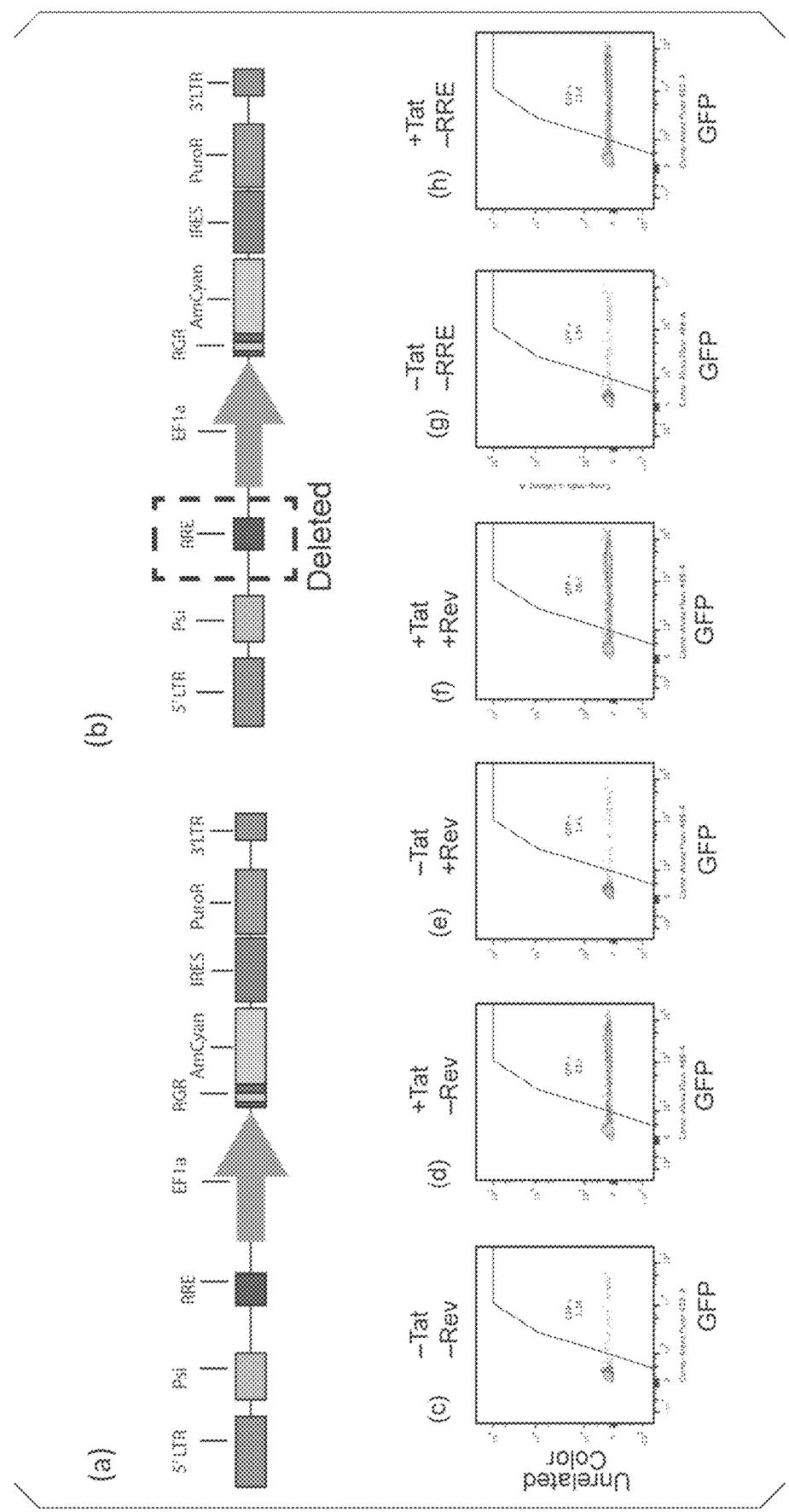
FIG. 22(a) is a schematic view showing the structure of an sgRNA expression vector including an RRE sequence.
FIG. 22(b) is a schematic view showing the structure of the expression vector obtained by removing the PRE sequence from the expression vector shown in FIG. 22(a).
FIGS. 22(c) to 22(h) are graphs showing the results of flow cytometry in Experimental Example 11.

Specifically, VLPs were produced in the presence or absence of the Rev protein and in the presence or absence of the RRE sequence, and the genome editing efficiency was examined. FIG. 22(a) is a schematic view showing the structure of an sgRNA expression vector (SEQ ID NO: 22) including the RRE sequence. FIG. 22(b) is a schematic view showing the structure of an expression vector (SEQ ID NO: 23) obtained by removing the PRE sequence from the expression vector shown in FIG. 22(a).

sgRNA is transcribed from the HIV LTR promoter, and the Tat protein of HIV is necessary to activate the HIV LTR promoter. Therefore, in the presence or absence of the Tat protein and in the presence or absence of the Rev protein, VLPs were prepared by letting sgRNA to be transcribed from the expression vector shown in FIG. 22(a), and the genome editing efficiency brought about by the prepared VLPs was analyzed.

Specifically, each of the VLPs was introduced into HEK293T EGxxFP reporter cells, and after 3 days, the proportion of GFP-positive cells was analyzed with a flow cytometer. FIGS. 22(c) to 22(f) are graphs showing the results of flow cytometry. In FIGS. 22(c) to 22(f), "−Tat" represents the result obtained from VLPs prepared in the absence of the Tat protein, "+Tat" represents the result obtained from VLPs prepared in the presence of the Tat protein, "−Rev" represents the result obtained from VLPs prepared in the absence of the Rev protein, and "+Rev" represents the result obtained from VLPs prepared in the presence of the Rev protein. As shown in the graphs, high genome editing efficiency was observed in the presence of the Tat protein. In addition, the genome editing efficiency in the presence of the Rev protein was approximately the same as that in the absence of the Rev protein.

Furthermore, in the presence or absence of the Tat protein, VLPs were prepared by letting sgRNA to be transcribed from the expression vector shown in FIG. 22(b), and the genome editing efficiency brought about by each of the prepared VLPs was analyzed. Specifically, each of the VLPs was introduced into HEK293T EGxxFP reporter cells, and after 3 days, the proportion of GFP-positive cells was analyzed with a flow cytometer.

FIGS. 22(g) and 22(h) are graphs showing the results of flow cytometry. In FIGS. 22(g) and 22(h), "−Tat" represents the result obtained from VLPs prepared in the absence of the Tat protein, "+Tat" represents the result obtained from VLPs prepared in the presence of the Tat protein, and "−PRE" represents the result obtained from VLPs prepared using the expression vector from which the PRE sequence has been removed. As a result, it was revealed that high genome editing efficiency is obtained even in the absence of the PRE sequence.

From the above results, it was revealed that the sgRNA expression vector does not require the RRE sequence, and the Rev protein is also unnecessary.

Experimental Example 12

(Examination 3 on Method of Encapsulating sgRNA in VLP)

As described above, sgRNA is transcribed from the HIV LTR promoter, and the Tat protein of HIV is necessary to activate the HIV LTR promoter. Therefore, by real-time PCR, the expression level of sgRNA in the VLP-producing cells in the presence and absence of the Tat protein in the VLP-producing cells was quantified. Furthermore, the amount of sgRNA in VLPs was also quantified in the same manner.

Figure 23:
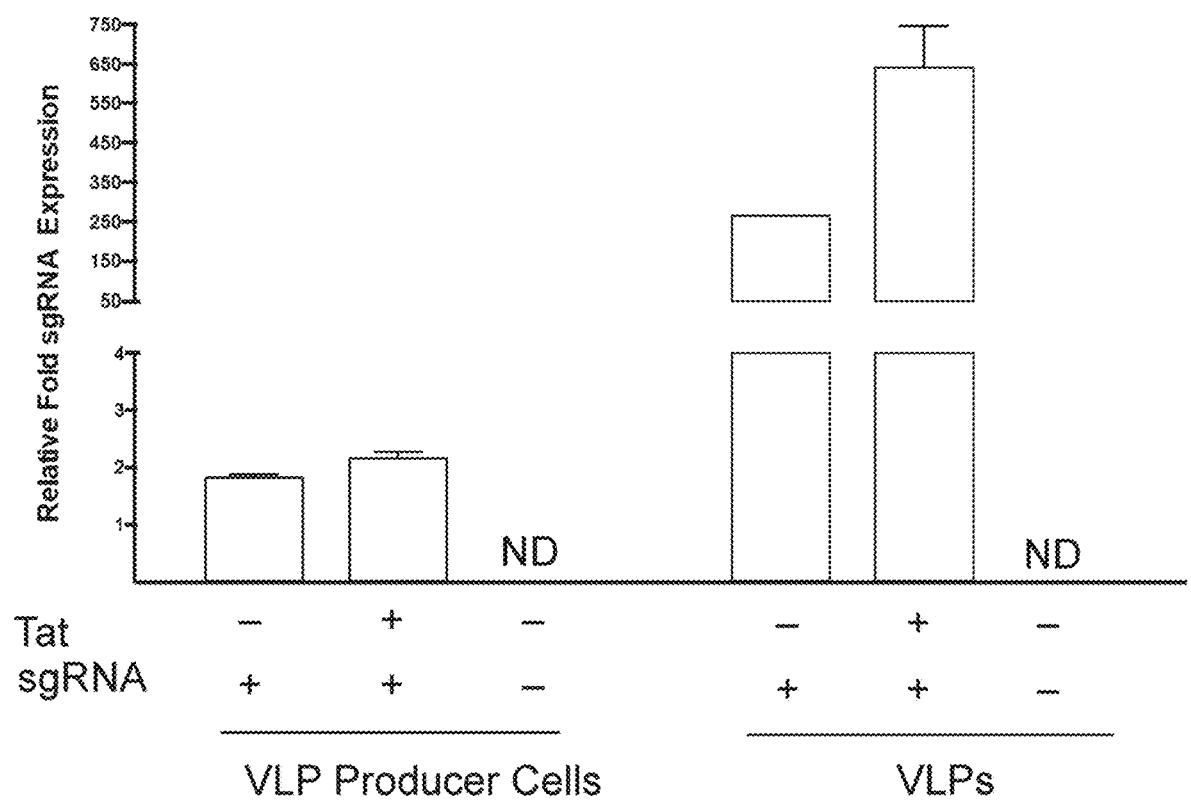
FIG. 23 is a graph showing the results of real-time PCR in Experimental Example 12.

FIG. 23 is a graph showing the results of real-time PCR. In FIG. 23, the ordinate shows the expression level (relative value) of sgRNA, "+" shows that the protein is present, "−" shows that the protein is absent, and "ND" shows that the amount of the protein is equal to or lower than the detection limit.

As shown in the graph, it was revealed that in a case where the Tat protein is co-expressed in the VLP-producing cells, the expression level of sgRNA and the amount of sgRNA encapsulated in VLPs can be increased.

Experimental Example 13

(Examination 4 on Method of Encapsulating sgRNA in VLP)

The effect of the packaging signal (Ψ+) in the sgRNA expression vector was examined. Specifically, VLPs were prepared using an SgRNA expression vector having Ψ+ or an sgRNA expression vector from which Ψ+ was deleted.

Figure 24:
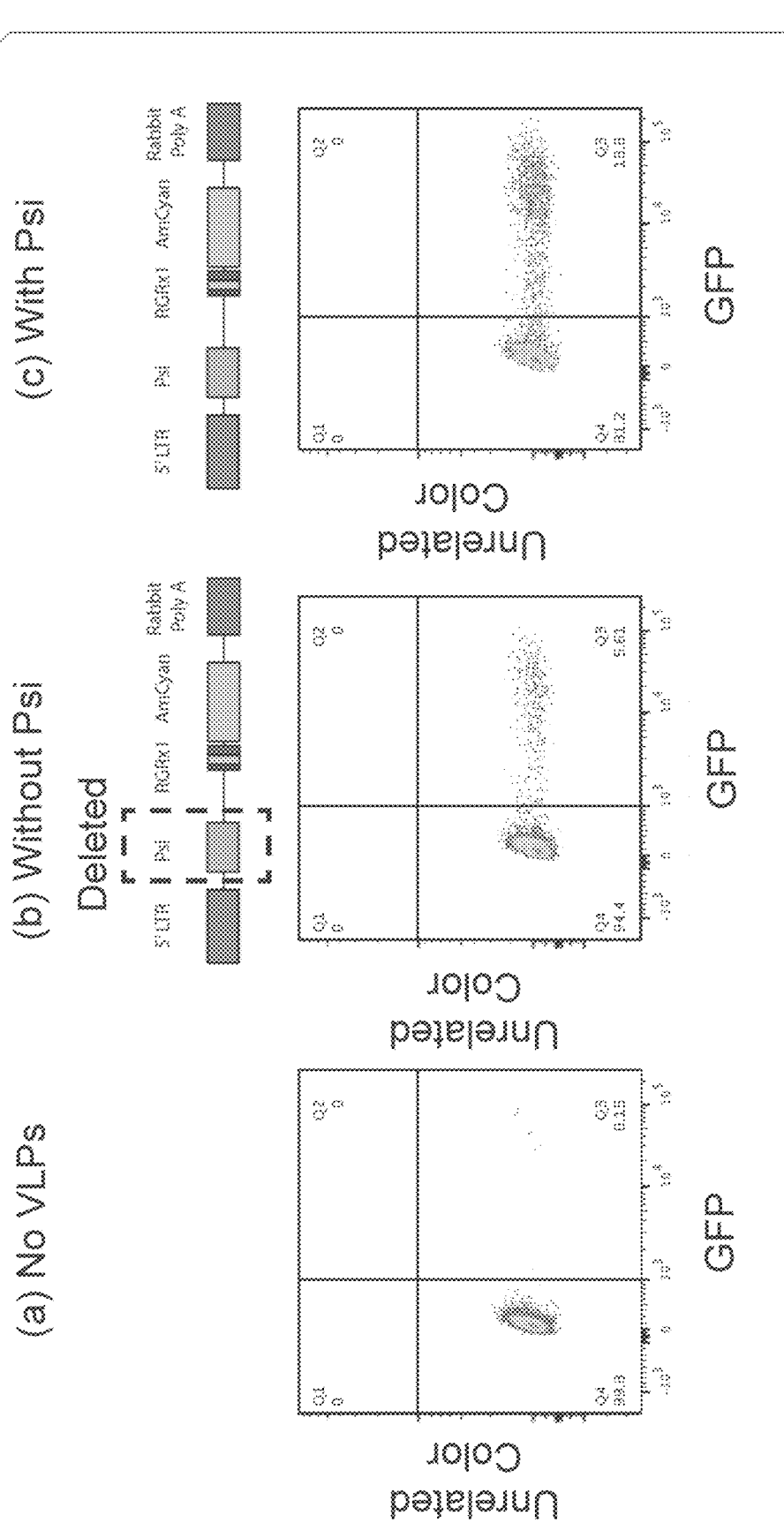
FIGS. 24(a) to 24(c) are graphs showing the results of flow cytometry in Experimental Example 13.

Then, each of the VLPs was introduced into HEK293T EGxxFP reporter cells, and after 3 days, the proportion of GFP-positive cells was analyzed with a flow cytometer. FIGS. 24(a) to 24(c) are graphs showing the results of flow cytometry. FIG. 24(a) shows the results obtained from control not being inoculated with VLPs. FIG. 24(b) shows the results obtained from the VLPs prepared using an sgRNA expression vector from which Ψ+ has been deleted. FIG. 24(c) shows the results obtained from VLPs prepared using the sgRNA expression vector having Ψ+.

As a result, it was revealed that the deletion of Ψ+ from the sgRNA expression vector reduces the VLP-mediated sgRNA delivery efficiency. This result indicates that the packaging signal is important for increasing the sgRNA encapsulation efficiency.

Experimental Example 14

(Examination on Copy Number of sgRNA in sgRNA Expression Vector)

In a vector expressing sgRNA interposed between ribozymes (hereinafter, called "RGR" in some cases) under the control of the EF1α promoter, the number of copies of sgRNA cassette was increased from 1 to 4, and the genome editing efficiency was examined.

Figure 25:
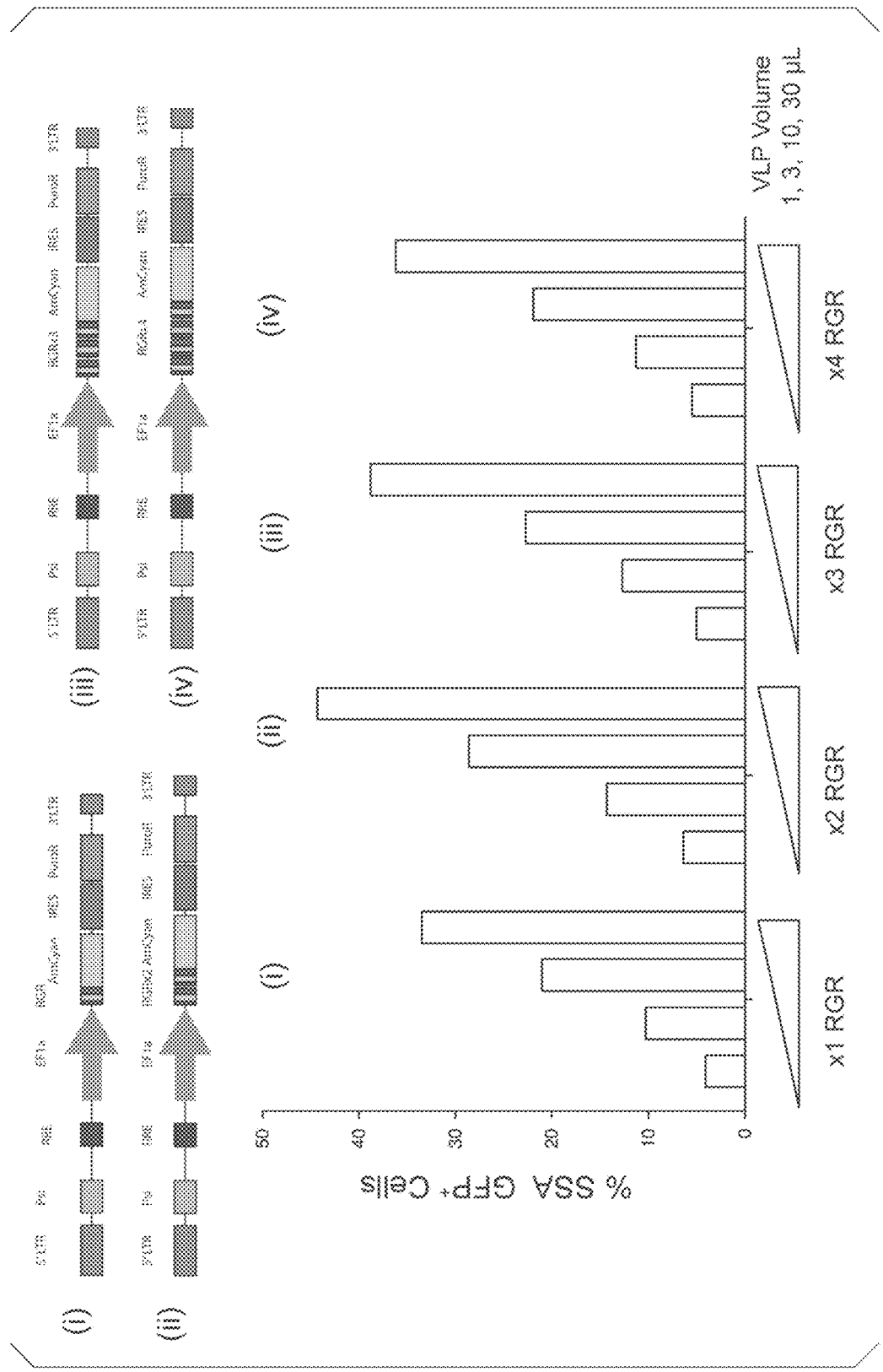
FIG. 25 is a graph showing the results of flow cytometry in Experimental Example 14.

Specifically, each of the VLPs was introduced into HEK293T EGxxFP reporter cells, and after 3 days, the proportion of GFP-positive cells was analyzed with a flow cytometer. FIG. 25 is graphs showing the results of flow cytometry. In FIG. 25, (i) is a schematic view showing the structure of an sgRNA expression vector having 1 copy of sgRNA cassette under the control of the EF1α promoter, (ii) is a schematic view showing the structure of an sgRNA expression vector having 2 copies of sgRNA cassette under the control of the EF1α promoter, (iii) is a schematic view showing the structure of an sgRNA expression vector having 3 copies of sgRNA cassette under the control of the EF1α promoter, and (iv) is a schematic view showing the structure of an sgRNA expression vector having 4 copies of sgRNA cassette under the control of the EF1α promoter.

As a result, it was revealed that even in a case where the copy number of sgRNA in the sgRNA expression vector is increased up to 4 under the control of the EF1α promoter, VLPs can be produced, sgRNA can be delivered, and genome editing can be induced.

Then, in a vector expressing sgRNA interposed between ribozymes (hereinafter, called "RGR" in some cases) under the control of the LTR promoter, the number of copies of sgRNA cassette was increased from 1 to 4, and the genome editing efficiency was examined.

Figure 26:
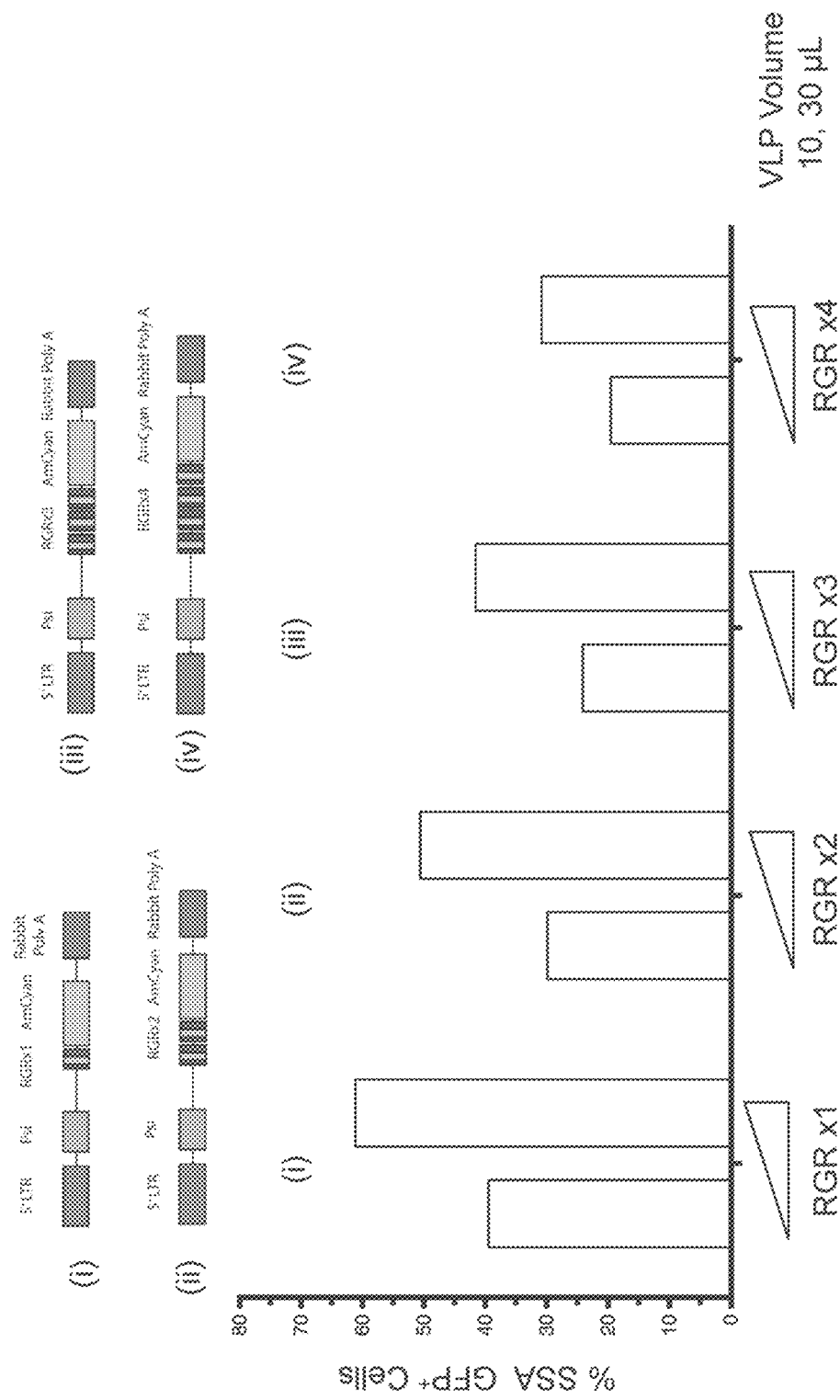
FIG. 26 is a graph showing the results of flow cytometry in Experimental Example 14.

Specifically, each of the VLPs was introduced into HEK293T EGxxFP reporter cells, and after 3 days, the proportion of GFP-positive cells was analyzed with a flow cytometer. FIG. 26 is graphs showing the results of flow cytometry. In FIG. 26, (i) is a schematic view showing the structure of an sgRNA expression vector having 1 copy of sgRNA cassette, (ii) is a schematic view showing the structure of an sgRNA expression vector having 2 copies of sgRNA cassette, (iii) is a schematic view showing the structure of an sgRNA expression vector having 3 copies of sgRNA cassette, and (iv) is a schematic view showing the structure of an sgRNA expression vector having 4 copies of sgRNA cassette.

As a result, it was revealed that even in a case where the copy number of sgRNA in the sgRNA expression vector is increased up to 4 under the control of the LTR promoter, VLPs can be produced, sgRNA can be delivered, and genome editing can be induced.

Experimental Example 15

(Simultaneous Delivery 1 of Cas9 Protein and sgRNA by VLP)

Figure 27:
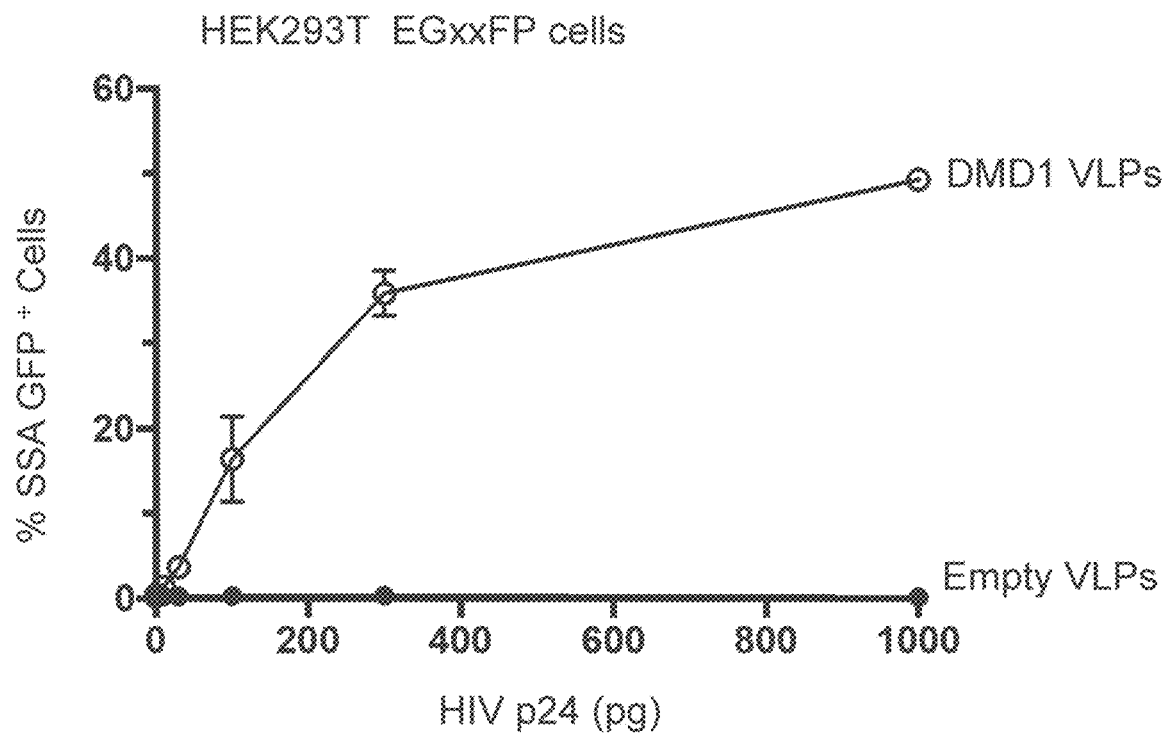
FIG. 27 is a graph showing the results of flow cytometry in Experimental Example 15.

VLPs encapsulating both the FRB-Cas9 protein and sgRNA (RGR) were prepared. Then, the prepared VLPs were introduced into HEK293T EGxxFP reporter cells, and after 3 days, the proportion of GFP-positive cells was analyzed with a flow cytometer. FIG. 27 is a graph showing the results of flow cytometry. As a result, genome editing activity was observed with extremely high efficiency depending on the dose of the VLPs.

Experimental Example 16

(Simultaneous Delivery 2 of Cas9 Protein and sgRNA by VLP)

Figure 28:
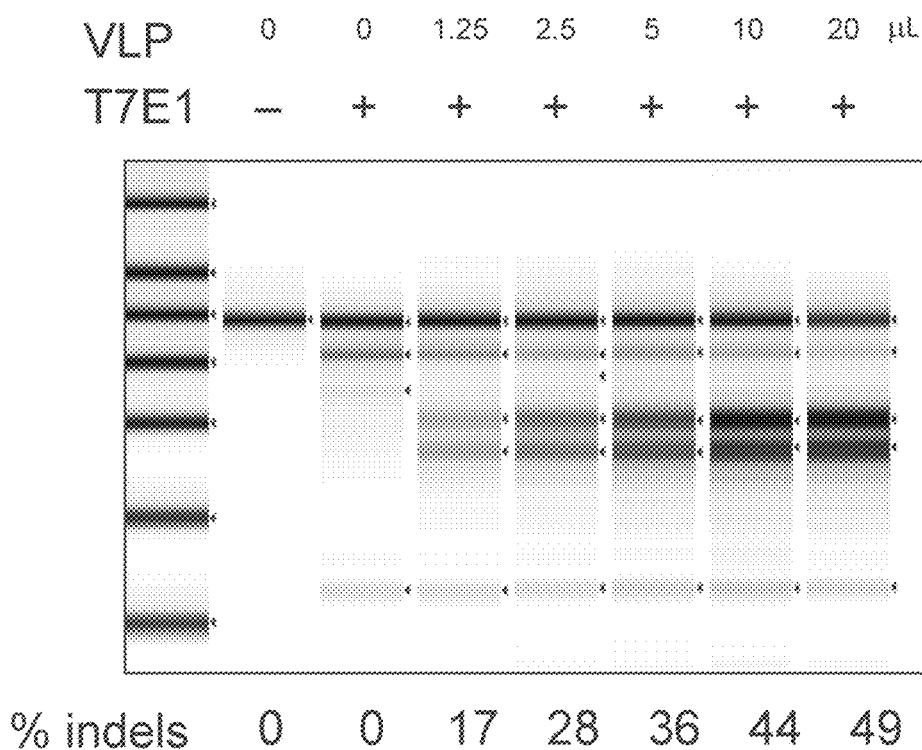
FIG. 28 is an image showing the results of the T7EI assay in Experimental Example 16.

VLPs encapsulating both the FRB-Cas9 protein and sgRNA (RGR) were prepared. Then, human iPS cells (404C2 strain) were prepared into which the prepared VLPs were introduced in amounts of 1.25 μL, 2.5 μL, 5 μL, 10 μL, and 20 μL. Subsequently, after 3 days, the genomic DNA was collected, the region of DMD gene which is the target base sequence was amplified by PCR, and the genome editing efficiency was examined by T7EI assay. FIG. 28 is an image showing the results of the T7EI assay. As a result, genome editing activity was observed with extremely high efficiency depending on the dose of the VLPs.

Experimental Example 17

(Comparison with Existing System)

A comparison was made between a system for delivering a Cas9 protein/sgRNA RNP complex by using exosome-like vesicles (Gesicle) (Gesicle system, Clontech Laboratories, Inc.) and a system using VLPs.

The Gesicle system is a system in which the Cas9 protein/sgRNA RNP complex and a red fluorescent protein Cherry Picker are associated with each other in Gesicle and efficiently encapsulated in Gesicle. The red fluorescent protein Cherry Picker is a fusion protein of a red fluorescent protein mCherry and a transferrin receptor membrane anchor domain.

Figure 29:
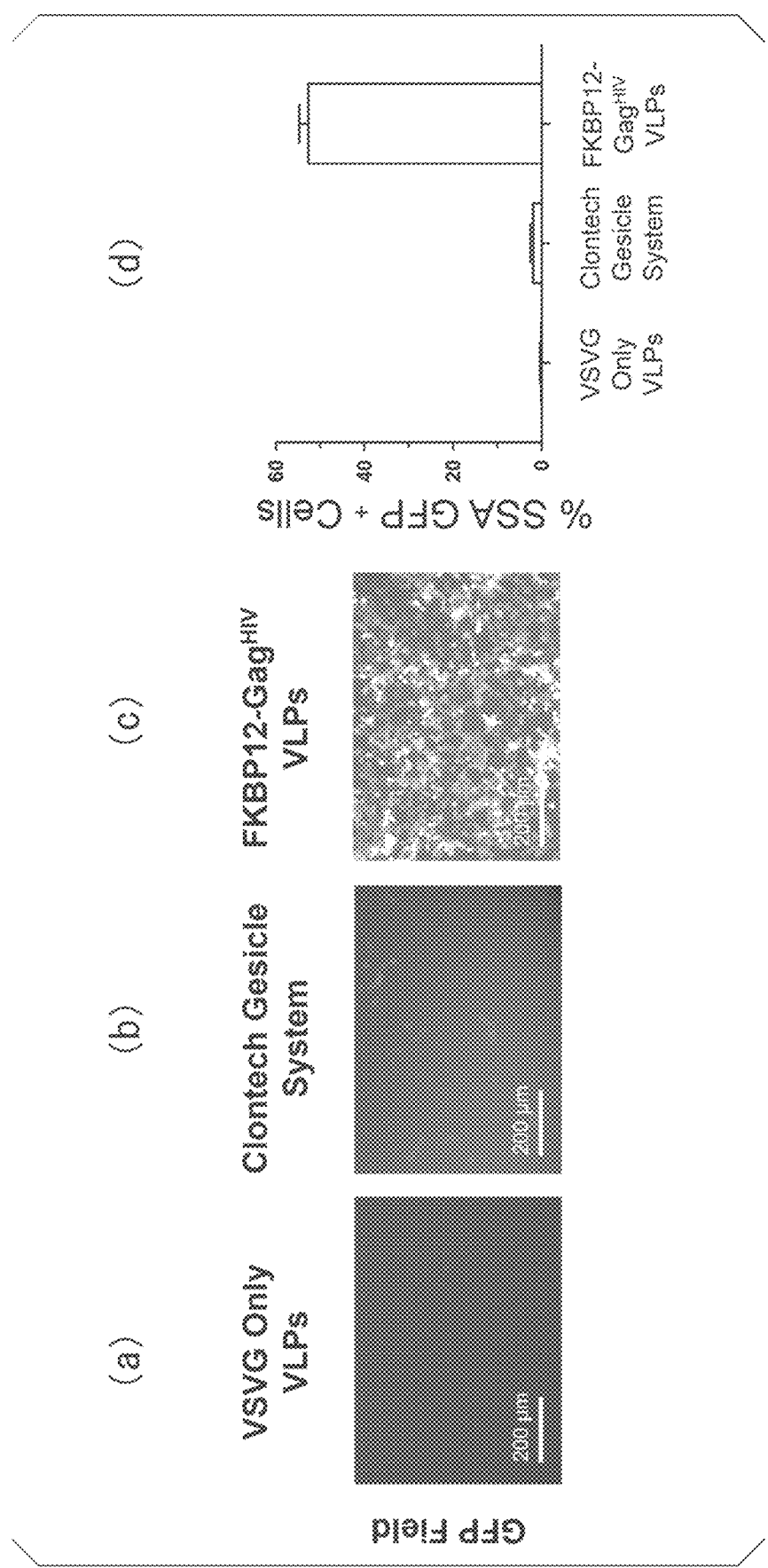
FIGS. 29(a) to 29(c) are fluorescence micrographs in Experimental Example 17.

In the present experimental example, first, VLPs were prepared using only VSV-G. Then, VLPs in which a Cas9 protein and sgRNA were encapsulated by means of free diffusion (represented by "VSVG Only VLP" in FIG. 29), Gesicle system (Clontech Laboratories, Inc. represented by "Clontech Gesicle System" in FIG. 29), and FKBP12-Gag$^{HIV}$ VLPs encapsulating sgRNA expressed from an sgRNA expression vector having an FRB-Cas9 protein and Ψ+(represented by "FKBP12-Gag$^{HIV}$ VLP" in FIG. 29) were prepared.

Thereafter, HEK293T EGxxFP reporter cells (2.5×10$^4$ cells) were inoculated with 5 μL of each of the VLPs or Gesicle, and after 72 hours, the cells were analyzed by fluorescence microscopy and flow cytometry.

FIGS. 29(a) to 29(c) are fluorescence micrographs showing the fluorescence of GFP observed. FIG. 29(d) is a graph showing the results of flow cytometry. In FIG. 29(d), the ordinate shows the proportion of GFP-positive cells. As a result, it was revealed that FKBP12-Gag$^{HIV}$ VLPs demonstrate markedly higher genome editing efficiency compared to other VLPs or Gesicle.

Experimental Example 18

(Simultaneous Delivery 3 of Cas9 Protein and sgRNA by VLP)

The Cas9 protein and sgRNA were simultaneously delivered by various VLPs, and the genome editing efficiency was examined.

Figure 30:
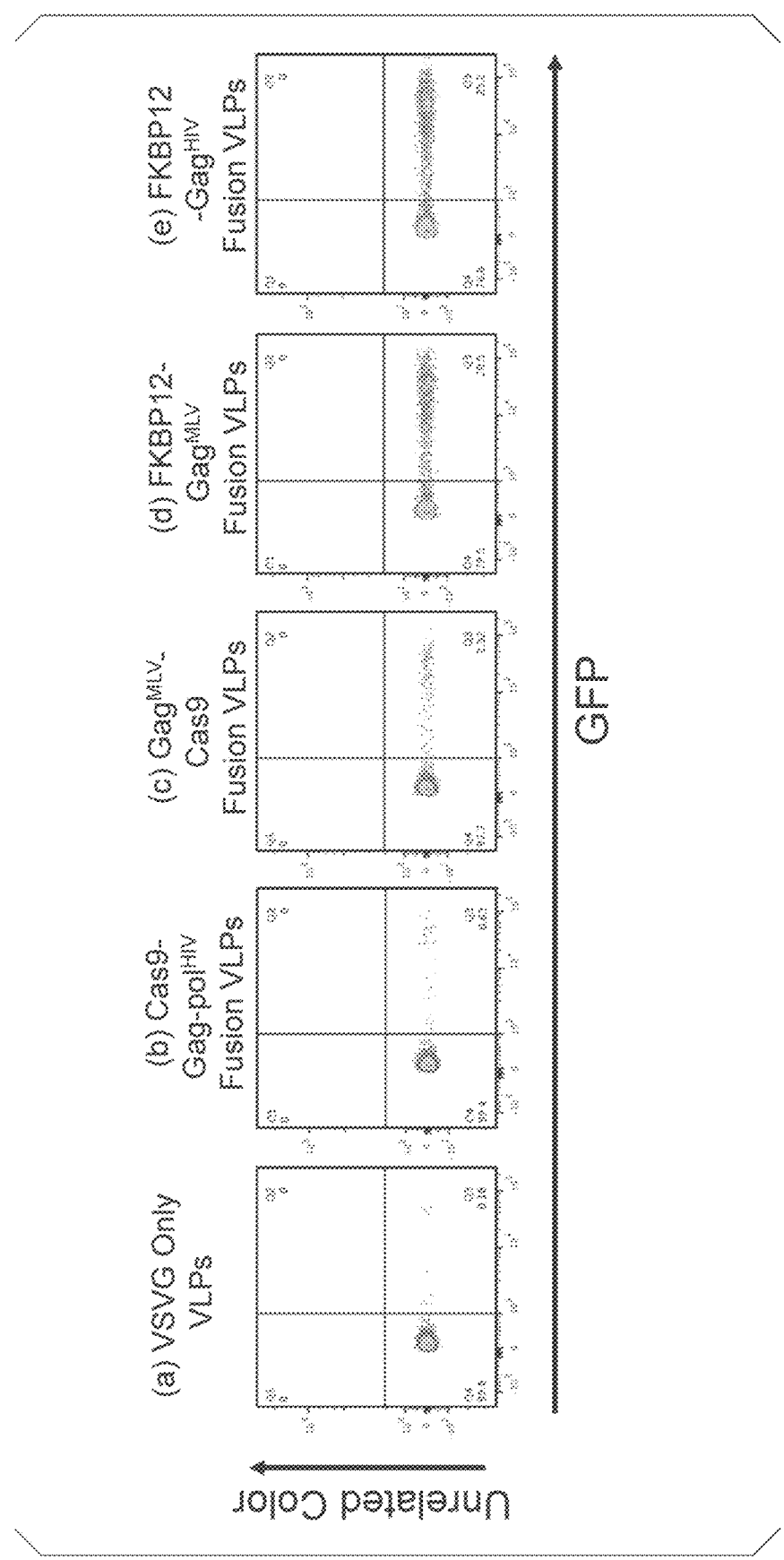
FIGS. 30(a) to 30(e) are graphs showing the results of flow cytometry in Experimental Example 18.

Specifically, first, the following VLPs (a) to (e) were prepared. (a) VLP made only of VSV-G and encapsulating a Cas9 protein and sgRNA by means of free diffusion (represented by "VSVG Only VLP" in FIG. 30). (b) VLP encapsulating Cas9 protein and Gag-$^{MLV}$ which is directly fused with the C-terminal of the Cas9 protein (represented by "Cas9-Gag-Pol$^{HIV}$ Fusion VLP" in FIG. 30). Gag-Pol$^{HIV}$ was added to accelerate the formation of VLP. (c) VLP encapsulating Cas9 protein and Gag$^{MLV}$ which is directly fused with the N-terminal of the Cas9 protein (represented by "Gag$^{MLV}$-Cas9 Fusion VLP" in FIG. 30). Gag-Pol$^{MLV}$ was added to accelerate the formation of VLP. (d) VLP encapsulating Cas9 by means of AP21967-mediated dimerization by the fusion of Cas9 with FRB and the fusion of Gag$^{MV}$ with FKBP12 (represented by "FKBP12-Gag$^{HIV}$ Fusion VLP" in FIG. 30). (e) VLP encapsulating Cas9 by means of AP21967-mediated dimerization by the fusion of Cas9 with FRB and the fusion of Gag$^{HIV}$ with FKBP12 (represented by "FKBP12-Gag$^{HIV}$ Fusion VLP" in FIG. 30).

Figure 31:
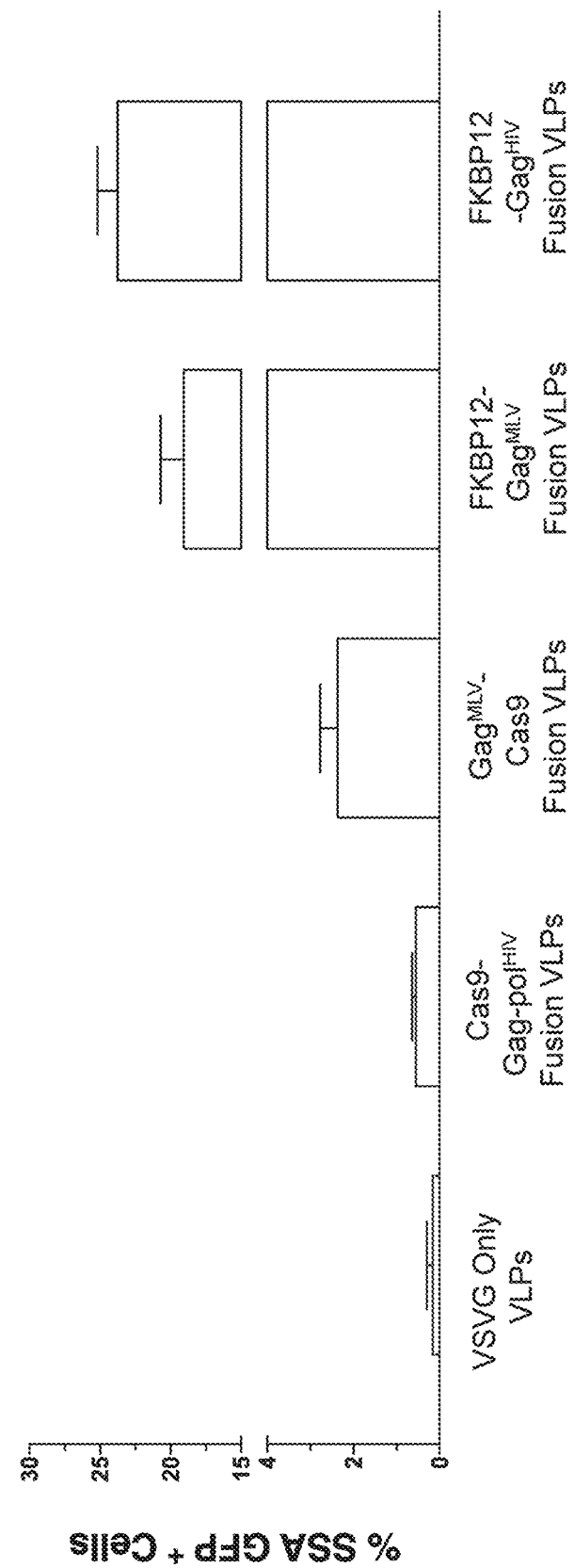
FIG. 31 is a graph numerically expressing the results shown in FIGS. 30(a) to 30(e).

Then, each of the prepared VLPs was introduced into HEK293T EGxxFP reporter cells, and after 3 days, the proportion of GFP-positive cells was analyzed with a flow cytometer. FIGS. 30(a) to 30(c) are graphs showing the results of flow cytometry. FIGS. 30(a) to 30(e) show the results of introducing the aforementioned VLPs (a) to (e) into the cells respectively. FIG. 31 is a graph numerically expressing the results shown in FIGS. 30(a) to 30(e). In FIG. 31, the ordinate shows the proportion of GFP-positive cells. As a result, extremely efficient genome editing activity was observed in FKBP12-Gag$^{HIV}$ Fusion VLP and FKBP12-Gag$^{HIV}$ Fusion VLP.

Experimental Example 19

(Examination 1 on Delivery of 2 Kinds of sgRNAs by VLP)

Figure 32:
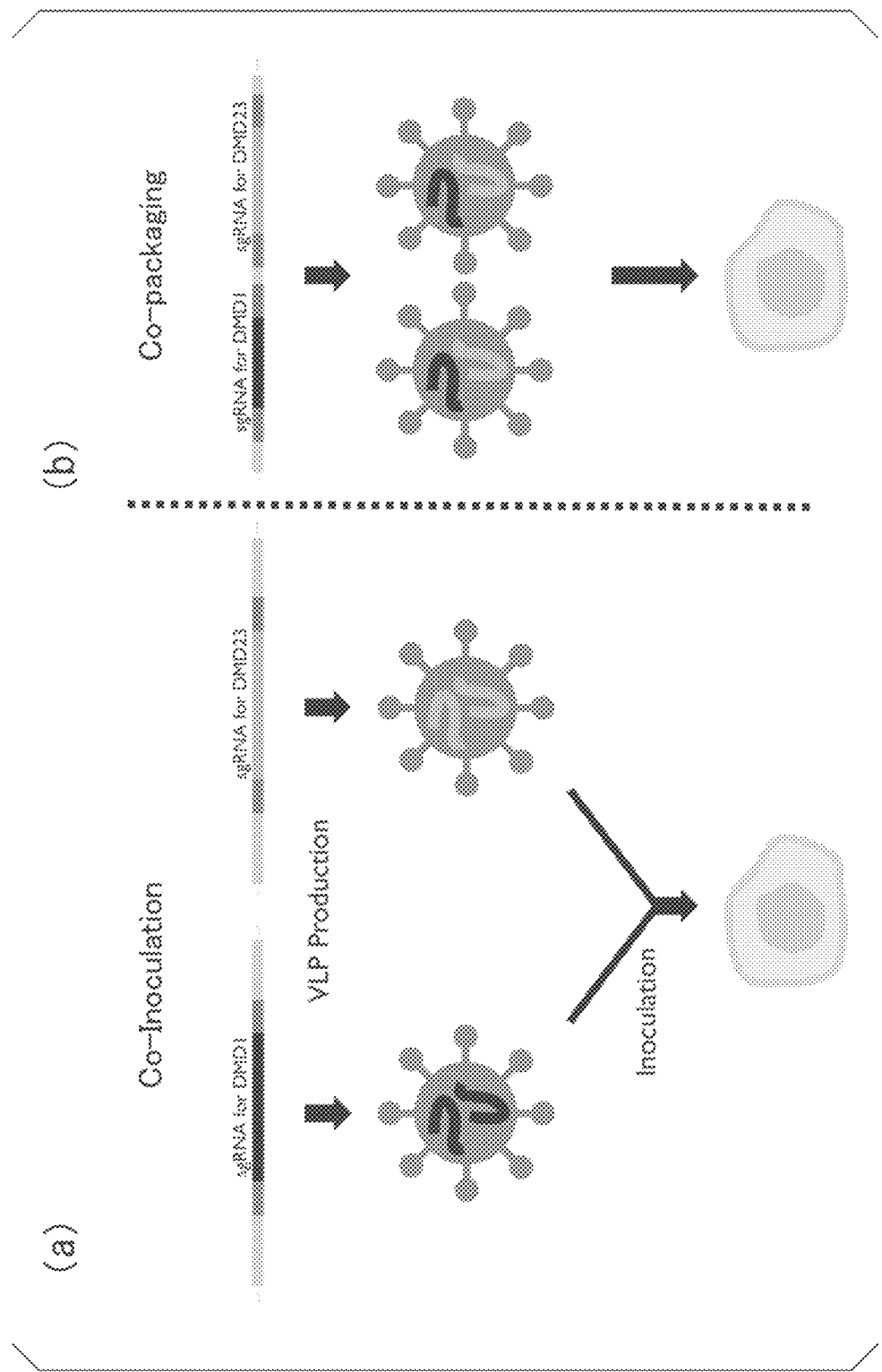
FIGS. 32(a) and 32(b) are schematic views illustrating a method of delivering two kinds of sgRNAs.

In order to deliver 2 kinds of sgRNAs into cells by VLPs, a method of co-introducing 2 kinds of VLPs encapsulating different sgRNAs and a method of introducing 1 kind of VLP encapsulating 2 kinds of sgRNAs may be considered. FIGS. 32(a) and 32(b) are schematic views illustrating these methods. FIG. 32(a) is a schematic view illustrating the method of co-introducing 2 kinds of VLPs encapsulating different sgRNAs. FIG. 32(b) is a schematic view illustrating the method of introducing 1 kind of VLP encapsulating 2 kinds of sgRNAs. In the present experimental example, the delivery of 2 kinds of sgRNAs into cells by these two methods was examined.

First, 2 kinds of VLPs, VLP encapsulating Cas9 and sgRNA DMD #1 (the target sequence is shown in SEQ ID NO: 15) targeting the 5' side (near the splicing acceptor) of exon 45 of the human DMD gene (hereinafter, called "DMD1 VLP" in some cases) and VLP encapsulating Cas9 and sgRNA DMD #23 (the target sequence is shown in SEQ ID NO: 24) targeting the 3' side (near the splicing donor) (hereinafter, called "DMD23 VLP" in some cases), were prepared.

Subsequently, 10 μL of each of these VLPs or 10 μL of a mixture of these VLPs was introduced into 4 kinds of 2.5×10$^4$ target iPS cells seeded on a 12-well plate. As the target iPS cells, a 404C2 strain and a 1383D2 strain which are iPS cell strains derived from healthy individuals, iPS cells derived from a patient with DMD caused by the deletion of exon 44 (hereinafter, called "ΔEx44 iPS Cells" in some cases), and iPS cells derived from a patient with DMD caused by the deletion of exons 46 and 47 (hereinafter, called "ΔEx46~47 iPS Cells" in some cases) were used. Then, genomic DNA was extracted from the respective iPS cells, and the genome editing efficiency at each target site was measured by T7EI assay.

Figure 33:
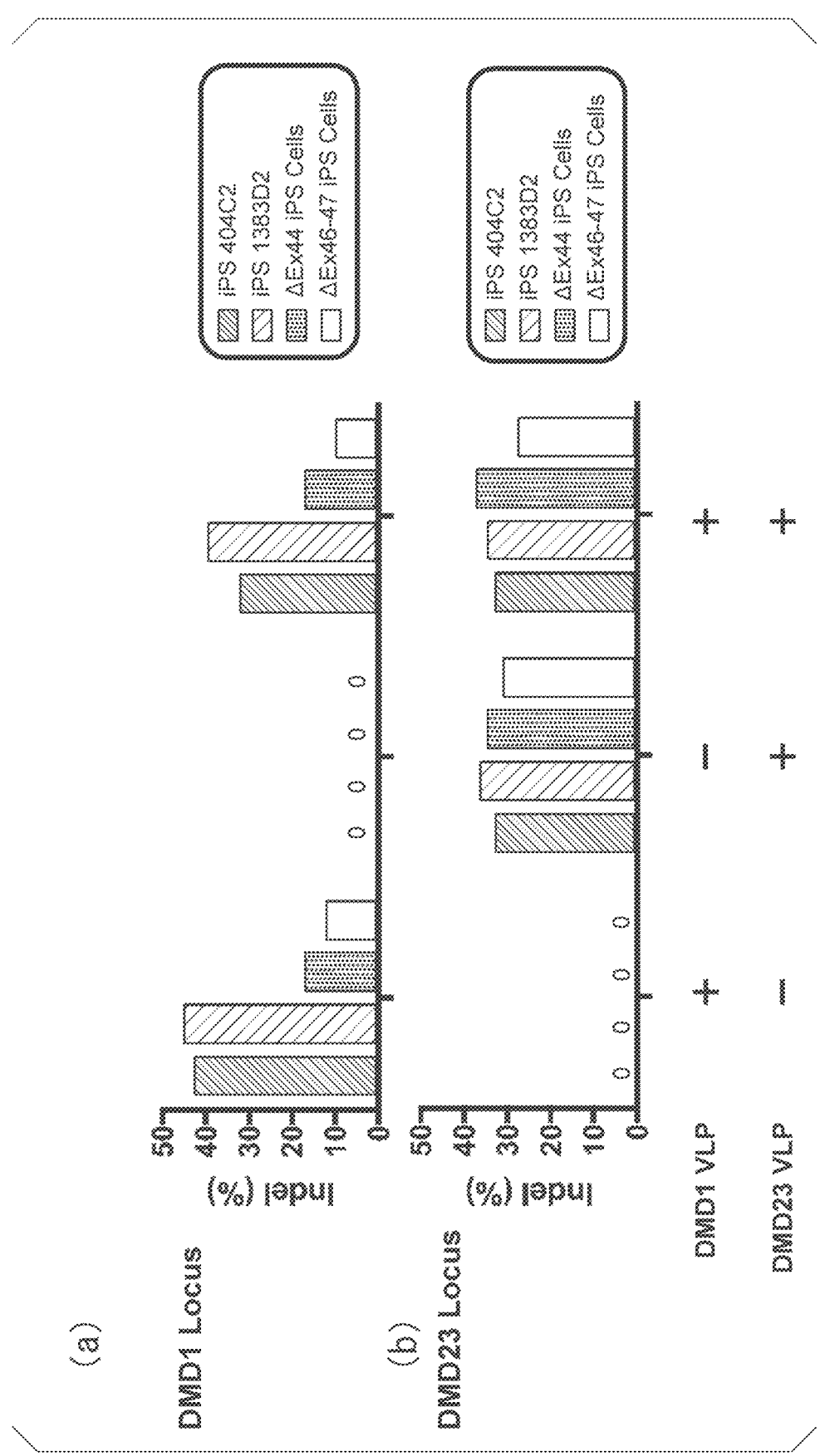
FIGS. 33(a) and 33(b) are graphs showing the results of the T7EI assay in Experimental Example 19.

FIGS. 33(a) and 33(b) are graphs showing the results of the T7EI assay. FIG. 33(a) is a graph showing the genome editing efficiency of sgRNA DMD #1 (the target sequence is shown in SEQ ID NO: 15) at the target site. FIG. 33(b) is a graph showing the genome editing efficiency of sgRNA DMD #23 (the target sequence is shown in SEQ ID NO: 24) at the target site.

As a result, it was confirmed that although the genome editing efficiency varies with the iPS cell strains, the co-introduction of VLP encapsulating sgRNA DMD #1 (the target sequence is shown in SEQ ID NO: 15) and VLP encapsulating sgRNA DMD #23 (the target sequence is shown in SEQ ID NO: 24) also brings about genome editing efficiency equivalent to the genome editing efficiency obtained by the introduction of 1 kind of VLP.

Experimental Example 20

(Examination 2 on Delivery of 2 Kinds of sgRNAs by VLP)

VLP encapsulating Cas9 and sgRNA DMD #1 (the target sequence is shown in SEQ ID NO: 15) and VLP encapsulating Cas9 and sgRNA DMD #23 (the target sequence is shown in SEQ ID NO: 24) were prepared in the same manner as in Experimental Example 19. Each of these VLPs (10 μL) or 10 μL of a mixture of these VLPs was introduced into 2 kinds of 2.5×10$^4$ target iPS cells seeded on 12-well plates. As the target iPS cells, a 404C2 strain and a 1383D2 strain which are iPS cell strains derived from healthy individuals were used. Subsequently, genomic DNA was extracted from the respective iPS cells, a region consisting of 300 bases including the target sites of both of sgRNAs was amplified by PCR, and analysis was performed using an electrophoresis system (2200 TapeStation, Agilent Technologies, Inc.).

Figure 34:
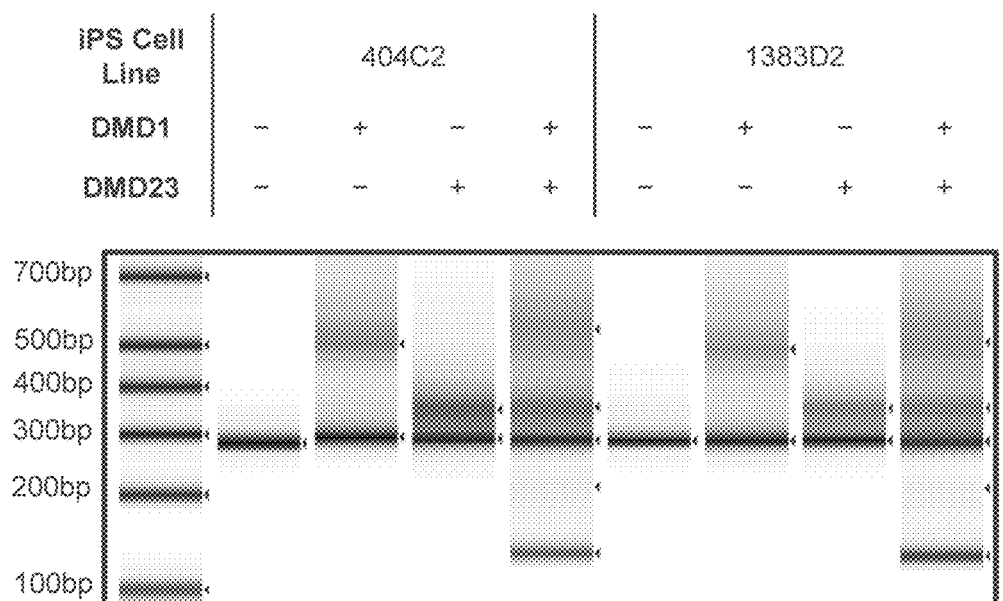
FIG. 34 is an image showing the results of electrophoresis in Experimental Example 20.

FIG. 34 is an image showing the results of electrophoresis. As a result, it was confirmed that the co-introduction of 2 kinds of VLPs can induce large deletion of about 150 bases constituting a genomic sequence cleaved from between the target sites of the two sgRNAs.

For example, in a case where a normal dystrophin protein cannot be expressed due to an out-of-frame mutation, this method can be used to induce exon skipping by deleting one specific exon or a plurality of specific exons so that the protein reading frame is restored.

Experimental Example 21

(Examination 3 on Delivery of 2 Kinds of sgRNAs by VLP)

sgRNA DMD #1 (the target sequence is shown in SEQ ID NO: 15) and sgRNA DMD #23 (the target sequence is shown in SEQ ID NO: 24) were loaded in tandem on one expression vector. By using this vector, 1 kind of VLP encapsulating Cas9 and 2 kinds of sgRNAs at the same time (hereinafter, called "Tandem 1/23" in some cases) was prepared.

Then, the prepared VLP was introduced into iPS cells derived from patients with DMD. As iPS cells derived from patients with DMD, iPS cells derived from a patient with DMD caused by the deletion of exon 44 (hereinafter, called "ΔEx44 iPS Cells" in some cases) and iPS cells derived from a patient with DMD caused by the deletion of exons 46 and 47 (hereinafter, called "ΔEx46-47 iPS Cells" in some cases) were used.

For comparison, cells were prepared into which a mixture of VLP encapsulating Cas9 and sgRNA DMD #1 (the target sequence is shown in SEQ ID NO: 15) and VLP encapsulating Cas9 and sgRNA DMD #23 (the target sequence is shown in SEQ ID NO: 24) prepared in the same manner as in Experimental Example 19 was introduced.

Subsequently, genomic DNA was extracted from the respective iPS cells, a region consisting of 300 bases including the target sites of both of the sgRNAs was amplified by PCR, and analysis was performed using an electrophoresis system (2200 TapeStation, Agilent Technologies, Inc.).

Figure 35:
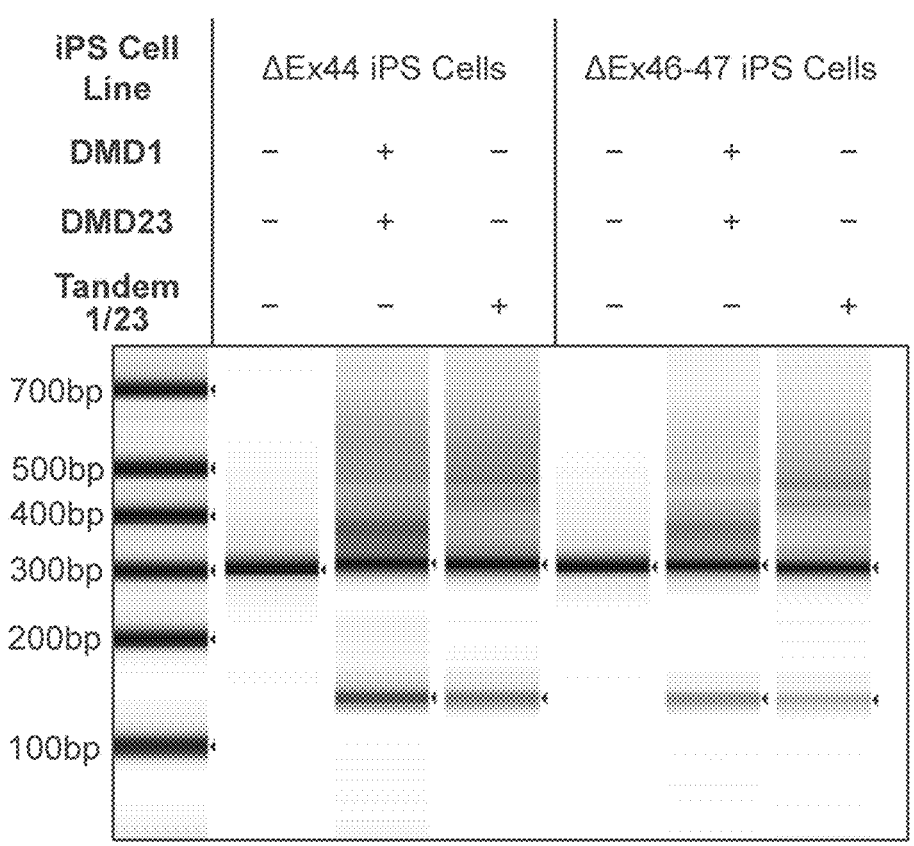
FIG. 35 is an image showing the results of electrophoresis in Experimental Example 21.

FIG. 35 is an image showing the results of electrophoresis. As a result, it was confirmed that even in a case where VLP encapsulating 2 kinds of sgRNAs at the same time is used, it is possible to induce large deletion of about 150 bases constituting a genomic sequence cleaved from between the target sites of the two sgRNAs.

Experimental Example 22

(Comparison 1 Between Method Using VLP and Other Methods)

Cas9 and sgRNA were introduced into HEK293T EGxxFP cells by a method using VLP and other methods. After 3 days, the fluorescence of the EGxxFP reporter construct of each cell sample was analyzed using a flow cytometer.

Figure 36:
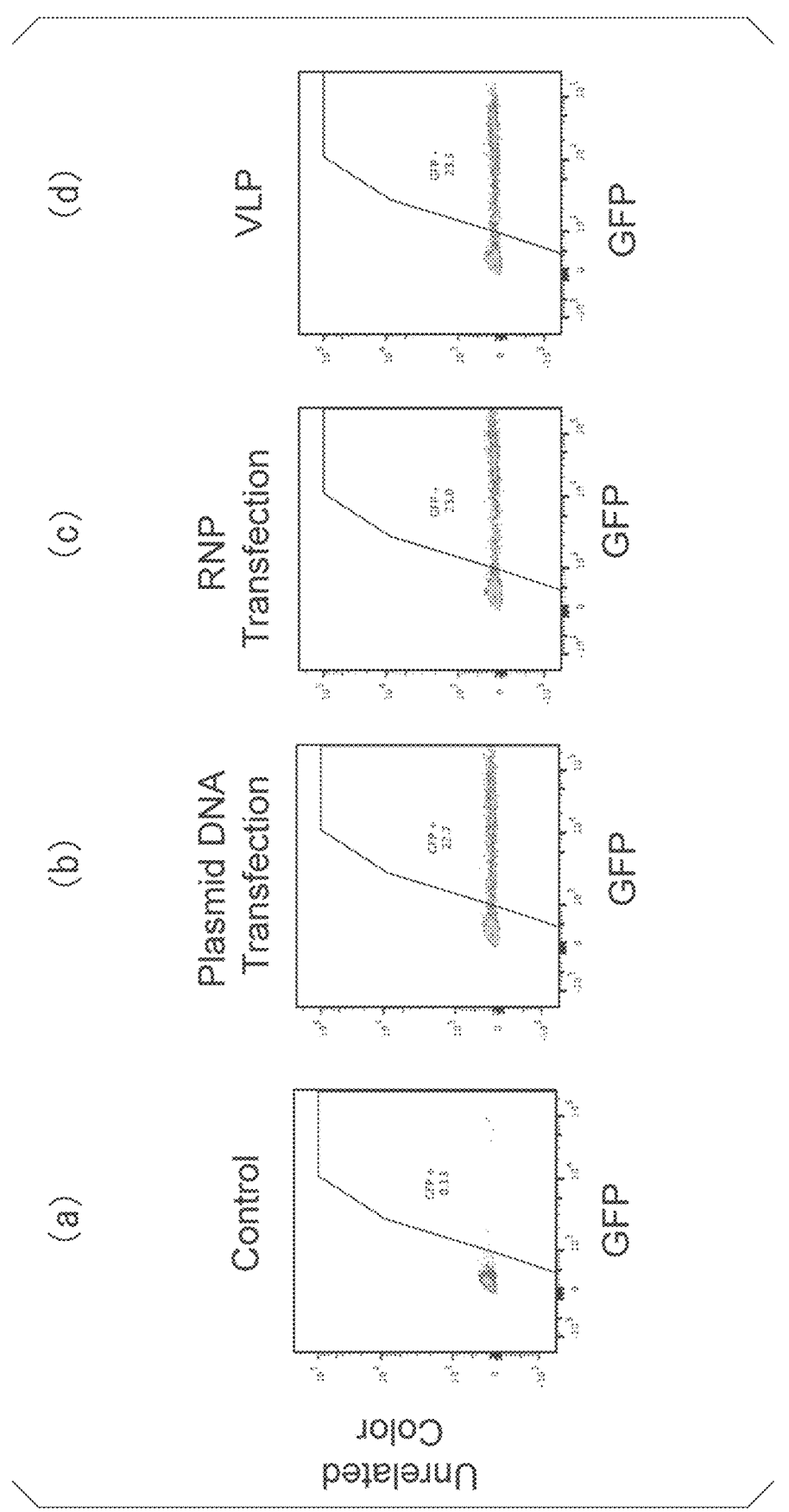
FIGS. 36(a) to 36(d) are graphs showing the results of flow cytometry in Experimental Example 22.

Specifically, Cas9 and sgRNA were introduced by the following methods (a) to (d). (a) As a control, cells into which none of Cas9 and sgRNA was introduced were prepared. (b) A Cas9 expression plasmid (0.5 µg) and 0.5 µg of an sgRNA expression plasmid were introduced into HEK293T EGxxFP cells by using a lipofection reagent (FuGENE 6 or FuGENE HD, Promega Corporation) (represented by "Plasmid DNA Transfection" in FIG. 36). (c) Purified Cas9 protein (1 µg) and sgRNA (0.25 µg) were mixed together to form a complex (ribonucleoprotein, RNP), and the complex was introduced into HEK293T EGxxFP cells by using a lipofection reagent (CRISPR-MAX, Thermo Fisher Scientific Inc.) (represented by "RNP transfection" in FIG. 36). (d) SpCas9 and sgRNA were introduced into HEK293T EGxxFP cells by using VLP (50 µL) (represented by "VLP" in FIG. 36).

FIGS. 36(a) to 36(d) are graphs showing the results of flow cytometry. FIGS. 36(a) to 36(d) are the results of analyzing the cells of (a) to (d) described above, respectively. Usually, genes can be introduced into HEK293T cells with high efficiency. Therefore, in these cells, plasmid DNA introduction or RNP introduction brings about sufficiently high genome editing efficiency. By the present experimental example, it was revealed that VLP exhibits genome editing activity equal to or higher than the genome editing activity obtained by such conventional methods.

Experimental Example 23

(Comparison 2 Between Method Using VLP and Other Methods)

By a method using VLP and other methods, Cas9 and sgRNA were introduced into 404C2 cells which are a human iPS cell strain. Then, after 2 days, by T7EI assay, the genome editing efficiency in a region of the 5' side (near the splicing acceptor) of exon 45 of the human DMD gene, which is the target site of sgRNA DMD #1 (the target sequence is shown in SEQ ID NO: 15), was examined.

Specifically, Cas9 and sgRNA were introduced by the following methods (a) to (f). (a) None of Cas9 and sgRNA was introduced into the cells, and T7 endonuclease I (T7EI) was not added during the T7EI assay (represented by "No Transfection, −T7EI" in FIG. 37). (b) None of Cas9 and sgRNA was introduced into the cells, but T7EI was added during the T7EI assay (represented by "No Transfection, +T7EI" in FIG. 37). (c) A Cas9 expression plasmid (0.5 µg) and 0.5 µg of an sgRNA expression plasmid were introduced into 404C2 cells by using a lipofection reagent (FuGENE 6 or FuGENE HD, Promega Corporation) (represented by "DNA Transfection, +T7EI" in FIG. 37). (d) Purified Cas9 protein (1 µg) and sgRNA (0.125 µg) were mixed together to form a complex (ribonucleoprotein, RNP), and the complex was introduced into 404C2 cells by using a lipofection reagent (CRISPR-MAX, Thermo Fisher Scientific Inc.) (represented by "RNP Transfection, +T7EI" in FIG. 37). (e) SpCas9 and sgRNA DMD #1 (the target sequence is shown in SEQ ID NO: 15) were introduced into 404C2 cells by using VLP (80 µL) (represented by "DMD1 VLP, +T7EI" in FIG. 37). (f) SpCas9 and sgRNA DMD #23 (the target sequence is shown in SEQ ID NO: 24) were introduced into 404C2 cells by using VLP (80 µL) (represented by "DMD23 VLP, +T7EI" in FIG. 37).

Figure 37:
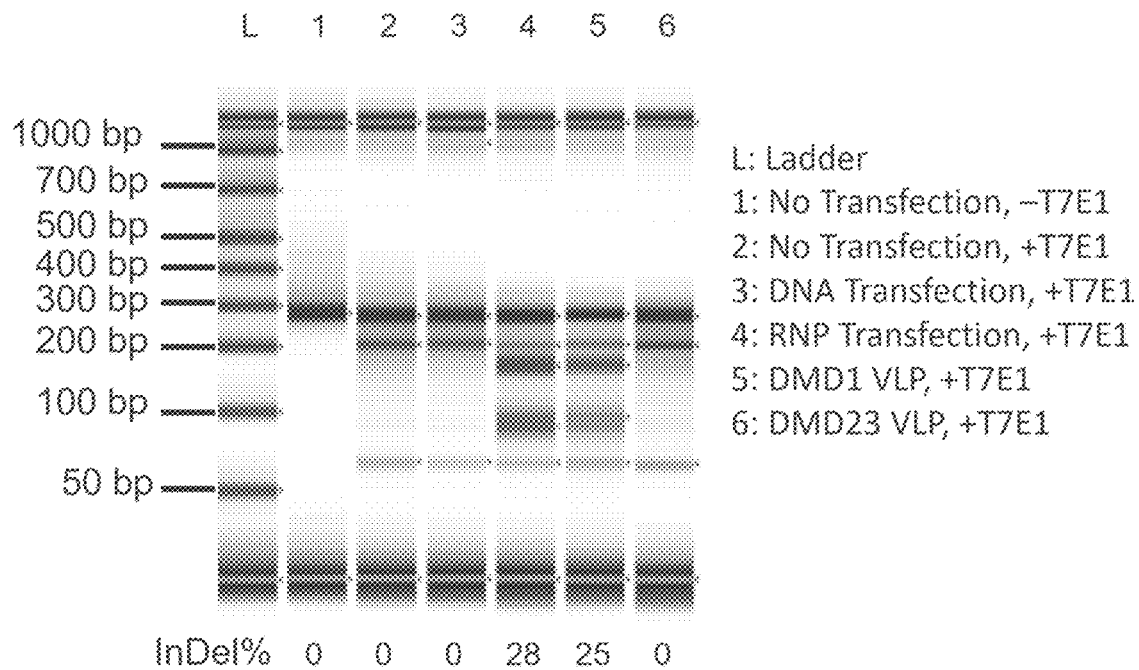
FIG. 37 is an image showing the results of electrophoresis in Experimental Example 23.

FIG. 37 is an image showing the results of electrophoresis. It is difficult to introduce plasmid DNA into human iPS cells by lipofection using FuGENE reagent, and RNP introduction can induce genome editing in these cells. By the present experimental example, it was revealed that VLP exhibits genome editing activity equivalent to the genome editing activity brought about by the RNP introduction.

Experimental Example 24

(Efficient Genome Editing 1 by Introduction of VLP into Muscle Cells)

An examination was performed on a method of inducing genome editing in a murine myoblast cell strain C2C12 by using VLP. Specifically, first, the murine myoblast cell strain C2C12 into which the EGxxFP reporter construct was introduced was seeded on a collagen I-coated 12-well plate at $2.5 \times 10^4$ cells/well.

Subsequently, the cells were inoculated with 0 µL, 1 µL, 3 µL, 10 µL, and 30 µL of VLPs encapsulating FRB-Cas9 and sgRNA DMD #1 (the target sequence is shown in SEQ ID NO: 15). Subsequently, after 3 days, the proportion of GFP-positive cells was analyzed with a flow cytometer.

Figure 38:
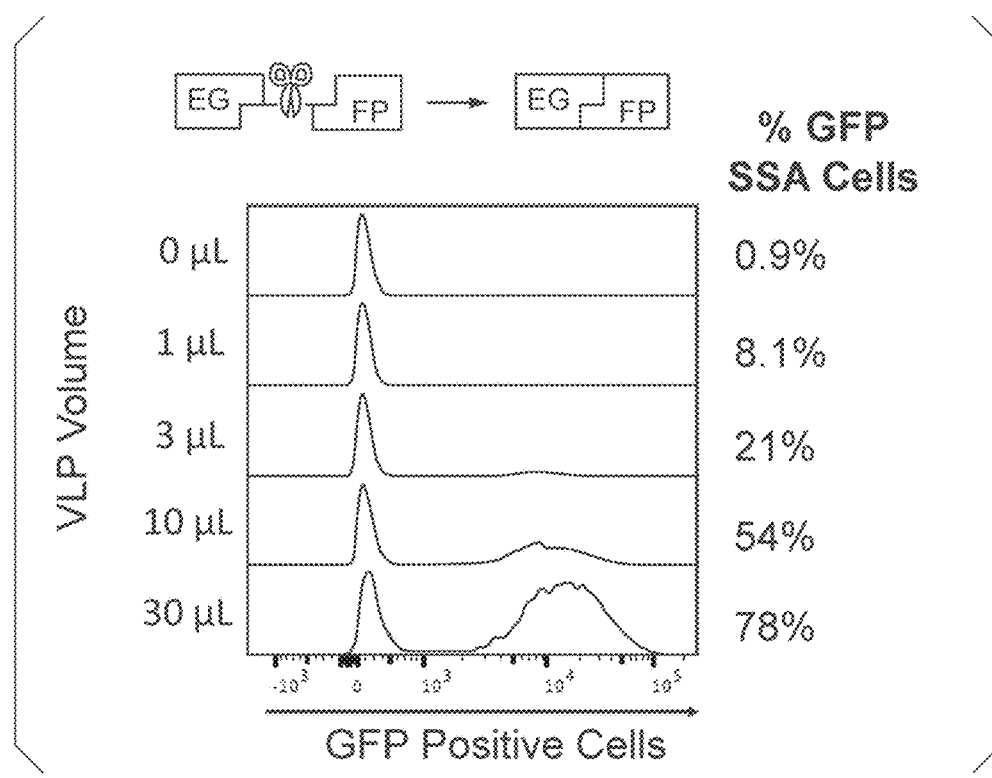
FIG. 38 is a graph showing the results of flow cytometry in Experimental Example 24.

FIG. 38 is a graph showing the results of flow cytometry. In FIG. 38, the ordinate shows the number of cells, and the abscissa shows the fluorescence intensity of GFP. The proportion of GFP-positive cells is shown on the right side of the graph. As a result, it was revealed that genome editing was induced with extremely high efficiency depending on the inoculation dose of VLP.

Experimental Example 25

(Efficient Genome Editing 2 by Introduction of VLP into Muscle Cells)

An examination was performed on a method of inducing a murine myoblast cell strain C2C12 to differentiate into muscle fibers and then inducing genome editing by using VLP. Specifically, first, the murine myoblast cell strain C2C12 into which the EGxxFP reporter construct was introduced was seeded on a collagen I-coated 12-well plate at $2.5 \times 10^4$ cells/well.

Then, the medium was replaced with a differentiation-inducing medium (DMEM, 5% horse serum, 100 mM sodium pyruvate, 100 mM 2 mercaptoethanol, penicillin, and streptomycin), and the cells were induced to differentiate into muscle fibers for 4 days.

Thereafter, the cells were inoculated with 20 µL of VLPs. The cells were inoculated with VLP encapsulating Cas9 and sgRNA DMD #1 (the target sequence is shown in SEQ ID NO: 15) (hereinafter, called "DMD1 VLP" in some cases) or with VLP encapsulating Cas9 and sgRNA DMD #23 (the target sequence is shown in SEQ ID NO: 24) (hereinafter, called "DMD23 VLP" in some cases). Subsequently, 4 days after inoculation, the fluorescence of the EGxxFP reporter construct was analyzed using a fluorescence microscope (Keyence Corporation) or flow cytometry.

Figure 39:
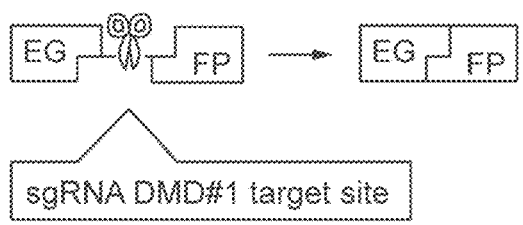
FIG. 39(a) is a schematic view illustrating the structure of an EGxxFP reporter construct used in Experimental Example 25.
FIG. 39(b) is photographs showing the results of fluorescence microscopy in Experimental Example 25.
FIG. 39(c) is a graph showing the results of flow cytometry in Experimental Example 25.
Figure 39:
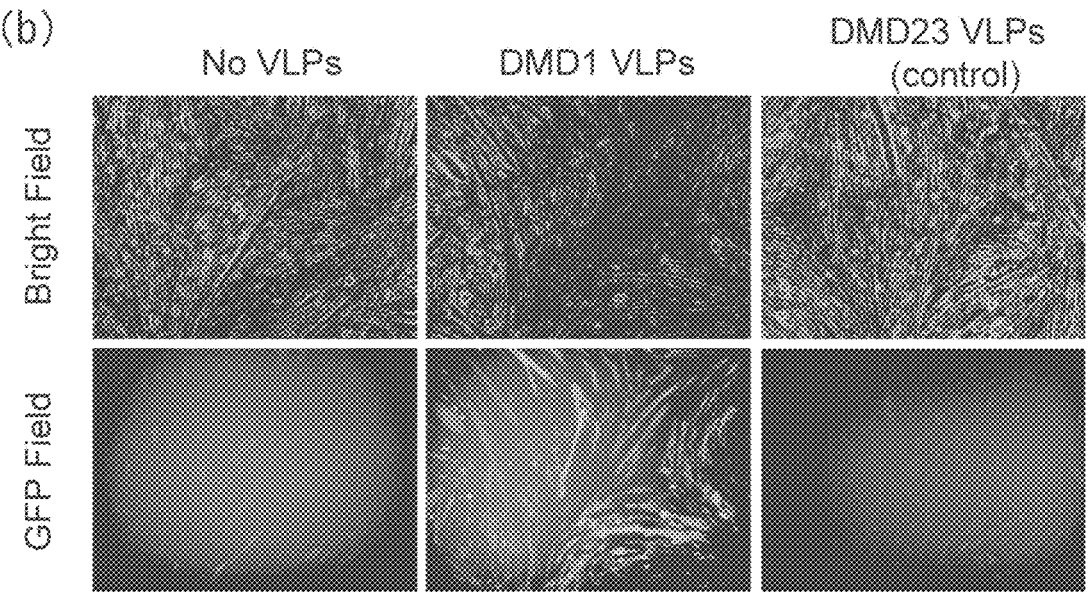
Figure 39:
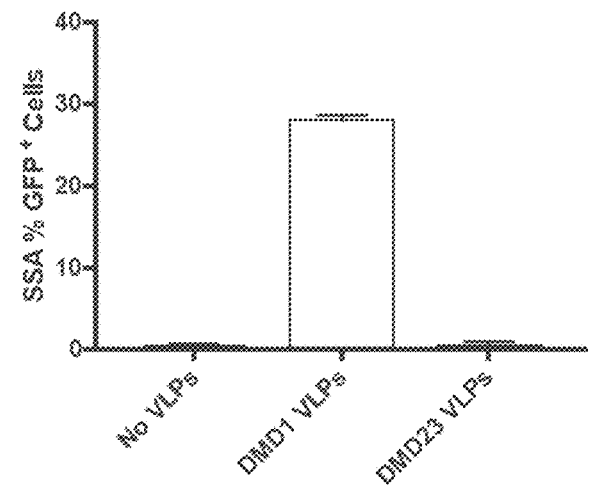

FIG. 39(a) is a schematic view illustrating the structure of the EGxxFP reporter construct used in the present experimental example. As shown in FIG. 39(a), the EGxxFP reporter construct has only the target sequence of sgRNA DMD #1 (the target sequence is shown in SEQ ID NO: 15) and does not have the target sequence of sgRNA DMD #23 (the target sequence is shown in SEQ ID NO: 24). Therefore, the cleavage of the EGxxFP reporter construct is induced only in a case where DMD1 VLP is inoculated.

FIG. 39(b) is photographs showing the results of fluorescence microscopy. In FIG. 39(b), "Bright Field" represents a bright field (phase contrast) observation image, and "GFP Field" represents a fluorescence detection image of GFP. As a result, it was revealed that only in a case where the DMD1 VLP is introduced into cells, genome editing is induced in the EGxxFP reporter construct, and the fluorescence of GFP is observed.

FIG. 39(c) is a graph showing the results of flow cytometry. In FIG. 39(c), the ordinate shows the proportion of GFP-positive cells. As a result, it was revealed that only in a case where the DMD1 VLP is introduced into cells, genome editing is induced in the EGxxFP reporter construct, and the fluorescence of GFP is observed.

Generally, after differentiation, cells stop growing. Therefore, it is difficult to introduce genes into the cells or induce genome editing in the cells. On the other hand, it was revealed that the use of VLP makes it possible to efficiently induce genome editing even in the differentiated cells.

Experimental Example 26

(Temporal Change in Genome Editing Activity by Introduction of VLP)

An examination was performed on the temporal change in the genome editing activity by the introduction of VLP. Specifically, first, 404C2 iPS cells were seeded at a cell density of $1.0 \times 10^5$ cells/24-well plate. Then, the cells were inoculated with VLPs encapsulating Cas9 and sgRNA. Subsequently, genomic DNA was collected over time, and genome editing efficiency was measured by T7EI assay.

Figure 40:
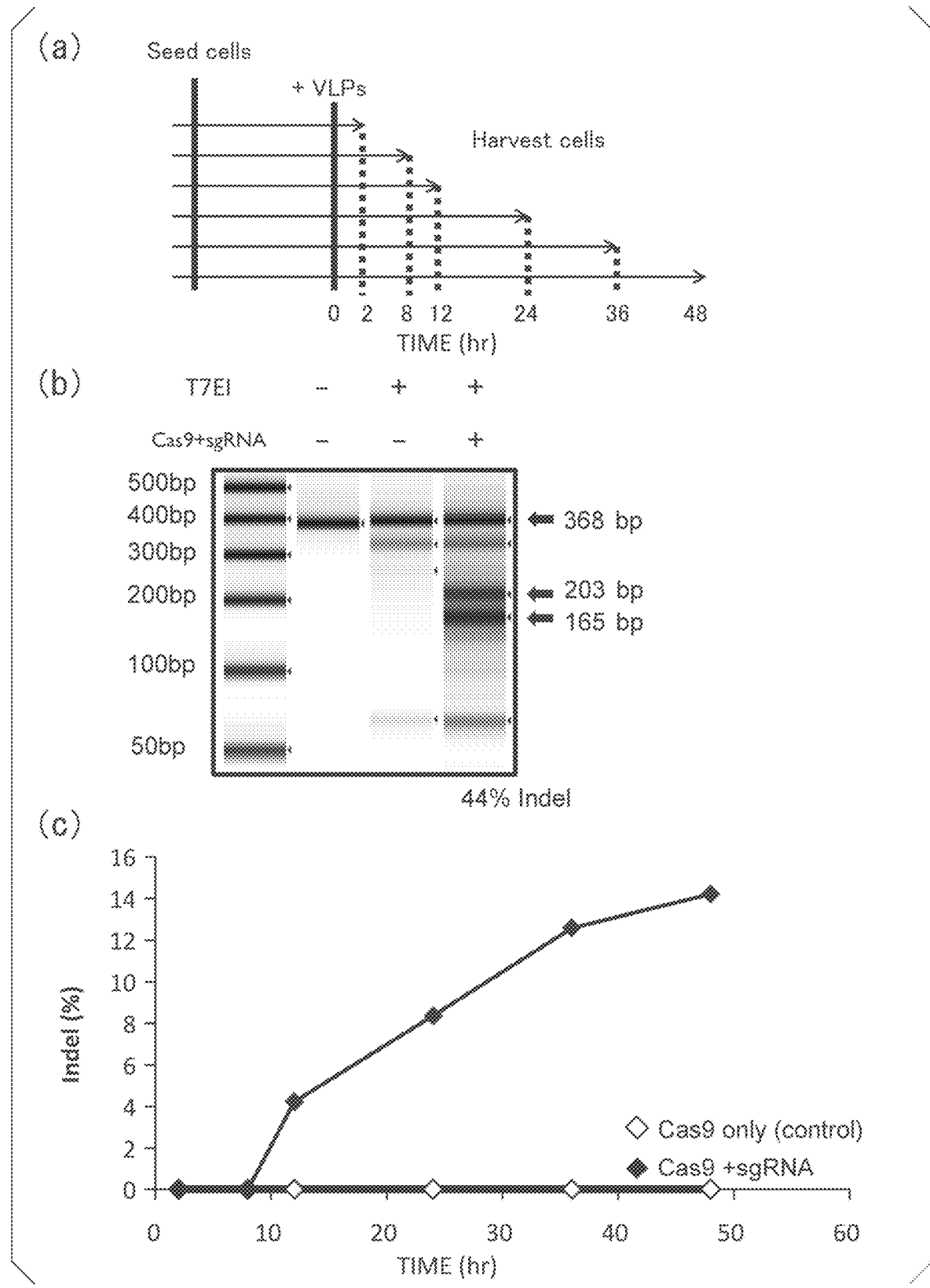
FIG. 40(a) is a view showing an experimental schedule of Experimental Example 26.
FIG. 40(b) is a typical image showing the results of the T7EI assay in Experimental Example 26.
FIG. 40(c) is a graph showing the temporal change in genome editing activity in Experimental Example 26.

FIG. 40(a) is a view showing an experiment schedule. FIG. 40(b) is a typical image showing the results of the T7EI assay. FIG. 40(c) is a graph showing the temporal change in genome editing activity. As a result, it was revealed that for 8 hours after the introduction of Cas9 and sgRNA by using VLP, no genome editing activity is exhibited. Furthermore, it was revealed that the genome editing activity gradually increases 12 hours after the introduction of VLP and then substantially reached a plateau 36 hours after the introduction of VLP.

Experimental Example 27

(Examination 1 on Safety of VLP System)

It has been reported that sgRNA (the target sequence is shown in SEQ ID NO: 25) targeting a VEGFA gene easily introduces a mutation into off-target sequences. Therefore, an examination was performed on the genome editing efficiency at a target site and an off-target site that is exhibited by the introduction of transiently expressed VLPs.

Figure 41:
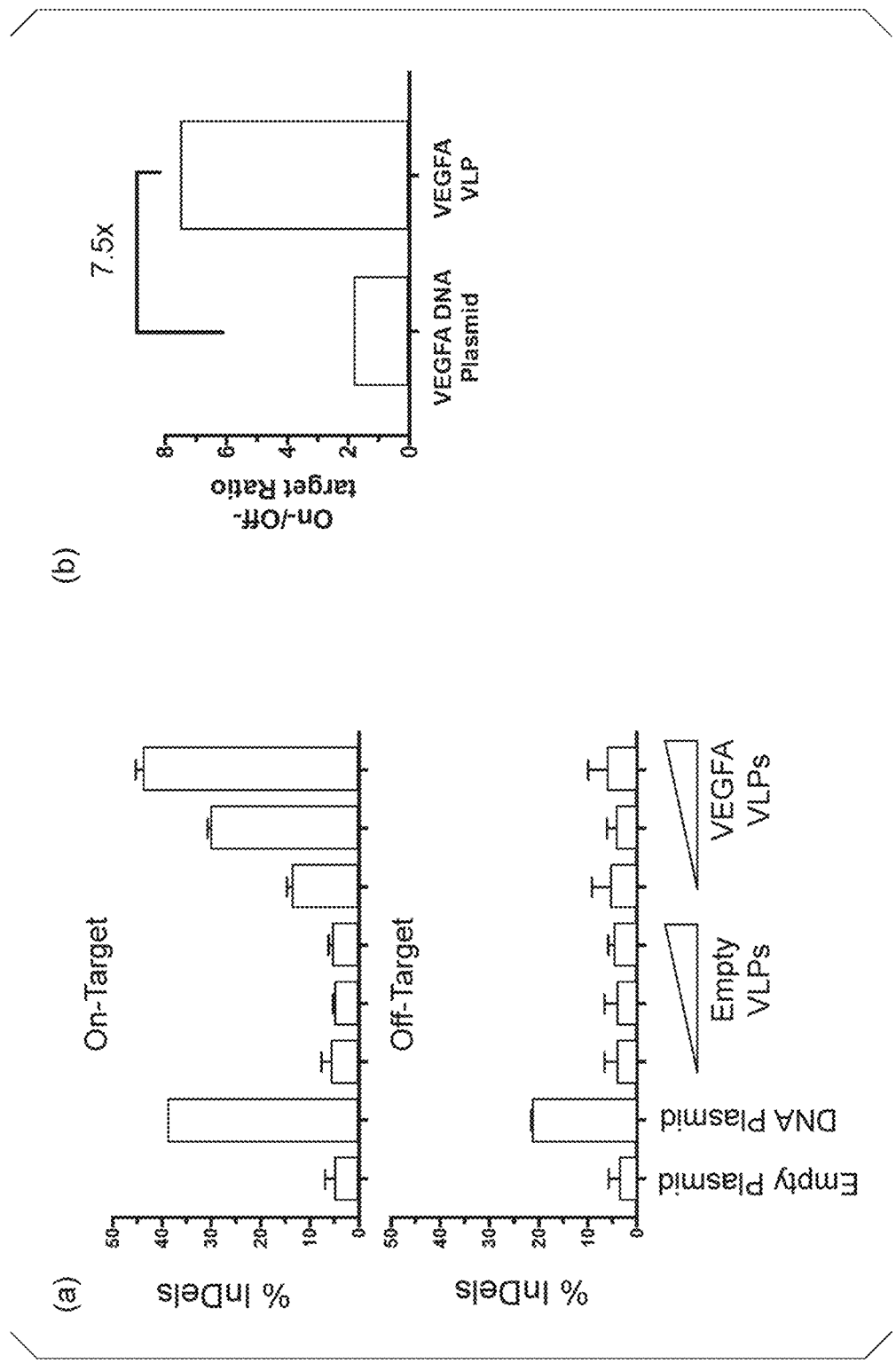
FIG. 41(a) is graphs showing the results of the T7EI assay in Experimental Example 27.
FIG. 41(b) is a graph showing the ratio of on-target cleavage to off-target cleavage in Experimental Example 27.

First, VLPs (represented by "VEGFA VLP" in FIG. 41) encapsulating Cas9 and sgRNA (the target sequence is shown in SEQ ID NO: 25) targeting a VEGFA gene were prepared. Then, $5 \times 10^4$ HEK293T cells were inoculated with 100, 200, and 300 ng (equivalent to the amount of p24) of the prepared VLPs.

For comparison, cells into which plasmid DNA expressing Cas9 and sgRNA was introduced were also prepared. Then, after 3 days, genomic DNA was collected from the respective cells, and the genome editing efficiency in a target site region (On-Target) of VEGFA was examined by T7EI assay. In addition, the genome editing efficiency in the off-target site region (Off-Target) similar to the target sequence was examined by T7EI assay.

Table 1 below shows the target sequence, the On-Target sequence, and the Off-Target sequence of sgRNA.

TABLE 1

|  | Sequence | PAM | SEQ ID NO: |
|---|---|---|---|
| Target sequence of sgRNA | GGTGAGTGAGTGTGTGCGTG | NGG | 25 |
| On-Target | GGTGAGTGAGTGTGTGCGTG | TGG | 26 |
| Off-Target | TGTGGGTGAGTGTGTGCGTG | AGG | 27 |

FIG. 41(a) is a graph showing the results of the T7EI assay. In FIG. 41(a), "DNA plasmid" represents the result of introduction of plasmid DNA expressing Cas9 and sgRNA, and "Empty plasmid" represents the result of the introduction of empty plasmid DNA.

FIG. 41(b) is a graph showing the ratio of on-target cleavage to off-target cleavage. In FIG. 41(b), "VEGFA DNA plasmid" represents the result of introduction of plasmid DNA expressing Cas9 and sgRNA, and "VEGFA VLP" represents the result of introduction of VLP.

As a result, in the target site region of the cells into which 300 ng (equivalent to the amount of p24) of VLP was introduced, genome editing efficiency was observed which was equal to or higher than genome editing efficiency in the cells into which the plasmid DNA was introduced.

In addition, it was confirmed that the introduction of the plasmid DNA results in the introduction of an unintended mutation into the off-target site. On the other hand, it was confirmed that the introduction of VLP does not result in the introduction of a mutation into the off-target site. It was confirmed that because Cas9 introduced into cells by VLP exists for a short period of time and disappears before a mutation is introduced into the off-target site, the introduction of VLP has higher specificity for a target base sequence compared to the introduction of plasmid DNA.

Experimental Example 28

(Examination 2 on Safety of VLP System)

VLPs (6 µL) encapsulating Cas9 and sgRNA DMD #1 (the target sequence is shown in SEQ ID NO: 15) were introduced into HEK293T EGxxFP cells ($1 \times 10^5$ cells) so that genome editing was induced. For comparison, cells into which the same amount of empty VLPs were introduced were also prepared.

Then, after 48 hours, the genome editing efficiency was measured using a flow cytometer. In addition, trypan blue staining was performed, and the number of living cells was counted using an automated cell counter (name "Countess II", Thermo Fisher Scientific Inc.).

Figure 42:
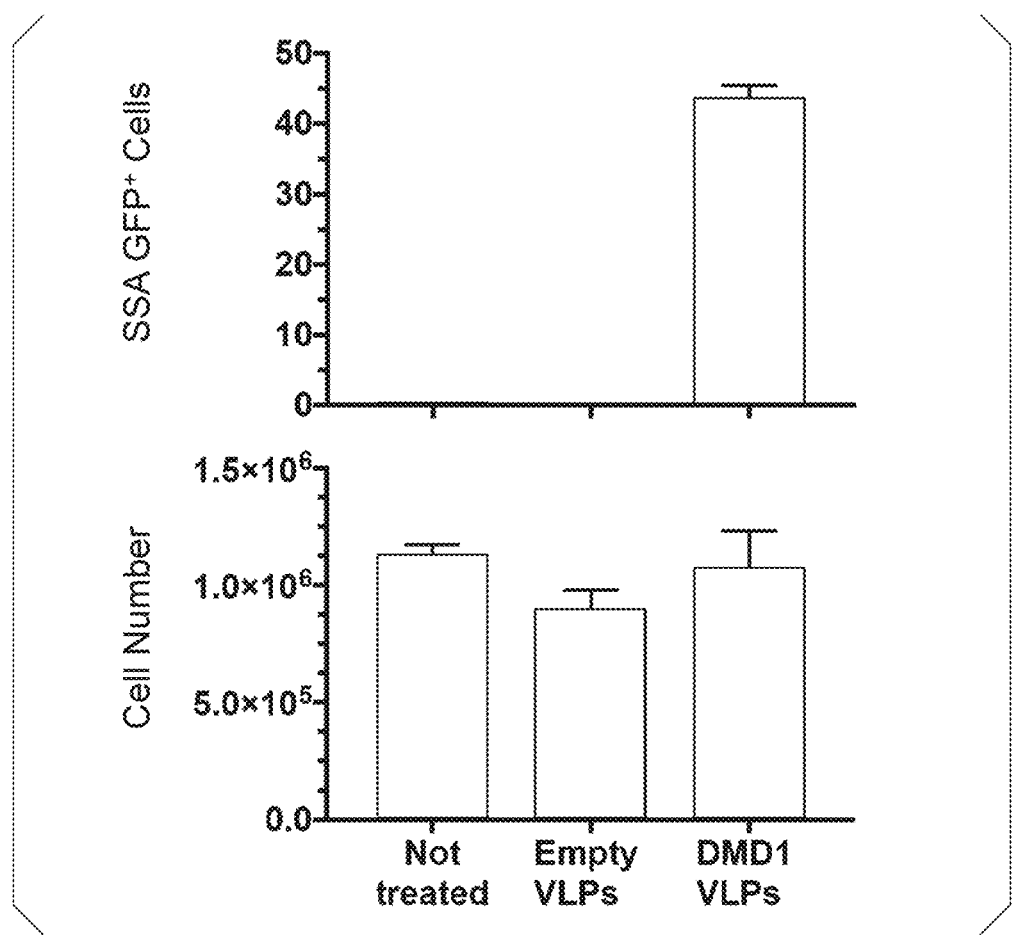
FIG. 42 is a graph showing the results of Experimental Example 28.

FIG. 42 is graphs showing the results. In FIG. 42, the upper graph shows the results of flow cytometry. The ordinate of the graph shows the proportion of GFP-positive cells. Furthermore, "DMD1 VLP" represents the result of the introduction of VLP encapsulating Cas9 and sgRNA DMD #1 (the target sequence is shown in SEQ ID NO: 15), "Empty VLP" represents the result of the introduction of empty VLP, and "Not treated" represents the result obtained from untreated HEK293T EGxxFP cells. In FIG. 42, the lower graph shows the number of living cells counted. The ordinate of the graph shows the number of cells. As a result, even though VLPs showing sufficient genome editing activity are introduced into the cells, the number of living cells substantially does not decrease, which shows that the VLPs have low cytotoxicity.

Experimental Example 29

(Induction of Exon Skipping in Human Skeletal Muscle Cells)

An examination was performed on whether or not VLPs according to the present invention can also induce exon skipping in human skeletal muscle cells. First, doxycycline was added to a medium containing iPS cells which were derived from a patent with DMD caused by the deletion of exon 44 and expressed MYOD1 gene in a doxycycline-inducible manner, so that the MYOD1 gene was overexpressed. In this way, the iPS cells were induced to differentiate into skeletal muscle cells.

Subsequently, VLP (hereinafter, called "DMD1 VLP" in some cases) encapsulating Cas9 and sgRNA DMD #1 (the target sequence is shown in SEQ ID NO: 15) and VLP (hereinafter, called "DMD23 VLP" in some cases) encapsulating Cas9 and sgRNA DMD #23 (the target sequence is shown in SEQ ID NO: 24) were prepared in the same manner as in Experimental Example 19. Then, 10 µL of each of the VLPs or 10 µL of a mixture of the VLPs was introduced into the obtained human skeletal muscle cells.

Subsequently, total RNA was extracted from each of the human skeletal muscle cells, and the region including exon 45 of cDNA of the DMD gene was amplified by RT-PCR and analyzed using an electrophoresis system (2200 TapeStation, Agilent Technologies, Inc.).

Figure 43:
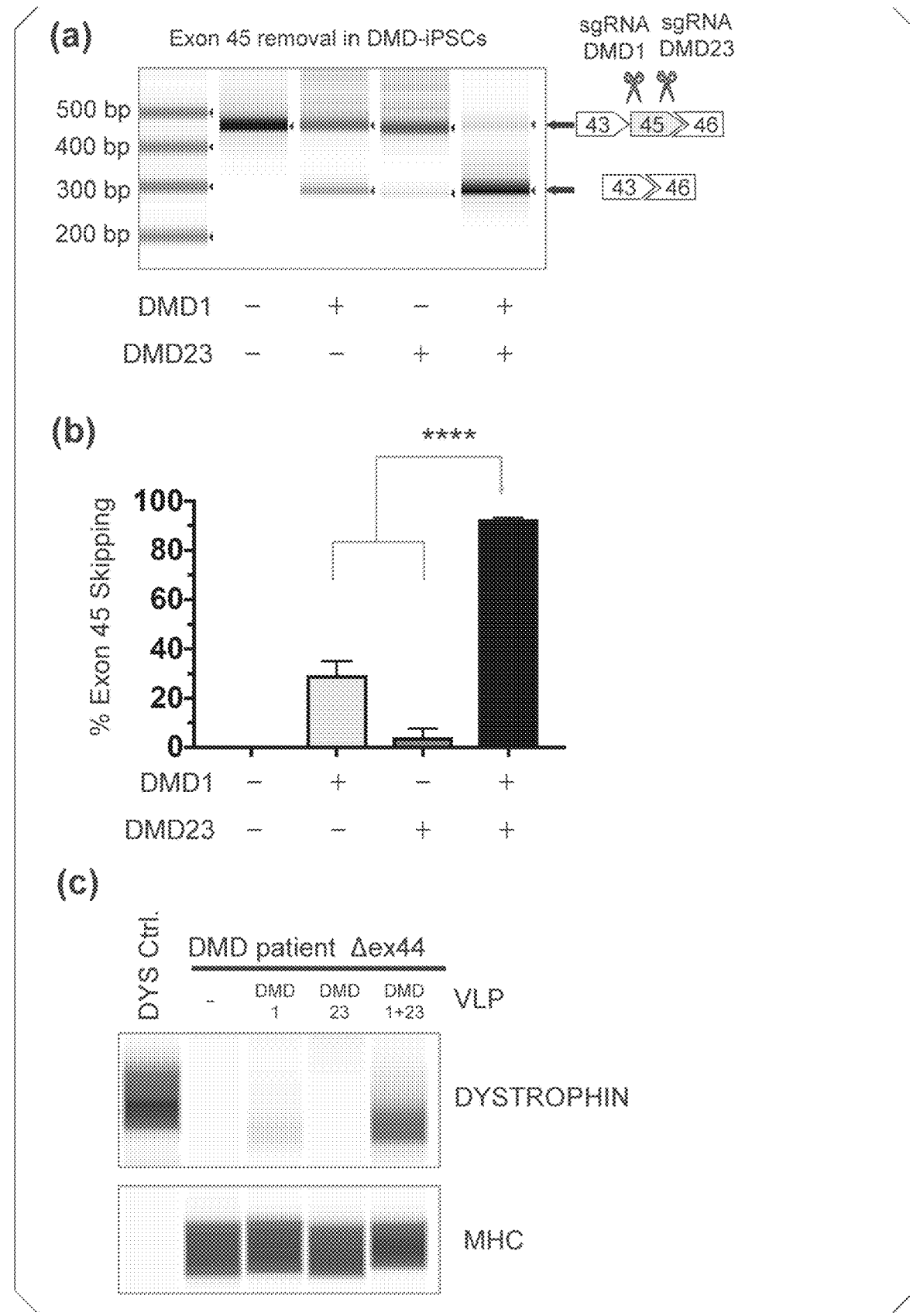
FIG. 43(a) is an image showing the results of electrophoresis in Experimental Example 29.
FIG. 43(b) is a graph numerically expressing the results shown in FIG. 43(a).
FIG. 43(c) is an image showing the results of Western blotting in Experimental Example 29.

FIG. 43(a) is an image showing the results of electrophoresis. The band indicated by the arrow on the upper side of FIG. 43(a) is derived from cDNA including exon 45. The band indicated by the arrow on the lower side in FIG. 43(a) is derived from cDNA that does not have exon 45 due to exon skipping.

FIG. 43(b) is a graph numerically expressing the results shown in FIG. 43(a). In FIG. 43(b), the ratio of the intensity of the lower band to the total intensity of the upper band and the lower band in FIG. 43(a) is represented by the exon skipping efficiency (%) for exon 45. In FIGS. 43(a) and 43(b), "DMD1" represents DMD1 VLP, "DMD23" represents DMD23 VLP, "+" shows that VLP was introduced into the human skeletal muscle cells, and "−" shows that VLP was not introduced into the human skeletal muscle cells. In FIG. 43(b), "****" shows a significant difference was found at P<0.0001 as a result of analysis by one-way ANOVA.

As a result, it was revealed that in a case where DMD1 VLP is introduced alone into the human skeletal muscle cells, skipping of exon 45 can be induced with an efficiency of about 36%. It was revealed that in a case where DMD23 VLP is introduced alone into the cells, the exon skipping efficiency is reduced. On the other hand, it was revealed that in a case where the 2 kinds of VLPs, DMD1 VLP and DMD23 VLP, are introduced together into the cells, exon skipping can be induced with extremely high efficiency of about 92%.

An examination was performed on the expression of dystrophin protein in human skeletal muscle cells. Specifically, Western blotting was performed using a fully automated Western blotting device Wes manufactured by ProteinSimple, Inc. and an anti-dystrophin antibody. In addition, a myosin heavy chain protein was detected as a loading control. Furthermore, as a control, HEK293T cells overexpressing dystrophin cDNA were analyzed in the same manner.

FIG. 43(c) is an image showing the results of Western blotting. In FIG. 43(c), "DYS Ctrl." represents the result obtained from the control, "DMD1" represents the result of the introduction of DMD1 VLP alone, "DMD23" represents the result of the introduction of DMD23 VLP alone, and "DMD1+23" represents the result of the co-introduction of DMD1 VLP and DMD23 VLP.

As a result, it was revealed that the expression level of dystrophin protein in human skeletal muscle cells is correlated with the exon skipping efficiency, and the co-introduction of 2 kinds of VLPs, DMD1 VLP and DMD23 VLP, can induce the high expression of dystrophin protein.

This result indicates that in a case where a normal dystrophin protein cannot be expressed due to an out-of-frame mutation, by deleting one specific exon or a plurality of specific exons, it is possible to induce exon skipping and to restore the protein reading frame.

Experimental Example 30

(Preparation of VLP Encapsulating Luciferase)

Figure 44:
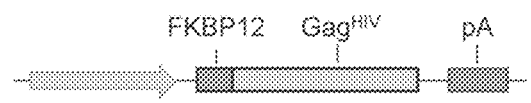
FIGS. 44(a) to 44(c) are schematic views illustrating the structure of VLP prepared in Experimental Example 30.
Figure 44:
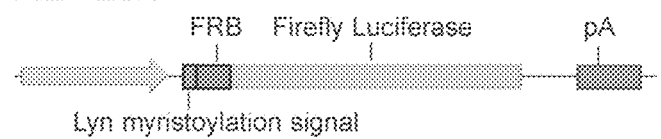
Figure 44:
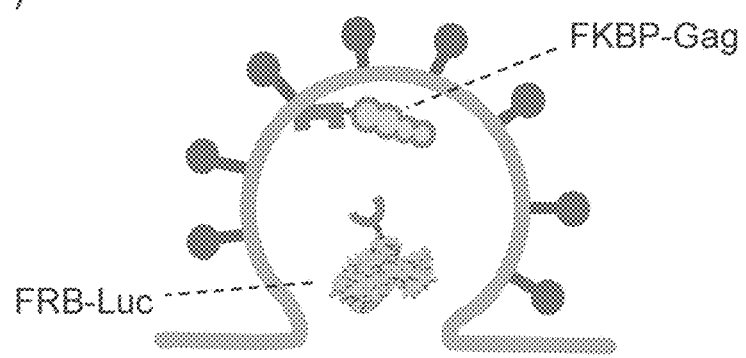

VLP encapsulating a luciferase protein was prepared. FIGS. 44(a) to 44(c) are schematic views illustrating the structure of VLP prepared in the present experimental example. FIG. 44(a) is a schematic view showing the structure of an expression construct of a fusion protein obtained by adding an FKBP12 domain to the N-terminal of Gag of HIV (hereinafter, called "FKBP12-Gag$^{HIV}$" in some cases). FIG. 44(b) is a schematic view showing the structure of an expression construct of a luciferase protein fused with an FRB domain (hereinafter, called "FRB-Luc" in some cases). FIG. 44(c) is a schematic view showing the way the FKBP12-Gag$^{HIV}$ and FRB-Luc are encapsulated in VLP.

Figure 45:
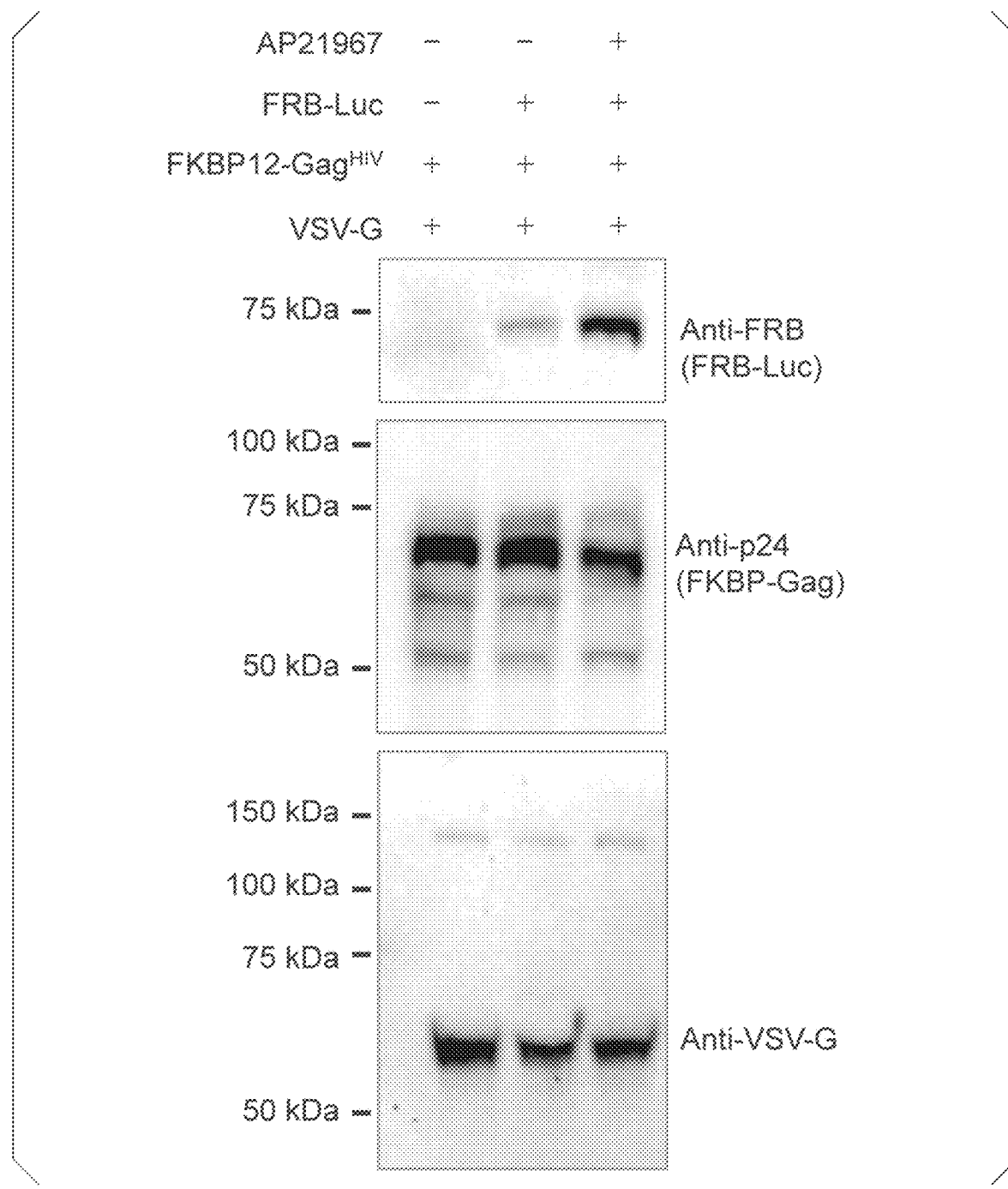
FIG. 45 is a photograph showing the results of Western blotting in Experimental Example 30.

In the presence or absence of AP21967 which is a drug similar to rapamycin, FRB-Luc, FKBP12-Gag$^{HIV}$, and VSV-G were combined as shown in FIG. 45 and expressed in HEK293T cells, thereby preparing VLPs. In FIG. 45, "+" shows that the protein was introduced into the cells, and "−" shows that the protein was not introduced into the cells.

Subsequently, FRB-Luc, FKBP12-Gag, and VSV-G in each of the above VLPs were quantified by Western blotting. FIG. 45 is photographs showing the results of Western blotting. As a result, it was revealed that the VLP prepared in the presence of AP21967 encapsulates more luciferase protein compared to VLP prepared in the absence of AP21967.

Figure 46:
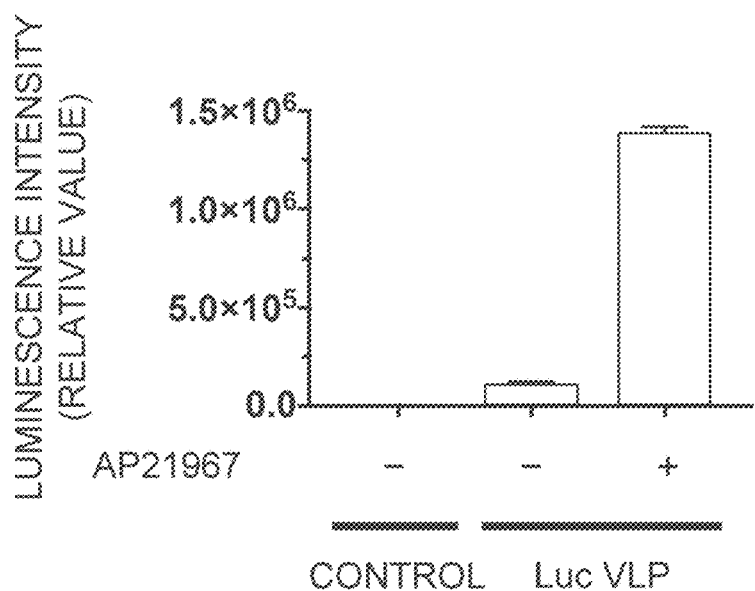
FIG. 46 is a graph showing the results of measuring luciferase activity in Experimental Example 30.

Then, HEK293T cells were seeded on a 96-well plate, and each of the above VLPs was introduced into the cells. Subsequently, after 16 hours, the cells were disrupted, and the luciferase activity was measured. FIG. 46 is a graph showing the results of measuring luciferase activity. In FIG. 46, "control" represents the result obtained from VLP devoid of FRB-Luc. In addition, "Luc VLP" represents the result obtained from VLP prepared to express FRB-Luc, FKBP12-Gag$^{HIV}$, and VSV-G. Furthermore, "−" represents the result obtained from VLP prepared in the absence of AP21967, and "+" represents the result obtained from VLP prepared in the presence of AP21967.

As a result, it was revealed that the amount of luciferase protein delivered to HEK293T cells by VLP prepared in the presence of AP21967 was 12 times greater than the amount of luciferase protein delivered to HEK293T cells by VLP prepared in the absence of AP21967.

Experimental Example 31

(In Vivo Delivery of Protein by Using VLP)

An examination was performed on in vivo delivery of proteins by using VLP. C57BL/6 mice were administered with 30 μL or 60 μL of Luc VLP prepared in Experimental Example 30 by means of injection into the gastrocnemius muscle. In addition, as a control, a group administered with PBS was prepared. Then, after 16 hours, 2 days, and 3 days, luminescence of luciferase was detected.

Specifically, 5 to 15 minutes before analysis, the mice were anesthetized with isoflurane, and 3 mg of luciferin was intravenously administered to each mouse. Then, by performing in vivo luminescence/fluorescence imaging with an IVIS imaging device (PerkinElmer), luminescence of luciferase was detected.

Figure 47:
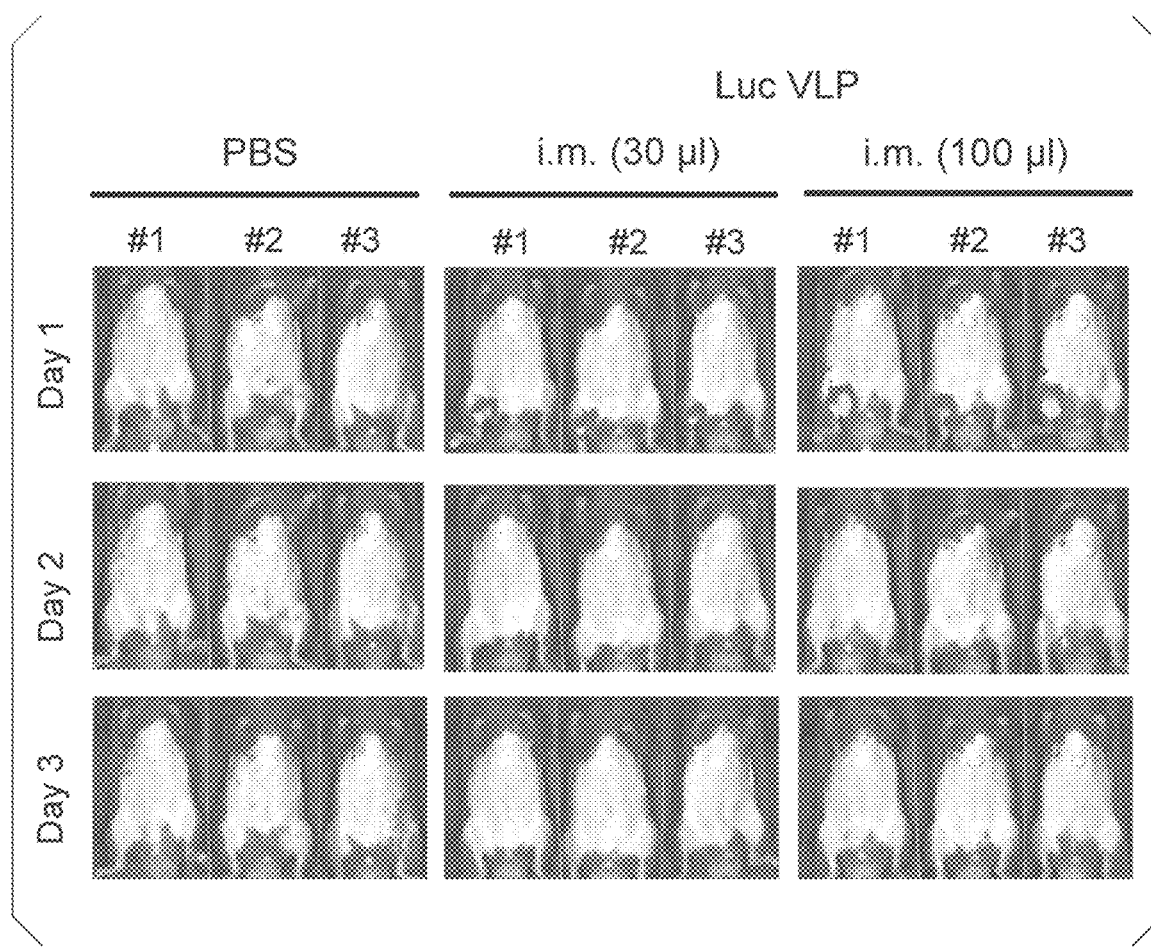
FIG. 47 is a graph showing the results of in vivo luminescence/fluorescence imaging in Experimental Example 31.
Figure 48:
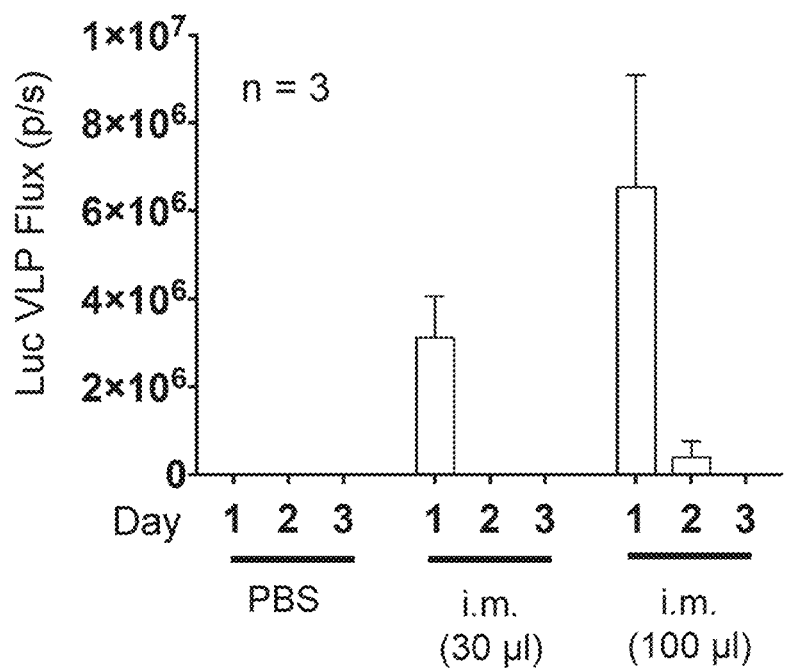
FIG. 48 is a graph numerically expressing the results shown in FIG. 47.

FIG. 47 is photographs showing the results of IVIS analysis. FIG. 48 is a graph numerically expressing the results shown in FIG. 47. As a result, dose-dependent luminescence of luciferase was observed near the muscle of the mice having Luc VLP injection. In addition, the leakage of luciferase to the liver or other organs was not substantially observed. Furthermore, the luciferase protein was found to completely disappear within 3 days after the introduction of Luc VLP. This result indicates that the protein delivered by VLP is transiently expressed.

Experimental Example 32

(In Vivo Induction of Exon Skipping)

Figure 49:
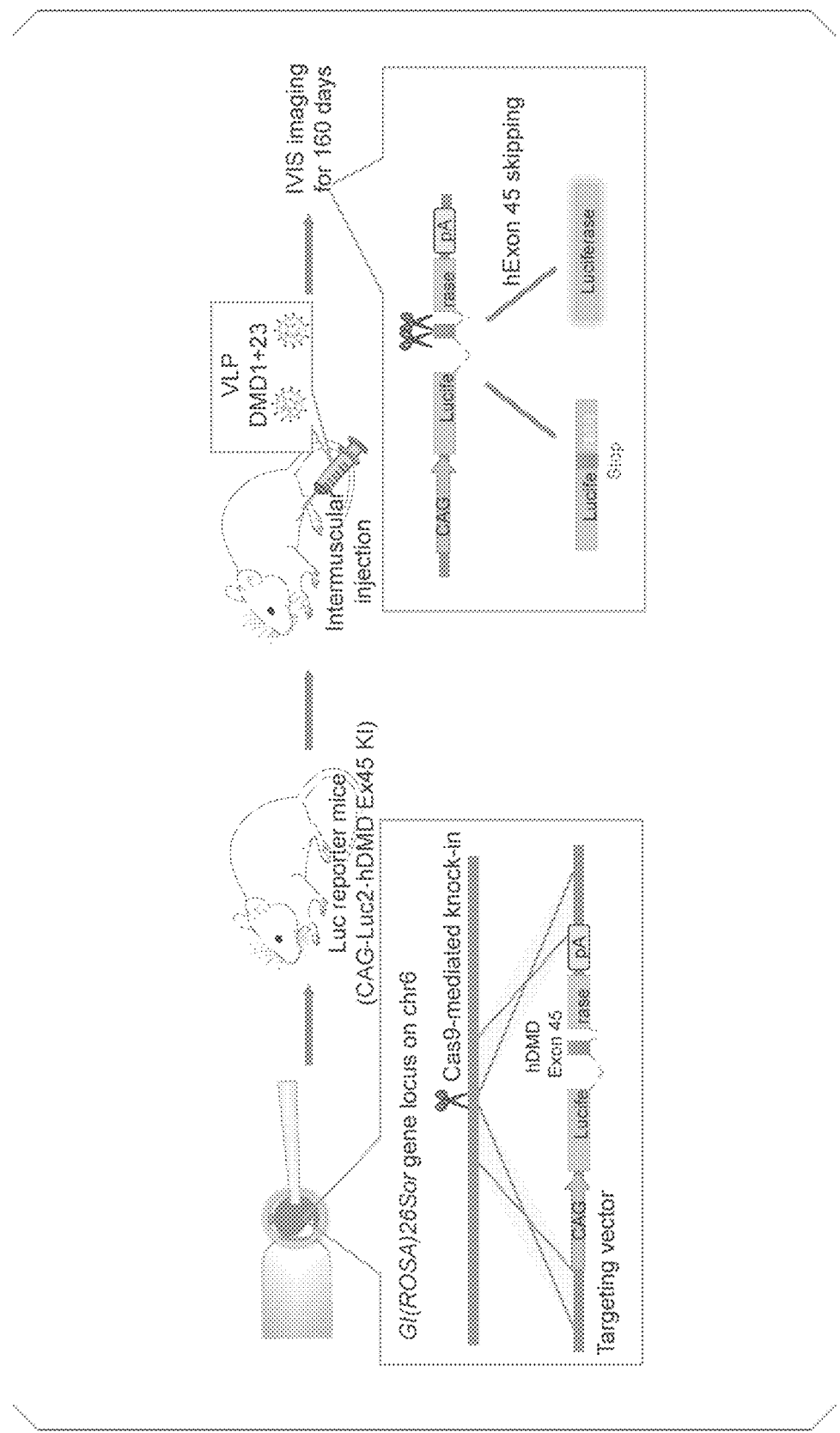
FIG. 49 is a view illustrating a gene-introduced luciferase reporter mouse model used in Experimental Example 32.

An examination was performed on in vivo induction of exon skipping by using VLP. FIG. 49 is a view illustrating a luciferase reporter knock-in mouse model used in the present experimental example. As shown in FIG. 49, a luciferase reporter gene was introduced into the Gt (ROSA) 26Sor locus of C57BL/6 mouse by genome editing, thereby inducing knock-in. Exon 45 of the human DMD gene and the 5' side and 3' side introns thereof were introduced into the luciferase reporter gene.

As shown in FIG. 49, in a case where exon 45 is incorporated into mRNA of luciferase in the process of splicing, out-of-frame deletion occurs, and hence a normal luciferase protein cannot be expressed. However, in a case where the same DMD1 VLP and DMD23 VLP as those in Experimental Example 19 are introduced into the luciferase reporter knock-in mouse model, skipping of exon 45 can be induced, and a normal luciferase protein can be expressed.

The same DMD1 VLP (50 μL) and DMD23 VLP (50 μL) as those in Experimental Example 19 were administered into the gastrocnemius muscle of the above luciferase reporter knock-in mouse model. Then, by performing in vivo luminescence/fluorescence imaging with an IVIS imaging device (PerkinElmer) in the same manner as in Experimental Example 31, luminescence of luciferase was detected over time.

Figure 50:
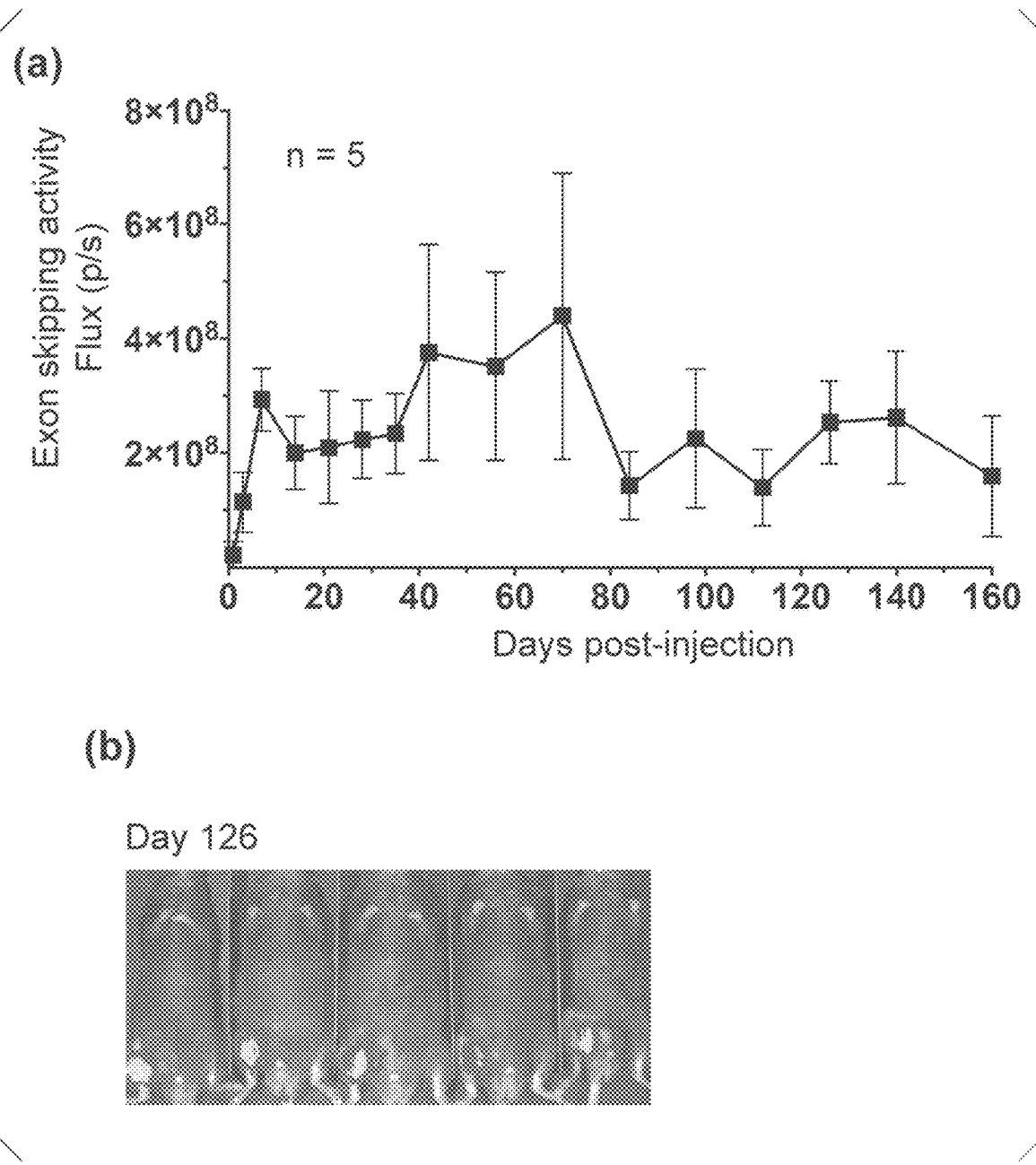
FIG. 50(a) is a photograph showing the results of in vivo luminescence/fluorescence imaging for 1 to 160 days after the administration of VLP in Experimental Example 32.
FIG. 50(b) is a typical photograph showing the results of in vivo luminescence/fluorescence imaging performed on the 126th day after the administration of VLP.

FIG. 50(a) is a photograph showing the results of IVIS analysis carried out for 1 to 160 days after the administration of VLP (n=5). FIG. 50(b) is typical photographs showing the results of IVIS analysis carried out on the 126th day after the administration of VLP. As a result, exon skipping-induced luciferase expression was observed specifically at the site having VLP injection.

Unlike in the mouse model having the Luc VLP injection, in the mouse model administered once with DMD1 VLP and DMD23 VLP, luciferase activity was observed 3 days after the administration, reached a plateau 7 days after the administration, and detected for at least 160 days thereafter. This result indicates that the exon 45 skipping activity was stably maintained in the mouse muscle.

Experimental Example 33

(Genome Editing in Various Cells by Using VLP)

VLPs encapsulating Cas9 and sgRNA for various target sequences were introduced into various cells, and the genome editing efficiency was examined.

<<T Lymphocyte>>

Figure 51:
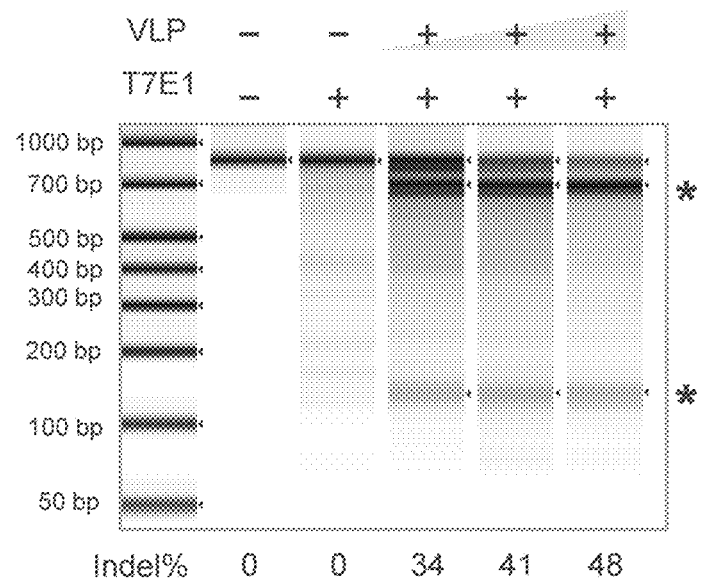
FIG. 51(a) is an image showing the results of introducing VLP into Jurkat cells, which are a human T lymphocyte cell strain, and performing T7EI assay in Experimental Example 33.
FIG. 51(b) is a graph numerically expressing the results shown in FIG. 51(a).
Figure 51:
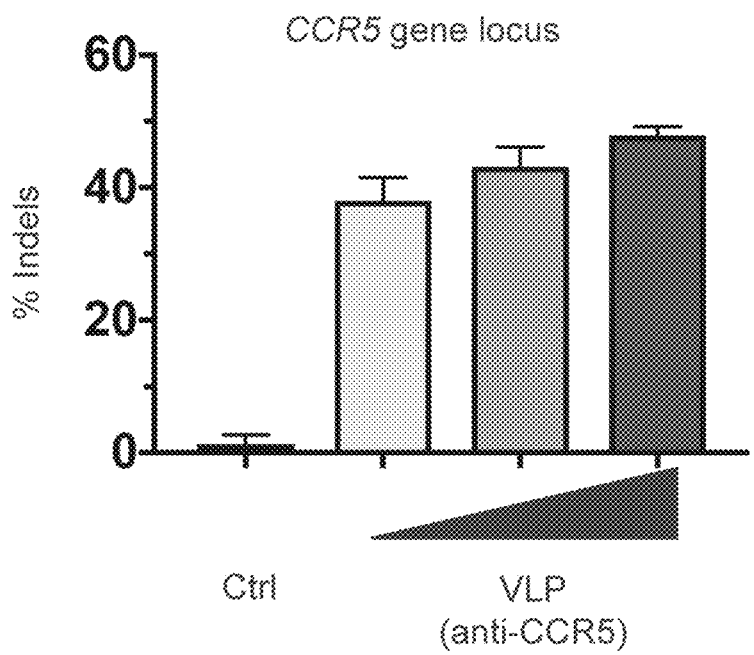

FIG. 51(a) is a photograph showing the results of introducing VLPs encapsulating sgRNA (the target sequence is shown in SEQ ID NO: 28) for CCR5 gene as a co-receptor of HIV and Cas9 into Jurkat cells as a human T lymphocyte strain and measuring the genome editing efficiency by T7EI assay. FIG. 51(b) is a graph numerically expressing the results shown in FIG. 51(a). As a result, it was revealed that the dose-dependent insertion/deletion mutation (Indel) is introduced by the introduction of VLPs, and the percentage of Indel increases up to 48%.

<<Monocyte>>

VLPs encapsulating sgRNA (the target sequence is shown in SEQ ID NO: 29) for the EGFP gene and Cas9 were introduced into cells (EGFP-U937) prepared by letting U937 cells as a human monocyte strain to stably express EFGP. As a control, VLPs encapsulating Cas9 and sgRNA (the target sequence shown in SEQ ID NO: 29) for the EGFP gene were introduced into cells prepared by letting U937 cells to stably express the SAMHD1 gene (SAMHD1-U937). Then, 3 days after the introduction of VLPs, the fluorescence of EGFP was analyzed by flow cytometry.

Figure 52:
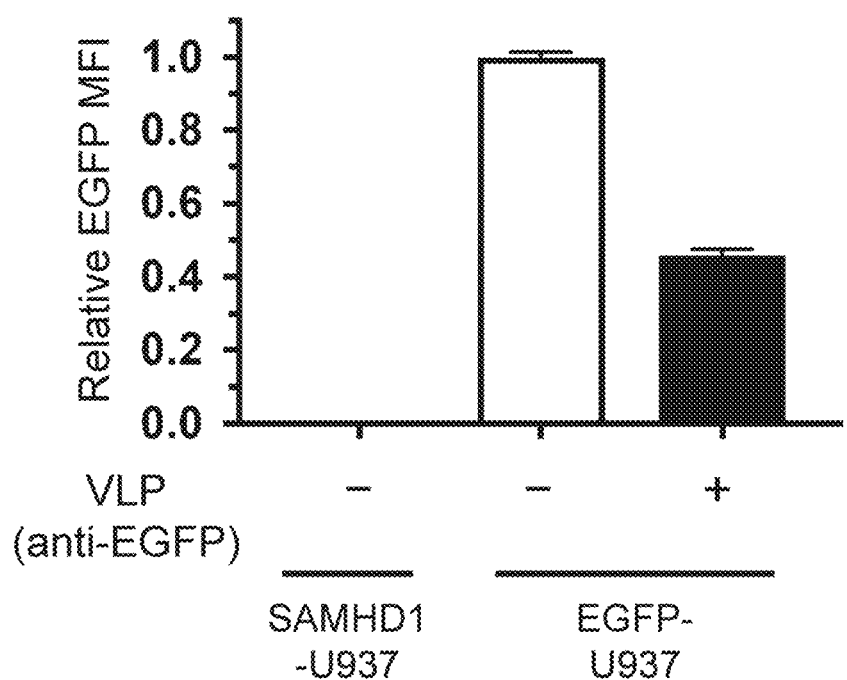
FIG. 52 is a graph showing the results of flow cytometry in Experimental Example 33.

FIG. 52 is a graph showing the results of flow cytometry. In FIG. 52, "−" represents cells into which VLPs are not introduced, and "+" represents cells into which VLPs are introduced. As a result, it was revealed that the average fluorescence intensity of EGFP in the group into which VLPs are introduced is about 50% of the average fluorescence intensity of EGFP in the group into which VLPs are not introduced.

<<Nerve Cell>>

The Neurogenin2 gene (NGN2-IRES-mCherry) was overexpressed in human iPS cells so that the cells were differentiated into cerebral cortical neuron-like nerve cells. Then, VLPs encapsulating sgRNA for the SAMHD1 gene and Cas9 were introduced into the obtained nerve cells. As sgRNA for the SAMHD1 gene, two kinds of sgRNAs, sgRNA #1 (the target sequence is shown in SEQ ID NO: 30) and sgRNA #2 (the target sequence is shown in SEQ ID NO: 31), were used.

Figure 53:
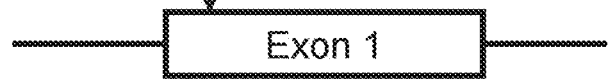
FIG. 53(a) is a schematic view showing the positions of sgRNA #1 (SEQ ID NO: 30) and sgRNA #2 (SEQ ID NO: 31) for an SAMHD1 gene used in Experimental Example 33.
FIG. 53(b) is a photograph of nerve cells differentiated from the human iPS cells in Experimental Example 33.
FIG. 53(c) is an image showing the results of the T7EI assay in Experimental Example 33.
Figure 53:
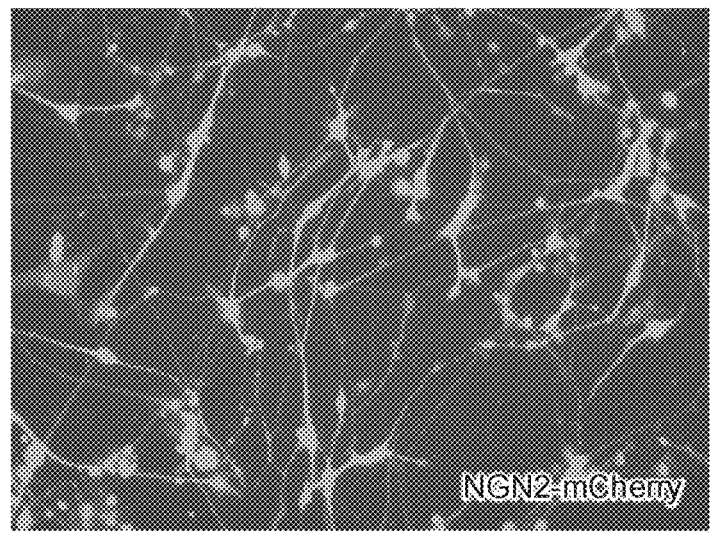
Figure 53:
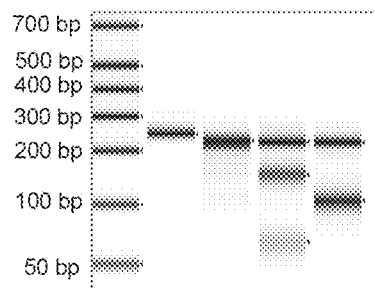

FIG. 53(a) is a schematic view showing the positions of sgRNA #1 and sgRNA #2 for the SAMHD1 gene. FIG. 53(b) is a photograph of nerve cells differentiated and induced from the human iPS cells. FIG. 53(c) is an image showing the results of measuring the genome editing efficiency by T7EI assay. In FIG. 53(c), "anti-SAMHD1 VLP" represents VLP encapsulating Cas9 and sgRNA for the SAMHD1 gene, "−" shows that VLP is not introduced into the cells, "#1" shows that VLP encapsulating sgRNA #1 is introduced into the cells, and "#2" shows that VLP encapsulating sgRNA #2 is introduced into the cells.

As a result, it was revealed that the introduction of VLP can efficiently edit the genome of the SAMHD1 gene which is a gene relating to congenital encephalopathy. Both the sgRNA #1 and sgRNA #2 used brought insertion/deletion mutation (Indel) introduction efficiency of about 36%.

Experimental Example 34

(Mass Production of VLP)

An examination was performed on a method for mass-producing VLPs for medical use without using animal-derived components (xeno-free). First, a HEK293 cell strain was established which expressed the SV40 large T antigen and can be suspension-cultured in a serum-free medium.

<<Examination on electroporation condition>>

By using a flow electroporation device ("MaxCyte STX", MaxCyte, Inc.), expression vectors for forming VLPs were introduced into the above HEK293 cells under "E4" condition in which low electroporation energy is used or under "E9" condition in which high electroporation energy is used.

As the expression vectors, an FKBP12-Gag$^{HIV}$ expression vector, an FRB-SpCas9 expression vector, an expression vector for sgRNA interposed between ribozymes (hereinafter, called "RGR" in some cases), a Tat$^{HIV}$ expression vector, and a VSVG expression vector were used.

After electroporation, cells were incubated for 40 minutes in the presence or absence of endonuclease ("benzonase", Merck). Then, AP21967 was added to the cell medium, and the cells were suspension-cultured with stirring at 100 rpm.

Thereafter, 36 to 48 hours after the electroporation, the culture supernatant was collected, cell debris was removed using a syringe filter having a pore size of 0.45 μm, and the filtrate was centrifuged for 3 hours at 100,000×g by using an Avanti JXN-30 centrifuge (Beckman Coulter, Inc.) so that VLPs were collected.

Then, VLPs prepared under the respective conditions were introduced into HEK293T cells into which the reporter construct EGxxFP was introduced (hereinafter, called "HEK293T EGxxFP cells" in some cases). Subsequently, after 3 days, the fluorescence of EGFP in each cell was measured using a flow cytometer, and the genome editing efficiency was measured.

Figure 54:
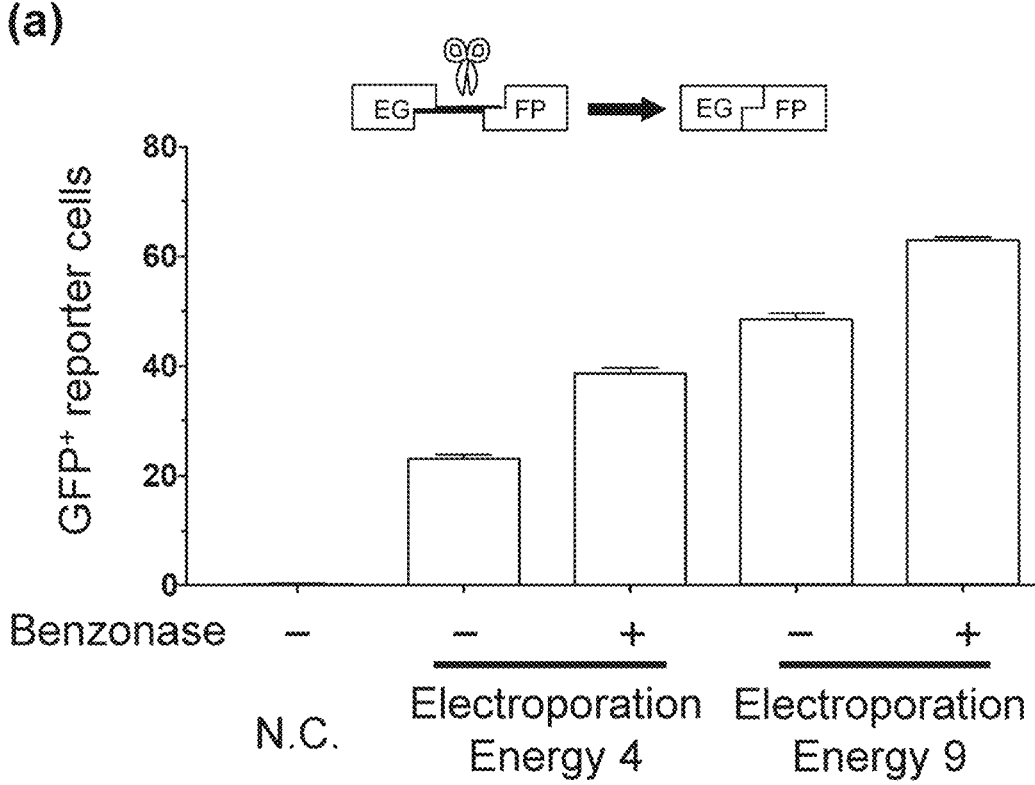
FIG. 54(a) and 54(b) are graphs showing the results of measuring the fluorescence of EGFP in Experimental Example 34.
Figure 54:
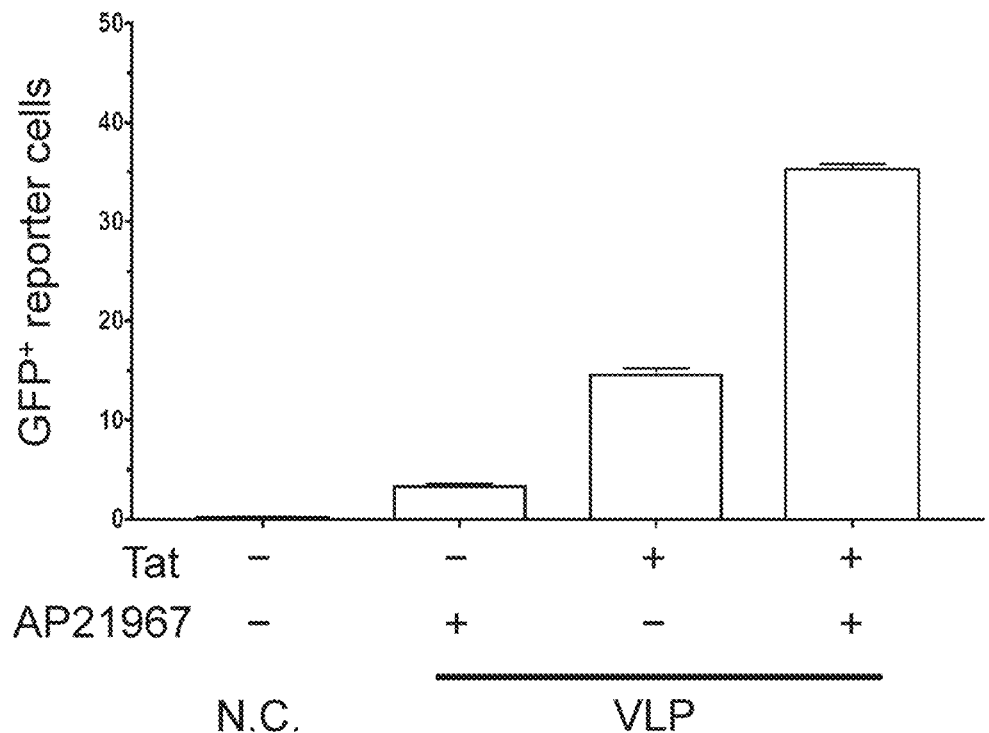

FIG. 54(a) is a graph showing the results of measuring the fluorescence of EGFP. As a result, it was revealed that the genome editing efficiency is the highest in a case where the cells are subjected to electroporation under "E9" condition and treated with endonuclease after electroporation. This result indicates that the amount of formed VLPs is the largest under the above condition.

<<Examination on Tat and AP21967>>

By using a flow electroporation device ("MaxCyte STX", MaxCyte, Inc.), VLPs were prepared under the E9 condition. Herein, examinations were performed on the preparation of VLPs in the presence or absence of the Tat$^{HIV}$ expression vector and on the preparation of VLPs in the presence or absence of AP21967.

Subsequently, VLPs prepared under the respective conditions were introduced into the HEK293T EGxxFP cells. Then, after 3 days, the fluorescence of EGFP in each cell was measured using a flow cytometer, and the genome editing efficiency was measured.

FIG. 54(b) is a graph showing the results of measuring the fluorescence of EGFP. As a result, it was revealed that the genome editing efficiency is the highest in a case where VLPs are prepared in the presence of Tat$^{HIV}$ and AP21967. This result further supports that the presence of Tat$^{HIV}$ and AP21967 is important for the encapsulation of sgRNA and Cas9 in VLPs.

<<Comparison Between Preparation of VLP by Adhesion Culture and Preparation of VLP by Suspension Culture>>

By using 48 10 cm dishes, HEK293T cells were adhesion-cultured in a medium containing 10% fetal bovine serum (FBS), and the respective expression vectors were introduced into the cells by using a lipofection reagent, thereby preparing VLPs on a scale of 480 mL in total.

In addition, by using two 1 L flasks each containing 240 mL of a medium, HEK293 cells were suspension-cultured in a serum-free medium devoid of animal-derived components, and the respective expression vectors were introduced into the cells by flow electroporation, thereby preparing VLPs on a scale of 480 mL.

Then, the VLPs were concentrated by being centrifuged overnight. Subsequently, the VLPs were lysed using Triton-X and reacted with a substrate (DNA having a dystrophin target sequence, 700 bp), and the abundance of an active Cas9/sgRNA RNP complex was quantified. For quantification, a standard curve was used which was prepared in the same manner as in Experimental Example 2 by using a recombinant spCas9 protein and chemically synthesized sgRNA.

Figure 55:
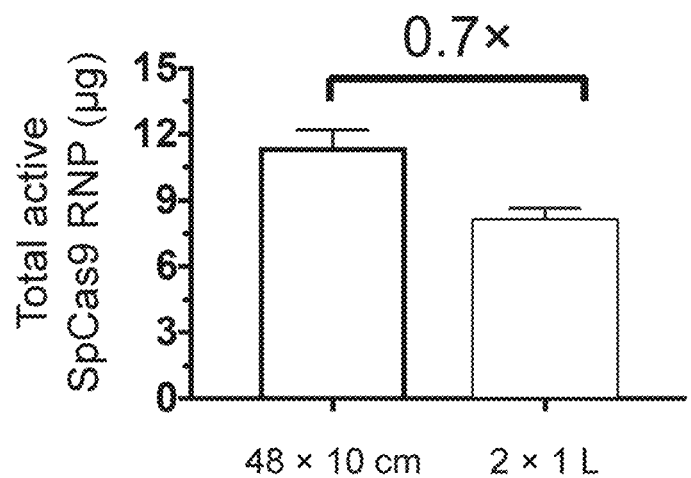
FIG. 55(a) is a graph showing the results of quantifying an active Cas9/sgRNA RNP complex in Experimental Example 34.
FIG. 55(b) is a graph showing the results of measuring the induction of an insertion/deletion mutation (Indel) in Experimental Example 34.
Figure 55:
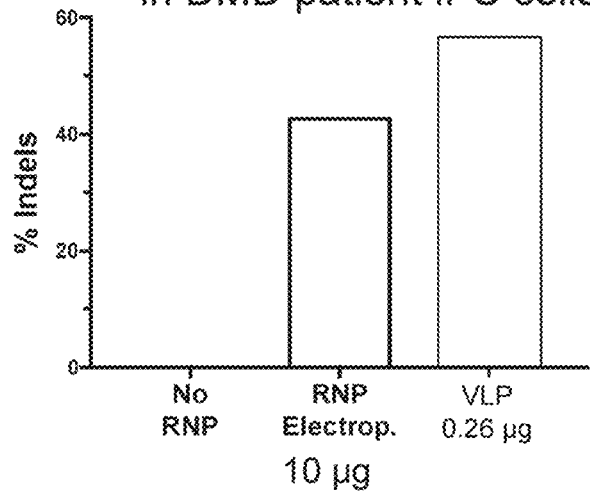

FIG. 55(a) is a graph showing the results of quantifying the active Cas9/sgRNA RNP complex. In FIG. 55(a), "48× 10 cm" represents the result obtained from VLPs prepared by adhesion culture, and "2×1 L" represents the result obtained from VLPs prepared by suspension culture.

As a result, it was revealed that a total of 8.1 μg of the Cas9/sgRNA RNP complex can be created by the suspension culture using a serum-free medium. This quantity is approximately 30% lower than the quantity of the same complex created using the VLPs prepared by adhesion culture using a serum-containing medium on the same scale. In order to use VLPs for medical purposes, animal-derived components should not be used in the VLPs. The above results indicate that suspension culture makes it possible to increase the amount of VLPs prepared and to produce VLPs industrially, and the prepared VLPs can be used for medical purposes.

FIG. 55(b) is a graph showing the results of introducing VLPs containing 0.26 μg of an active RNP complex having sgRNA DMD #1 (the target sequence is shown in SEQ ID NO: 15) into iPS cells derived from a patient with DMD and measuring the induction of an insertion/deletion mutation (Indel). In FIG. 55(b), "No RNP" shows that the Cas9/sgRNA RNP complex was not introduced into the cells, and "RNP Electrop." shows that the Cas9/sgRNA RNP complex was introduced into the cells by electroporation.

As a result, it was revealed that in a case where VLPs are used, an insertion/deletion mutation is more efficiently induced than in a case where 10 μg of recombinant RNP is introduced into the iPS cells by electroporation. This result indicates that VLPs efficiently deliver CRISPR-Cas9 RNP to target cells and exhibit high cleavage activity.

Experimental Example 35

(Analysis of VLP)

The size of VLPs and the number of molecules of the active Cas9/sgRNA RNP complex in one VLP were analyzed. First, VLPs were adsorbed onto a monolithic silica column. Then, extraction was performed using buffers with NaCl concentration adjusted to 0.1 M, 0.2 M, 0.65 M, and 1 M, and the extracts were purified. Subsequently, VLPs contained in the elution fraction eluted at each salt concentration was subjected to Western blotting, and a SpCas9 protein and capsid (CA, also called p24) were detected.

Figure 56:
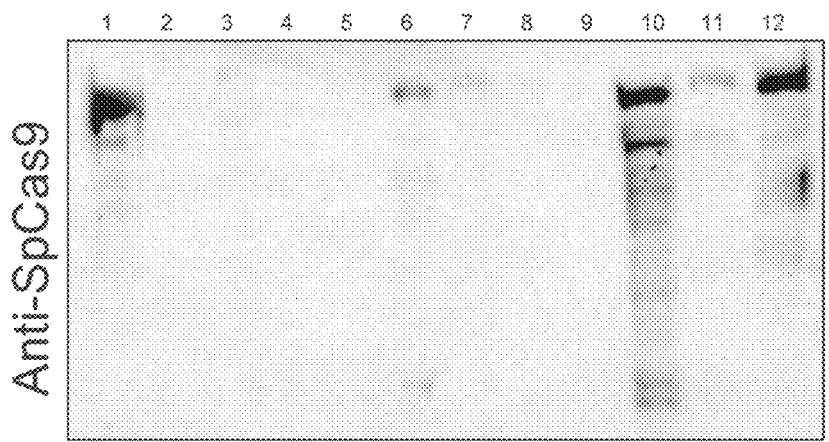
FIGS. 56(a) and 56(b) are photographs showing the results of Western blotting in Experimental Example 35.
Figure 56:
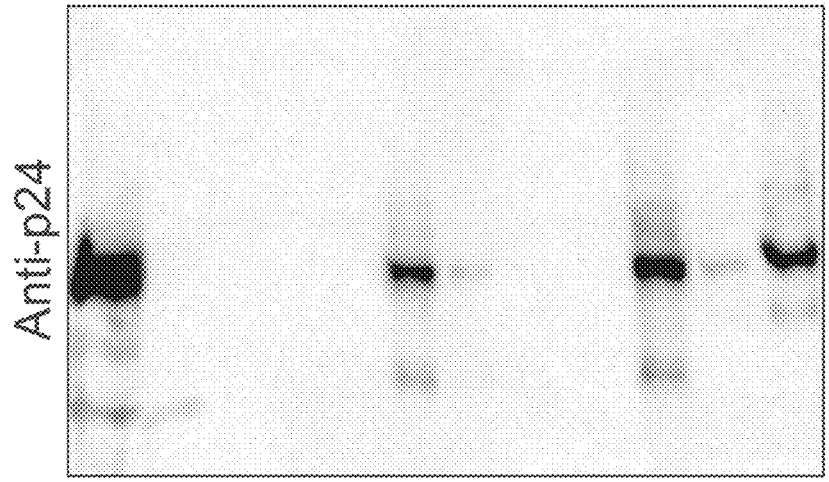

FIG. 56(a) is a photograph showing the results of Western blotting on SpCas9 protein. FIG. 56(b) is a photograph showing the results of Western blotting on p24. As a result, it was considered that VLPs were contained in the elution fractions having a salt concentration of 0.65 M and a salt concentration of 1 M.

<<Measurement of Particle Size>>

Figure 57:
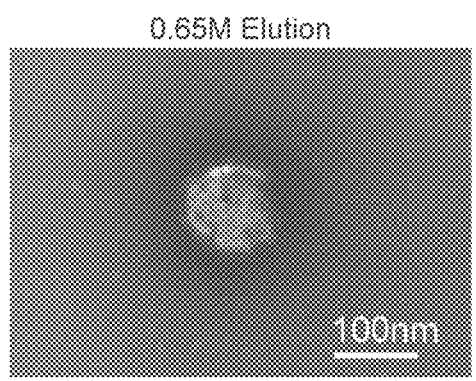
FIGS. 57(a) and 57(b) are typical electron micrographs of VLPs captured in Experimental Example 35.
FIGS. 57(c) and 57(d) are graphs showing the results of measuring the particle size of VLP in Experimental Example 35.
Figure 57:
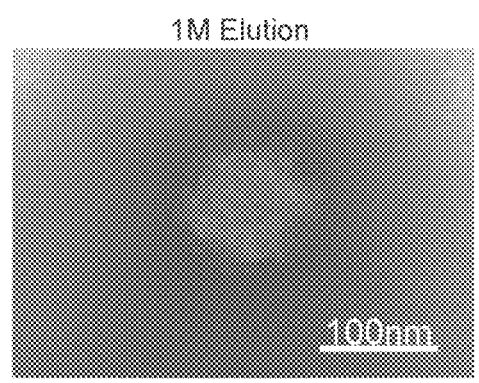
Figure 57:
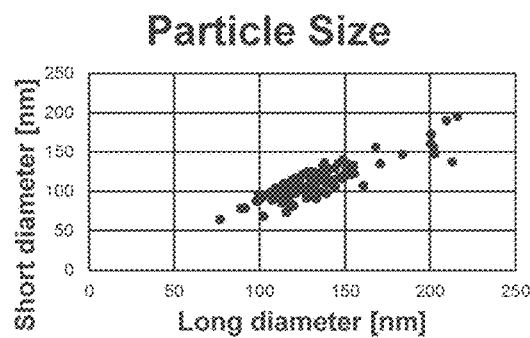
Figure 57:
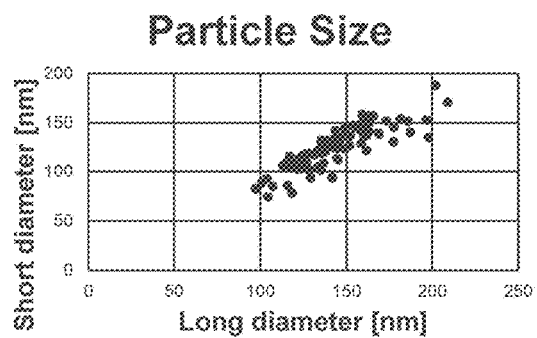

Subsequently, the purified VLPs were observed with an electron microscope, and the particle size was measured. FIG. 57(a) is a typical electron micrograph of VLPs contained in the elution fraction having a salt concentration of 0.65 M. FIG. 57(b) is a typical electron micrograph of VLPs contained in the elution fraction having a salt concentration of 1 M. FIG. 57(c) is a graph showing the results of measuring the particle size (long diameter and short diameter) of VLPs contained in the elution fraction having a salt concentration of 0.65 M based on an electron micrograph. FIG. 57(d) is a graph showing the results of measuring the particle size (long diameter and short diameter) of VLPs contained in the elution fraction having a salt concentration of 1 M based on an electron micrograph.

Figure 58:
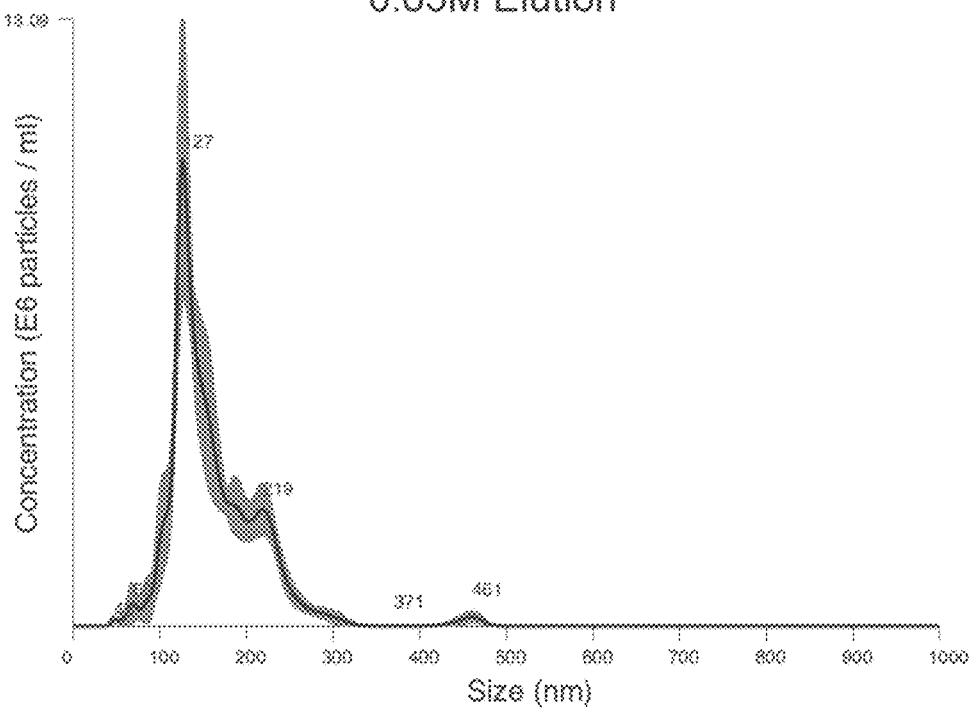
FIGS. 58(a) and (b) are graphs showing the particle size of VLP measured by observing the Brownian motion in Experimental Example 35.
Figure 58:
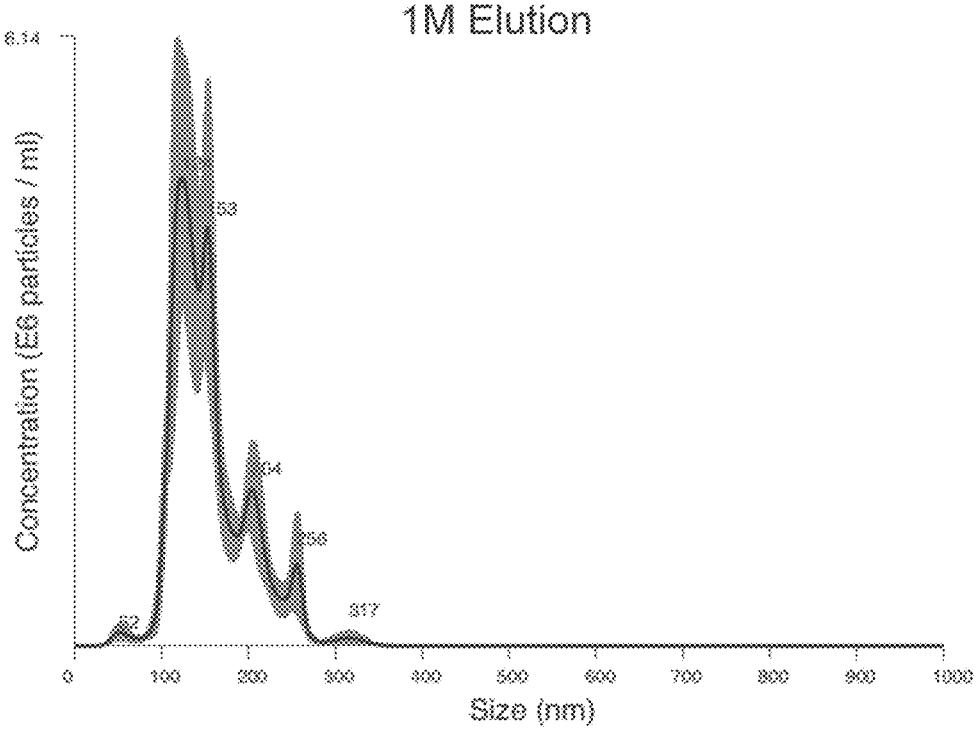

FIG. 58(a) is a graph showing the results of measuring the particle size of VLPs contained in the elution fraction having a salt concentration of 0.65 M by using a commercially available device ("NanoSight", Malvern Panalytical). FIG. 58(b) is a graph showing the results of measuring the particle size of VLPs contained in the elution fraction having a salt concentration of 1 M by using a commercially available device ("NanoSight", Malvern Panalytical). In FIGS. 58(a) and 58(b), the ordinate shows the concentration of VLPs ($10^6$ particles/mL), and the abscissa shows the particle size (nm).

<<Analysis of the Number of Molecules of Cas9>>

The number of Cas9 protein molecules in one VLP (number of molecules of an active Cas9/sgRNA RNP complex) was analyzed. First, by using Triton-X, VLPs contained in the elution fraction having a salt concentration of 0.65M and VLPs contained in the elution fraction having a salt concentration of 1M were lysed. Then, the VLPs were reacted with a substrate (DNA having a dystrophin target sequence, 700 bp), and the abundance of the active Cas9/sgRNA RNP complex was quantified. For quantification, a standard curve was used which was prepared in the same manner as in Experimental Example 2 by using a recombinant spCas9 protein and chemically synthesized sgRNA.

Figure 59:
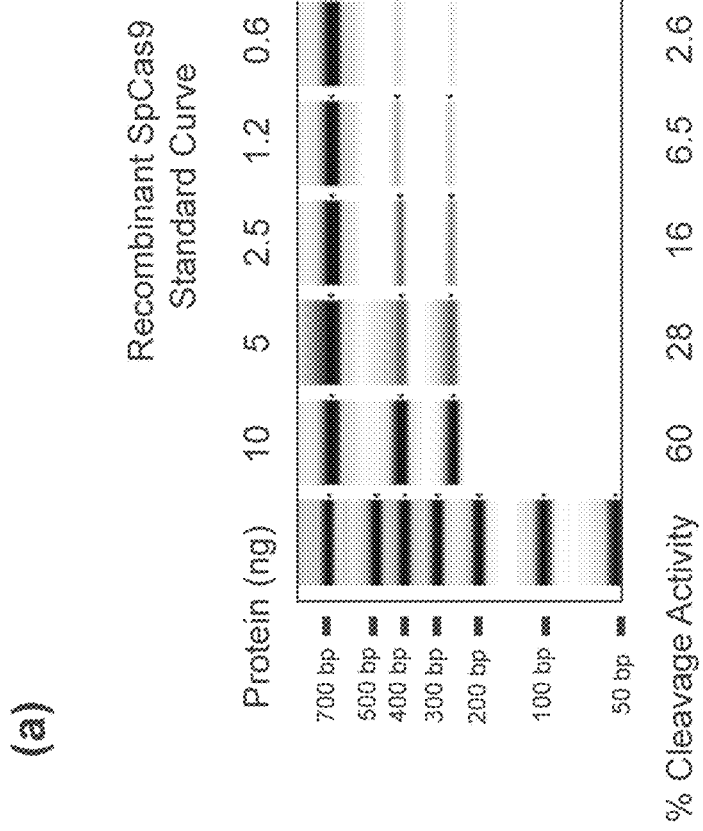
FIG. 59(a) is an image showing a standard curve of DNA cleavage activity in Experimental Example 35.
FIG. 59(b) is an image showing the results of cleaving a substrate by using the Cas9/sgRNA RNP complex in VLP.

FIG. 59(a) is an image showing a standard curve. FIG. 59(b) is an image showing the results of cleaving the substrate (DNA having a dystrophin target sequence, 700 bp) by using the Cas9/sgRNA RNP complex in VLPs contained in the elution fractions having salt concentrations of 0.65 M and 1 M respectively. In FIGS. 59(a) and 59(b), "% Cleavage Activity" represents the percentage of the cleaved substrate (cleavage activity).

As a result, the concentration of the Cas9 protein in the elution fraction having a salt concentration of 0.65 M was calculated to be 3.4 μg/mL. The concentration of the Cas9 protein in the elution fraction having a salt concentration of 1 M was calculated to be 13.3 μg/mL. The following Table 2 shows the particle size of VLPs, the concentration of VLPs, the concentration of the Cas9 protein, and the number of Cas9 protein molecules in one VLP calculated as above.

TABLE 2

| Salt concentration for elution | 0.65M | 1M |
|---|---|---|
| Particle size determined using electron microscope (nm) | 132 ± 23 | 144 ± 23 |
| Particle size determined using NanoSight (nm) | 155 ± 44 | 162 ± 56 |
| Concentration of VLP observed using NanoSight (particle/mL) | $3 \times 10^{12}$ | $6 \times 10^{12}$ |
| Cas9 protein concentration (μg/mL) | 3.4 | 13.3 |
| Cas9 protein concentration (molecule/mL) | $1.2 \times 10^{13}$ | $4.8 \times 10^{13}$ |
| Number of Cas9 protein molecules (molecule/particle) | 3.5 | 7.9 |

INDUSTRIAL APPLICABILITY

According to the present invention, it is possible to provide a technique for efficiently encapsulating a target protein in a virus-like particle.

The invention claimed is:

1. A virus-like particle encapsulating a Cas family protein and a gRNA, comprising:
   a fusion protein of FKBP12 and Gag protein and a fusion protein of FRB and the Cas family protein, or a fusion protein of FRB and Gag protein and a fusion protein of FKBP12 and a Cas family protein;
   an mRNA or a self-cleavage product of the mRNA wherein the mRNA having the gRNA sequence interposed between a first ribozyme sequence and a second ribozyme sequence and a packaging signal sequence; and
   a rapamycin or a rapamycin derivative;
   wherein the FKBP12, the rapamycin or the rapamycin derivative, and the FRB are bound together and the Gag protein forms a dimer with the Cas family protein.

2. A method for manufacturing a genome-edited cell, comprising:
   inoculating the cell with the virus-like particle according to claim 1.

3. A kit for manufacturing the virus-like particle according to claim 1, comprising:
   an expression vector for a fusion protein of FKBP12 and Gag protein and an expression vector for a fusion protein of FRB and the Cas family protein; or an expression vector for a fusion protein of FRB and Gag protein and an expression vector for a fusion protein of FKBP12 and the Cas family protein; and
   an expression vector for mRNA having a base sequence of a target RNA or a multiple cloning site, which is interposed between a first ribozyme sequence and a second ribozyme sequence, and a packaging signal sequence.

4. A method for treating diseases caused by genetic mutation, infections, or cancer, comprising:
   administering an effective dose of the virus-like particle according to claim 1 to a patient in need of treatment.

5. A method for manufacturing a virus-like particle encapsulating a Cas family protein and a gRNA, comprising the following (1) and (2):
   (1) letting a cell to express:
      a fusion protein of FKBP12 and Gag protein and a fusion protein of FRB and the Cas family protein, or a fusion protein of FRB and Gag protein and a fusion protein of FKBP12 and a Cas family protein, and
      an mRNA having the gRNA sequence interposed between a first ribozyme sequence and a second ribozyme sequence and a packaging signal sequence in the presence of rapamycin or a rapamycin derivative; and
   (2) obtaining a medium containing the virus-like particle encapsulating the Cas family protein and the gRNA.

6. The method for manufacturing according to claim 5, wherein in (1), a nucleic acid encoding the fusion protein or the mRNA is introduced into the cell by lipofection or electroporation.

\* \* \* \* \*

SEQUENCE LISTING

```
<160> NUMBER OF SEQ ID NOS: 31

<210> SEQ ID NO 1
<211> LENGTH: 533
<212> TYPE: PRT
<213> ORGANISM: Human immunodeficiency virus

<400> SEQUENCE: 1

Gly Ala Ile Lys Ser Lys Arg Lys Asp Asn Leu Asn Asp Asp Glu Arg
1               5                   10                  15

Arg Ala Glu Phe Thr Leu Ala Ala Arg Ala Ser Val Leu Ser Gly Gly
            20                  25                  30

Glu Leu Asp Arg Trp Glu Lys Ile Arg Leu Arg Pro Gly Gly Lys Lys
        35                  40                  45

Lys Tyr Lys Leu Lys His Ile Val Trp Ala Ser Arg Glu Leu Glu Arg
    50                  55                  60

Phe Ala Val Asn Pro Gly Leu Leu Glu Thr Ser Glu Gly Cys Arg Gln
```

```
            65                  70                  75                  80
Ile Leu Gly Gln Leu Gln Pro Ser Leu Gln Thr Gly Ser Glu Glu Leu
                    85                  90                  95

Arg Ser Leu Tyr Asn Thr Val Ala Thr Leu Tyr Cys Val His Gln Arg
                100                 105                 110

Ile Glu Ile Lys Asp Thr Lys Glu Ala Leu Asp Lys Ile Glu Glu Glu
                115                 120                 125

Gln Asn Lys Ser Lys Lys Ala Gln Gln Ala Ala Ala Asp Thr Gly
    130                 135                 140

His Ser Ser Gln Val Ser Gln Asn Tyr Pro Ile Val Gln Asn Ile Gln
145                 150                 155                 160

Gly Gln Met Val His Gln Ala Ile Ser Pro Arg Thr Leu Asn Ala Trp
                165                 170                 175

Val Lys Val Val Glu Glu Lys Ala Phe Ser Pro Glu Val Ile Pro Met
                180                 185                 190

Phe Ser Ala Leu Ser Glu Gly Ala Thr Pro Gln Asp Leu Asn Thr Met
                195                 200                 205

Leu Asn Thr Val Gly Gly His Gln Ala Ala Met Gln Met Leu Lys Glu
    210                 215                 220

Thr Ile Asn Glu Glu Ala Ala Glu Trp Asp Arg Val His Pro Val His
225                 230                 235                 240

Ala Gly Pro Ile Ala Pro Gly Gln Met Arg Glu Pro Arg Gly Ser Asp
                245                 250                 255

Ile Ala Gly Thr Thr Ser Thr Leu Gln Glu Gln Ile Gly Trp Met Thr
                260                 265                 270

Asn Asn Pro Pro Ile Pro Val Gly Glu Ile Tyr Lys Arg Trp Ile Ile
                275                 280                 285

Leu Gly Leu Asn Lys Ile Val Arg Met Tyr Ser Pro Thr Ser Ile Leu
    290                 295                 300

Asp Ile Arg Gln Gly Pro Lys Glu Pro Phe Arg Asp Tyr Val Asp Arg
305                 310                 315                 320

Phe Tyr Lys Thr Leu Arg Ala Glu Gln Ala Ser Gln Glu Val Lys Asn
                325                 330                 335

Trp Met Thr Glu Thr Leu Leu Val Gln Asn Ala Asn Pro Asp Cys Lys
                340                 345                 350

Thr Ile Leu Lys Ala Leu Gly Pro Ala Ala Thr Leu Glu Glu Met Met
                355                 360                 365

Thr Ala Cys Gln Gly Val Gly Gly Pro Gly His Lys Ala Arg Val Leu
    370                 375                 380

Ala Glu Ala Met Ser Gln Val Thr Asn Thr Ala Thr Ile Met Met Gln
385                 390                 395                 400

Arg Gly Asn Phe Arg Asn Gln Arg Lys Met Val Lys Cys Phe Asn Cys
                405                 410                 415

Gly Lys Glu Gly His Thr Ala Arg Asn Cys Arg Ala Pro Arg Lys Lys
                420                 425                 430

Gly Cys Trp Lys Cys Gly Lys Glu Gly His Gln Met Lys Asp Cys Thr
                435                 440                 445

Glu Arg Gln Ala Asn Phe Leu Gly Lys Ile Trp Pro Ser Tyr Lys Gly
    450                 455                 460

Arg Pro Gly Asn Phe Leu Gln Ser Arg Pro Glu Pro Thr Ala Pro Pro
465                 470                 475                 480

Phe Leu Gln Ser Arg Pro Glu Thr Ala Pro Glu Glu Ser Phe
                485                 490                 495
```

Arg Ser Gly Val Glu Thr Thr Thr Pro Pro Gln Lys Gln Glu Pro Ile
            500                 505                 510

Asp Lys Glu Leu Tyr Pro Leu Thr Ser Leu Arg Ser Leu Phe Gly Asn
            515                 520                 525

Asp Pro Ser Ser Gln
            530

<210> SEQ ID NO 2
<211> LENGTH: 538
<212> TYPE: PRT
<213> ORGANISM: Murine leukemia virus

<400> SEQUENCE: 2

Met Gly Gln Thr Val Thr Thr Pro Leu Ser Leu Thr Leu Gly His Trp
1               5                   10                  15

Lys Asp Val Glu Arg Ile Ala His Asn Gln Ser Val Asp Val Lys Lys
            20                  25                  30

Arg Arg Trp Val Thr Phe Cys Ser Ala Glu Trp Pro Thr Phe Asn Val
        35                  40                  45

Gly Trp Pro Arg Asp Gly Thr Phe Asn Arg Asp Leu Ile Thr Gln Val
    50                  55                  60

Lys Ile Lys Val Phe Ser Pro Gly Pro His Gly His Pro Asp Gln Val
65                  70                  75                  80

Pro Tyr Ile Val Thr Trp Glu Ala Leu Ala Phe Asp Pro Pro Pro Trp
                85                  90                  95

Val Lys Pro Phe Val His Pro Lys Pro Pro Pro Leu Pro Pro Ser
            100                 105                 110

Ala Pro Ser Leu Pro Leu Glu Pro Pro Arg Ser Thr Pro Pro Arg Ser
        115                 120                 125

Ser Leu Tyr Pro Ala Leu Thr Pro Ser Leu Gly Ala Lys Pro Lys Pro
    130                 135                 140

Gln Val Leu Ser Asp Ser Gly Gly Pro Leu Ile Asp Leu Leu Thr Glu
145                 150                 155                 160

Asp Pro Pro Pro Tyr Arg Asp Pro Arg Pro Pro Pro Ser Asp Arg Asp
                165                 170                 175

Gly Asn Gly Gly Glu Ala Thr Pro Ala Gly Glu Ala Pro Asp Pro Ser
            180                 185                 190

Pro Met Ala Ser Arg Leu Arg Gly Arg Arg Glu Pro Pro Val Ala Asp
        195                 200                 205

Ser Thr Thr Ser Gln Ala Phe Pro Leu Arg Ala Gly Gly Asn Gly Gln
    210                 215                 220

Leu Gln Tyr Trp Pro Phe Ser Ser Ser Asp Leu Tyr Asn Trp Lys Asn
225                 230                 235                 240

Asn Asn Pro Ser Phe Ser Glu Asp Pro Gly Lys Leu Thr Ala Leu Ile
                245                 250                 255

Glu Ser Val Leu Ile Thr His Gln Pro Thr Trp Asp Asp Cys Gln Gln
            260                 265                 270

Leu Leu Gly Thr Leu Leu Thr Gly Glu Glu Lys Gln Arg Val Leu Leu
        275                 280                 285

Glu Ala Arg Lys Ala Val Arg Gly Asp Asp Gly Arg Pro Thr Gln Leu
    290                 295                 300

Pro Asn Glu Val Asp Ala Ala Phe Pro Leu Glu Arg Pro Asp Trp Asp
305                 310                 315                 320

Tyr Thr Thr Gln Ala Gly Arg Asn His Leu Val His Tyr Arg Gln Leu

-continued

```
                    325                 330                 335
Leu Leu Ala Gly Leu Gln Asn Ala Gly Arg Ser Pro Thr Asn Leu Ala
                340                 345                 350
Lys Val Lys Gly Ile Thr Gln Gly Pro Asn Glu Ser Pro Ser Ala Phe
                355                 360                 365
Leu Glu Arg Leu Lys Glu Ala Tyr Arg Arg Tyr Thr Pro Tyr Asp Pro
            370                 375                 380
Glu Asp Pro Gly Gln Glu Thr Asn Val Ser Met Ser Phe Ile Trp Gln
385                 390                 395                 400
Ser Ala Pro Asp Ile Gly Arg Lys Leu Glu Arg Leu Glu Asp Leu Lys
                405                 410                 415
Asn Lys Thr Leu Gly Asp Leu Val Arg Glu Ala Glu Lys Ile Phe Asn
            420                 425                 430
Lys Arg Glu Thr Pro Glu Glu Arg Glu Glu Arg Ile Arg Arg Glu Thr
                435                 440                 445
Glu Glu Lys Glu Glu Arg Arg Arg Thr Glu Asp Glu Gln Lys Glu Lys
            450                 455                 460
Glu Arg Asp Arg Arg Arg His Arg Glu Met Ser Lys Leu Leu Ala Thr
465                 470                 475                 480
Val Val Ser Gly Gln Lys Gln Asp Arg Gln Gly Gly Glu Arg Arg Arg
                485                 490                 495
Ser Gln Leu Asp Arg Asp Gln Cys Ala Tyr Cys Lys Leu Lys Gly His
            500                 505                 510
Trp Ala Lys Asp Cys Pro Lys Lys Pro Arg Gly Pro Arg Gly Pro Arg
            515                 520                 525
Pro Gln Thr Ser Leu Leu Thr Leu Asp Asp
            530                 535

<210> SEQ ID NO 3
<211> LENGTH: 512
<212> TYPE: PRT
<213> ORGANISM: Vesicular stomatitis virus

<400> SEQUENCE: 3

Met Lys Cys Leu Leu Tyr Leu Ala Phe Leu Phe Ile Gly Val Asn Cys
1               5                   10                  15
Lys Phe Thr Ile Val Phe Pro His Asn Gln Lys Gly Asn Trp Lys Asn
                20                  25                  30
Val Pro Ser Asn Tyr His Tyr Cys Pro Ser Ser Ser Asp Leu Asn Trp
            35                  40                  45
His Asn Asp Leu Ile Gly Thr Ala Leu Gln Val Lys Met Pro Lys Ser
        50                  55                  60
His Lys Ala Ile Gln Ala Asp Gly Trp Met Cys His Ala Ser Lys Trp
65                  70                  75                  80
Val Thr Thr Cys Asp Phe Arg Trp Tyr Gly Pro Lys Tyr Ile Thr His
                85                  90                  95
Ser Ile Arg Ser Phe Thr Pro Ser Val Glu Gln Cys Lys Glu Ser Ile
            100                 105                 110
Glu Gln Thr Lys Gln Gly Thr Trp Leu Asn Pro Gly Phe Pro Pro Gln
            115                 120                 125
Ser Cys Gly Tyr Ala Thr Val Thr Asp Ala Glu Ala Val Ile Val Gln
        130                 135                 140
Val Thr Pro His His Val Leu Val Asp Glu Tyr Thr Gly Glu Trp Val
145                 150                 155                 160
```

-continued

Asp Ser Gln Phe Ile Asn Gly Lys Cys Ser Asn Tyr Ile Cys Pro Thr
            165                 170                 175

Val His Asn Ser Thr Thr Trp His Ser Asp Tyr Lys Val Lys Gly Leu
        180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
        210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
        435                 440                 445

Asn Pro Ile Glu Leu Val Glu Gly Trp Phe Ser Ser Trp Lys Ser Ser
    450                 455                 460

Ile Ala Ser Phe Phe Ile Ile Gly Leu Ile Gly Leu Phe Leu
465                 470                 475                 480

Val Leu Arg Val Gly Ile His Leu Cys Ile Lys Leu Lys His Thr Lys
                485                 490                 495

Lys Arg Gln Ile Tyr Thr Asp Ile Glu Met Asn Arg Leu Gly Lys Leu
            500                 505                 510

<210> SEQ ID NO 4
<211> LENGTH: 1415
<212> TYPE: PRT
<213> ORGANISM: Streptococcus pyogenes

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

```
Lys Val Leu Gly Asn Thr Asp Arg His Ser Ile Lys Lys Asn Leu Ile
    35                  40                  45

Gly Ala Leu Leu Phe Asp Ser Gly Glu Thr Ala Glu Ala Thr Arg Leu
 50                  55                  60

Lys Arg Thr Ala Arg Arg Tyr Thr Arg Arg Lys Asn Arg Ile Cys
 65                  70                  75              80

Tyr Leu Gln Glu Ile Phe Ser Asn Glu Met Ala Lys Val Asp Asp Ser
                 85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
        370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445
```

-continued

```
Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
```

```
                865                 870                 875                 880
Asn Tyr Trp Arg Gln Leu Leu Asn Ala Lys Leu Ile Thr Gln Arg Lys
                    885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275
```

-continued

```
Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ser Gly Lys Arg Pro Ala Ala Thr Lys Lys Ala Gly Gln Ala Lys
    1370                1375                1380

Lys Lys Lys Gly Ser Tyr Pro Tyr Asp Val Pro Asp Tyr Ala Tyr
    1385                1390                1395

Pro Tyr Asp Val Pro Asp Tyr Ala Tyr Pro Tyr Asp Val Pro Asp
    1400                1405                1410

Tyr Ala
    1415

<210> SEQ ID NO 5
<211> LENGTH: 109
<212> TYPE: PRT
<213> ORGANISM: Homo sapiens

<400> SEQUENCE: 5

Ser Arg Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
            20                  25                  30

Glu Asp Gly Lys Lys Phe Asp Ser Ser Arg Asp Arg Asn Lys Pro Phe
        35                  40                  45

Lys Phe Met Leu Gly Lys Gln Glu Val Ile Arg Gly Trp Glu Glu Gly
    50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu
            100                 105

<210> SEQ ID NO 6
<211> LENGTH: 97
<212> TYPE: PRT
<213> ORGANISM: Homo sapiens

<400> SEQUENCE: 6

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60
```

Ala Gln Glu Trp Cys Arg Lys Tyr Met Lys Ser Gly Asn Val Lys Asp
 65                  70                  75                  80

Leu Leu Gln Ala Trp Asp Leu Tyr Tyr His Val Phe Arg Arg Ile Ser
             85                  90                  95

Lys

<210> SEQ ID NO 7
<211> LENGTH: 120
<212> TYPE: DNA
<213> ORGANISM: Human immunodeficiency virus

<400> SEQUENCE: 7
gcaggactcg gcttgctgaa gcgcgcacgg caagaggcga ggggcggcga ctggtgagta    60
cgccaaaaat tttgactagc ggaggctaga aggagagaga tgggtgcgag agcgtcggta   120

<210> SEQ ID NO 8
<211> LENGTH: 558
<212> TYPE: DNA
<213> ORGANISM: Human immunodeficiency virus

<400> SEQUENCE: 8
gcaggactcg gcttgctgaa gcgcgcacgg caagaggcga ggggcggcga ctggtgagta    60
cgccaaaaat tttgactagc ggaggctaga aggagagaga tgggtgcgag agcgtcggta   120
ttaagcgggg gagaattaga taatgggaa aaaattcggt taaggccagg gggaaagaaa   180
caatataaac taaacatat agtatgggca agcagggagc tagaacgatt cgcagttaat   240
cctggccttt tagagacatc agaaggctgt agacaaatac tgggacagct acaaccatcc   300
cttcagacag gatcagaaga acttagatca ttatataata caatagcagt cctctattgt   360
gtgcatcaaa ggatagatgt aaaagacacc aaggaagcct tagataagat agaggaagag   420
caaaacaaaa gtaagaaaaa ggcacagcaa gcagcagctg acacaggaaa caacagccag   480
gtcagccaaa attaccctat agtgcagaac ctccaggggc aaatggtaca tcaggccata   540
tcacctagaa ctttaaat                                                  558

<210> SEQ ID NO 9
<211> LENGTH: 43
<212> TYPE: DNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (1)..(6)
<223> OTHER INFORMATION: n is a, c, g, or t

<400> SEQUENCE: 9
nnnnnnctga tgagtccgtg aggacgaaac gagtaagctc gtc                      43

<210> SEQ ID NO 10
<211> LENGTH: 68
<212> TYPE: DNA
<213> ORGANISM: Hepatitis D virus

<400> SEQUENCE: 10
ggccggcatg gtcccagcct cctcgctggc gccggctggg caacatgctt cggcatggcg    60
aatgggac                                                             68

<210> SEQ ID NO 11

```
<211> LENGTH: 20
<212> TYPE: DNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (1)..(20)
<223> OTHER INFORMATION: n is a, c, g, or t

<400> SEQUENCE: 11
nnnnnnnnnn nnnnnnnnnn                                                  20

<210> SEQ ID NO 12
<211> LENGTH: 42
<212> TYPE: RNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (1)..(20)
<223> OTHER INFORMATION: n is a, c, g, or u

<400> SEQUENCE: 12
nnnnnnnnnn nnnnnnnnnn guuuuagagc uaugcuguuu ug                         42

<210> SEQ ID NO 13
<211> LENGTH: 70
<212> TYPE: RNA
<213> ORGANISM: Artificial Sequence
<220> FEATURE:
<223> OTHER INFORMATION: Synthesized oligonucleotide

<400> SEQUENCE: 13
caaaacagca uagcaaguua aaauaaggcu aguccguuau caacuugaaa aaguggcacc      60
gagucggugc                                                             70

<210> SEQ ID NO 14
<211> LENGTH: 103
<212> TYPE: RNA
<213> ORGANISM: Artificial Sequence
<220> FEATURE:
<223> OTHER INFORMATION: Synthesized oligonucleotide
<220> FEATURE:
<221> NAME/KEY: misc_feature
<222> LOCATION: (1)..(20)
<223> OTHER INFORMATION: n is a, c, g, or u

<400> SEQUENCE: 14
nnnnnnnnnn nnnnnnnnnn guuuuagagc uagaaauagc aaguuaaaau aaggcuaguc      60
cguuaucaac uugaaaaagu ggcaccgagu cggugcuuuu uuu                        103

<210> SEQ ID NO 15
<211> LENGTH: 19
<212> TYPE: DNA
<213> ORGANISM: Homo sapiens

<400> SEQUENCE: 15
ggtatcttac aggaactcc                                                   19

<210> SEQ ID NO 16
<211> LENGTH: 6388
<212> TYPE: DNA
<213> ORGANISM: Artificial Sequence
<220> FEATURE:
<223> OTHER INFORMATION: Synthesized vector
```

<400> SEQUENCE: 16

```
gaaaagtgcc acctgacgtc gctagcgttt aaacccgggc gatcgctcta gattgtctca      60
tgagcggata catatttgaa tgtatttaga aaataaaca aatagggtt ccgcgcacat       120
ttccccgaaa agtgccacct gggactagct ttttgcaaaa gcctaggcct ccaaaaaagc     180
ctcctcacta cttctggaat agctcagagg ccgaggcggc ctcggcctct gcataaataa     240
aaaaaattag tcagccatgg ggcggagaat gggcggaact gggcggagtt aggggcggga    300
tgggcggagt taggggcggg actatggttg ctgactaatt gagatgagct tgcatgccga    360
cattgattat tgactagtcc ctaagaaacc attcttatca tgacattaac ctataaaaat    420
aggcgtatca cgaggcctag actagtgcgg ccgctgcaga agctttgcaa agatggataa    480
agttttaaac agagaggaat ctttgcagct aatggacctt ctaggtcttg aaaggagtgg    540
gaattggctc cggtgcccgt cagtgggcag agcgcacatc gcccacagtc cccgagaagt    600
tggggggagg ggtcggcaat tgaaccggtg cctagagaag gtggcgcggg gtaaactggg    660
aaagtgatgt cgtgtactgg ctccgccttt ttcccgaggg tgggggagaa ccgtatataa    720
gtgcagtagt cgccgtgaac gttcttttc gcaacgggtt tgccgccaga acacaggtaa    780
gtgccgtgtg tggttcccgc gggcctggcc tctttacggg ttatggccct tgcgtgcctt    840
gaattacttc cacgccctg gctgcagtac gtgattcttg atcccgagct tcgggttgga    900
agtgggtggg agagttcgag gccttgcgct taaggagccc cttcgcctcg tgcttgagtt    960
gaggcctggc ctgggcgctg gggccgccgc gtgcgaatct ggtggcacct tcgcgcctgt   1020
ctcgctgctt tcgataagtc tctagccatt taaaattttt gatgacctgc tgcgacgctt   1080
tttttctggc aagatagtct tgtaaatgcg ggccaagatc tgcacactgg tatttcggtt   1140
tttgggccg cgggcggcga cggggcccgt gcgtcccagc gcacatgttc ggcgaggcgg   1200
ggcctgcgag cgcggccacc gagaatcgga cgggggtagt ctcaagctgg ccggcctgct   1260
ctggtgcctg gcctcgcgcc gccgtgtatc gccccgccct gggcggcaag gctggcccgg   1320
tcggcaccag ttgcgtgagc ggaaagatgg ccgcttcccg gccctgctgc agggagctca   1380
aaatggagga cgcggcgctc gggagagcgg gcgggtgagt cacccacaca aaggaaaagg   1440
gcctttccgt cctcagccgt cgcttcatgt gactccacgg agtaccgggc gccgtccagg   1500
cacctcgatt agttctcgag cttttggagt acgtcgtctt taggttgggg ggagggggttt   1560
tatgcgatgg agtttcccca cactgagtgg gtggagactg aagttaggcc agcttggcac   1620
ttgatgtaat tctccttgga atttgccctt tttgagtttg gatcttggtt cattctcaag   1680
cctcagacag tggttcaaag ttttttttctt ccatttcagg tgtcgtgaga attagcggtg   1740
gcggccatca caagtttgta caaaaaagca ggctggcgcc ggaaccaatt cagtcgactg   1800
gatccggtac cgaattcgcg gcccgaattg ccaccatggg agctattaaa tcaaaaagga   1860
aagacgatcc accggcatct agaggagtgc aggtggaaac catctcccca ggagacgggc   1920
gcaccttccc caagcgcggc cagacctgcg tggtgcacta caccgggatg cttgaagatg   1980
gaaagaaatt tgattcctcc cgggacagaa acaagccctt taagtttatg ctaggcaagc   2040
aggaggtgat ccgaggctgg gaagaagggg ttgcccagat gagtgtgggt cagagagcca   2100
aactgactat atctccagat tatgcctatg gtgccactgg gcacccaggc atcatcccac   2160
cacatgccac tctcgtcttc gatgtggagc ttcaaaact ggaactggcc gcagggcca   2220
gcgtgctgag cggcggcgag ctggacaggt gggagaagat caggctgagg cccggcggca   2280
```

```
agaagaagta taagctgaag cacatcgtgt gggccagcag ggagctggag aggttcgccg    2340
tgaaccccgg cctgctggag accagcgagg gctgcaggca gatcctgggc cagctgcagc    2400
ccagcctgca gaccggcagc gaggagctga ggagcctgta caacaccgtg ccaccctgt     2460 actgcgtgca ccagaggatc gagatcaagg acaccaagga ggccctggac aagatcgagg    2520
aggagcagaa caagtccaag aagaaggccc agcaggccgc cgccgacacc ggccacagca    2580
gccaggtgag ccagaactac cccatcgtgc agaacatcca gggccagatg gtgcaccagg    2640
ccatcagccc caggaccctg aacgcctggg tgaaggtggt ggaggagaag gccttcagcc    2700
ccgaggtgat ccccatgttc agcgccctga gcgagggagc cacccccccag gacctgaaca    2760 ccatgctgaa caccgtgggc ggccaccagg ccgccatgca gatgctgaag gagaccatca    2820
acgaggaggc cgccgagtgg gacagggtgc accccgtgca cgccggcccc atcgccccg     2880 gccagatgag ggagccccgc ggcagcgaca tcgccggcac caccagcacc ctgcaggagc    2940
agatcggctg gatgaccaac aaccccccca tccccgtggg cgaaatctac aagaggtgga    3000
tcatcctggg cctgaacaag atcgtgagga tgtacagccc caccagcatc ctggatatca    3060
ggcagggccc caaagagccc ttcagggact acgtggacag gttctacaag accctgcgcg    3120
ccgagcaggc cagccaggag gtgaagaact ggatgaccga ccctgctg gtgcagaacg      3180 ccaacccga ctgcaagacc atcctgaagg ccctgggacc cgccgccacc ctggaggaga    3240
tgatgaccgc ctgccaggc gtgggcggcc ccggccacaa ggccagggtg ctggccgagg    3300
ccatgagcca ggtgaccaac accgccacca tcatgatgca gaggggcaac ttcaggaacc    3360
agaggaagat ggtgaagtgc ttcaactgcg gcaaggaggg ccacaccgcc aggaactgcc    3420
gcgcccccag gaagaagggc tgctggaagt gcggcaagga gggccaccag atgaaggact    3480
gcaccgagag gcaggctaat ttttaggga agatctggcc ttcctacaag ggaaggccag    3540
ggaattttct tcagagcaga ccagagccaa cagcccccacc atttcttcag agcagaccag    3600
agccaacagc cccaccagaa gagagcttca ggtctgggt agagacaaca actcccctc      3660 agaagcagga gccgatagac aaggaactgt atcctttaac ttccctcaga tcactctttg    3720
gcaacgaccc ctcgtcacaa tgatcgagat atctagaccc agctttcttg tacaaagtgg    3780
tgatctagct aaaacgcggc ctcgaatcga attcgattcg aatgtacaga tctggatcct    3840
aggcttaagt atacctcgag ttaaattcac tcctcaggtg caggctgcct atcagaaggt    3900
ggtggctggt gtggccaatg ccctggctca caaataccac tgagatcttt ttccctctgc    3960
caaaaattat ggggacatca tgaagccct tgagcatctg acttctggct aataaaggaa     4020 atttatttc attgcaatag tgtgttggaa ttttttgtgt ctctcactcg aaggacata      4080 tgggagggca aatcatttaa acatcagaa tgagtatttg gtttagagtt tggcaacata     4140
tgcccatatg ctggctgcca tgaacaaagg ttggctataa agaggtcatc agtatatgaa    4200 acagcccct gctgtccatt ccttattcca tagaaaagcc ttgacttgag gttagatttt     4260 tttatattt tgttttgtgt tatttttttc tttaacatcc ctaaaatttt ccttacatgt    4320
tttactagcc agattttcc tcctctcctg actactccca gtcatagctg tccctcttct    4380
cttatggaga tccctcgact taattaaacc ggtcagctgc attaatgaat cggccaacgc    4440
gcggggagag gcggtttgcg tattgggcgc tcttccgctt cctcgctcac tgactcgctg    4500
cgctcggtcg ttcggctgcg gcgagcggta tcagctcact caaaggcggt aatacggtta    4560
tccacagaat caggggataa cgcaggaaag aacatgtgag caaaaggcca gcaaaaggcc    4620
aggaaccgta aaaaggccgc gttgctggcg ttttttccata ggctccgccc ccctgacgag    4680
```

| | |
|---|---:|
| catcacaaaa atcgacgctc aagtcagagg tggcgaaacc cgacaggact ataaagatac | 4740 |
| caggcgtttc ccctggaag ctccctcgtg cgctctcctg ttccgaccct gccgcttacc | 4800 |
| ggatacctgt ccgcctttct cccttcggga agcgtggcgc tttctcatag ctcacgctgt | 4860 |
| aggtatctca gttcggtgta ggtcgttcgc tccaagctgg gctgtgtgca cgaaccccc | 4920 |
| gttcagcccg accgctgcgc cttatccggt aactatcgtc ttgagtccaa cccggtaaga | 4980 |
| cacgacttat cgccactggc agcagccact ggtaacagga ttagcagagc gaggtatgta | 5040 |
| ggcggtgcta cagagttctt gaagtggtgg cctaactacg gctacactag aagaacagta | 5100 |
| tttggtatct gcgctctgct gaagccagtt accttcggaa aaagagttgg tagctcttga | 5160 |
| tccggcaaac aaaccaccgc tggtagcggt ggtttttttg tttgcaagca gcagattacg | 5220 |
| cgcagaaaaa aaggatctca agaagatcct ttgatctttt ctacggggtc tgacgctcag | 5280 |
| tggaacgaaa actcacgtta agggattttg gtcatgagat tatcaaaaag gatcttcacc | 5340 |
| tagatccttt taaattaaaa atgaagtttt aaatcaatct aaagtatata tgagtaaact | 5400 |
| tggtctgaca gttaccaatg cttaatcagt gaggcaccta tctcagcgat ctgtctattt | 5460 |
| cgttcatcca tagttgcctg actccccgtc gtgtagataa ctacgatacg ggagggctta | 5520 |
| ccatctggcc ccagtgctgc aatgataccg cgagacccac gctcaccggc tccagattta | 5580 |
| tcagcaataa accagccagc cggaagggcc gagcgcagaa gtggtcctgc aactttatcc | 5640 |
| gcctccatcc agtctattaa ttgttgccgg gaagctagag taagtagttc gccagttaat | 5700 |
| agtttgcgca acgttgttgc cattgctaca ggcatcgtgg tgtcacgctc gtcgtttggt | 5760 |
| atggcttcat tcagctccgg ttcccaacga tcaaggcgag ttacatgatc ccccatgttg | 5820 |
| tgcaaaaaag cggttagctc cttcggtcct ccgatcgttg tcagaagtaa gttggccgca | 5880 |
| gtgttatcac tcatggttat ggcagcactg cataattctc ttactgtcat gccatccgta | 5940 |
| agatgctttt ctgtgactgg tgagtactca accaagtcat tctgagaata gtgtatgcgg | 6000 |
| cgaccgagtt gctcttgccc ggcgtcaata cgggataata ccgcgccaca tagcagaact | 6060 |
| ttaaaagtgc tcatcattgg aaaacgttct cggggcgaaa actctcaag gatcttaccg | 6120 |
| ctgttgagat ccagttcgat gtaacccact cgtgcaccca actgatcttc agcatctttt | 6180 |
| actttcacca gcgtttctgg gtgagcaaaa acaggaaggc aaaatgccgc aaaaaaggga | 6240 |
| ataagggcga cacggaaatg ttgaatactc atactcttcc tttttcaata ttattgaagc | 6300 |
| atttatcagg gttattgtct catgagcgga tacatatttg aatgtattta gaaaaataaa | 6360 |
| caaatagggg ttccgcgcac atttcccc | 6388 |

<210> SEQ ID NO 17
<211> LENGTH: 9010
<212> TYPE: DNA
<213> ORGANISM: Artificial Sequence
<220> FEATURE:
<223> OTHER INFORMATION: Synthesized vector

<400> SEQUENCE: 17

| | |
|---|---:|
| gaaaagtgcc acctgacgtc gctagcgttt aaacccgggc gatcgctcta gattgtctca | 60 |
| tgagcggata catatttgaa tgtatttaga aaaataaaca aataggggtt ccgcgcacat | 120 |
| ttccccgaaa agtgccacct gggactagct ttttgcaaaa gcctaggcct ccaaaaaagc | 180 |
| ctcctcacta cttctggaat agctcagagg ccgaggcggc ctcggcctct gcataaataa | 240 |
| aaaaaattag tcagccatgg ggcggagaat gggcggaact gggcggagtt aggggcggga | 300 |

```
tgggcggagt taggggcggg actatggttg ctgactaatt gagatgagct tgcatgccga    360
cattgattat tgactagtcc ctaagaaacc attcttatca tgacattaac ctataaaaat    420
aggcgtatca cgaggcctag actagtgcgg ccgctgcaga agctttgcaa agatggataa    480
agttttaaac agagaggaat ctttgcagct aatggacctt ctaggtcttg aaaggagtgg    540
gaattggctc cggtgcccgt cagtgggcag agcgcacatc gcccacagtc cccgagaagt    600 tgggggggagg ggtcggcaat tgaaccggtg cctagagaag gtggcgcggg gtaaactggg    660
aaagtgatgt cgtgtactgg ctccgccttt ttcccgaggg tgggggagaa ccgtatataa    720
gtgcagtagt cgccgtgaac gttcttttc gcaacgggtt tgccgccaga acacaggtaa     780
gtgccgtgtg tggttcccgc gggcctggcc tctttacggg ttatggccct tgcgtgcctt    840
gaattacttc cacgccctg gctgcagtac gtgattcttg atcccgagct tcgggttgga     900
agtgggtggg agagttcgag gccttgcgct taaggagccc cttcgcctcg tgcttgagtt    960
gaggcctggc ctgggcgctg gggccgccgc gtgcgaatct ggtggcacct tcgcgcctgt    1020
ctcgctgctt tcgataagtc tctagccatt taaaattttt gatgacctgc tgcgacgctt    1080
tttttctggc aagatagtct tgtaaatgcg ggccaagatc tgcacactgg tatttcggtt    1140
tttggggccg cgggcggcga cggggcccgt gcgtcccagc gcacatgttc ggcgaggcgg    1200
ggcctgcgag cgcggccacc gagaatcgga cggggtagt ctcaagctgg ccggcctgct     1260
ctggtgcctg gcctcgcgcc gccgtgtatc gccccgccct gggcggcaag gctggcccgg    1320
tcggcaccag ttgcgtgagc ggaaagatgg ccgcttcccg gccctgctgc agggagctca    1380
aaatggagga cgcggcgctc gggagagcgg gcgggtgagt cacccacaca aaggaaaagg    1440
gcctttccgt cctcagccgt cgcttcatgt gactccacgg agtaccgggc gccgtccagg    1500
cacctcgatt agttctcgag cttttggagt acgtcgtctt taggttgggg ggaggggttt    1560
tatgcgatgg agtttcccca cactgagtgg gtggagactg aagttaggcc agcttggcac    1620
ttgatgtaat tctccttgga atttgccctt tttgagtttg gatcttggtt cattctcaag    1680
cctcagacag tggttcaaag ttttttttctt ccatttcagg tgtcgtgaga attagcggtg    1740
gcggccatca caagtttgta caaaaaagca ggctgtcgag ccgccaccat ggcttctaga    1800
atcctctggc atgagatgtg gcatgaaggc ctggaagagg catctcgttt gtactttggg    1860
gaaaggaacg tgaaaggcat gtttgaggtg ctggagccct tgcatgctat gatgaacgg     1920 ggcccccaga ctctgaagga acatcctttt aatcaggcct atggtcgaga tttaatggag    1980
gcccaagagt ggtgcaggaa gtacatgaaa tcagggaatg tcaaggacct cctccaagcc    2040
tgggacctct attatcatgt gttccgacga atctcaaagt cgaccatgga taagaaatac    2100
agcattggac tggacattgg gacaaactcc gtgggatggg ccgtgattac agacgaatac    2160
aaagtgcctt caaagaagtt caaggtgctg ggcaacaccg atagacacag catcaagaaa    2220
aatctgattg gagccctgct gttcgactcc ggcgagacag ctgaagcaac tcggctgaaa    2280
agaactgctc ggagaaggta tacccgccga aagaatagga tctgctacct gcaggagatt    2340
ttcagcaacg aaatggccaa ggtggacgat agtttctttc accgcctgga ggaatcattc    2400
ctggtcgagg aagataagaa acacgagcgg catcccatct tggcaacat tgtgacgag     2460 gtcgcttatc acgaaaagta ccctaccatc tatcatctga ggaagaaact ggtggactcc    2520
acagataaag cagacctgcg cctgatctat ctggccctgg ctcacatgat taagttccgg    2580
ggccattttc tgatcgaggg ggatctgaac ccagacaatt ctgatgtgga caagctgttc    2640
atccagctgg tccagacata caatcagctg tttgaggaaa accccattaa tgcatctggc    2700
```

```
gtggacgcaa aagccatcct gagtgccaga ctgtctaaga gtcggagact ggagaacctg    2760
atcgctcagc tgccagggga aaagaaaaac ggcctgtttg gaatctgat  tgcactgtca    2820 ctggactga  ctcccaactt caagagcaat tttgatctgg ccgaggacgc taaactgcag    2880
ctgtccaagg acacctatga cgatgacctg gataacctgc tggctcagat cggggatcag    2940
tacgcagacc tgttcctggc cgctaagaat ctgtctgacg ccatcctgct gagtgatatt    3000
ctgcgcgtga acaccgagat tacaaaagcc ccctgtcag  ctagcatgat caagagatat    3060
gacgagcacc atcaggatct gaccctgctg aaggctctgg tgaggcagca gctgcctgag    3120
aagtacaagg aaatcttctt tgatcagtct aagaacggat acgccggcta tattgacggc    3180
ggggctagtc aggaggagtt ctacaagttt atcaaaccca ttctggagaa gatggatggc    3240
acagaggaac tgctggtgaa actgaatcgg aagacctgc  tgaggaagca gcgcactttt    3300
gataacggaa gcatccctca ccagattcat ctgggagagc tgcacgcaat cctgaggcgc    3360
caggaagact tctacccatt tctgaaggat aacaggaga  gatcgaaaaa aattctgaca    3420
ttccgcatcc cctactatgt gggccctctg caagaggca  acagccggtt tgcctggatg    3480
actcgcaaat ctgaggaaac aatcactccc tggaacttcg aggaagtggt cgataagggc    3540
gcttccgcac agtctttcat tgagcggatg acaaacttcg acaagaacct gccaaacgaa    3600
aaagtgctgc ccaagcactc tctgctgtac gagtatttca cagtctataa cgaactgact    3660
aaggtgaaat acgtcaccga ggggatgaga aagcctgcct tcctgagtgg agaacagaag    3720
aaagctatcg tggacctgct gtttaaaacc aataggaagg tgacagtcaa gcagctgaaa    3780
gaggactatt tcaagaaaat tgaatgtttc gattctgtgg agatcagtgg cgtcgaagac    3840
aggtttaacg cctccctggg gacctaccac gatctgctga agatcattaa ggataaagac    3900
ttcctggaca acgaggaaaa tgaggatatc ctggaagaca ttgtgctgac cctgacactg    3960
tttgaggata gggaaatgat cgaggaacgc ctgaagacct atgcccatct gttcgatgac    4020
aaagtgatga acagctgaa  gcgacggaga tacacaggat ggggccgact gtctcggaag    4080
ctgatcaatg ggattcgcga caaacagagt ggaaagacca tcctggactt tctgaaatca    4140
gatggcttcg ccaaccggaa cttcatgcag ctgattcacg atgacagcct gacattcaaa    4200
gaggatatcc agaaggcaca ggtgtccggg cagggagact ctctgcacga gcatatcgca    4260
aacctggccg gcagccctgc catcaagaaa gggattctgc agaccgtgaa ggtggtggac    4320
gagctggtga agtcatggg  aagacataag ccagaaaaca tcgtgattga gatggccagg    4380
gaaaatcaga ccacacagaa aggccagaag aactcaaggg agcgcatgaa aagaatcgag    4440
gaaggaatta aggaactggg cagccagatc ctgaaagagc accccgtgga aaacacacag    4500
ctgcagaatg agaagctgta tctgtactat ctgcagaatg gacgcgatat gtacgtggac    4560
caggagctgg atattaaccg actgtccgat tacgacgtgg atcatatcgt cccacagtca    4620
ttcctgaaag atgacagcat tgacaataag gtgctgaccc gctctgacaa aaaccgaggc    4680
aagagtgata atgtcccctc agaggaagtg gtcaagaaaa tgaagaacta ctggaggcag    4740
ctgctgaatg ccaaactgat cacacagcga aagtttgata acctgactaa agctgagcgg    4800
ggaggcctga gtgaactgga caaagcaggc ttcattaagc gacagctggt ggagacacgg    4860
cagatcacaa agcacgtcgc ccagattctg gattcaagaa tgaacactaa gtacgatgag    4920
aatgacaaac tgatcagaga agtgaaggtc attaccctga agtcaaaact ggtgagcgac    4980
tttcggaaag atttccagtt ttataaggtc agagagatca acaactacca ccatgctcat    5040
```

```
gacgcatacc tgaacgcagt ggtcggcaca gccctgatta agaaataccc taaactggag    5100
tccgagttcg tgtacgggga ctataaggtg tacgatgtca gaaaaatgat cgccaagtct    5160
gagcaggaaa ttggcaaagc cactgctaag tatttctttt acagtaacat catgaatttc    5220
tttaagactg agatcaccct ggcaaatggg gaaatccgaa agcggccact gattgagact    5280
aacggcgaga caggagaaat cgtgtgggac aaaggaagag attttgctac cgtgaggaag    5340
gtcctgagca tgccccaagt gaatattgtc aagaaaacag aggtgcagac tgggggattc    5400
agtaaggaat caattctgcc taaacgcaac tccgataagc tgatcgcccg aaagaaagac    5460
tgggacccca agaagtatgg cgggttcgac tccccaactg tggcttactc tgtcctggtg    5520
gtcgcaaagg tggagaaggg aaaaagcaag aaactgaaat ccgtcaagga actgctgggc    5580
atcaccatta tggagcgcag ctccttcgaa aagaatccta tcgattttct ggaggccaaa    5640
ggctataagg aagtgaagaa agacctgatc atcaagctgc caaagtactc actgtttgag    5700
ctggaaaacg ggagaaagag gatgctggca agcgccgggg agctgcagaa aggaaatgaa    5760
ctggccctgc cctccaagta cgtgaacttc ctgtatctgg ctagccacta cgagaagctg    5820
aaagggtccc ctgaggataa cgaacagaaa cagctgtttg tggagcagca caagcattat    5880
ctggacgaga tcattgaaca gattagcgag ttctccaaaa gagtgatcct ggctgacgca    5940
aatctggata aggtcctgag cgcatacaac aaacaccggg ataagccaat cagagagcag    6000
gccgaaaata tcattcatct gttcactctg accaacctgg gagcccccgc agccttcaag    6060
tattttgaca ctaccatcga tcgcaaacga tacacaagca taaggaggt gctggacgct    6120 accctgattc atcagagcat tactggcctg tatgaaacaa ggattgacct gtctcagctg    6180
ggcggcgact ccggaaaaag gccggcggcc acgaaaaagg ccggccaggc aaaaaagaaa    6240
aagggatcct acccatacga tgttccagat tacgcttacc catacgatgt tccagattac    6300
gcttacccat acgatgttcc agattacgct taatccggag ctgacccaa gaagaagagg    6360 aaggtgtgag acctctagac ccagctttct tgtacaaagt ggtgatctag ctaaaacgcg    6420
gcctcgaatc gaattcgatt cgaatgtaca gatctggatc ctaggcttaa gtatacctcg    6480
agttaaattc actcctcagg tgcaggctgc ctatcagaag gtggtggctg gtgtggccaa    6540
tgccctggct cacaaatacc actgagatct ttttccctct gccaaaaatt atggggacat    6600
catgaagccc cttgagcatc tgacttctgg ctaataaagg aaatttattt tcattgcaat    6660
agtgtgttgg aattttttgt gtctctcact cggaaggaca tatgggaggg caaatcattt    6720
aaaacatcag aatgagtatt tggtttagag tttggcaaca tatgcccata tgctggctgc    6780
catgaacaaa ggttggctat aaagaggtca tcagtatatg aaacagcccc tgctgtccca    6840
ttccttattc catagaaaag ccttgacttg aggttagatt ttttttatat tttgttttgt    6900
gttatttttt tctttaacat ccctaaaatt tccttacat gttttactag ccagattttt    6960
cctcctctcc tgactactcc cagtcatagc tgtccctctt ctcttatgga gatccctcga    7020
cttaattaaa ccggtcagct gcattaatga atcggccaac gcgcggggag aggcggtttg    7080
cgtattgggc gctcttccgc ttcctcgctc actgactcgc tgcgctcggt cgttcggctg    7140
cggcgagcgg tatcagctca ctcaaaggcg gtaatacggt tatccacaga atcagggat    7200 aacgcaggaa agaacatgtg agcaaaaggc cagcaaaagg ccaggaaccg taaaaaggcc    7260
gcgttgctgg cgtttttcca taggctccgc cccctgacg agcatcacaa aaatcgacgc    7320
tcaagtcaga ggtggcgaaa cccgacagga ctataaagat accaggcgtt ccccctggaa    7380 gctccctcg tgcgctctcc tgttccgacc ctgccgctta ccggatacct gtccgccttt    7440
```

| | |
|---|---:|
| ctcccttcgg gaagcgtggc gctttctcat agctcacgct gtaggtatct cagttcggtg | 7500 |
| taggtcgttc gctccaagct gggctgtgtg cacgaacccc ccgttcagcc cgaccgctgc | 7560 |
| gccttatccg gtaactatcg tcttgagtcc aacccggtaa gacacgactt atcgccactg | 7620 |
| gcagcagcca ctggtaacag gattagcaga gcgaggtatg taggcggtgc tacagagttc | 7680 |
| ttgaagtggt ggcctaacta cggctacact agaagaacag tatttggtat ctgcgctctg | 7740 |
| ctgaagccag ttaccttcgg aaaaagagtt ggtagctctt gatccggcaa acaaaccacc | 7800 |
| gctggtagcg gtggtttttt tgtttgcaag cagcagatta cgcgcagaaa aaaggatct | 7860 |
| caagaagatc ctttgatctt ttctacgggg tctgacgctc agtggaacga aaactcacgt | 7920 |
| taagggattt tggtcatgag attatcaaaa aggatcttca cctagatcct tttaaattaa | 7980 |
| aaatgaagtt ttaaatcaat ctaaagtata tatgagtaaa cttggtctga cagttaccaa | 8040 |
| tgcttaatca gtgaggcacc tatctcagcg atctgtctat ttcgttcatc catagttgcc | 8100 |
| tgactccccg tcgtgtagat aactacgata cgggagggct taccatctgg ccccagtgct | 8160 |
| gcaatgatac cgcgagaccc acgctcaccg gctccagatt tatcagcaat aaaccagcca | 8220 |
| gccggaaggg ccgagcgcag aagtggtcct gcaactttat ccgcctccat ccagtctatt | 8280 |
| aattgttgcc gggaagctag agtaagtagt tcgccagtta atagtttgcg caacgttgtt | 8340 |
| gccattgcta caggcatcgt ggtgtcacgc tcgtcgtttg gtatggcttc attcagctcc | 8400 |
| ggttcccaac gatcaaggcg agttacatga tcccccatgt tgtgcaaaaa agcggttagc | 8460 |
| tccttcggtc ctccgatcgt tgtcagaagt aagttggccg cagtgttatc actcatggtt | 8520 |
| atggcagcac tgcataattc tcttactgtc atgccatccg taagatgctt ttctgtgact | 8580 |
| ggtgagtact caaccaagtc attctgagaa tagtgtatgc ggcgaccgag ttgctcttgc | 8640 |
| ccggcgtcaa tacgggataa taccgcgcca catagcagaa ctttaaaagt gctcatcatt | 8700 |
| ggaaaacgtt cttcggggcg aaaactctca aggatcttac cgctgttgag atccagttcg | 8760 |
| atgtaaccca ctcgtgcacc caactgatct tcagcatctt ttactttcac cagcgtttct | 8820 |
| gggtgagcaa aaacaggaag gcaaaatgcc gcaaaaaagg gaataagggc gacacggaaa | 8880 |
| tgttgaatac tcatactctt cctttttcaa tattattgaa gcatttatca gggttattgt | 8940 |
| ctcatgagcg gatacatatt tgaatgtatt tagaaaaata aacaaatagg ggttccgcgc | 9000 |
| acatttcccc | 9010 |

<210> SEQ ID NO 18
<211> LENGTH: 6284
<212> TYPE: DNA
<213> ORGANISM: Artificial Sequence
<220> FEATURE:
<223> OTHER INFORMATION: Synthesized vecter

<400> SEQUENCE: 18

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt gcggccgctg aagggctaa | 420 |

-continued

```
tttggtccca aaaaagacaa gagatccttg atctgtggat ctaccacaca caaggctact    480
tccctgattg gcagaactac acaccagggc cagggatcag atatccactg acctttggat    540
ggtgcttcaa gttagtacca gttgaaccag agcaagtaga agaggccaaa taaggagaga    600
agaacagctt gttacaccct atgagccagc atgggatgga ggacccggag ggagaagtat    660
tagtgtggaa gtttgacagc ctcctagcat ttcgtcacat ggcccgagag ctgcatccgg    720
agtactacaa agactgctga catcgagctt tctacaaggg actttccgct ggggactttc    780
cagggaggtg tggcctgggc gggactgggg agtggcgagc cctcagatgc tacatataag    840
cagctgcttt ttgcctgtac tgggtctctc tggttagacc agatctgagc ctgggagctc    900
tctggctaac tagggaaccc actgcttaag cctcaataaa gcttgccttg agtgctcaaa    960
gtagtgtgtg cccgtctgtt gtgtgactct ggtaactaga gatccctcag acccttttag   1020
tcagtgtgga aaatctctag cagtggcgcc cgaacaggga cttgaaagcg aaagtaaagc   1080
cagaggagat ctctcgacgc aggactcggc ttgctgaagc gcgcacggca agaggcgagg   1140
ggcggcgact ggtgagtacg ccaaaaattt tgactagcgg aggctagaag agagagatg    1200 ggtgcgagag cgtcggtatt aagcggggga gaattagata aatgggaaaa aattcggtta   1260
aggccagggg gaaagaaaca atataaacta aaacatatag tatgggcaag cagggagcta   1320
gaacgattcg cagttaatcc tggccttta gagacatcag aaggctgtag acaaatactg    1380
ggacagctac aaccatccct tcagacagga tcagaagaac ttagatcatt atataataca   1440
atagcagtcc tctattgtgt gcatcaaagg atagatgtaa aagacaccaa ggaagcctta   1500
gataagatag aggaagagca aaacaaaagt aagaaaaagg cacagcaagc agcagctgac   1560
acaggaaaca acagccaggt cagccaaaat taccctatag tgcagaacct ccaggggcaa   1620
atggtacatc aggccatatc acctagaact ttaaattaag acagcagtac aaatggcagt   1680
attcatccac aattttaaaa gaaaaggggg gattgggggg tacagtgcag gggaagaat   1740 agtagacata atagcaacag acatacaaac taaagaatta caaaaacaaa ttacaaaaat   1800
tcaaaatttt cgggtttatt acagggacag cagagatcca gtttggaaag gaccagcaaa   1860
gctcctctgg aaaggtgaag gggcagtagt aatacaagat aatagtgaca taaaagtagt   1920
gccaagaaga aaagcaaaga tcatcaggga ttatggaaaa cagatggcag gtgatgattg   1980
tgtggcaagt agacaggatg aggattaaca catggaaaag attagtaaaa caccatagct   2040
ctagagcgat ccgatcttca gacctggagg aggcgatatg agggacaatt acaagtttgt   2100
acaaaaaagc aggctggcgc cggaaccaat tcagtcgact ggatccggta ccgaattcgc   2160
ggccataccc ctgatgagtc cgtgaggacg aaacgagtaa gctcgtcggg tatcttacag   2220
gaactccgtt ttagagctat gctggaaaca gcatagcaag ttaaaataag gctagtccgt   2280
tatcaacttg aaaaagtggc accgagtcgg tgcttttttt ttggccggca tggtcccagc   2340
ctcctcgctg gcgccggctg gcaacatgc ttcggcatgg cgaatgggac ggccgctcta   2400
gaactagtgg atcccccgcc accatggccc tgtccaacaa gttcatcggc gacgacatga   2460
agatgaccta ccacatggac ggctgcgtga acggccacta cttcaccgtg aagggcgagg   2520
gcagcggcaa gccctacgag ggcacccaga cctccacctt caaggtgacc atggccaacg   2580 gcggcccct ggccttctcc ttcgacatcc tgtccaccgt gttcatgtac ggcaaccgct   2640
gcttcaccgc ctaccccacc agcatgcccg actacttcaa gcaggccttc cccgacggca   2700
tgtcctacga gagaaccttc acctacgagg acggcggcgt ggccaccgcc agctgggaga   2760
tcagcctgaa gggcaactgc ttcgagcaca gtccaccctt ccacggcgtg aacttccccg   2820
```

```
ccgacggccc cgtgatggcc aagaagacca ccggctggga cccctccttc gagaagatga    2880
ccgtgtgcga cggcatcttg aagggcgacg tgaccgcctt cctgatgctg cagggcggcg    2940
gcaactacag atgccagttc cacacctcct acaagaccaa gaagcccgtg accatgcccc    3000
ccaaccacgt ggtggagcac cgcatcgcca gaaccgacct ggacaagggc ggcaacagcg    3060
tgcagctgac cgagcacgcc gtggcccaca tcacctccgt ggtgcccttc tgagggctgc    3120
aggaattcga tatcaagctt atcgataccg tcgacctcga gatatctaga cccagctttc    3180
ttgtacaaag tggtgatcta gctaaaacgc ggcctcgaat cgaattcgat tcgaatgtac    3240
agatctggat cctaggctta agtatacctc gagttaaatt cactcctcag gtgcaggctg    3300
cctatcagaa ggtggtggct ggtgtggcca atgccctggc tcacaaatac cactgagatc    3360
tttttccctc tgccaaaaat tatggggaca tcatgaagcc ccttgagcat ctgacttctg    3420
gctaataaag gaaatttatt ttcattgcaa tagtgtgttg aattttttg tgtctctcac    3480 tcggaaggac atatgggagg gcaaatcatt taaaacatca gaatgagtat ttggtttaga    3540
gtttggcaac atatgcccat atgctggctg ccatgaacaa aggttggcta taagaggtc    3600 atcagtatat gaaacagccc cctgctgtcc attccttatt ccatagaaaa gccttgactt    3660
gaggttagat ttttttata ttttgttttg tgttatttt tctttaaca tccctaaaat    3720 tttccttaca tgttttacta gccagatttt tcctcctctc ctgactactc ccagtcatag    3780
ctgtccctct tctcttatgg agatcaattc tagcttggcg taatcatggt catagctgtt    3840
cctgtgtgaa attgttatcc gctcacaatt ccacacaaca tacgagccgg aagcataaag    3900
tgtaaagcct ggggtgccta atgagtgagc taactcacat taattgcgtt gcgctcactg    3960
cccgctttcc agtcgggaaa cctgtcgtgc cagctgcatt aatgaatcgg ccaacgcgcg    4020
gggagaggcg gtttgcgtat tgggcgctct tccgcttcct cgctcactga ctcgctgcgc    4080
tcggtcgttc ggctgcggcg agcggtatca gctcactcaa aggcggtaat acggttatcc    4140
acagaatcag gggataacgc aggaaagaac atgtgagcaa aaggccagca aaaggccagg    4200
aaccgtaaaa aggccgcgtt gctggcgttt ttccataggc tccgcccccc tgacgagcat    4260
cacaaaaatc gacgctcaag tcagaggtgg cgaaacccga caggactata aagataccag    4320
gcgtttcccc ctggaagctc cctcgtgcgc tctcctgttc cgaccctgcc gcttaccgga    4380
tacctgtccg cctttctccc ttcgggaagc gtggcgcttt ctcaatgctc acgctgtagg    4440
tatctcagtt cggtgtaggt cgttcgctcc aagctgggct gtgtgcacga accccccgtt    4500
cagcccgacc gctgcgcctt atccggtaac tatcgtcttg agtccaaccc ggtaagacac    4560
gacttatcgc cactggcagc agccactggt aacaggatta gcagagcgag gtatgtaggc    4620
ggtgctacag agttcttgaa gtggtggcct aactacggct acactagaag gacagtattt    4680
ggtatctgcg ctctgctgaa gccacttacc ttcggaaaaa gagttggtag ctcttgatcc    4740
ggcaaacaaa ccaccgctgg tagcggtggt ttttttgttt gcaagcagca gattacgcgc    4800
agaaaaaaag gatctcaaga agatcctttg atcttttcta cggggtctga cgctcagtgg    4860
aacgaaaact cacgttaagg gattttggtc atgagattat caaaaaggat cttcacctag    4920
atccttttaa attaaaaatg aagttttaaa tcaatctaaa gtatatatga gtaaacttgg    4980
tctgacagtt accaatgctt aatcagtgag gcacctatct cagcgatctg tctatttcgt    5040
tcatccatag ttgcctgact ccccgtcgtg tagataacta cgatacggga gggcttacca    5100
tctggcccca gtgctgcaat gataccgcga gacccacgct caccggctcc agatttatca    5160
```

| | |
|---|---|
| gcaataaacc agccagccgg aagggccgag cgcagaagtg gtcctgcaac tttatccgcc | 5220 |
| tccatccagt ctattaattg ttgccgggaa gctagagtaa gtagttcgcc agttaatagt | 5280 |
| ttgcgcaacg ttgtgccatt gctacaggca tcgtggtgtc acgctcgtcg tttggtatgg | 5340 |
| cttcattcag ctccggttcc caacgatcaa ggcgagttac atgatccccc atgttgtgca | 5400 |
| aaaaagcggt tagctccttc ggtcctccga tcgttgtcag aagtaagttg gccgcagtgt | 5460 |
| tatcactcat ggttatggca gcactgcata attctcttac tgtcatgcca tccgtaagat | 5520 |
| gcttttctgt gactggtgag tactcaacca agtcattctg agaatagtgt atgcggcgac | 5580 |
| cgagttgctc ttgcccggcg tcaatacggg ataataccgc gccacatagc agaactttaa | 5640 |
| aagtgctcat cattggaaaa cgttcttcgg ggcgaaaact ctcaaggatc ttaccgctgt | 5700 |
| tgagatccag ttcgatgtaa cccactcgtg cacccaactg atcttcagca tcttttactt | 5760 |
| tcaccagcgt ttctgggtga gcaaaaacag gaaggcaaaa tgccgcaaaa aagggaataa | 5820 |
| gggcgacacg gaaatgttga atactcatac tcttcctttt tcaatattat tgaagcattt | 5880 |
| atcagggtta ttgtctcatg agcggataca tatttgaatg tatttagaaa aataaacaaa | 5940 |
| taggggttcc gcgcacattt ccccgaaaag tgccacctgg gactagcttt ttgcaaaagc | 6000 |
| ctaggcctcc aaaaaagcct cctcactact tctggaatag ctcagaggcc gaggcggcct | 6060 |
| cggcctctgc ataaataaaa aaaattagtc agccatgggg cggagaatgg gcggaactgg | 6120 |
| gcggagttag gggcgggatg gcggagtta ggggcgggac tatggttgct gactaattga | 6180 |
| gatgtagctt gcatgccgac atggattatt gactagtccc taagaaacca ttattatcat | 6240 |
| gacattaacc tataaaaata ggcgtatcac gaggccctttt cgtc | 6284 |

<210> SEQ ID NO 19
<211> LENGTH: 5133
<212> TYPE: DNA
<213> ORGANISM: Artificial Sequence
<220> FEATURE:
<223> OTHER INFORMATION: Synthesized vector

<400> SEQUENCE: 19

| | |
|---|---|
| acattgatta ttgactagtt attaatagta atcaattacg gggtcattag ttcatagccc | 60 |
| atatatggag ttccgcgtta cataacttac ggtaaatggc ccgcctggct gaccgcccaa | 120 |
| cgacccccgc ccattgacgt caataatgac gtatgttccc atagtaacgc caatagggac | 180 |
| tttccattga cgtcaatggg tggactattt acggtaaact gcccacttgg cagtacatca | 240 |
| agtgtatcat atgccaagta cgccccctat tgacgtcaat gacggtaaat ggcccgcctg | 300 |
| gcattatgcc cagtacatga ccttatggga ctttcctact tggcagtaca tctacgtatt | 360 |
| agtcatcgct attaccatgg tgatgcggtt ttggcagtac atcaatgggc gtggatagcg | 420 |
| gtttgactca cggggatttc caagtctcca ccccattgac gtcaatggga gtttgttttg | 480 |
| gcaccaaaat caacgggact ttccaaaatg tcgtaacaac tccgccccat tgacgcaaat | 540 |
| gggcggtagg cgtgtacggt gggaggtcta tataagcaga gctctctggc taactagaga | 600 |
| acccactgct tactggctta tcgaaattaa tacgactcac tatagggaga cccaagcttg | 660 |
| tcgacatagc agaataggcg ttactcaaca gaggagagca agaaatggag ccagtagatc | 720 |
| ctagactaga gccctggaag catccaggaa gtcagcctaa aactgcttgt accacttgct | 780 |
| attgtaaaaa gtgttgcttt cattgccaag tttgtttcac aacaaaagcc ttaggcatct | 840 |
| cctatgcag gaagaagcgg agacagcgac gaagacctcc tcaaggcagt cagactcatc | 900 |
| aagtttctct atcaaagcag taagtagtac atgtaatgca acctatacaa atagcaatag | 960 |

-continued

```
cagcattagt agtagcaata ataatagcaa tagttgtgtg gtccggatcc actagtaacg     1020
gccgccagtg tgctggaatt ctgcagatat ccatcacact ggcggccgct cgagcatgca     1080
tctagagggc cctattctat agtgtcacct aaatgctaga ggatctttgt gaaggaacct     1140
tacttctgtg gtgtgacata attggacaaa ctacctacag agatttaaag ctctaaggta     1200
aatataaaat ttttaagtgt ataatgtgtt aaactactga ttctaattgt ttgtgtattt     1260
tagattccaa cctatggaac tgatgaatgg gagcagtggt ggaatgcctt taatgaggaa     1320
aacctgtttt gctcagaaga aatgccatct agtgatgatg aggctactgc tgactctcaa     1380
cattctactc ctccaaaaaa gaagagaaag gtagaagacc ccaaggactt ccttcagaa      1440 ttgctaagtt ttttgagtca tgctgtgttt agtaatagaa ctcttgcttg ctttgctatt     1500
tacaccacaa aggaaaaagc tgcactgcta taagaaaaa ttatggaaaa atatttgatg      1560
tatagtgcct tgactagaga tcataatcag ccataccaca tttgtagagg ttttacttgc     1620
tttaaaaaac ctcccacacc tcccctgaa cctgaaacat aaaatgaatg caattgttgt      1680
tgttaacttg tttattgcag cttataatgg ttacaaataa agcaatagca tcacaaattt     1740
cacaaataaa gcattttttt cactgcattc tagttgtggt ttgtccaaac tcatcaatgt     1800
atcttatcat gtctggatca tcccgccatg gtatcaacgc catatttcta tttacagtag     1860
ggacctcttc gttgtgtagg taccgctgta ttcctaggga aatagtagag gcaccttgaa     1920
ctgtctgcat cagccatata gccccgctg ttcgacttac aaacacaggc acagtactga      1980
caaacccata cacctcctct gaaatacccca tagttgctag ggctgtctcc gaactcatta    2040
caccctccaa agtcagagct gtaatttcgc catcaagggc agcgagggct tctccagata    2100
aaatagcttc tgccgagagt cccgtaaggg tagacacttc agctaatccc tcgatgaggt    2160
ctactagaat agtcagtgcg gctcccattt tgaaaattca cttacttgat cagcttcaga    2220
agatggcgga gggcctccaa cacagtaatt ttcctcccga ctcttaaaat agaaaatgtc    2280
aagtcagtta agcaggaagt ggactaactg acgcagctgg ccgtgcgaca tcctctttta    2340
attagttgct aggcaacgcc ctccagaggg cgtgtggttt tgcaagagga agcaaaagcc    2400
tctccaccca ggcctagaat gtttccaccc aatcattact atgacaacag ctgtttttt     2460 tagtattaag cagaggccgg ggaccctgg gcccgcttac tctggagaaa agaagagag      2520 gcattgtaga ggcttccaga ggcaacttgt caaaacagga ctgcttctat ttctgtcaca    2580
ctgtctggcc ctgtcacaag gtccagcacc tccatacccc ctttaataag cagtttggga    2640
acgggtgcgg gtcttactcc gcccatcccg cccctaactc cgcccagttc cgcccattct    2700
ccgccccatg gctgactaat ttttttatt tatgcagagg ccgaggccgc ctcggcctct    2760
gagctattcc agaagtagtg aggaggcttt tttggaggcc taggcttttg caaaaagcta    2820
attcggcgta atctgctgct tgcaaacaaa aaaccaccg ctaccagcgg tggtttgttt     2880
gccggatcaa gagctaccaa ctctttttcc gaaggtaact ggcttcagca gagcgcagat    2940
accaaatact gtccttctag tgtagccgta gttaggccac acttcaaga actctgtagc     3000 accgcctaca tacctcgctc tgctaatcct gttaccagtg ctgctgcca gtggcgataa    3060 gtcgtgtctt accgggttgg actcaagacg atagttaccg gataaggcgc agcggtcggg    3120
ctgaacgggg ggttcgtgca cacagcccag cttggagcga acgacctaca ccgaactgag    3180
atacctacag cgtgagcatt gagaaagcgc cacgcttccc gaaggagaa aggcggacag     3240 gtatccggta agcggcaggg tcggaacagg agagcgcacg agggagcttc caggggaa     3300
```

```
cgcctggtat ctttatagtc ctgtcgggtt tcgccacctc tgacttgagc gtcgattttt    3360
gtgatgctcg tcaggggggc ggagcctatg gaaaaacgcc agcaacgcaa gctagcttct    3420
agctagaaat tgtaaacgtt aatattttgt taaaattcgc gttaaatttt tgttaaatca    3480
gctcattttt taaccaatag gccgaaatcg gcaaaatccc ttataaatca aaagaatagc    3540
ccgagatagg gttgagtgtt gttccagttt ggaacaagag tccactatta agaacgtgg    3600
actccaacgt caaagggcga aaaccgtct atcagggcga tggccgccca ctacgtgaac    3660
catcacccaa atcaagtttt tggggtcga ggtgccgtaa agcactaaat cggaaccct a    3720
aagggagccc ccgatttaga gcttgacggg gaaagccggc gaacgtggcg agaaaggaag    3780
ggaagaaagc gaaaggagcg ggcgctaggg cgctggcaag tgtagcggtc acgctgcgcg    3840
taaccaccac acccgccgcg cttaatgcgc cgctacaggg cgcgtactat ggttgctttg    3900
acgagcacgt ataacgtgct ttcctcgttg gaatcagagc gggagctaaa caggaggccg    3960
attaaaggga tttagacag gaacggtacg ccagctggac ccgaaagggc ctcgtgatac    4020
gcctattttt ataggttaat gtcatgataa taatggtttc ttagacgtca ggtggcactt    4080
ttcggggaaa tgtgcgcgga acccctattt gtttattttt ctaaatacat tcaaatatgt    4140
atccgctcat gagacaataa ccctgataaa tgcttcaata atattgaaaa aggaagagta    4200
tgagtattca acatttccgt gtcgccctta ttccctttt tgcggcattt tgccttcctg    4260
tttttgctca cccagaaacg ctggtgaaag taaaagatgc tgaagatcag ttgggtgcac    4320
gagtgggtta catcgaactg gatctcaaca gcggtaagat ccttgagagt tttcgccccg    4380
aagaacgttt tccaatgatg agcacttta aagttctgct atgtggcgcg gtattatccc    4440
gtgttgacgc cgggcaagag caactcggtc gccgcataca ctattctcag aatgacttgg    4500
ttgagtactc accagtcaca gaaaagcatc ttacggatgg catgacagta agagaattat    4560
gcagtgctgc cataaccatg agtgataaca ctgcggccaa cttacttctg acaacgatcg    4620
gaggaccgaa ggagctaacc gcttttttgc acaacatggg ggatcatgta actcgccttg    4680
atcgttggga accggagctg aatgaagcca taccaaacga cgagcgtgac accacgatgc    4740
ctgcagcaat ggcaacaacg ttgcgcaaac tattaactgg cgaactactt actctagctt    4800
cccggcaaca attaatagac tggatggagg cggataaagt tgcaggacca cttctgcgct    4860
cggcccttcc ggctggctgg tttattgctg ataaatctgg agccggtgag cgtgggtctc    4920
gcggtatcat tgcagcactg gggccagatg gtaagccctc ccgtatcgta gttatctaca    4980
cgacggggag tcaggcaact atggatgaac gaaatagaca gatcgctgag ataggtgcct    5040
cactgattaa gcattggtaa ctgtcagacc aagtttactc atatatactt tagattgatt    5100
taaaacttca tttttaattt ctctagcgcg ttg                                 5133
```

<210> SEQ ID NO 20
<211> LENGTH: 6508
<212> TYPE: DNA
<213> ORGANISM: Artificial Sequence
<220> FEATURE:
<223> OTHER INFORMATION: Synthesized vector

<400> SEQUENCE: 20

```
gcggccgctc tagagagctt ggcccattgc atacgttgta tccatatcat aatatgtaca      60
tttatattgg ctcatgtcca acattaccgc catgttgaca ttgattattg actagttatt     120
aatagtaatc aattacgggg tcattagttc atagcccata tatggagttc cgcgttacat     180
aacttacggt aaatggcccg cctggctgac cgcccaacga cccccgccca ttgacgtcaa     240
```

```
taatgacgta tgttcccata gtaacgccaa tagggacttt ccattgacgt caatgggtgg    300
agtatttacg gtaaactgcc cacttggcag tacatcaagt gtatcatatg ccaagtacgc    360
cccctattga cgtcaatgac ggtaaatggc ccgcctggca ttatgcccag tacatgacct    420
tatgggactt tcctacttgg cagtacatct acgtattagt catcgctatt accatggtga    480
tgcggttttg gcagtacatc aatgggcgtg gatagcggtt tgactcacgg ggatttccaa    540
gtctccaccc cattgacgtc aatgggagtt tgttttggca ccaaaatcaa cgggactttc    600
caaaatgtcg taacaactcc gccccattga cgcaaatggg cggtaggcgt gtacggtggg    660
aggtctatat aagcagagct cgtttagtga accgtcagat cgcctggaga cgccatccac    720
gctgttttga cctccataga agacaccggg accgatccag cctccggtcg accgatcctg    780
agaacttcag ggtgagtttg ggacccttga ttgttctttc tttttcgct  attgtaaaat    840 tcatgttata tggaggggc aaagttttca gggtgttgtt tagaatggga agatgtccct    900
tgtatcacca tggaccctca tgataatttt gtttctttca ctttctactc tgttgacaac    960
cattgtctcc tcttattttc ttttcatttt ctgtaacttt ttcgttaaac tttagcttgc   1020
atttgtaacg aatttttaaa ttcacttttg tttatttgtc agattgtaag tactttctct   1080
aatcactttt ttttcaaggc aatcagggta tattatattg tacttcagca cagttttaga   1140
gaacaattgt tataattaaa tgataaggta gaatatttct gcatataaat tctggctggc   1200
gtggaaatat tcttattggt agaaacaact acaccctggt catcatcctg cctttctctt   1260
tatggttaca atgatataca ctgtttgaga tgaggataaa atactctgag tccaaaccgg   1320
gcccctctgc taaccatgtt catgccttct tctctttcct acagctcctg gcaacgtgc    1380 tggttgttgt gctgtctcat cattttggca aagaattcct cgacggatcc ctcgaggaat   1440
tctgacacta tgaagtgcct tttgtactta gcctttttat tcattgggt gaattgcaag    1500 ttcaccatag ttttccaca caaccaaaaa ggaaactgga aaaatgttcc ttctaattac    1560
cattattgcc cgtcaagctc agatttaaat tggcataatg acttaatagg cacagcctta   1620
caagtcaaaa tgcccaagag tcacaaggct attcaagcag acggttggat gtgtcatgct   1680
tccaaatggg tcactacttg tgatttccgc tggtatggac cgaagtatat aacacattcc   1740
atccgatcct tcactccatc tgtagaacaa tgcaaggaaa gcattgaaca acgaaacaa    1800 ggaacttggc tgaatccagg cttccctcct caaagttgtg gatatgcaac tgtgacggat   1860
gccgaagcag tgattgtcca ggtgactcct caccatgtgc tggttgatga atacacagga   1920
gaatgggttg attcacagtt catcaacgga aaatgcagca attacatatg ccccactgtc   1980
cataactcta caacctggca ttctgactat aaggtcaaag gctatgtga ttctaacctc    2040 atttccatgg acatcacctt cttctcagag acggagagc tatcatccct gggaaaggag   2100
ggcacagggt tcagaagtaa ctactttgct tatgaaactg gaggcaaggc ctgcaaaatg   2160
caatactgca agcattgggg agtcagactc ccatcaggtg tctggttcga gatggctgat   2220
aaggatctct ttgctgcagc cagattccct gaatgcccag aagggtcaag tatctctgct   2280
ccatctcaga cctcagtgga tgtaagtcta attcaggacg ttgagaggat cttggattat   2340
tccctctgcc aagaaacctg gagcaaaatc agagcgggtc ttccaatctc tccagtggat   2400
ctcagctatc ttgctcctaa aaacccagga accggtcctg ctttcaccat aatcaatggt   2460
accctaaaat actttgagac cagatacatc agagtcgata ttgctgctcc aatcctctca   2520
agaatggtcg gaatgatcag tggaactacc acagaaaggg aactgtggga tgactgggca   2580
```

```
ccatatgaag acgtggaaat tggacccaat ggagttctga ggaccagttc aggatataag    2640
tttcctttat acatgattgg acatggtatg ttggactccg atcttcatct tagctcaaag    2700
gctcaggtgt tcgaacatcc tcacattcaa gacgctgctt cgcaacttcc tgatgatgag    2760
agtttatttt ttggtgatac tgggctatcc aaaaatccaa tcgagcttgt agaaggttgg    2820
ttcagtagtt ggaaaagctc tattgcctct ttttctttta tcatagggtt aatcattgga    2880
ctattcttgg ttctccgagt tggtatccat ctttgcatta aattaaagca caccaagaaa    2940
agacagattt atacagacat agagatgaac cgacttggaa agtaactcaa atcctgcaca    3000
acagattctt catgtttgga ccaaatcaac ttgtgatacc atgctcaaag aggcctcaat    3060
tatatttgag tttttaattt ttatgaaaaa aaaaaaaaa aacggaattc ctcgagggat    3120
ccgtcgagga attcactcct caggtgcagg ctgcctatca gaaggtggtg ctggtgtgg    3180 ccaatgccct ggctcacaaa taccactgag atctttttcc ctctgccaaa aattatgggg    3240
acatcatgaa gcccccttgag catctgactt ctggctaata aaggaaattt attttcattg    3300
caatagtgtg ttggaatttt ttgtgtctct cactcggaag gacatatggg agggcaaatc    3360
atttaaaaca tcagaatgag tatttggttt agagtttggc aacatatgcc catatgctgg    3420
ctgccatgaa caaaggttgg ctataaagag gtcatcagta tatgaaacag cccccctgctg    3480 tccattcctt attccataga aaagccttga cttgaggtta gattttttt atattttgtt    3540 ttgtgttatt ttttctttta acatccctaa aattttcctt acatgtttta ctagccagat    3600
ttttcctcct ctcctgacta ctcccagtca tagctgtccc tcttctctta tggagatccc    3660
tcgacggatc ggccgcaatt cgtaatcatg tcatagctgt ttcctgtgtg aaattgttat    3720
ccgctcacaa ttccacacaa catacgagcc ggaagcataa agtgtaaagc ctggggtgcc    3780
taatgagtga gctaactcac attaattgcg ttgcgctcac tgcccgcttt ccagtcggga    3840
aacctgtcgt gccagctgca ttaatgaatc ggccaacgcg cggggagagg cggtttgcgt    3900
attgggcgct cttccgcttc ctcgctcact gactcgctgc gctcggtcgt tcggctgcgg    3960
cgagcggtat cagctcactc aaaggcggta atacggttat ccacagaatc aggggataac    4020
gcaggaaaga acatgtgagc aaaaggccag caaaaggcca ggaaccgtaa aaaggccgcg    4080
ttgctggcgt ttttccatag gctccgcccc cctgacgagc atcacaaaaa tcgacgctca    4140
agtcagaggt ggcgaaaccc gacaggacta taaagatacc aggcgtttcc ccctggaagc    4200
tccctcgtgc gctctcctgt tccgaccctg ccgcttaccg gatacctgtc cgcctttctc    4260
ccttcgggaa gcgtggcgct ttctcatagc tcacgctgta ggtatctcag ttcggtgtag    4320
gtcgttcgct ccaagctggg ctgtgtgcac gaaccccccg ttcagcccga ccgctgcgcc    4380
ttatccggta actatcgtct tgagtccaac ccggtaagac acgacttatc gccactggca    4440
gcagccactg gtaacaggat tagcagagcg aggtatgtag gcggtgctac agagttcttg    4500
aagtggtggc ctaactacgg ctacactaga agaacagtat ttggtatctg cgctctgctg    4560
aagccagtta ccttcggaaa aagagttggt agctcttgat ccggcaaaca aaccaccgct    4620
ggtagcggtg gtttttttgt ttgcaagcag cagattacgc gcagaaaaaa aggatctcaa    4680
gaagatcctt tgatcttttc tacggggtct gacgctcagt ggaacgaaaa ctcacgttaa    4740
gggattttgg tcatgagatt atcaaaaagg atcttcacct agatcctttt aaattaaaaa    4800
tgaagtttta aatcaatcta agtatatat gagtaaactt ggtctgacag ttaccaatgc    4860
ttaatcagtg aggcacctat ctcagcgatc tgtctatttc gttcatccat agttgcctga    4920
ctccccgtcg tgtagataac tacgatacgg gagggcttac catctggccc cagtgctgca    4980
```

```
atgataccgc gagacccacg ctcaccggct ccagatttat cagcaataaa ccagccagcc      5040
ggaagggccg agcgcagaag tggtcctgca actttatccg cctccatcca gtctattaat      5100
tgttgccggg aagctagagt aagtagttcg ccagttaata gtttgcgcaa cgttgttgcc      5160
attgctacag gcatcgtggt gtcacgctcg tcgtttggta tggcttcatt cagctccggt      5220
tcccaacgat caaggcgagt tacatgatcc cccatgttgt gcaaaaaagc gggttagctc      5280
cttcggtcct ccgatcgttg tcagaagtaa gttggccgca gtgttatcac tcatggttat      5340
ggcagcactg cataattctc ttactgtcat gccatccgta agatgctttt ctgtgactgg      5400
tgagtactca accaagtcat tctgagaata gtgtatgcgg cgaccgagtt gctcttgccc      5460
ggcgtcaata cgggataata ccgcgccaca tagcagaact ttaaaagtgc tcatcattgg      5520
aaaacgttct cggggcgaaa actctcaag gatcttaccg ctgttgagat ccagttcgat       5580
gtaacccact cgtgcaccca actgatcttc agcatctttt actttcacca gcgtttctgg      5640
gtgagcaaaa acaggaaggc aaaatgccgc aaaaaaggga ataagggcga cacggaaatg      5700
ttgaatactc atactcttcc ttttcaata ttattgaagc atttatcagg gttattgtct        5760
catgagcgga tacatatttg aatgtattta gaaaaataaa caataggggg ttccgcgcac      5820
atttccccga aaagtgccac ctaaattgta agcgttaata ttttgttaaa attcgcgtta      5880
aatttttgtt aaatcagctc atttttttaac caataggccg aaatcggcaa atcccttat      5940 aaatcaaaag aatagaccga gataggggttg agtgttgttc cagtttggaa caagagtcca     6000
ctattaaaga acgtggactc caacgtcaaa gggcgaaaaa ccgtctatca gggcgatggc      6060
ccactacgtg aaccatcacc ctaatcaagt tttttggggt cgaggtgccg taaagcacta      6120
aatcggaacc ctaaagggag cccccgattt agagcttgac ggggaaagcc ggcgaacgtg      6180
gcgagaaagg aagggaagaa agcgaaagga gcgggcgcta gggcgctggc aagtgtagcg      6240
gtcacgctgc gcgtaaccac cacacccgcc gcgcttaatg cgccgctaca gggcgcgtcc      6300
cattcgccat tcaggctgcg caactgttgg gaagggcgat cggtgcgggc ctcttcgcta      6360
ttacgccagc tggcgaaagg gggatgtgct gcaaggcgat taagttgggt aacgccaggg      6420
ttttcccagt cacgacgttg taaaacgacg gccagtgagc gcgcgtaata cgactcacta      6480
tagggcgaat tggagctcca ccgcggtg                                          6508
```

<210> SEQ ID NO 21
<211> LENGTH: 7194
<212> TYPE: DNA
<213> ORGANISM: Artificial Sequence
<220> FEATURE:
<223> OTHER INFORMATION: Synthesized reporter construct

<400> SEQUENCE: 21

```
gaaaagtgcc acctgacgtc atctgttaac attatacgcg tttaacccta gaaagataat        60
catattgtga cgtacgttaa agataatcat gcgtaaaatt gacgcatgtg ttttatcggt       120
ctgtatatcg aggtttattt attaatttga atagatatta agttttatta tatttacact       180
tacatactaa taataaattc aacaaacaat ttatttatgt ttatttattt attaaaaaaa       240
aacaaaaact caaatttct tctataaagt aacaaaactt ttaaacattc tctcttttac        300
aaaaataaac ttattttgta ctttaaaaac agtcatgttg tattataaaa taagtaatta      360
gcttaaccta tacataatag aaacaaatta tacttattag tcagtcagaa acaactttgg     420
cacatatcaa tattatgctc tgctagcgtt taaacccggg cgatcgctct agactagtgc      480
```

```
ggccgctgca gaagctttgc aaagatggat aaagttttaa acagagagga atctttgcag    540
ctaatggacc ttctaggtct tgaaaggagt gggaattggc tccggtgccc gtcagtgggc    600
agagcgcaca tcgcccacag tccccgagaa gttgggggga ggggtcggca attgaaccgg    660
tgcctagaga aggtggcgcg gggtaaactg ggaaagtgat gtcgtgtact ggctccgcct    720
ttttcccgag ggtgggggag aaccgtatat aagtgcagta gtcgccgtga acgttctttt    780
tcgcaacggg tttgccgcca gaacacaggt aagtgccgtg tgtggttccc gcgggcctgg    840
cctctttacg ggttatggcc cttgcgtgcc ttgaattact tccacgcccc tggctgcagt    900
acgtgattct tgatcccgag cttcgggttg gaagtgggtg ggagagttcg aggccttgcg    960
cttaaggagc cccttcgcct cgtgcttgag ttgaggcctg gcctgggcgc tggggccgcc   1020
gcgtgcgaat ctggtggcac cttcgcgcct gtctcgctgc tttcgataag tctctagcca   1080
tttaaaattt ttgatgacct gctgcgacgc ttttttttctg gcaagatagt cttgtaaatg   1140
cgggccaaga tctgcacact ggtatttcgg ttttggggc cgcgggcggc gacggggccc   1200
gtgcgtccca gcgcacatgt tcggcgaggc ggggcctgcg agcgcggcca ccgagaatcg   1260
gacgggggta gtctcaagct ggccggcctg ctctggtgcc tggcctcgcg ccgccgtgta   1320
tcgccccgcc ctgggcggca aggctggccc ggtcggcacc agttgcgtga gcggaaagat   1380
ggccgcttcc cggccctgct gcagggagct caaaatggag gacgcggcgc tcggagagc   1440 gggcgggtga gtcacccaca caaggaaaa gggccttttcc gtcctcagcc gtcgcttcat   1500
gtgactccac ggagtaccgg gcgccgtcca ggcacctcga ttagttctcg agcttttgga   1560
gtacgtcgtc tttaggttgg ggggagggt tttatgcgat ggagtttccc cacactgagt   1620
gggtggagac tgaagttagg ccagcttggc acttgatgta attctccttg gaatttgccc   1680
tttttgagtt tggatcttgg ttcattctca agcctcagac agtggttcaa agtttttttc   1740
ttccatttca ggtgtcgtga gaattagcgg tggcggccat cacaagtttg tacaaaaaag   1800
caggctggcg ccggaaccaa ttcagtcgac ggtaccgcgg gcccgggatc caccggtcgc   1860
caccatggtg agcaagggcg aggagctgtt caccggggtg gtgcccatcc tggtcgagct   1920
ggacggcgac gtaaacggcc acaagttcag cgtgtccggc gagggcgagg gcgatgccac   1980
ctacggcaag ctgaccctga agttcatctg caccaccggc aagctgcccg tgccctggcc   2040
caccctcgtg accaccctga cctacggcgt gcagtgcttc agccgctacc ccgaccacat   2100
gaagcgccac gacttcttca agtccgccat gcccgaaggc tacgtccagg agcgcaccat   2160
cttcttcaag gacgacggca actacaagac ccgcgccgag gtgaagttcg agggcgacac   2220
cctggtgaac cgcatcgagc tgaagggcat cgacttcaag gaggacggca acatcctggg   2280
gcacaagctg gagtacaact acaacagcca caacgtctat atcatggccg acaagcagta   2340
gggtctctgt cgtgcctttt tggtatctta caggaactcc aggatggcat tgggcagcgg   2400
caaactgttg tcagaacatg gtaccgtgag acctagagga gcgcaccatc ttcttcaagg   2460
acgacggcaa ctacaagacc cgcgccgagg tgaagttcga gggcgacacc ctggtgaacc   2520
gcatcgagct gaagggcatc gacttcaagg aggacggcaa catcctgggg cacaagctgg   2580
agtacaacta caacagccac aacgtctata tcatggccga caagcagaag aacggcatca   2640
aggtgaactt caagacccgc cacaacatcg aggacggcag cgtgcagctc gccgaccact   2700
accagcagaa caccccatc ggcgacggcc ccgtgctgct gcccgacaac cactacctga   2760
gcacccagtc cgccctgagc aaagacccca acgagaagcg cgatcacatg gtcctgctgg   2820
agttcgtgac cgccgccggg atcactctcg gcatggacga gctgtacaag taaagcggcc   2880
```

```
gcactcgaga tatctagacc cagctttctt gtacaaagtg gtgatctagc taaaacgcgg      2940
cctcgaatcg aattccgccc ccccccctct ccctcccccc cccctaacgt tactggccga      3000
agccgcttgg aataaggccg gtgtgcgttt gtctatatgt tattttccac catattgccg      3060
tcttttggca atgtgagggc ccggaaacct ggccctgtct tcttgacgag cattcctagg      3120
ggtctttccc ctctcgccaa aggaatgcaa ggtctgttga atgtcgtgaa ggaagcagtt      3180
cctctggaag cttcttgaag acaaacaacg tctgtagcga cccttttgcag gcagcggaac     3240
cccccacctg gcgacaggtg cctctgcggc caaaagccac gtgtataaga tacacctgca      3300
aaggcggcac aaccccagtg ccacgttgtg agttggatag ttgtggaaag agtcaaatgg      3360
ctctcctcaa gcgtattcaa caaggggctg aaggatgccc agaaggtacc ccattgtatg      3420
ggatctgatc tggggcctcg gtgcacatgc tttacatgtg tttagtcgag gttaaaaaaa      3480
cgtctaggcc ccccgaacca cggggacgtg gttttccttt gaaaaacacg atgataatat      3540
ggccacaacc atgaccgagt acaagcccac ggtgcgcctc gccacccgcg acgacgtccc      3600
cagggccgta cgcacccctcg ccgccgcgtt cgccgactac cccgccacgc gccacaccgt     3660
cgatccggac cgccacatcg agcgggtcac cgagctgcaa gaactcttcc tcacgcgcgt      3720
cgggctcgac atcggcaagg tgtgggtcgc ggacgacggc gccgcggtgg cggtctggac      3780
cacgccggag agcgtcgaag cggggcggt gttcgccgag atcggcccgc gcatggccga       3840
gttgagcggt tcccggctgg ccgcgcagca acagatggaa ggcctcctgg cgccgcaccg      3900
gcccaaggag cccgcgtggt tcctggccac cgtcggcgtc tcgcccgacc accagggcaa      3960
gggtctgggc agcgccgtcg tgctccccgg agtggaggcg gccgagcgcg ccggggtgcc      4020
cgccttcctg gagacctccg cgccccgcaa cctcccccttc tacgagcggc tcggcttcac     4080
cgtcaccgcc gacgtcgagg tgcccgaagg accgcgcacc tggtgcatga cccgcaagcc     4140
cggtgcctga cgcccgcccc acgacccgca gcgcccgacc gaaaggagcg cacgacccca     4200
tgcatcgatt cgaatgtaca gatctggatc ctaggcttaa gtatacctcg agttaaattc      4260
actcctcagg tgcaggctgc ctatcagaag gtggtggctg gtgtggccaa tgccctggct      4320
cacaaatacc actgagatct ttttccctct gccaaaaatt atggggacat catgaagccc      4380
cttgagcatc tgacttctgg ctaataaagg aaatttatttt tcattgcaat agtgtgttgg     4440
aatttttttgt gtctctcact cggaaggaca tatgggaggg caaatcattt aaaacatcag     4500
aatgagtatt tggtttagag tttggcaaca tatgcccata tgctggctgc catgaacaaa      4560
ggttggctat aaagaggtca tcagtatatg aaacagcccc ctgctgtcca ttccttattc      4620
catagaaaag ccttgacttg aggttagatt tttttttatat tttgttttgt gttattttt      4680
tctttaacat ccctaaaatt ttccttacat gttttactag ccagatttt cctcctctcc       4740
tgactactcc cagtcatagc tgtccctctt ctcttatgga gatccctcga cttaattaac      4800
caacaagctc gtcatcgctt tgcagaagag cagagaggat atgctcatcg tctaaagaac      4860
tacccatttt attatatatt agtcacgata tctataacaa gaaatatat atataataag       4920
ttatcacgta agtagaacat gaaataacaa tataattatc gtatgagtta aatcttaaaa      4980
gtcacgtaaa agataatcat gcgtcatttt gactcacgcg gtcgttatag ttcaaaatca      5040
gtgacactta ccgcattgac aagcacgcct cacgggagct ccaagcggcg actgagatgt      5100
cctaaatgca cagcgacgga ttcgcgctat ttagaaagag agagcaatat ttcaagaatg      5160
catgcgtcaa ttttacgcag actatctttc tagggttaat acgtataata catatgattc      5220
```

| | |
|---|---|
| agctgcatta atgaatcggc caacgcgcgg ggagaggcgg tttgcgtatt gggcgctctt | 5280 |
| ccgcttcctc gctcactgac tcgctgcgct cggtcgttcg gctgcggcga gcggtatcag | 5340 |
| ctcactcaaa ggcggtaata cggttatcca cagaatcagg ggataacgca ggaaagaaca | 5400 |
| tgtgagcaaa aggccagcaa aaggccagga accgtaaaaa ggccgcgttg ctggcgtttt | 5460 |
| tccataggct ccgccccect gacgagcatc acaaaaatcg acgctcaagt cagaggtggc | 5520 |
| gaaacccgac aggactataa agataccagg cgtttccccc tggaagctcc ctcgtgcgct | 5580 |
| ctcctgttcc gaccctgccg cttaccggat acctgtccgc ctttctccct tcgggaagcg | 5640 |
| tggcgctttc tcatagctca cgctgtaggt atctcagttc ggtgtaggtc gttcgctcca | 5700 |
| agctgggctg tgtgcacgaa ccccccgttc agcccgaccg ctgcgcctta ccggtaact | 5760 |
| atcgtcttga gtccaacccg gtaagacacg acttatcgcc actggcagca gccactggta | 5820 |
| acaggattag cagagcgagg tatgtaggcg gtgctacaga gttcttgaag tggtggccta | 5880 |
| actacggcta cactagaaga acagtatttg gtatctgcgc tctgctgaag ccagttacct | 5940 |
| tcggaaaaag agttggtagc tcttgatccg gcaaacaaac caccgctggt agcggtggtt | 6000 |
| ttttgtttg caagcagcag attacgcgca gaaaaaagg atctcaagaa gatcctttga | 6060 |
| tcttttctac ggggtctgac gctcagtgga acgaaaactc acgttaaggg attttggtca | 6120 |
| tgagattatc aaaaaggatc ttcacctaga tccttttaaa ttaaaaatga agttttaaat | 6180 |
| caatctaaag tatatatgag taaacttggt ctgacagtta ccaatgctta atcagtgagg | 6240 |
| cacctatctc agcgatctgt ctatttcgtt catccatagt tgcctgactc cccgtcgtgt | 6300 |
| agataactac gatacgggag ggcttaccat ctggccccag tgctgcaatg ataccgcgag | 6360 |
| acccacgctc accggctcca gatttatcag caataaacca gccagccgga agggccgagc | 6420 |
| gcagaagtgg tcctgcaact ttatccgcct ccatccagtc tattaattgt tgccgggaag | 6480 |
| ctagagtaag tagttcgcca gttaatagtt tgcgcaacgt tgttgccatt gctacaggca | 6540 |
| tcgtggtgtc acgctcgtcg tttggtatgg cttcattcag ctccggttcc caacgatcaa | 6600 |
| ggcgagttac atgatccccc atgttgtgca aaaaagcggt tagctccttc ggtcctccga | 6660 |
| tcgttgtcag aagtaagttg gccgcagtgt tatcactcat ggttatggca gcactgcata | 6720 |
| attctcttac tgtcatgcca tccgtaagat gcttttctgt gactggtgag tactcaacca | 6780 |
| agtcattctg agaatagtgt atgcggcgac cgagttgctc ttgcccggcg tcaatacggg | 6840 |
| ataataccgc gccacatagc agaactttaa aagtgctcat cattggaaaa cgttcttcgg | 6900 |
| ggcgaaaact ctcaaggatc ttaccgctgt tgagatccag ttcgatgtaa cccactcgtg | 6960 |
| cacccaactg atcttcagca tcttttactt tcaccagcgt ttctgggtga gcaaaaacag | 7020 |
| gaaggcaaaa tgccgcaaaa aagggaataa gggcgacacg gaaatgttga atactcatac | 7080 |
| tcttcctttt tcaatattat tgaagcattt atcagggtta ttgtctcatg agcggataca | 7140 |
| tatttgaatg tatttagaaa aataaacaaa tagggggttcc gcgcacattt cccc | 7194 |

<210> SEQ ID NO 22
<211> LENGTH: 9240
<212> TYPE: DNA
<213> ORGANISM: Artificial Sequence
<220> FEATURE:
<223> OTHER INFORMATION: Synthesized vector

<400> SEQUENCE: 22

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |

```
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt gcggccgctg aagggctaa    420 tttggtccca aaaagacaa gagatccttg atctgtggat ctaccacaca caaggctact    480
tccctgattg gcagaactac acaccagggc cagggatcag atatccactg acctttggat    540
ggtgcttcaa gttagtacca gttgaaccag agcaagtaga agaggccaaa taaggagaga    600
agaacagctt gttacaccct atgagccagc atgggatgga ggacccggag ggagaagtat    660
tagtgtggaa gtttgacagc ctcctagcat tcgtcacat ggcccgagag ctgcatccgg      720
agtactacaa agactgctga catcgagctt tctacaaggg actttccgct ggggactttc    780
cagggaggtg tggcctgggc gggactgggg agtggcgagc cctcagatgc tacatataag    840
cagctgcttt ttgcctgtac tgggtctctc tggttagacc agatctgagc ctgggagctc    900
tctggctaac tagggaaccc actgcttaag cctcaataaa gcttgccttg agtgctcaaa    960
gtagtgtgtg cccgtctgtt gtgtgactct ggtaactaga gatccctcag acccttttag   1020
tcagtgtgga aaatctctag cagtggcgcc cgaacaggga cttgaaagcg aaagtaaagc   1080
cagaggagat ctctcgacgc aggactcggc ttgctgaagc gcgcacggca agaggcgagg   1140
ggcggcgact ggtgagtacg ccaaaaattt tgactagcgg aggctagaag agagagatg    1200 ggtgcgagag cgtcggtatt aagcggggga gaattagata aatgggaaaa aattcggtta   1260
aggccagggg gaaagaaaca atataaacta aaacatatag tatgggcaag cagggagcta   1320
gaacgattcg cagttaatcc tggccttta gagacatcag aaggctgtag acaaatactg     1380
ggacagctac aaccatccct tcagacagga tcagaagaac ttagatcatt atataataca   1440
atagcagtcc tctattgtgt gcatcaaagg atagatgtaa aagacaccaa ggaagcctta   1500
gataagatag aggaagagca aaacaaaagt aagaaaaagg cacagcaagc agcagctgac   1560
acaggaaaca acagccaggt cagccaaaat taccctatag tgcagaaccct ccaggggcaa   1620 atggtacatc aggccatatc acctagaact ttaaattaag acagcagtac aaatggcagt   1680
attcatccac aatttaaaa gaaaggggg gattgggggg tacagtgcag gggaaagaat      1740
agtagacata atagcaacag acatacaaac taaagaatta caaaacaaa ttacaaaaat     1800 tcaaaatttt cgggtttatt acaggacag cagagatcca gtttggaaag gaccagcaaa     1860
gctcctctgg aaaggtgaag gggcagtagt aatacaagat aatagtgaca taaaagtagt   1920
gccaagaaga aaagcaaaga tcatcaggga ttatggaaaa cagatggcag gtgatgattg   1980
tgtggcaagt agacaggatg aggattaaca catggaaaag attagtaaaa caccatagct   2040
ctagagcgat ccgatcttca gacctggagg aggcgatatg agggacaatt ggagaagtga   2100
attatataaa tataaagtag taaaaattga accattagga gtagcaccca ccaaggcaaa   2160
gagaagagtg gtgcagagag aaaaaagagc agtgggaata ggagctttgt tccttgggtt   2220
cttgggagca gcaggaagca ctatgggctg cacgtcaatg acgctgacgg tacaggccag   2280
acaattattg tctgatatag tgcagcagca gaacaatttg ctgagggcta ttgaggcgca   2340
acagcatctg ttgcaactca cagtctgggg catcaaacag ctccaggcaa gaatcctggc   2400
tgtggaaaga tacctaaagg atcaacagct cctggggatt tggggttgct ctggaaaact   2460
```

```
catttgcacc actgctgtgc cttggaatgc tagttggagt aataaatctc tggaacagat  2520
ttggaataac atgacctgga tggagtggga cagagaaatt aacaattaca caagcttggt  2580
aggtttaaga atagtttttg ctgtactttc tatagtgaat agagttaggc agggatattc  2640
accattatcg tttcagaccc acctcccaat cccgagggga cccgacaggc ccgaaggaat  2700
agaagaagaa ggtggagaga gagacagaga cagatccatt cgattagtga acggatcccg  2760
aacaagcttt gcaaagatgg ataaagtttt aaacagagag gaatctttgc agctaatgga  2820
ccttctaggt cttgaaagga gtgggaattg gctccggtgc ccgtcagtgg gcagagcgca  2880
catcgcccac agtccccgag aagttggggg gaggggtcgg caattgaacc ggtgcctaga  2940
gaaggtggcg cggggtaaac tgggaaagtg atgtcgtgta ctggctccgc cttttttccg  3000
agggtggggg agaaccgtat ataagtgcag tagtcgccgt gaacgttctt tttcgcaacg  3060
ggtttgccgc cagaacacag gtaagtgccg tgtgtggttc ccgcgggcct ggcctcttta  3120
cgggttatgg cccttgcgtg ccttgaatta cttccacgcc cctggctgca gtacgtgatt  3180
cttgatcccg agcttcgggt tggaagtggg tgggagagtt cgaggccttg cgcttaagga  3240
gccccttcgc ctcgtgcttg agttgaggcc tggcctgggc gctggggccg ccgcgtgcga  3300
atctggtggc accttcgcgc ctgtctcgct gctttcgata agtctctagc catttaaaat  3360
ttttgatgac ctgctgcgac gcttttttc tggcaagata gtcttgtaaa tgcgggccaa  3420
gatctgcaca ctggtatttc ggttttggg gccgcgggcg cgacggggc ccgtgcgtcc  3480
cagcgcacat gttcggcgag gcggggcctg cgagcgcggc caccgagaat cggacggggg  3540
tagtctcaag ctggccggcc tgctctggtg cctggcctcg cgccgccgtg tatcgccccg  3600
ccctgggcgg caaggctggc ccggtcggca ccagttgcgt gagcggaaag atggccgctt  3660
cccggccctg ctgcagggag ctcaaaatgg aggacgcggc gctcgggaga gcgggcgggt  3720
gagtcaccca cacaaaggaa aagggccttt ccgtcctcag ccgtcgcttc atgtgactcc  3780
acggagtacc gggcgccgtc caggcacctc gattagttct cgagcttttg gagtacgtcg  3840
tcttaggtt ggggggaggg gttttatgcg atggagtttc cccacactga gtgggtggag  3900
actgaagtta ggccagcttg gcacttgatg taattctcct tggaatttgc ccttttttgag  3960
tttggatctt ggttcattct caagcctcag acagtggttc aaagtttttt tcttccattt  4020
caggtgtcgt gagaattagc ggtggcggcc atcacaagtt tgtacaaaaa agcaggctgg  4080
cgccggaacc aattcagtcg actggatccg gtaccgaatt cgcggccata cccctgatga  4140
gtccgtgagg acgaaacgag taagctcgtc gggtatctta caggaactcc gttttagagc  4200
tatgctggaa acagcatagc aagttaaaat aaggctagtc cgttatcaac ttgaaaaagt  4260
ggcaccgagt cggtgctttt ttttttggccg gcatggtccc agcctcctcg ctggcgccgg  4320
ctgggcaaca tgcttcggca tggcgaatgg gacggccgct ctagaactag tggatccccc  4380
gccaccatgg ccctgtccaa caagttcatc ggcgacgaca tgaagatgac ctaccacatg  4440
gacggctgcg tgaacggcca ctacttcacc gtgaagggcg agggcagcgg caagccctac  4500
gagggcaccc agaccctccac cttcaaggtg accatggcca acggcggccc cctggccttc  4560
tccttcgaca tcctgtccac cgtgttcatg tacggcaacc gctgcttcac cgcctacccc  4620
accagcatgc ccgactactt caagcaggcc ttccccgacg catgtcctta cgagagaacc  4680
ttcacctacg aggacggcgg cgtggccacc gccagctggg agatcagcct gaagggcaac  4740
tgcttcgagc acaagtccac cttccacggc gtgaacttcc ccgccgacgg ccccgtgatg  4800
gccaagaaga ccaccggctg ggaccctcc ttcgagaaga tgaccgtgtg cgacggcatc  4860
```

```
ttgaagggcg acgtgaccgc cttcctgatg ctgcagggcg gcggcaacta cagatgccag    4920
ttccacacct cctacaagac caagaagccc gtgaccatgc cccccaacca cgtggtggag    4980
caccgcatcg ccagaaccga cctggacaag ggcggcaaca gcgtgcagct gaccgagcac    5040
gccgtggccc acatcacctc cgtggtgccc ttctgagggc tgcaggaatt cgatatcaag    5100
cttatcgata ccgtcgacct cgagatatct agacccagct ttcttgtaca aagtggtgat    5160
ctagctaaaa cgcggcctcg aatcgaattc cgccccccc cctctccctc ccccccccct    5220
aacgttactg gccgaagccg cttggaataa ggccggtgtg cgtttgtcta tatgttattt    5280
tccaccatat tgccgtcttt tggcaatgtg agggcccgga acctggccc tgtcttcttg    5340 acgagcattc ctaggggtct ttcccctctc gccaaaggaa tgcaaggtct gttgaatgtc    5400
gtgaaggaag cagttcctct ggaagcttct tgaagacaaa caacgtctgt agcgaccctt    5460
tgcaggcagc ggaaccccc acctggcgac aggtgcctct gcggccaaaa gccacgtgta    5520
taagatacac ctgcaaaggc ggcacaaccc cagtgccacg ttgtgagttg atagttgtg    5580 gaaagagtca aatggctctc ctcaagcgta ttcaacaagg gctgaagga tgcccagaag    5640 gtacccatt gtatgggatc tgatctgggg cctcggtgca catgctttac atgtgtttag    5700
tcgaggttaa aaaacgtct aggcccccg aaccacgggg acgtggtttt cctttgaaaa    5760
acacgatgat aatatggcca caaccatgac cgagtacaag cccacggtgc gcctcgccac    5820
ccgcgacgac gtccccaggg ccgtacgcac cctcgccgcc gcgttcgccg actacccgc    5880 cacgcgccac accgtcgatc cggaccgcca catcgagcgg gtcaccgagc tgcaagaact    5940
cttcctcacg cgcgtcgggc tcgacatcgg caaggtgtgg gtcgcggacg acggcgccgc    6000
ggtggcggtc tggaccacgc cggagagcgt cgaagcgggg gcggtgttcg ccagatcgg    6060 cccgcgcatg gccgagttga gcggttcccg gctggccgcg cagcaacaga tggaaggcct    6120
cctggcgccg caccggccca aggagcccgc gtggttcctg gccaccgtcg gcgtctcgcc    6180
cgaccaccag ggcaagggtc tgggcagcgc cgtcgtgctc cccggagtgg aggcggccga    6240
gcgcgccggg gtgcccgcct tcctggagac ctccgcgccc cgcaacctcc ccttctacga    6300
gcggctcggc ttcaccgtca ccgccgacgt cgaggtgccc gaaggaccgc gcacctggtg    6360
catgacccgc aagcccggtg cctgacgccc gccccacgac ccgcagcgcc cgaccgaaag    6420
gagcgcacga cccatgcat cgatttcgaa cccggggtac ctttaagacc aatgacttac    6480
aaggcagctg tagatcttag ccacttttta aagaaaagg ggggactgga agggctaatt    6540
cactcccaaa gaagacaaga tctgcttttt gcctgtactg ggtctctctg gttagaccag    6600
atctgagcct gggagctctc tggctaacta gggaacccac tgcttaagcc tcaataaagc    6660
ttgccttgag tgcttcaagt agtgtgtgcc cgtctgttgt gtgactctgg taactagaga    6720
tccctcagac cctttagtc agtgtggaaa atctctagca gaattctagc ttggcgtaat    6780
catggtcata gctgttcctg tgtgaaattg ttatccgctc acaattccac acaacatacg    6840
agccggaagc ataaagtgta aagcctgggg tgcctaatga gtgagctaac tcacattaat    6900
tgcgttgcgc tcactgcccg ctttccagtc gggaaacctg tcgtgccagc tgcattaatg    6960
aatcggccaa cgcgcgggga gaggcggttt gcgtattggg cgctcttccg cttcctcgct    7020
cactgactcg ctgcgctcgg tcgttcggct gcggcgagcg gtatcagctc actcaaaggc    7080
ggtaatacgg ttatccacag aatcagggga taacgcagga agaacatgtg agcaaaaggc    7140
ccagcaaaag gccaggaacc gtaaaaaggc cgcgttgctg gcgtttttcc ataggctccg    7200
```

```
cccccctgac gagcatcaca aaaatcgacg ctcaagtcag aggtggcgaa acccgacagg    7260
actataaaga taccaggcgt ttccccctgg aagctccctc gtgcgctctc ctgttccgac    7320
cctgccgctt accggatacc tgtccgcctt tctcccttcg ggaagcgtgg cgctttctca    7380
atgctcacgc tgtaggtatc tcagttcggt gtaggtcgtt cgctccaagc tgggctgtgt    7440
gcacgaaccc cccgttcagc ccgaccgctg cgccttatcc ggtaactatc gtcttgagtc    7500
caacccggta agacacgact tatcgccact ggcagcagcc actggtaaca ggattagcag    7560
agcgaggtat gtaggcggtg ctacagagtt cttgaagtgg tggcctaact acggctacac    7620
tagaaggaca gtatttggta tctgcgctct gctgaagcca cttaccttcg gaaaaagagt    7680
tggtagctct tgatccggca aacaaaccac cgctggtagc ggtggttttt ttgtttgcaa    7740
gcagcagatt acgcgcagaa aaaaaggatc tcaagaagat cctttgatct tttctacggg    7800
gtctgacgct cagtggaacg aaaactcacg ttaagggatt ttggtcatga gattatcaaa    7860
aaggatcttc acctagatcc ttttaaatta aaaatgaagt tttaaatcaa tctaaagtat    7920
atatgagtaa acttggtctg acagttacca atgcttaatc agtgaggcac ctatctcagc    7980
gatctgtcta tttcgttcat ccatagttgc ctgactcccc gtcgtgtaga taactacgat    8040
acgggagggc ttaccatctg gccccagtgc tgcaatgata ccgcgagacc cacgctcacc    8100
ggctccagat ttatcagcaa taaaccagcc agccggaagg gccgagcgca gaagtggtcc    8160
tgcaacttta tccgcctcca tccagtctat taattgttgc cgggaagcta gagtaagtag    8220
ttcgccagtt aatagtttgc gcaacgttgt tgccattgct acaggcatcg tggtgtcacg    8280
ctcgtcgttt ggtatggctt cattcagctc cggttcccaa cgatcaaggc gagttacatg    8340
atcccccatg ttgtgcaaaa aagcggttag ctccttcggt cctccgatcg ttgtcagaagt   8400
aagttggccg cagtgttatc actcatggtt atggcagcac tgcataattc tcttactgtc    8460
atgccatccg taagatgctt ttctgtgact ggtgagtact caaccaagtc attctgagaa    8520
tagtgtatgc ggcgaccgag ttgctcttgc ccggcgtcaa tacgggataa taccgcgcca    8580
catagcagaa ctttaaaagt gctcatcatt ggaaaacgtt cttcggggcg aaaactctca    8640
aggatcttac cgctgttgag atccagttcg atgtaaccca ctcgtgcacc caactgatct    8700
tcagcatctt ttactttcac cagcgtttct gggtgagcaa aaacaggaag gcaaaatgcc    8760
gcaaaaaagg gaataagggc gacacggaaa tgttgaatac tcatactctt cctttttcaa    8820
tattattgaa gcatttatca gggttattgt ctcatgagcg gatacatatt tgaatgtatt    8880
tagaaaaata aacaaatagg ggttccgcgc acatttcccc gaaaagtgcc acctgggact    8940
agcttttgc aaaagcctag gcctccaaaa aagcctcctc actacttctg gaatagctca    9000
gaggccgagg cggcctcggc ctctgcataa ataaaaaaaa ttagtcagcc atggggcgga    9060
gaatgggcgg aactgggcgg agttaggggc gggatgggcg gagttagggg cgggactatg    9120
gttgctgact aattgagatg tagcttgcat gccgacatgg attattgact agtccctaag    9180
aaaccattat tatcatgaca ttaacctata aaaataggcg tatcacgagg ccctttcgtc    9240
```

<210> SEQ ID NO 23
<211> LENGTH: 8405
<212> TYPE: DNA
<213> ORGANISM: Artificial Sequence
<220> FEATURE:
<223> OTHER INFORMATION: Synthesized vector

<400> SEQUENCE: 23

```
tcgcgcgttt cggtgatgac ggtgaaaacc tctgacacat gcagctcccg gagacggtca      60
```

```
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta cgccagggt       360 tttcccagtc acgacgttgt aaaacgacgg ccagtgaatt gcggccgctg aagggctaa      420 tttggtccca aaaagacaa gagatccttg atctgtggat ctaccacaca caaggctact      480
tccctgattg gcagaactac acaccagggc cagggatcag atatccactg acctttggat      540
ggtgcttcaa gttagtacca gttgaaccag agcaagtaga agaggccaaa taaggagaga      600
agaacagctt gttacaccct atgagccagc atgggatgga ggacccggag ggagaagtat      660
tagtgtggaa gtttgacagc ctcctagcat ttcgtcacat ggcccgagag ctgcatccgg      720
agtactacaa agactgctga catcgagctt tctacaaggg actttccgct ggggactttc      780
cagggaggtg tggcctgggc gggactgggg agtggcgagc cctcagatgc tacatataag      840
cagctgcttt ttgcctgtac tgggtctctc tggttagacc agatctgagc ctgggagctc      900
tctggctaac tagggaaccc actgcttaag cctcaataaa gcttgccttg agtgctcaaa      960
gtagtgtgtg cccgtctgtt gtgtgactct ggtaactaga gatccctcag acccttttag     1020
tcagtgtgga aaatctctag cagtggcgcc cgaacaggga cttgaaagcg aaagtaaagc     1080
cagaggagat ctctcgacgc aggactcggc ttgctgaagc gcgcacggca agaggcgagg     1140
ggcggcgact ggtgagtacg ccaaaaattt tgactagcgg aggctagaag gagagagatg     1200
ggtgcgagag cgtcggtatt aagcggggga gaattagata aatgggaaaa aattcggtta     1260
aggccagggg gaaagaaaca atataaacta aaacatatag tatgggcaag cagggagcta     1320
gaacgattcg cagttaatcc tggccttta gagacatcag aaggctgtag acaaatactg      1380
ggacagctac aaccatccct tcagacagga tcagaagaac ttagatcatt atataataca     1440
atagcagtcc tctattgtgt gcatcaaagg atagatgtaa aagacaccaa ggaagcctta     1500
gataagatag aggaagagca aaacaaaagt aagaaaaagg cacagcaagc agcagctgac     1560
acaggaaaca acagccaggt cagccaaaat taccctatag tgcagaacct ccaggggcaa     1620
atggtacatc aggccatatc acctagaact ttaaattaag acagcagtac aaatggcagt     1680
attcatccac aattttaaaa gaaaggggg gattgggggg tacagtgcag gggaagaat      1740 agtagacata atagcaacag acatacaaac taaagaatta caaaacaaa ttacaaaaat     1800 tcaaaatttt cgggtttatt acagggacag cagagatcca gtttggaaag gaccagcaaa     1860
gctcctctgg aaaggtgaag gggcagtagt aatacaagat aatagtgaca taaaagtagt     1920
gccaagaaga aaagcaaaga tcatcaggga ttatggaaaa cagatggcag gtgatgattg     1980
tgtggcaagt agacaggatg aggattaaca catggaaaag attagtaaaa caccatagct     2040
ctagagcgat ccgatcttca gacctggagg aggcgatatg agggacaatt gaaccggtgc     2100
ctagagaagg tggcgcgggg taaactggga aagtgatgtc gtgtactggc tccgcctttt     2160
tcccgagggt ggggagaac cgtatataag tgcagtagtc gccgtgaacg ttctttttcg      2220
caacgggttt gccgccagaa cacaggtaag tgccgtgtgt ggttcccgcg ggcctggcct     2280
ctttacgggg tatggccctt gcgtgccttg aattacttcc acgcccctgg ctgcagtacg     2340
tgattcttga tcccgagctt cggggttgaa gtgggtggga gagttcgagg ccttgcgctt     2400
```

```
aaggagcccc ttcgcctcgt gcttgagttg aggcctggcc tgggcgctgg ggccgccgcg   2460
tgcgaatctg gtggcacctt cgcgcctgtc tcgctgcttt cgataagtct ctagccattt   2520 aaaattttg atgacctgct gcgacgcttt ttttctggca agatagtctt gtaaatgcgg    2580
gccaagatct gcacactggt atttcggttt ttggggccgc gggcggcgac ggggcccgtg   2640
cgtcccagcg cacatgttcg gcgaggcggg gcctgcgagc gcggccaccg agaatcggac   2700
gggggtagtc tcaagctggc cggcctgctc tggtgcctgg cctcgcgccg ccgtgtatcg   2760
ccccgccctg ggcggcaagg ctggcccggt cggcaccagt tgcgtgagcg gaaagatggc   2820
cgcttcccgg ccctgctgca gggagctcaa aatggaggac gcggcgctcg ggagagcggg   2880
cgggtgagtc acccacacaa aggaaaaggg cctttccgtc ctcagccgtc gcttcatgtg   2940
actccacgga gtaccgggcg ccgtccaggc acctcgatta gttctcgagc ttttggagta   3000 cgtcgtctt aggttggggg gaggggtttt atgcgatgga gtttccccac actgagtggg    3060
tggagactga agttaggcca gcttggcact tgatgtaatt ctccttggaa tttgcccttt   3120
ttgagtttgg atcttggttc attctcaagc ctcagacagt ggttcaaagt ttttttcttc   3180
catttcaggt gtcgtgagaa ttagcggtgg cggccatcac aagtttgtac aaaaaagcag   3240
gctggcgccg gaaccaattc agtcgactgg atccggtacc gaattcgcgg ccataccct    3300 gatgagtccg tgaggacgaa acgagtaagc tcgtcgggta tcttacagga actccgtttt   3360
agagctatgc tggaaacagc atagcaagtt aaaataaggc tagtccgtta tcaacttgaa   3420
aaagtggcac cgagtcggtg ctttttttt ggccggcatg gtcccagcct cctcgctggc    3480
gccggctggg caacatgctt cggcatggcg aatgggacgg ccgctctaga actagtggat   3540
cccccgccac catggccctg tccaacaagt tcatcggcga cgacatgaag atgacctacc   3600
acatggacgc ctgcgtgaac ggccactact tcaccgtgaa gggcgagggc agcggcaagc   3660
cctacgaggg cacccagacc tccaccttca aggtgaccat ggccaacggc ggccccctgg   3720
ccttctcctt cgacatcctg tccaccgtgt tcatgtacgg caaccgctgc ttcaccgcct   3780
accccaccag catgcccgac tacttcaagc aggccttccc cgacggcatg tcctacgaga   3840
gaaccttcac ctacgaggac ggcggcgtgg ccaccgccag ctgggagatc agcctgaagg   3900
gcaactgctt cgagcacaag tccaccttcc acggcgtgaa cttccccgcc gacggccccg   3960
tgatggccaa gaagaccacc ggctgggacc cctccttcga aagatgacc gtgtgcgacg    4020 gcatcttgaa gggcgacgtg accgccttcc tgatgctgca gggcggcggc aactacagat   4080
gccagttcca cacctcctac aagaccaaga gagcccgtgac catgccccc aaccacgtgg    4140 tggagcaccg catcgccaga accgacctgg acaagggcgg caacagcgtg cagctgaccg   4200
agcacgccgt ggcccacatc acctccgtgg tgcccttctg agggctgcag gaattcgata   4260
tcaagcttat cgataccgtc gacctcgaga tatctagacc cagctttctt gtacaaagtg   4320
gtgatctagc taaaacgcgg cctcgaatcg aattccgccc ccccctct ccctccccc      4380 cccctaacgt tactggccga agccgcttgg aataaggccg gtgtgcgttt gtctatatgt   4440
tattttccac catattgccg tcttttggca atgtgagggc ccggaaacct ggccctgtct   4500
tcttgacgag cattcctagg ggtctttccc ctctcgccaa aggaatgcaa ggtctgttga   4560
atgtcgtgaa ggaagcagtt cctctggaag cttcttgaag acaaacaacg tctgtagcga   4620 cccttttgcag gcagcggaac cccccacctg gcgacaggtg cctctgcggc caaaagccac   4680
gtgtataaga tacctgcaa aaggcggcac aaccccagtg ccacgttgtg agttggatag    4740
ttgtggaaag agtcaaatgg ctctcctcaa gcgtattcaa caagggctg aaggatgccc     4800
```

```
agaaggtacc ccattgtatg ggatctgatc tggggcctcg gtgcacatgc tttacatgtg    4860
tttagtcgag gttaaaaaaa cgtctaggcc ccccgaacca cggggacgtg gttttccttt    4920
gaaaaacacg atgataatat ggccacaacc atgaccgagt acaagcccac ggtgcgcctc    4980
gccacccgcg acgacgtccc cagggccgta cgcaccctcg ccgccgcgtt cgccgactac    5040
cccgccacgc gccacaccgt cgatccggac cgccacatcg agcgggtcac cgagctgcaa    5100
gaactcttcc tcacgcgcgt cgggctcgac atcggcaagg tgtgggtcgc ggacgacggc    5160
gccgcggtgg cggtctggac cacgccggag agcgtcgaag cggggcggt gttcgccgag    5220 atcggcccgc gcatggccga gttgagcggt tcccggctgg ccgcgcagca acagatggaa    5280
ggcctcctgg cgccgcaccg gcccaaggag cccgcgtggt tcctggccac cgtcggcgtc    5340
tcgcccgacc accagggcaa gggtctgggc agcgccgtcg tgctccccgg agtggaggcg    5400
gccgagcgcg ccggggtgcc cgccttcctg gagacctccg cgccccgcaa cctccccttc    5460
tacgagcggc tcggcttcac cgtcaccgcc gacgtcgagg tgcccgaagg accgcgcacc    5520
tggtgcatga cccgcaagcc cggtgcctga cgcccgcccc acgacccgca gcgcccgacc    5580
gaaaggagcg cacgacccca tgcatcgatt tcgaacccgg ggtacccttta agaccaatga    5640 cttacaaggc agctgtagat cttagccact ttttaaaaga aaaggggga ctggaagggc    5700 taattcactc ccaaagaaga caagatctgc ttttttgcctg tactgggtct ctctggttag    5760
accagatctg agcctgggag ctctctggct aactagggaa cccactgctt aagcctcaat    5820
aaagcttgcc ttgagtgctt caagtagtgt gtgcccgtct gttgtgtgac tctggtaact    5880
agagatccct cagacccttt tagtcagtgt ggaaaatctc tagcagaatt ctagcttggc    5940
gtaatcatgg tcatagctgt tcctgtgtga aattgttatc cgctcacaat tccacacaac    6000
atacgagccg gaagcataaa gtgtaaagcc tggggtgcct aatgagtgag ctaactcaca    6060
ttaattgcgt tgcgctcact gcccgctttc cagtcgggaa acctgtcgtg ccagctgcat    6120
taatgaatcg gccaacgcgc ggggagaggc ggtttgcgta ttgggcgctc ttccgcttcc    6180
tcgctcactg actcgctgcg ctcggtcgtt cggctgcggc gagcggtatc agctcactca    6240
aaggcggtaa tacggttatc cacagaatca ggggataacg caggaaagaa catgtgagca    6300
aaaggccagc aaaaggccag gaaccgtaaa aaggccgcgt tgctggcgtt tttccatagg    6360
ctccgccccc ctgacgagca tcacaaaaat cgacgctcaa gtcagaggtg gcgaaacccg    6420
acaggactat aaagatacca ggcgtttccc cctggaagct ccctcgtgcg ctctcctgtt    6480
ccgaccctgc cgcttaccgg atacctgtcc gcctttctcc cttcgggaag cgtggcgctt    6540
tctcaatgct cacgctgtag gtatctcagt tcggtgtagg tcgttcgctc caagctgggc    6600
tgtgtgcacg aaccccccgt tcagcccgac cgctgcgcct tatccggtaa ctatcgtctt    6660
gagtccaacc cggtaagaca cgacttatcg ccactggcag cagccactgg taacaggatt    6720
agcagagcga ggtatgtagg cggtgctaca gagttcttga agtggtggcc taactacggc    6780
tacactagaa ggacagtatt tggtatctgc gctctgctga agccacttac cttcggaaaa    6840
agagttggta gctcttgatc cggcaaacaa accaccgctg gtagcggtgg tttttttgtt    6900
tgcaagcagc agattacgcg cagaaaaaaa ggatctcaag aagatccttt gatcttttct    6960
acggggtctg acgctcagtg gaacgaaaac tcacgttaag ggattttggt catgagatta    7020
tcaaaaagga tcttcaccta gatccttttta aattaaaaat gaagttttaa atcaatctaa    7080
agtatatatg agtaaacttg gtctgacagt taccaatgct taatcagtga ggcacctatc    7140
```

-continued

```
tcagcgatct gtctatttcg ttcatccata gttgcctgac tccccgtcgt gtagataact    7200
acgatacggg agggcttacc atctggcccc agtgctgcaa tgataccgcg agacccacgc    7260
tcaccggctc cagatttatc agcaataaac cagccagccg aagggccga gcgcagaagt     7320
ggtcctgcaa ctttatccgc ctccatccag tctattaatt gttgccggga agctagagta    7380
agtagttcgc cagttaatag tttgcgcaac gttgtgccat tgctacaggc atcgtggtgt    7440
cacgctcgtc gtttggtatg gcttcattca gctccggttc ccaacgatca aggcgagtta    7500
catgatcccc catgttgtgc aaaaaagcgg ttagctcctt cggtcctccg atcgttgtca    7560
gaagtaagtt ggccgcagtg ttatcactca tggttatggc agcactgcat aattctctta    7620
ctgtcatgcc atccgtaaga tgcttttctg tgactggtga gtactcaacc aagtcattct    7680
gagaatagtg tatgcggcga ccgagttgct cttgcccggc gtcaatacgg gataataccg    7740
cgccacatag cagaacttta aaagtgctca tcattggaaa acgttcttcg ggcgaaaac     7800
tctcaaggat cttaccgctg ttgagatcca gttcgatgta acccactcgt gcacccaact    7860
gatcttcagc atctttact ttcaccagcg tttctgggtg agcaaaaaca ggaaggcaaa     7920
atgccgcaaa aaagggaata agggcgacac ggaaatgttg aatactcata ctcttccttt    7980
ttcaatatta ttgaagcatt tatcagggtt attgtctcat gagcggatac atatttgaat    8040
gtatttagaa aaataaacaa atagggcttc cgcgcacatt tccccgaaaa gtgccacctg    8100
ggactagctt tttgcaaaag cctaggcctc caaaaaagcc tcctcactac ttctggaata    8160
gctcagaggc cgaggcggcc tcggcctctg cataaataaa aaaaattagt cagccatggg    8220
gcggagaatg ggcggaactg gcggagtta ggggcgggat gggcggagtt aggggcggga     8280
ctatggttgc tgactaattg agatgtagct tgcatgccga catggattat tgactagtcc    8340
ctaagaaacc attattatca tgacattaac ctataaaaat aggcgtatca cgaggccctt    8400
tcgtc                                                                8405
```

<210> SEQ ID NO 24
<211> LENGTH: 20
<212> TYPE: DNA
<213> ORGANISM: Homo sapiens

<400> SEQUENCE: 24
agctgtcaga cagaaaaaag    20

<210> SEQ ID NO 25
<211> LENGTH: 20
<212> TYPE: DNA
<213> ORGANISM: Homo sapiens

<400> SEQUENCE: 25
ggtgagtgag tgtgtgcgtg    20

<210> SEQ ID NO 26
<211> LENGTH: 23
<212> TYPE: DNA
<213> ORGANISM: Homo sapiens

<400> SEQUENCE: 26
ggtgagtgag tgtgtgcgtg tgg    23

<210> SEQ ID NO 27
<211> LENGTH: 23
<212> TYPE: DNA
<213> ORGANISM: Homo sapiens

```
<400> SEQUENCE: 27
tgtgggtgag tgtgtgcgtg agg                                              23

<210> SEQ ID NO 28
<211> LENGTH: 20
<212> TYPE: DNA
<213> ORGANISM: Homo sapiens

<400> SEQUENCE: 28
tgacatcaat tattatacat                                                  20

<210> SEQ ID NO 29
<211> LENGTH: 20
<212> TYPE: DNA
<213> ORGANISM: Homo sapiens

<400> SEQUENCE: 29
gggcacgggc agcttgccgg                                                  20

<210> SEQ ID NO 30
<211> LENGTH: 20
<212> TYPE: DNA
<213> ORGANISM: Homo sapiens

<400> SEQUENCE: 30
gtcatcgcaa cggggacgct                                                  20

<210> SEQ ID NO 31
<211> LENGTH: 20
<212> TYPE: DNA
<213> ORGANISM: Homo sapiens

<400> SEQUENCE: 31
ctcaaacacc ccttccgcag                                                  20
```